US011795228B2

(12) United States Patent
Tomasevic et al.

(10) Patent No.: US 11,795,228 B2
(45) Date of Patent: Oct. 24, 2023

(54) ANTI-CD94 ANTIBODIES AND METHODS OF USE THEREOF

(71) Applicant: Dren Bio, Inc., Redwood City, CA (US)

(72) Inventors: Nenad Tomasevic, Foster City, CA (US); Ruo Shi Shi, San Mateo, CA (US)

(73) Assignee: Dren Bio, Inc., Foster City, CA (US)

( * ) Notice: Subject to any disclaimer, the term of this patent is extended or adjusted under 35 U.S.C. 154(b) by 51 days.

(21) Appl. No.: 17/489,385

(22) Filed: Sep. 29, 2021

(65) Prior Publication Data

US 2022/0127365 A1 Apr. 28, 2022

Related U.S. Application Data

(60) Provisional application No. 63/088,926, filed on Oct. 7, 2020, provisional application No. 63/085,932, filed on Sep. 30, 2020.

(51) Int. Cl.
*C07K 16/28* (2006.01)
*A61K 38/20* (2006.01)
*A61K 39/395* (2006.01)
*A61K 39/00* (2006.01)

(52) U.S. Cl.
CPC ...... *C07K 16/2851* (2013.01); *A61K 38/2013* (2013.01); *A61K 39/3955* (2013.01); *C07K 16/283* (2013.01); *A61K 2039/505* (2013.01); *C07K 2317/21* (2013.01); *C07K 2317/24* (2013.01); *C07K 2317/33* (2013.01); *C07K 2317/40* (2013.01); *C07K 2317/565* (2013.01); *C07K 2317/622* (2013.01); *C07K 2317/732* (2013.01); *C07K 2317/76* (2013.01); *C07K 2317/77* (2013.01)

(58) Field of Classification Search
CPC .......... A61K 2039/505; C07K 2317/33; C07K 2317/565; C07K 2317/77
See application file for complete search history.

(56) References Cited

U.S. PATENT DOCUMENTS

| | | |
|---|---|---|
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0260186 A1 | 11/2005 | Bookbinder et al. |
| 2006/0104968 A1 | 5/2006 | Bookbinder et al. |
| 2008/0274047 A1 * | 11/2008 | Romagne ................ A61P 13/12 424/1.49 |
| 2008/0274475 A1 | 11/2008 | Braud et al. |
| 2017/0355756 A1 * | 12/2017 | Julien ..................... A61P 25/00 |
| 2022/0185895 A1 | 6/2022 | Tomasevic et al. |

FOREIGN PATENT DOCUMENTS

| | | | |
|---|---|---|---|
| WO | WO-1991011465 A1 | 8/1991 | |
| WO | WO-2000061739 A1 | 10/2000 | |
| WO | WO-2001029246 A1 | 4/2001 | |
| WO | WO-2003084570 A1 | 10/2003 | |
| WO | WO-2003085119 A1 | 10/2003 | |
| WO | WO-2004056312 A2 | 7/2004 | |
| WO | WO-2005035586 A1 | 4/2005 | |
| WO | WO-2005035778 A1 | 4/2005 | |
| WO | WO-2005053742 A1 | 6/2005 | |
| WO | WO-2005105848 A1 | 11/2005 | |
| WO | WO-2006070286 A2 | 7/2006 | |
| WO | WO-2007042573 A2 * | 4/2007 | ............... A61P 1/04 |
| WO | WO-2008009545 A1 | 1/2008 | |
| WO | WO-2009092805 A1 | 7/2009 | |
| WO | WO-2012172102 A1 | 12/2012 | |
| WO | WO-2016041947 A1 | 3/2016 | |

OTHER PUBLICATIONS

Koenig et al. Mutational landscape of antibody variable domains reveals a switch modulating the interdomain conformational dynamics and antigen binding.PNAS Jan. 24, 2017 114(4)E486-E495;firstpublished Jan. 5, 2017. (Year: 2017).*
Kussie et al. A single engineered amino acid substitution changes antibody fine specificity.J Immunol. Jan. 1, 1994;152(1):146-52. (Year: 1994).*
Wu et al. Humanization of a murine monoclonal antibody by simultaneous optimization of framework and CDR residues. J Mol Biol. Nov. 19, 1999;294(1):151-62. (Year: 1999).*
Edwards et al. The remarkable flexibility of the human antibody repertoire;isolation of over one thousand different antibodies to a single protein,BLyS. J Mol Biol Nov. 14, 2003;334(1):103-18. (Year: 2003).*
Chen et al. Enhancement and destruction of antibody function by somatic mutation: unequal occurrence is controlled by V gene combinatorial associations. EMBO J.Jun. 15, 1995; 14(12): 2784-94. (Year: 1995).*
Rudikoff S et al. Single amino acid substitution altering antigen-binding specificity. Proc Natl Acad Sci U S A. Mar. 1982;79(6):1979-83. (Year: 1982).*
Almagro JC, Fransson J. Humanization of antibodies. Front Biosci. Jan. 1, 2008;13:1619-33. (Year: 2008).*

(Continued)

*Primary Examiner* — Aurora M Fontainhas
*Assistant Examiner* — Jennifer A Benavides
(74) *Attorney, Agent, or Firm* — MORRISON & FOERSTER LLP

(57) ABSTRACT

The present disclosure relates to antibodies that bind to human CD94, as well as methods, uses, polynucleotides, vectors, host cells, and pharmaceutical compositions related thereto. In some embodiments, the antibodies are human or humanized antibodies that bind to human CD94 and do not block binding between CD94 and HLA-E. In some embodiments, the antibodies cross-react with cynomolgus CD94. In some embodiments, the antibodies do not promote internalization of surface-expressed CD94 to the extent of existing antibodies. In some embodiments, the antibodies promote ADCC targeting cells that express human CD94, e.g., on the cell surface.

75 Claims, 50 Drawing Sheets

Specification includes a Sequence Listing.

(56) References Cited

OTHER PUBLICATIONS

Peipp M et al. Antibody fucosylation differentially impacts cytotoxicity mediated by NK and PMN effector cells. Blood. Sep. 15, 2008; 112(6):2390-9. (Year: 2008).*

Iwasaki K, Uno Y, Utoh M, Yamazaki H. Importance of cynomolgus monkeys in development of monoclonal antibody drugs. Drug Metab Pharmacokinet. Feb. 2019;34(1):55-63. (Year: 2019).*

Ackerman et al., (2011). "A robust, high-throughput assay to determine the phagocytic activity of clinical antibody samples," Journal of Immunological Methods, 366(1-2):8-19.

Alekshun et al., (2007). "Diseases of large granular lymphocytes," Cancer Control, 14(2):141-150.

Aletaha et al., (2010). "2010 Rheumatoid arthritis classification criteria: an American College of Rheumatology/European League Against Rheumatism collaborative initiative," Annals of Rheumatic Diseases, 69(9):1580-1588.

Bajaj (2019). "The T cell predominance: Peripheral T cell lymphoma-not otherwise specified," International Journal of Hematology and Therapy, 5(1), 7 pages.

Barmeyer et al., (2016). "ENaC Dysregulation Through Activation of MEK1/2 Contributes to Impaired Na+ Absorption in Lymphocytic Colitis," Inflamm. Bowel Dis., 22(3):539-547.

Biolegend Purified anti-human CD94 antibody (clone DX22)—technical data sheet (Revision Date: Nov. 30, 2012). Available online at <https://www.biolegend.com/en-us/search-results/purified-anti-human-cd94-antibody-649>, 2 pages.

Bourgault-Rouxel et al., (2008). "Clinical spectrum of γδ T cell LGL leukemia: Analysis of 20 cases," Leuk Res., 32(1):45-48.

Brekke et al., (2003). "New technologies in therapeutic antibody development," Curr. Opin. Phamacol., 3(5):544-550.

Cairo et al., (2004). "Tumour lysis syndrome: new therapeutic strategies and classification," Br J Haematol, 127(1):3-11.

Capel et al., (1994). "Heterogeneity of human IgG Fc receptors," Immunomethods, 4(1):25-34.

Carter et al., (1992). "Humanization of an anti-p185$^{HER2}$ antibody for human cancer therapy," PNAS, 89(10):4285-4289.

Chothia et al., (1987). "Canonical structures for the hypervariable regions of immunoglobulins," Mol. Biol., 196(4):901-917.

Conrad et al., (2005). "Considerations on antibody-phage display methodology," Comb. Chem. High Throughput Screen., 8(2):117-126.

Dall'Ozzo et al., (2004). "Rituximab-dependent cytotoxicity by natural killer cells: influence of FCGR3A polymorphism on the concentration-effect relationship," Cancer Res., 64(13):4664-4469.

Dantas-Barbosa et al., (2005). "Construction of a human Fab phage display library from antibody repertoires of osteosarcoma patients," Genet. Mol. Res., 4(2):126-140.

De Haas et al., (1995). "Fcγ receptors of phagocytes," J. Leg. Clin. Med., 126(4):330-341.

Drake et al., (2007). "A rigorous multiple independent binding site model for determining cell-based equilibrium dissociation constants," J. Immunol. Methods, 318(1-2):147-152.

Ferrara et al., (2011). "Unique carbohydrate-carbohydrate interactions are required for high affinity binding between FcγRIII and antibodies lacking core fucose," Proc. Natl. Acad. Sci., 108(31):12669-12674.

Gomez-Roman et al., (2006). "A simplified method for the rapid fluorometric assessment of antibody-dependent cell-mediated cytotoxicity," J. Immunol. Methods, 308(1-2):53-67.

Goranzon et al., (2013). "Immunohistochemical characterization of lymphocytes in microscopic colitis," J. Crohns Colitis, 7(10):e434-e442.

Green et al., (1994). "Antigen-specific human monoclonal antibodies from mice engineered with human Ig heavy and light chain YACs," Nature Genetics, 7:13-21.

Green et al., (1999). "Antibody engineering via genetic engineering of the mouse: XenoMouse strains are a vehicle for the facile generation of therapeutic human monoclonal antibodies," J. Immunol. Methods, 231(1-2):11-23.

Hisamatsu et al., (2016). "The Role of T-Cell Subsets in Chronic Inflammation in Celiac Disease and Inflammatory Bowel Disease Patients: More Common Mechanisms or More Differences?" Inflamm. Intest. Dis., 1(2):52-62.

Huang et al., (2016). "Depletion of major pathogenic cells in asthma by targeting CRTh2," JCI Insight, 1(7):e86689, 20 pages.

International Search Report and Written Opinion received for International Patent Application No. PCT/US2020/025012 dated Jun. 10, 2020, 15 pages.

International Search Report and Written Opinion received for International Patent Application No. PCT/US2021/052668 dated Nov. 30, 2021, 14 pages.

Invitrogen CD94 Monoclonal Antibody (HP-3D9), APC—Datasheet, (2021). Available online at <https://www.thermofisher.com/antibody/product/CD94-Antibody-clone-HP-3D9-Monoclonal/17-5094-42>, 2 pages.

Jones et al., (1986). "Replacing the complementarity-determining regions in a human antibody with those from a mouse," Nature, 321(6069):522-525.

Köhler et al., (1975). "Continuous cultures of fused cells secreting antibody of predefined specificity," Nature, 256(5517):495-497.

Kolbeck et al., (2010). "MEDI-563, a humanized anti-IL-5 receptor alpha mAb with enhanced antibody-dependent cell-mediated cytotoxicity function," J Allergy Clin Immunol., 125(6):1344-1353.

Kwong et al., (2012). "SMILE for natural killer/T-cell lymphoma: analysis of safety and efficacy from the Asia Lymphoma Study Group," Blood, 120(15):2973-2980.

Lamy et al., (2017). "LGL leukemia: from pathogenesis to treatment," Blood, 129(9):1082-1094.

Lazar et al., (2006). "Engineered antibody Fc variants with enhanced effector function," PNAS, 103(11):4005-4010.

Lefranc (1999). "The IMGT unique numbering for immunoglobulins, T-cell receptors, and Ig-like domains," Immunologist, 7(4):132-136.

Lonberg et al., (1994). "Antigen-specific human antibodies from mice comprising four distinct genetic modifications," Nature, 368(6474):856-859.

Losman et al., (1990). "Baboon anti-idiotype antibodies mimic a carcinoembryonic antigen epitope," Int J Cancer., 46(2):310-314.

Loughran (1993). "Clonal diseases of large granular lymphocytes," Blood, 82(1):1-14.

Mancini et al., (2004). "Phage display for the production of human monoclonal antibodies against human pathogens," New Microbiol., 27(4):315-328.

Mori et al., (2004). "Engineering Chinese hamster ovary cells to maximize effector function of produced antibodies using FUT8 siRNA," Biotechnology and Bioengineering, 88(7):901-908.

Okazaki et al., (2004). "Fucose depletion from human IgG1 oligosaccharide enhances binding enthalpy and association rate between IgG1 and FcγRIIIa," J. Mol. Biol., 336(5):1239-1249.

Oshimi, (2017). "Clinical Features, Pathogenesis, and Treatment of Large Granular Lymphocyte Leukemias," Internal Medicine, 56:1759-1769.

Ravetch et al., (1991). "Fc receptors," Annu Rev Immunol., 9:457-492.

Richards et al., (2008). "Optimization of antibody binding to FcγRIIa enhances macrophage phagocytosis of tumor cells," Mol Cancer Ther., 7(8):2517-2527.

Riechmann et al., (1988). "Reshaping human antibodies for therapy," Nature, 332(6162):323-327.

Ripka et al., (1986). "Two Chinese hamster ovary glycosylation mutants affected in the conversion of GDP-mannose to GDP-fucose," Arch. Biochem. Biophys., 249(2):533-545.

Sandhu (1992). "Protein engineering of antibodies," Crit. Rev. Biotech., 12(5-6):437-462.

Santa Cruz Anti-CD94 Antibody (H-3): sc-390776—Datasheet. (2021). Available online at <https://www.scbt.eom/p/cd94-antibody-h-3>, 1 page.

Santa Cruz Anti-CD94 Antibody (HP-3B1): sc-59143—Datasheet. (2021). Available online at <https://www.scbt.com/p/cd94-antibody-hp-3b1>, 1 page.

(56) References Cited

OTHER PUBLICATIONS

Semenzato et al., (1997). "The lymphoproliferative disease of granular lymphocytes: updated criteria for diagnosis," Blood, 89(1):256-260.
Shegarfi et al., (2012). "Natural killer cells and their role in rheumatoid arthritis: friend or foe?" Scientific World Journal, 2012:491974, 10 pages.
Shields et al., (2001). "High resolution mapping of the binding site on human IgG1 for FcγRI, FcγRII, FcγRIII, and FcRn and design of IgG1 variants with improved binding to the FcγR," J. Biol. Chem., 276(9):6591-6604.
Shields, (2002). "Lack of Fucose on Human IgG1 N-linked Oligosaccharide Improves Binding to Human FcγRIII and Antibody-dependent Cellular Toxicity," The Journal of Biological Chemistry, 277(30):26733-26740.
Singer et al., (1993). "Optimal humanization of 1B4, an anti-CD18 murine monoclonal antibody, is achieved by correct choice of human V-region framework sequences," J. Immun., 150(7):2844-2857.
Stewart et al., (2011). "A variant human IgG1-Fc mediates improved ADCC," Protein Engineering, Design and Selection, 24(9):671-678.
Swerdlow et al., (2016). "The 2016 revision of the World Health Organization classification of lymphoid neoplasms," Blood, 127(20):2375-2390.
Taylor et al., (1994). "Human immunoglobulin transgenes undergo rearrangement, somatic mutation and class switching in mice that lack endogenous IgM," Int. Immun., 6(4):579-591.
Tempest et al., (1991). "Reshaping a human monoclonal antibody to inhibit human Yespiratory syncytial virus infection in vivo," Biotechnology, 9(3):266-271.
Tomasevic et al., (2014). "A high affinity recombinant antibody to the human EphA3 receptor with enhanced ADCC activity," Growth Factors, 32(6):223-235.
Verhoeyen et al., (1988). "Reshaping human antibodies: grafting an antilysozyme activity," Science, 239(4847):1534-1536.
Yamane-Ohnuki et al., (2004). "Establishment of FUT8 knockout Chinese hamster ovary cells: an ideal host cell line for producing completely defucosylated antibodies with enhanced antibody-dependent cellular cytotoxicity," Biotech. Bioeng., 87(5):614-622.
Zambello et al., (2014). "Are T-LGL Leukemia and NK-Chronic Lymphoproliferative Disorder really two distinct diseases?" Transl Med UniSa., 8:4-11.
Beckman Coulter, Inc., (2022). "CD159a-APC Conjugated Antibody, Z199, 0.5 mL, ASR", Available online at <https://www.beckman.com/reagents/coulter-flow-cytometry/antibodies-and-kits/singlecolor-antibodies/cd159a/a60797>, 4 pages.
Extended European Search Report and Written Opinion received for European Patent Application No. 20785240.1 dated Nov. 18, 2022, 19 pages.
Shashidharamurthy et al., (2010). "Analysis of cross-species IgG binding to human and mouse Fcgamma receptors (FcgammaRs) (138.29)," J Immunol, 184(1 Supplement), 2 pages. Abstract Only.
Velders et al., (1998). "The Impact Of Antigen Density And Antibody Affinity On Antibody-Dependent Cellular Cytotoxicity: Relevance For Immunotherapy Of Carcinomas," British Journal Of Cancer, 78(4):478-483.
Wolff et al., (2007). "American Society of Clinical Oncology/College of American Pathologists Guideline Recommendations for Human Epidermal Growth Factor Receptor 2 Testing in Breast Cancer," Arch Pathol Lab Med, 131:18-43.
Zahavi et al., (2018). "Enhancing antibody-dependent cell-mediated cytotoxicity: a strategy for improving antibody-based immunotherapy," Antibody Therapeutics, 1(1):7-12.

\* cited by examiner

| Antibody | Affinity on human NK cells | Cyno CD94 cross-reactivity | HLA-E blocking | Antibody competition | Antibody internalization from 0.5-24 hours at 37 °C | ADCC activity in normal NK cells | ADCC activity in normal non-targeted cells | ADCC activity in LGL1 | ADCC activity in LGL1 non-targeted cells |
|---|---|---|---|---|---|---|---|---|---|
| HP-3D9 | 0.07nM | No | 99% | Partially with 18H3 | 52% | N/A | N/A | N/A | N/A |
| DX22 | 0.15nM | No | 95% | None | 56% | N/A | N/A | N/A | N/A |
| HP-3B1 | 3nM | No | 99.8% | None | N/A | N/A | N/A | N/A | N/A |
| 131412 | 11nM | No | 40% | None | N/A | N/A | N/A | N/A | N/A |
| 12K45 | 7nM | Yes | 47% | Partially with 1E4 | N/A | N/A | N/A | N/A | N/A |
| 18H3 | 2.6nM | Yes | 0% | Partially with HP-3D9 | 24% | IC50: 0.02ug/ml | None | IC50: 0.059ug/ml | None |
| 1M4 | 7nM | Yes | 0% | 1E4 | 32% | N/A | N/A | N/A | N/A |
| 1E4 | 75nM | Yes | 0% | 1M4; Partially with 12K45 | 18% | Depletion observed; IC50 ND | None | N/A | None |

FIG. 11

SEQUENCE LISTING

```
<160> NUMBER OF SEQ ID NOS: 118

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Ser Tyr Trp Ile Gly
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Pro Phe Asp Tyr Gly Gly Ser Pro Gly Tyr Phe Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Arg Ala Ser Gln Ser Ile Arg Ser Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Lys Ala Ser Ser Leu Glu Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Construct

<400> SEQUENCE: 6

Gln Gln Tyr Asn Thr Phe Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Construct

<400> SEQUENCE: 7

Asn Tyr Ala Met Asn
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 8

Val Ile Ser Gly Ser Gly Asp Thr Thr Tyr Cys Ala Asp Ser Val Lys
1               5                   10                  15

Gly

<210> SEQ ID NO 9
<211> LENGTH: 14
<212> TYPE: PRT
<213> ORGANISM: Artificial Sequence
<220> FEATURE:
<223> OTHER INFORMATION: Synthetic Construct

<400> SEQUENCE: 9

Asn Cys Tyr Gly Ser Gly Ser Tyr Tyr Asn His Phe Asp Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Synthetic Construct

<400> SEQUENCE: 10

Lys Ser Ser Gln Ser Val Leu Tyr Ser Ser Asn Arg Met Asn Tyr Leu
1               5                   10                  15

Ala

<210> SEQ ID NO 11
<211> LENGTH: 7
<212> TYPE: PRT
<213> ORGANISM: Artificial Sequence
<220> FEATURE:
<223> OTHER INFORMATION: Synthetic Construct

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Gln Gln Tyr Tyr Ser Ile Pro Leu Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Thr Ser Asp Leu Cys Val Ser
1               5

<210> SEQ ID NO 14
<211> LENGTH: 16
<212> TYPE: PRT
```

```
<213> ORGANISM: Artificial Sequence
<220> FEATURE:
<223> OTHER INFORMATION: Synthetic Construct

<400> SEQUENCE: 14

Leu Ile Asp Trp Asn Asp Asp Lys Tyr Tyr Ser Thr Ser Leu Gln Thr
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: Synthetic Construct

<400> SEQUENCE: 15

Thr Ile Ala Ala Ala Gly Pro Tyr Asp Ala Phe Asp Ile
1               5                   10

<210> SEQ ID NO 16
<211> LENGTH: 17
<212> TYPE: PRT
<213> ORGANISM: Artificial Sequence
<220> FEATURE:
<223> OTHER INFORMATION: Synthetic Construct

<400> SEQUENCE: 16

Lys Ser Ser Gln Ser Val Leu Tyr Gly Ser Asn Asn Lys Asn Tyr Leu
1               5                   10                  15

Ala

<210> SEQ ID NO 17
<211> LENGTH: 7
<212> TYPE: PRT
<213> ORGANISM: Artificial Sequence
<220> FEATURE:
<223> OTHER INFORMATION: Synthetic Construct

<400> SEQUENCE: 17

Trp Ala Ser Thr Arg Lys Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic Construct

<400> SEQUENCE: 18

Gln Glu Tyr Tyr Ser Leu Arg Phe Thr
1               5

<210> SEQ ID NO 19
<211> LENGTH: 122
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Arg Phe Thr Ser Tyr
                20                  25                  30
```

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Ile Ile Ser Ala Asp Lys Ser Ile Thr Thr Ala Phe
65                  70                  75                  80

Leu Gln Trp Ser Ser Leu Lys Ala Ser Asp Thr Ala Met Tyr Tyr Cys
                85                  90                  95

Ala Arg Pro Phe Asp Tyr Gly Gly Ser Pro Gly Tyr Phe Asp Tyr Trp
            100                 105                 110

Gly Gln Gly Thr Leu Val Thr Val Ser Ser
            115                 120

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
 50                 55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Phe Trp Thr
                85                  90                  95

Phe Gly Gln Gly Thr Lys Val Glu Ile Lys
            100                 105

<210> SEQ ID NO 21
<211> LENGTH: 121
<212> TYPE: PRT
<213> ORGANISM: Artificial Sequence
<220> FEATURE:
<223> OTHER INFORMATION: Synthetic Construct

<400> SEQUENCE: 21

Gln Leu Val Glu Ser Gly Gly Gly Leu Val Gln Pro Gly Gly Ser Leu
1               5                   10                  15

Arg Leu Ala Cys Ala Ala Ser Gly Phe Thr Phe Ser Asn Tyr Ala Met
            20                  25                  30

Asn Trp Val Arg Gln Ala Pro Gly Lys Gly Leu Glu Trp Val Ser Val
            35                  40                  45

Ile Ser Gly Ser Gly Asp Thr Thr Tyr Cys Ala Asp Ser Val Lys Gly
 50                 55                  60

Arg Phe Thr Ile Ser Arg Asp Asn Ser Lys Thr Leu His Leu Gln
65                  70                  75                  80

Leu Asn Ser Leu Arg Ala Glu Asp Thr Ala Val Tyr Tyr Cys Ala Lys
                85                  90                  95

Asn Cys Tyr Gly Ser Gly Ser Tyr Tyr Asn His Phe Asp Tyr Trp Gly
            100                 105                 110

```
Gln Gly Thr Leu Val Thr Val Ser Ser
        115                 120

<210> SEQ ID NO 22
<211> LENGTH: 113
<212> TYPE: PRT
<213> ORGANISM: Artificial Sequence
<220> FEATURE:
<223> OTHER INFORMATION: Synthetic Construct

<400> SEQUENCE: 22

Glu Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Arg Met Asn Tyr Leu Ala Trp Tyr Gln Gln Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Ile Pro Leu Thr Phe Gly Gly Gly Thr Lys Val Glu Ile
            100                 105                 110

Lys

<210> SEQ ID NO 23
<211> LENGTH: 123
<212> TYPE: PRT
<213> ORGANISM: Artificial Sequence
<220> FEATURE:
<223> OTHER INFORMATION: Synthetic Construct

<400> SEQUENCE: 23

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Asp Leu Cys Val Ser Trp Ile Arg Gln Pro Pro Gly Lys Ala Leu Glu
        35                  40                  45

Trp Leu Ala Leu Ile Asp Trp Asn Asp Asp Lys Tyr Tyr Ser Thr Ser
    50                  55                  60

Leu Gln Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Thr Ile Ala Ala Ala Gly Pro Tyr Asp Ala Phe Asp Ile
            100                 105                 110

Trp Gly Gln Gly Thr Met Val Thr Val Ser Ser
        115                 120

<210> SEQ ID NO 24
<211> LENGTH: 113
<212> TYPE: PRT
<213> ORGANISM: Artificial Sequence
<220> FEATURE:
<223> OTHER INFORMATION: Synthetic Construct
```

<400> SEQUENCE: 24

Asp Ile Val Met Thr Gln Ser Pro Asp Ser Leu Ser Val Ser Leu Gly
1               5                   10                  15

Glu Arg Ala Thr Ile Asn Cys Lys Ser Ser Gln Ser Val Leu Tyr Gly
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Lys Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Glu
                85                  90                  95

Tyr Tyr Ser Leu Arg Phe Thr Phe Gly Pro Gly Thr Lys Val Asp Ile
            100                 105                 110

Lys

<210> SEQ ID NO 25
<211> LENGTH: 179
<212> TYPE: PRT
<213> ORGANISM: Homo sapiens

<400> SEQUENCE: 25

Met Ala Val Phe Lys Thr Thr Leu Trp Arg Leu Ile Ser Gly Thr Leu
1               5                   10                  15

Gly Ile Ile Cys Leu Ser Leu Met Ser Thr Leu Gly Ile Leu Leu Lys
            20                  25                  30

Asn Ser Phe Thr Lys Leu Ser Ile Glu Pro Ala Phe Thr Pro Gly Pro
        35                  40                  45

Asn Ile Glu Leu Gln Lys Asp Ser Asp Cys Cys Ser Cys Gln Glu Lys
50                  55                  60

Trp Val Gly Tyr Arg Cys Asn Cys Tyr Phe Ile Ser Ser Glu Gln Lys
65                  70                  75                  80

Thr Trp Asn Glu Ser Arg His Leu Cys Ala Ser Gln Lys Ser Ser Leu
                85                  90                  95

Leu Gln Leu Gln Asn Thr Asp Glu Leu Asp Phe Met Ser Ser Ser Gln
            100                 105                 110

Gln Phe Tyr Trp Ile Gly Leu Ser Tyr Ser Glu Glu His Thr Ala Trp
        115                 120                 125

Leu Trp Glu Asn Gly Ser Ala Leu Ser Gln Tyr Leu Phe Pro Ser Phe
130                 135                 140

Glu Thr Phe Asn Thr Lys Asn Cys Ile Ala Tyr Asn Pro Asn Gly Asn
145                 150                 155                 160

Ala Leu Asp Glu Ser Cys Glu Asp Lys Asn Arg Tyr Ile Cys Lys Gln
                165                 170                 175

Gln Leu Ile

<210> SEQ ID NO 26
<211> LENGTH: 180
<212> TYPE: PRT
<213> ORGANISM: Homo sapiens

<400> SEQUENCE: 26

Met Ala Val Phe Lys Thr Thr Leu Trp Arg Leu Ile Ser Gly Thr Leu
1               5                   10                  15

```
Gly Ile Ile Cys Leu Ser Leu Met Ser Thr Leu Gly Ile Leu Leu Lys
                20                  25                  30

Asn Ser Phe Thr Lys Leu Ser Ile Glu Pro Ala Phe Thr Pro Gly Pro
            35                  40                  45

Asn Ile Glu Leu Gln Lys Asp Ser Asp Cys Cys Ser Cys Gln Glu Lys
50                      55                  60

Trp Val Gly Tyr Arg Cys Asn Cys Tyr Phe Ile Ser Ser Glu Gln Lys
65                  70                  75                  80

Thr Trp Asn Glu Ser Arg His Leu Cys Ala Ser Gln Lys Ser Ser Leu
                85                  90                  95

Leu Gln Leu Gln Asn Thr Asp Glu Leu Gln Asp Phe Met Ser Ser Ser
            100                 105                 110

Gln Gln Phe Tyr Trp Ile Gly Leu Ser Tyr Ser Glu Glu His Thr Ala
        115                 120                 125

Trp Leu Trp Glu Asn Gly Ser Ala Leu Ser Gln Tyr Leu Phe Pro Ser
    130                 135                 140

Phe Glu Thr Phe Asn Thr Lys Asn Cys Ile Ala Tyr Asn Pro Asn Gly
145                 150                 155                 160

Asn Ala Leu Asp Glu Ser Cys Glu Asp Lys Asn Arg Tyr Ile Cys Lys
                165                 170                 175

Gln Gln Leu Ile
            180

<210> SEQ ID NO 27
<211> LENGTH: 208
<212> TYPE: PRT
<213> ORGANISM: Homo sapiens

<400> SEQUENCE: 27

Met Ala Ala Phe Thr Lys Leu Ser Ile Glu Pro Ala Phe Thr Pro Gly
1               5                   10                  15

Pro Asn Ile Glu Leu Gln Lys Asp Ser Asp Cys Cys Ser Cys Gln Glu
            20                  25                  30

Lys Trp Val Gly Tyr Arg Cys Asn Cys Tyr Phe Ile Ser Ser Glu Gln
        35                  40                  45

Lys Thr Trp Asn Glu Ser Arg His Leu Cys Ala Ser Gln Lys Ser Ser
    50                  55                  60

Leu Leu Gln Leu Gln Asn Thr Asp Glu Leu Asp Phe Met Ser Ser Ser
65                  70                  75                  80

Gln Gln Phe Tyr Trp Ile Gly Leu Ser Tyr Ser Glu Glu His Thr Ala
                85                  90                  95

Trp Leu Trp Glu Asn Gly Ser Ala Leu Ser Gln Tyr Leu Phe Pro Ser
            100                 105                 110

Phe Glu Thr Phe Asn Thr Lys Asn Cys Ile Ala Tyr Asn Pro Asn Gly
        115                 120                 125

Asn Ala Leu Asp Glu Ser Cys Glu Asp Lys Asn Arg Tyr Ile Cys Lys
    130                 135                 140

Gln Gln Leu Ile Ser Tyr Ser Glu Glu His Thr Ala Trp Leu Trp Glu
145                 150                 155                 160

Asn Gly Ser Ala Leu Ser Gln Tyr Leu Phe Pro Ser Phe Glu Thr Phe
                165                 170                 175

Asn Thr Lys Asn Cys Ile Ala Tyr Asn Pro Asn Gly Asn Ala Leu Asp
            180                 185                 190

Glu Ser Cys Glu Asp Lys Asn Arg Tyr Ile Cys Lys Gln Gln Leu Ile
        195                 200                 205
```

<210> SEQ ID NO 28
<211> LENGTH: 254
<212> TYPE: PRT
<213> ORGANISM: Homo sapiens

<400> SEQUENCE: 28

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 29
<211> LENGTH: 254
<212> TYPE: PRT
<213> ORGANISM: Homo sapiens

<400> SEQUENCE: 29

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

-continued

```
Val Asp Asp Ser Gly Glu Tyr Arg Cys Gln Thr Asn Leu Ser Thr Leu
            85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
            210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 30
<211> LENGTH: 5
<212> TYPE: PRT
<213> ORGANISM: Artificial Sequence
<220> FEATURE:
<223> OTHER INFORMATION: Synthetic Construct

<400> SEQUENCE: 30

Ser Tyr Gly Val Ser
1               5

<210> SEQ ID NO 31
<211> LENGTH: 17
<212> TYPE: PRT
<213> ORGANISM: Artificial Sequence
<220> FEATURE:
<223> OTHER INFORMATION: Synthetic Construct

<400> SEQUENCE: 31

Trp Ile Ser Pro Tyr Asn Gly Asn Thr Asn Tyr Ala His Asn Leu Gln
1               5                   10                  15

Gly

<210> SEQ ID NO 32
<211> LENGTH: 12
<212> TYPE: PRT
<213> ORGANISM: Artificial Sequence
<220> FEATURE:
<223> OTHER INFORMATION: Synthetic Construct

<400> SEQUENCE: 32

Asp Arg Gly Arg Phe Gly Glu Leu Phe Phe Asp Tyr
1               5                   10

<210> SEQ ID NO 33
<211> LENGTH: 11
<212> TYPE: PRT
```

<213> ORGANISM: Artificial Sequence
<220> FEATURE:
<223> OTHER INFORMATION: Synthetic Construct

<400> SEQUENCE: 33

Arg Ala Ser Gln Gly Ile Ser Asn Tyr Leu Ala
1               5                   10

<210> SEQ ID NO 34
<211> LENGTH: 7
<212> TYPE: PRT
<213> ORGANISM: Artificial Sequence
<220> FEATURE:
<223> OTHER INFORMATION: Synthetic Construct

<400> SEQUENCE: 34

Ala Ala Ser Ser Leu Gln Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

Leu Gln His Asn Ser Tyr Pro Phe Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Synthetic Construct

<400> SEQUENCE: 36

Ser Tyr Gly Ile Ser
1               5

<210> SEQ ID NO 37
<211> LENGTH: 17
<212> TYPE: PRT
<213> ORGANISM: Artificial Sequence
<220> FEATURE:
<223> OTHER INFORMATION: Synthetic Construct

<400> SEQUENCE: 37

Trp Ile Ser Ala Tyr Asn Gly Asn Thr Asn Tyr Ala Gln Lys Phe Gln
1               5                   10                  15

Gly

<210> SEQ ID NO 38
<211> LENGTH: 12
<212> TYPE: PRT
<213> ORGANISM: Artificial Sequence
<220> FEATURE:
<223> OTHER INFORMATION: Synthetic Construct

<400> SEQUENCE: 38

Asp Arg Gly Arg Phe Gly Glu Leu Leu Ser Asp Tyr
1               5                   10

<210> SEQ ID NO 39
<211> LENGTH: 17

```
<212> TYPE: PRT
<213> ORGANISM: Artificial Sequence
<220> FEATURE:
<223> OTHER INFORMATION: Synthetic Construct

<400> SEQUENCE: 39

Trp Ile Ser Ala Tyr Asn Gly Asn Thr Asn Tyr Ala Gln Lys Leu Gln
1               5                   10                  15

Gly

<210> SEQ ID NO 40
<211> LENGTH: 12
<212> TYPE: PRT
<213> ORGANISM: Artificial Sequence
<220> FEATURE:
<223> OTHER INFORMATION: Synthetic Construct

<400> SEQUENCE: 40

Asp Arg Gly Arg Phe Gly Glu Leu Phe Phe Asp His
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Synthetic Construct

<400> SEQUENCE: 41

Ser Ile Ile Tyr Tyr Trp Gly
1               5

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Ser Ile Tyr Tyr Ser Gly Ser Thr Tyr Tyr Asn Pro Ser Leu Lys Ser
1               5                   10                  15

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Leu Pro Leu Thr Gly Glu Phe Ala Phe Asp Ile
1               5                   10

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct

<400> SEQUENCE: 44

Arg Ala Ser Gln Ser Val Ser Thr Tyr Leu Ala
1               5                   10

<210> SEQ ID NO 45
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 45

Gly Ala Ser Ser Arg Ala Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Construct

<400> SEQUENCE: 46

Gln Gln Tyr Gly Ser Ser Pro Ile Thr
1               5

<210> SEQ ID NO 47
<211> LENGTH: 5
<212> TYPE: PRT
<213> ORGANISM: Artificial Sequence
<220> FEATURE:
<223> OTHER INFORMATION: Synthetic Construct

<400> SEQUENCE: 47

Ser Tyr Ser Met Asn
1               5

<210> SEQ ID NO 48
<211> LENGTH: 17
<212> TYPE: PRT
<213> ORGANISM: Artificial Sequence
<220> FEATURE:
<223> OTHER INFORMATION: Synthetic Construct

<400> SEQUENCE: 48

Ser Ile Ser Thr Ser Ser Asn Phe Ile Tyr Tyr Ala Asp Ser Val Lys
1               5                   10                  15

Gly

<210> SEQ ID NO 49
<211> LENGTH: 13
<212> TYPE: PRT
<213> ORGANISM: Artificial Sequence
<220> FEATURE:
<223> OTHER INFORMATION: Synthetic Construct

<400> SEQUENCE: 49

Asp Met Gly Pro Phe Tyr Ser Phe Tyr Tyr Met Asp Val
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Synthetic Construct

<400> SEQUENCE: 50

Arg Ala Ser Gln Ser Val Ser Ser Ser Tyr Leu Ala
1               5                   10
```

```
<210> SEQ ID NO 51
<211> LENGTH: 7
<212> TYPE: PRT
<213> ORGANISM: Artificial Sequence
<220> FEATURE:
<223> OTHER INFORMATION: Synthetic Construct

<400> SEQUENCE: 51

Gly Ala Ser Asn Arg Ala Thr
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic Construct

<400> SEQUENCE: 52

Leu Gln His Asn Ser Tyr Pro Pro Thr
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Construct

<400> SEQUENCE: 53

Ser Arg Tyr Trp Trp Thr
1               5

<210> SEQ ID NO 54
<211> LENGTH: 16
<212> TYPE: PRT
<213> ORGANISM: Artificial Sequence
<220> FEATURE:
<223> OTHER INFORMATION: Synthetic Construct

<400> SEQUENCE: 54

Glu Ile Tyr His Ser Gly Thr Thr Asn Tyr Asn Pro Ser Leu Glu Ser
1               5                   10                  15

<210> SEQ ID NO 55
<211> LENGTH: 13
<212> TYPE: PRT
<213> ORGANISM: Artificial Sequence
<220> FEATURE:
<223> OTHER INFORMATION: Synthetic Construct

<400> SEQUENCE: 55

Ser Pro Asn Trp Gly Tyr Tyr Tyr Tyr Tyr Met Asp Val
1               5                   10

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Gln Gln Tyr Gly Arg Ser Leu Thr
1               5

<210> SEQ ID NO 57
```

```
<211> LENGTH: 5
<212> TYPE: PRT
<213> ORGANISM: Artificial Sequence
<220> FEATURE:
<223> OTHER INFORMATION: Synthetic Construct

<400> SEQUENCE: 57

Gly Ser Thr Ile Gln
1               5

<210> SEQ ID NO 58
<211> LENGTH: 19
<212> TYPE: PRT
<213> ORGANISM: Artificial Sequence
<220> FEATURE:
<223> OTHER INFORMATION: Synthetic Construct

<400> SEQUENCE: 58

Arg Ile Arg Ser Lys Ala Asn Ser Tyr Ala Thr Ala Ser Ala Ala Ser
1               5                   10                  15

Val Lys Gly

<210> SEQ ID NO 59
<211> LENGTH: 17
<212> TYPE: PRT
<213> ORGANISM: Artificial Sequence
<220> FEATURE:
<223> OTHER INFORMATION: Synthetic Construct

<400> SEQUENCE: 59

Glu Gly Leu Gly Tyr Tyr Asn Val Gly Tyr Tyr Phe Tyr Met Asp
1               5                   10                  15

Val

<210> SEQ ID NO 60
<211> LENGTH: 11
<212> TYPE: PRT
<213> ORGANISM: Artificial Sequence
<220> FEATURE:
<223> OTHER INFORMATION: Synthetic Construct

<400> SEQUENCE: 60

Arg Ala Ser Gln Ser Ile Ser Ser Tyr Leu Asn
1               5                   10

<210> SEQ ID NO 61
<211> LENGTH: 9
<212> TYPE: PRT
<213> ORGANISM: Artificial Sequence
<220> FEATURE:
<223> OTHER INFORMATION: Synthetic Construct

<400> SEQUENCE: 61

Gln Gln Ser Tyr Ser Thr Pro Ile Thr
1               5

<210> SEQ ID NO 62
<211> LENGTH: 11
<212> TYPE: PRT
<213> ORGANISM: Artificial Sequence
<220> FEATURE:
<223> OTHER INFORMATION: Synthetic Construct

<400> SEQUENCE: 62

Asp Leu Gly Arg Tyr Tyr Tyr Tyr Met Asp Val
1               5                   10
```

<210> SEQ ID NO 63
<211> LENGTH: 11
<212> TYPE: PRT
<213> ORGANISM: Artificial Sequence
<220> FEATURE:
<223> OTHER INFORMATION: Synthetic Construct

<400> SEQUENCE: 63

Arg Ala Ser Gln Ser Ile Ser Ser Trp Leu Ala
1               5                   10

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Gln Lys Tyr Asn Ser Ala Pro Phe Thr
1               5

<210> SEQ ID NO 65
<211> LENGTH: 121
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Val Gln Ser Gly Ala Glu Val Lys Lys Pro Gly Ala
1               5                   10                  15

Ser Leu Lys Val Ser Cys Lys Ala Ser Gly Tyr Thr Phe Thr Ser Tyr
            20                  25                  30

Gly Val Ser Trp Val Arg Gln Ala Pro Gly Gln Gly Leu Glu Trp Val
        35                  40                  45

Gly Trp Ile Ser Pro Tyr Asn Gly Asn Thr Asn Tyr Ala His Asn Leu
    50                  55                  60

Gln Gly Arg Val Ala Met Thr Thr Asp Thr Ser Thr Ser Thr Ala Tyr
65                  70                  75                  80

Met Glu Leu Arg Ser Leu Arg Ser Asp Asp Met Ala Val Tyr Tyr Cys
                85                  90                  95

Ala Arg Asp Arg Gly Arg Phe Gly Glu Leu Phe Phe Asp Tyr Trp Gly
            100                 105                 110

Gln Gly Thr Leu Val Thr Val Ser Ser
        115                 120

<210> SEQ ID NO 66
<211> LENGTH: 107
<212> TYPE: PRT
<213> ORGANISM: Artificial Sequence
<220> FEATURE:
<223> OTHER INFORMATION: Synthetic Construct

<400> SEQUENCE: 66

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
                100                 105

<210> SEQ ID NO 67
<211> LENGTH: 121
<212> TYPE: PRT
<213> ORGANISM: Artificial Sequence
<220> FEATURE:
<223> OTHER INFORMATION: Synthetic Construct

<400> SEQUENCE: 67

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Phe
        50                  55                  60

Gln Gly Arg Val Thr Met Thr Thr Asp Thr Ser Thr Asn Thr Ala Tyr
65                  70                  75                  80

Met Glu Leu Arg Ser Leu Arg Ser Asp Thr Ala Val Tyr Tyr Cys
                85                  90                  95

Ala Arg Asp Arg Gly Arg Phe Gly Glu Leu Leu Ser Asp Tyr Trp Gly
                100                 105                 110

Gln Gly Thr Leu Val Thr Val Ser Ser
            115                 120

<210> SEQ ID NO 68
<211> LENGTH: 107
<212> TYPE: PRT
<213> ORGANISM: Artificial Sequence
<220> FEATURE:
<223> OTHER INFORMATION: Synthetic Construct

<400> SEQUENCE: 68

Asp Ile Val Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln His Asn Ser Tyr Pro Phe
                85                  90                  95

Thr Phe Gly Pro Gly Thr Lys Val Asp Ile Lys
                100                 105
```

```
<210> SEQ ID NO 69
<211> LENGTH: 121
<212> TYPE: PRT
<213> ORGANISM: Artificial Sequence
<220> FEATURE:
<223> OTHER INFORMATION: Synthetic Construct

<400> SEQUENCE: 69
```

| Gln | Val | Gln | Leu | Val | Gln | Ser | Gly | Ala | Glu | Val | Lys | Lys | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Val | Ser | Cys | Lys | Ala | Ser | Gly | Tyr | Thr | Phe | Thr | Ser | Tyr |
|---|---|---|---|---|---|---|---|---|---|---|---|---|---|---|---|
| | | | 20 | | | | | 25 | | | | | 30 | | |

| Gly | Ile | Ser | Trp | Val | Arg | Gln | Ala | Pro | Gly | Gln | Gly | Leu | Glu | Trp | Met |
|---|---|---|---|---|---|---|---|---|---|---|---|---|---|---|---|
| | | 35 | | | | | 40 | | | | | 45 | | | |

| Gly | Trp | Ile | Ser | Ala | Tyr | Asn | Gly | Asn | Thr | Asn | Tyr | Ala | Gln | Lys | Leu |
|---|---|---|---|---|---|---|---|---|---|---|---|---|---|---|---|
| | 50 | | | | | 55 | | | | | 60 | | | | |

| Gln | Gly | Arg | Val | Thr | Met | Thr | Thr | Asp | Thr | Ser | Thr | Ser | Thr | Ala | Tyr |
|---|---|---|---|---|---|---|---|---|---|---|---|---|---|---|---|
| 65 | | | | | 70 | | | | | 75 | | | | | 80 |

| Met | Glu | Val | Arg | Ser | Leu | Arg | Ser | Asp | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Asp | Arg | Gly | Arg | Phe | Gly | Glu | Leu | Phe | Phe | Asp | His | Trp | Gly |
|---|---|---|---|---|---|---|---|---|---|---|---|---|---|---|---|
| | | | 100 | | | | | 105 | | | | | 110 | | |

| Gln | Gly | Thr | Leu | Val | Thr | Val | Ser | Ser |
|---|---|---|---|---|---|---|---|---|
| | | 115 | | | | | 120 | |

```
<210> SEQ ID NO 70
<211> LENGTH: 107
<212> TYPE: PRT
<213> ORGANISM: Artificial Sequence
<220> FEATURE:
<223> OTHER INFORMATION: Synthetic Construct

<400> SEQUENCE: 70
```

| Asp | Ile | Val | Met | Thr | Gln | Ser | Pro | Ser | Ser | Val | Ser | Ala | Ser | Val | Gly |
|---|---|---|---|---|---|---|---|---|---|---|---|---|---|---|---|
| 1 | | | | 5 | | | | | 10 | | | | | 15 | |

| Asp | Arg | Val | Thr | Ile | Thr | Cys | Arg | Ala | Ser | Gln | Gly | Ile | Ser | Asn | Tyr |
|---|---|---|---|---|---|---|---|---|---|---|---|---|---|---|---|
| | | | 20 | | | | | 25 | | | | | 30 | | |

| Leu | Ala | Trp | Tyr | Gln | Gln | Lys | Pro | Gly | Lys | Ala | Pro | Lys | Leu | Leu | Ile |
|---|---|---|---|---|---|---|---|---|---|---|---|---|---|---|---|
| | | 35 | | | | | 40 | | | | | 45 | | | |

| Tyr | Ala | Ala | Ser | Ser | Leu | Gln | Ser | Gly | Val | Pro | Ser | Arg | Phe | Ser | Gly |
|---|---|---|---|---|---|---|---|---|---|---|---|---|---|---|---|
| | 50 | | | | | 55 | | | | | 60 | | | | |

| Ser | Gly | Ser | Gly | Thr | Asp | Phe | Thr | Leu | Thr | Ile | Ser | Ser | Leu | Gln | Pro |
|---|---|---|---|---|---|---|---|---|---|---|---|---|---|---|---|
| 65 | | | | | 70 | | | | | 75 | | | | | 80 |

| Glu | Asp | Phe | Ala | Thr | Tyr | Tyr | Cys | Leu | Gln | His | Asn | Ser | Tyr | Pro | Phe |
|---|---|---|---|---|---|---|---|---|---|---|---|---|---|---|---|
| | | | | 85 | | | | | 90 | | | | | 95 | |

| Thr | Phe | Gly | Pro | Gly | Thr | Lys | Val | Asp | Ile | Lys |
|---|---|---|---|---|---|---|---|---|---|---|
| | | | 100 | | | | | 105 | | |

```
<210> SEQ ID NO 71
<211> LENGTH: 121
<212> TYPE: PRT
<213> ORGANISM: Artificial Sequence
<220> FEATURE:
<223> OTHER INFORMATION: Synthetic Construct

<400> SEQUENCE: 71
```

| Gln | Val | Gln | Leu | Gln | Gln | Ser | Gly | Pro | Gly | Leu | Val | Lys | Pro | Ser | Glu |
|---|---|---|---|---|---|---|---|---|---|---|---|---|---|---|---|
| 1 | | | | 5 | | | | | 10 | | | | | 15 | |

| Thr | Leu | Ser | Leu | Thr | Cys | Thr | Val | Ser | Gly | Gly | Ser | Ile | Ser | Ser | Ile |
|---|---|---|---|---|---|---|---|---|---|---|---|---|---|---|---|
| | | | 20 | | | | | 25 | | | | | 30 | | |

```
Ile Tyr Tyr Trp Gly Trp Ile Arg Gln Pro Pro Gly Lys Gly Leu Glu
            35                  40                  45

Trp Ile Gly Ser Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
65                  70                  75                  80

Ser Leu Asn Leu Ser Ser Val Thr Ala Ala Asp Thr Ala Val Tyr Tyr
                85                  90                  95

Cys Ala Arg Leu Pro Leu Thr Gly Glu Phe Ala Phe Asp Ile Trp Gly
            100                 105                 110

Gln Gly Thr Met Val Thr Val Ser Ser
            115                 120

<210> SEQ ID NO 72
<211> LENGTH: 107
<212> TYPE: PRT
<213> ORGANISM: Artificial Sequence
<220> FEATURE:
<223> OTHER INFORMATION: Synthetic Construct

<400> SEQUENCE: 72

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Tyr
            20                  25                  30

Leu Ala Trp Phe Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Ile
                85                  90                  95

Thr Phe Gly Gln Gly Thr Arg Leu Glu Ile Lys
            100                 105

<210> SEQ ID NO 73
<211> LENGTH: 122
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Gln Glu Ser Gly Gly Gly Leu Val Gln Pro Gly Gly
1               5                   10                  15

Ser Leu Lys Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Thr Ser Ser Asn Phe Ile Tyr Tyr Ala Asp Ser Val
 50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Asp Met Gly Pro Phe Tyr Ser Phe Tyr Tyr Met Asp Val Trp
```

```
                    100                 105                 110

Gly Asn Gly Thr Thr Val Thr Val Ser Ser
            115                 120

<210> SEQ ID NO 74
<211> LENGTH: 108
<212> TYPE: PRT
<213> ORGANISM: Artificial Sequence
<220> FEATURE:
<223> OTHER INFORMATION: Synthetic Construct

<400> SEQUENCE: 74

Asp Ile Gln Val Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Asn Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Leu Gln His Asn Ser Tyr Pro
                85                  90                  95

Pro Thr Phe Gly Gly Gly Thr Lys Val Asp Ile Lys
            100                 105

<210> SEQ ID NO 75
<211> LENGTH: 122
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Gln Gln Ser Gly Pro Gly Leu Val Lys Pro Ser Gly
1               5                   10                  15

Thr Leu Ser Leu Thr Cys Ala Val Ser Gly Gly Ser Ile Ser Ser Arg
            20                  25                  30

Tyr Trp Trp Thr Trp Val Arg Gln Pro Pro Gly Lys Gly Leu Glu Trp
        35                  40                  45

Ile Gly Glu Ile Tyr His Ser Gly Thr Thr Asn Tyr Asn Pro Ser Leu
    50                  55                  60

Glu Ser Arg Val Thr Ile Ser Val Asp Lys Ser Lys Asn Gln Phe Ser
65                  70                  75                  80

Leu Lys Val Ser Ser Val Thr Ala Ala Asp Thr Ala Val Tyr Tyr Cys
                85                  90                  95

Ala Arg Ser Pro Asn Trp Gly Tyr Tyr Tyr Tyr Met Asp Val Trp
            100                 105                 110

Gly Lys Gly Thr Thr Val Thr Val Ser Ser
            115                 120

<210> SEQ ID NO 76
<211> LENGTH: 107
<212> TYPE: PRT
<213> ORGANISM: Artificial Sequence
<220> FEATURE:
<223> OTHER INFORMATION: Synthetic Construct

<400> SEQUENCE: 76
```

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Ser Glu Asp Phe Ala Val Tyr Tyr Cys Gln Gln Tyr Gly Arg Ser Leu
                85                  90                  95

Thr Phe Gly Gly Gly Thr Lys Val Glu Ile Lys
            100                 105
```

<210> SEQ ID NO 77
<211> LENGTH: 128
<212> TYPE: PRT
<213> ORGANISM: Artificial Sequence
<220> FEATURE:
<223> OTHER INFORMATION: Synthetic Construct

<400> SEQUENCE: 77

```
Gln Val Gln Leu Gln Glu Ser Gly Gly Leu Val Gln Pro Gly Gly
1               5                   10                  15

Ser Leu Lys Leu Ser Cys Ala Ala Ser Gly Phe Thr Phe Ser Gly Ser
            20                  25                  30

Thr Ile Gln Trp Val Arg Gln Ala Ser Gly Lys Gly Leu Glu Trp Val
        35                  40                  45

Gly Arg Ile Arg Ser Lys Ala Asn Ser Tyr Ala Thr Ala Ser Ala Ala
    50                  55                  60

Ser Val Lys Gly Arg Phe Thr Ile Ser Arg Asp Asp Ser Lys Asn Met
65                  70                  75                  80

Ala Tyr Leu Gln Met Asn Ser Leu Lys Thr Glu Asp Thr Ala Val Tyr
                85                  90                  95

Tyr Cys Thr Arg Glu Gly Leu Gly Tyr Tyr Asn Val Gly Tyr Tyr Tyr
            100                 105                 110

Phe Tyr Met Asp Val Trp Gly Lys Gly Thr Thr Val Thr Val Ser Ser
        115                 120                 125
```

<210> SEQ ID NO 78
<211> LENGTH: 107
<212> TYPE: PRT
<213> ORGANISM: Artificial Sequence
<220> FEATURE:
<223> OTHER INFORMATION: Synthetic Construct

<400> SEQUENCE: 78

```
Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Ser Tyr Ser Thr Pro Ile
                    85                  90                  95

Thr Phe Gly Gln Gly Thr Arg Leu Glu Ile Lys
            100                 105

<210> SEQ ID NO 79
<211> LENGTH: 115
<212> TYPE: PRT
<213> ORGANISM: Artificial Sequence
<220> FEATURE:
<223> OTHER INFORMATION: Synthetic Construct

<400> SEQUENCE: 79

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Ala Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Phe Asp Tyr Trp Gly Gln Gly Thr Leu Val Thr
            100                 105                 110

Val Ser Ser
        115

<210> SEQ ID NO 80
<211> LENGTH: 107
<212> TYPE: PRT
<213> ORGANISM: Artificial Sequence
<220> FEATURE:
<223> OTHER INFORMATION: Synthetic Construct

<400> SEQUENCE: 80

Glu Ile Val Leu Thr Gln Ser Pro Ser Thr Leu Ser Ala Ser Val Gly
1               5                   10                  15

Asp Arg Val Thr Ile Thr Cys Arg Val Ser Gln Gly Ile Ser Ser Tyr
            20                  25                  30

Leu Asn Trp Tyr Arg Gln Lys Pro Gly Lys Val Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 81
<211> LENGTH: 120
<212> TYPE: PRT
<213> ORGANISM: Artificial Sequence
<220> FEATURE:
```

-continued

<223> OTHER INFORMATION: Synthetic Construct

<400> SEQUENCE: 81

Glu Val Gln Leu Leu Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Thr Ser Ser Asn Phe Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Gly Arg Tyr Tyr Tyr Met Asp Val Trp Gly Lys
            100                 105                 110

Gly Thr Thr Val Thr Val Ser Ser
        115                 120

<210> SEQ ID NO 82
<211> LENGTH: 107
<212> TYPE: PRT
<213> ORGANISM: Artificial Sequence
<220> FEATURE:
<223> OTHER INFORMATION: Synthetic Construct

<400> SEQUENCE: 82

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Phe
                85                  90                  95

Thr Phe Gly Pro Gly Thr Lys Val Asp Ile Lys
            100                 105

<210> SEQ ID NO 83
<211> LENGTH: 5
<212> TYPE: PRT
<213> ORGANISM: Artificial Sequence
<220> FEATURE:
<223> OTHER INFORMATION: Synthetic Construct

<400> SEQUENCE: 83

Ser Tyr Trp Met Ser
1               5

<210> SEQ ID NO 84
<211> LENGTH: 17
<212> TYPE: PRT
<213> ORGANISM: Artificial Sequence
<220> FEATURE:
<223> OTHER INFORMATION: Synthetic Construct

<400> SEQUENCE: 84

Asn Ile Lys Gln Asp Gly Ser Ala Lys Tyr Tyr Val Asp Ser Val Lys
1               5                   10                  15

Gly

<210> SEQ ID NO 85
<211> LENGTH: 6
<212> TYPE: PRT
<213> ORGANISM: Artificial Sequence
<220> FEATURE:
<223> OTHER INFORMATION: Synthetic Construct

<400> SEQUENCE: 85

Gly Tyr Tyr Phe Asp Tyr
1               5

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

Arg Val Ser Gln Gly Ile Ser Ser Tyr Leu Asn
1               5                   10

<210> SEQ ID NO 87
<211> LENGTH: 8
<212> TYPE: PRT
<213> ORGANISM: Artificial Sequence
<220> FEATURE:
<223> OTHER INFORMATION: Synthetic Construct

<400> SEQUENCE: 87

Gly Tyr Thr Phe Thr Ser Tyr Gly
1               5

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct

<400> SEQUENCE: 88

Ile Ser Pro Tyr Asn Gly Asn Thr
1               5

<210> SEQ ID NO 89
<211> LENGTH: 14
<212> TYPE: PRT
<213> ORGANISM: Artificial Sequence
<220> FEATURE:
<223> OTHER INFORMATION: Synthetic Construct

<400> SEQUENCE: 89

Ala Arg Asp Arg Gly Arg Phe Gly Glu Leu Phe Phe Asp Tyr
1               5                   10

<210> SEQ ID NO 90
<211> LENGTH: 6
<212> TYPE: PRT
<213> ORGANISM: Artificial Sequence
<220> FEATURE:

```
<223> OTHER INFORMATION: Synthetic Construct

<400> SEQUENCE: 90

Gln Gly Ile Ser Asn Tyr
1               5

<210> SEQ ID NO 91
<211> LENGTH: 3
<212> TYPE: PRT
<213> ORGANISM: Artificial Sequence
<220> FEATURE:
<223> OTHER INFORMATION: Synthetic Construct

<400> SEQUENCE: 91

Ala Ala Ser
1

<210> SEQ ID NO 92
<211> LENGTH: 8
<212> TYPE: PRT
<213> ORGANISM: Artificial Sequence
<220> FEATURE:
<223> OTHER INFORMATION: Synthetic Construct

<400> SEQUENCE: 92

Ile Ser Ala Tyr Asn Gly Asn Thr
1               5

<210> SEQ ID NO 93
<211> LENGTH: 14
<212> TYPE: PRT
<213> ORGANISM: Artificial Sequence
<220> FEATURE:
<223> OTHER INFORMATION: Synthetic Construct

<400> SEQUENCE: 93

Ala Arg Asp Arg Gly Arg Phe Gly Glu Leu Leu Ser Asp Tyr
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic Construct

<400> SEQUENCE: 94

Ala Arg Asp Arg Gly Arg Phe Gly Glu Leu Phe Phe Asp His
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic Construct

<400> SEQUENCE: 95

Gly Gly Ser Ile Ser Ser Ile Ile Tyr Tyr
1               5                   10

<210> SEQ ID NO 96
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 96

Ile Tyr Tyr Ser Gly Ser Thr
1               5

<210> SEQ ID NO 97
<211> LENGTH: 13
<212> TYPE: PRT
<213> ORGANISM: Artificial Sequence
<220> FEATURE:
<223> OTHER INFORMATION: Synthetic Construct

<400> SEQUENCE: 97

Ala Arg Leu Pro Leu Thr Gly Glu Phe Ala Phe Asp Ile
1               5                   10

<210> SEQ ID NO 98
<211> LENGTH: 6
<212> TYPE: PRT
<213> ORGANISM: Artificial Sequence
<220> FEATURE:
<223> OTHER INFORMATION: Synthetic Construct

<400> SEQUENCE: 98

Gln Ser Val Ser Thr Tyr
1               5

<210> SEQ ID NO 99
<211> LENGTH: 3
<212> TYPE: PRT
<213> ORGANISM: Artificial Sequence
<220> FEATURE:
<223> OTHER INFORMATION: Synthetic Construct

<400> SEQUENCE: 99

Gly Ala Ser
1

<210> SEQ ID NO 100
<211> LENGTH: 9
<212> TYPE: PRT
<213> ORGANISM: Artificial Sequence
<220> FEATURE:
<223> OTHER INFORMATION: Synthetic Construct

<400> SEQUENCE: 100

Gln Gln Tyr Gly Ser Ser Pro Ile Thr
1               5

<210> SEQ ID NO 101
<211> LENGTH: 8
<212> TYPE: PRT
<213> ORGANISM: Artificial Sequence
<220> FEATURE:
<223> OTHER INFORMATION: Synthetic Construct

<400> SEQUENCE: 101

Gly Phe Thr Phe Ser Gly Ser Thr
1               5

<210> SEQ ID NO 102
<211> LENGTH: 10
<212> TYPE: PRT
<213> ORGANISM: Artificial Sequence
<220> FEATURE:
<223> OTHER INFORMATION: Synthetic Construct
```

```
<400> SEQUENCE: 102

Ile Arg Ser Lys Ala Asn Ser Tyr Ala Thr
1               5                   10

<210> SEQ ID NO 103
<211> LENGTH: 19
<212> TYPE: PRT
<213> ORGANISM: Artificial Sequence
<220> FEATURE:
<223> OTHER INFORMATION: Synthetic Construct

<400> SEQUENCE: 103

Thr Arg Glu Gly Leu Gly Tyr Tyr Asn Val Gly Tyr Tyr Tyr Phe Tyr
1               5                   10                  15

Met Asp Val

<210> SEQ ID NO 104
<211> LENGTH: 6
<212> TYPE: PRT
<213> ORGANISM: Artificial Sequence
<220> FEATURE:
<223> OTHER INFORMATION: Synthetic Construct

<400> SEQUENCE: 104

Gln Ser Ile Ser Ser Tyr
1               5

<210> SEQ ID NO 105
<211> LENGTH: 8
<212> TYPE: PRT
<213> ORGANISM: Artificial Sequence
<220> FEATURE:
<223> OTHER INFORMATION: Synthetic Construct

<400> SEQUENCE: 105

Gly Phe Thr Phe Ser Ser Tyr Trp
1               5

<210> SEQ ID NO 106
<211> LENGTH: 8
<212> TYPE: PRT
<213> ORGANISM: Artificial Sequence
<220> FEATURE:
<223> OTHER INFORMATION: Synthetic Construct

<400> SEQUENCE: 106

Ile Lys Gln Asp Gly Ser Ala Lys
1               5

<210> SEQ ID NO 107
<211> LENGTH: 8
<212> TYPE: PRT
<213> ORGANISM: Artificial Sequence
<220> FEATURE:
<223> OTHER INFORMATION: Synthetic Construct

<400> SEQUENCE: 107

Ala Arg Gly Tyr Tyr Phe Asp Tyr
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic Construct
```

```
<400> SEQUENCE: 108

Gln Gly Ile Ser Ser Tyr
1               5

<210> SEQ ID NO 109
<211> LENGTH: 8
<212> TYPE: PRT
<213> ORGANISM: Artificial Sequence
<220> FEATURE:
<223> OTHER INFORMATION: Synthetic Construct

<400> SEQUENCE: 109

Gly Phe Thr Phe Ser Ser Tyr Ser
1               5

<210> SEQ ID NO 110
<211> LENGTH: 8
<212> TYPE: PRT
<213> ORGANISM: Artificial Sequence
<220> FEATURE:
<223> OTHER INFORMATION: Synthetic Construct

<400> SEQUENCE: 110

Ile Ser Thr Ser Ser Asn Phe Ile
1               5

<210> SEQ ID NO 111
<211> LENGTH: 13
<212> TYPE: PRT
<213> ORGANISM: Artificial Sequence
<220> FEATURE:
<223> OTHER INFORMATION: Synthetic Construct

<400> SEQUENCE: 111

Ala Arg Asp Leu Gly Arg Tyr Tyr Tyr Tyr Met Asp Val
1               5                   10

<210> SEQ ID NO 112
<211> LENGTH: 6
<212> TYPE: PRT
<213> ORGANISM: Artificial Sequence
<220> FEATURE:
<223> OTHER INFORMATION: Synthetic Construct

<400> SEQUENCE: 112

Gln Ser Ile Ser Ser Trp
1               5

<210> SEQ ID NO 113
<211> LENGTH: 3
<212> TYPE: PRT
<213> ORGANISM: Artificial Sequence
<220> FEATURE:
<223> OTHER INFORMATION: Synthetic Construct

<400> SEQUENCE: 113

Ala Ser Ser
1

<210> SEQ ID NO 114
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 114

Val Arg Asp Met Gly Pro Phe Tyr Ser Phe Tyr Tyr Met Asp Val
1               5                   10                  15

<210> SEQ ID NO 115
<211> LENGTH: 7
<212> TYPE: PRT
<213> ORGANISM: Artificial Sequence
<220> FEATURE:
<223> OTHER INFORMATION: Synthetic Construct

<400> SEQUENCE: 115

Gln Ser Val Ser Ser Ser Tyr
1               5

<210> SEQ ID NO 116
<211> LENGTH: 9
<212> TYPE: PRT
<213> ORGANISM: Artificial Sequence
<220> FEATURE:
<223> OTHER INFORMATION: Synthetic Construct

<400> SEQUENCE: 116

Gly Gly Ser Ile Ser Ser Arg Tyr Trp
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic Construct

<400> SEQUENCE: 117

Ile Tyr His Ser Gly Thr Thr
1               5

<210> SEQ ID NO 118
<211> LENGTH: 15
<212> TYPE: PRT
<213> ORGANISM: Artificial Sequence
<220> FEATURE:
<223> OTHER INFORMATION: Synthetic Construct

<400> SEQUENCE: 118

Ala Arg Ser Pro Asn Trp Gly Tyr Tyr Tyr Tyr Met Asp Val
1               5                   10                  15
```

ANTI-CD94 ANTIBODIES AND METHODS OF USE THEREOF

CROSS-REFERENCE TO RELATED APPLICATIONS

This application claims priority to U.S. Provisional Application Ser. No. 63/085,932, filed Sep. 30, 2020, and 63/088,926, filed Oct. 7, 2020, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 186542000300SEQLIST.TXT, date recorded: Sep. 28, 2021, size: 52,165 bytes).

FIELD OF THE INVENTION

The present disclosure relates to antibodies that bind to CD94 and to uses thereof for treating diseases and disorders associated with NK cells and/or T cells.

BACKGROUND OF THE INVENTION

Natural Killer (NK)/T cell lymphomas and leukemias are characterized by a clonal expansion of NK and/or CD8+ and CD4+ T cells. NK/T cell lymphomas represent a small percentage of non-Hodgkin's lymphomas (NHL), and have a 5-year survival rate of less than 50% (Kwong, 2012). There are approximately 4,000-7,000 new patients each year in the United States alone, with higher frequencies in Asian populations (Bajaj, A. (2019) Int. J. Hemat. Ther 5:1-7). NK/T cell lymphoma can occur at any age, and more than half of NHL patients are 65 or older (Bajaj, 2019). There are also NK and T cell-based leukemias such as LGL and aggressive NK leukemia. Other examples of diseases and disorders in which NK cells play a role include LGL leukemia (e.g., T-cell LGL leukemia), chronic lymphoproliferative disorders of NK cells (CLPD-NK, formerly NK-LGL), Rheumatoid arthritis, Felty's syndrome, aggressive NK leukemia (e.g., aggressive natural killer leukemia (ANKL) and extranodal NKL nasal type (ENKL)), IBM, and IBD.

There are thirteen distinct diseases involving NK/T cell lymphoma: extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, and subcutaneous panniculitis TCL (Bajaj, 2019). The major subtypes of NK/T cell lymphoma, which are mostly cytotoxic cell-driven (NK/CD8+ T cells), include extranodal NK/T cell lymphoma, hepatosplenic TCL, enteropathy-associated TCL, monomorphic epitheliotropic intestinal TCL, epidermotropic CD8+ cutaneous TCL, primary cutaneous gamma/delta TCL, and subcutaneous panniculitis TCL. NK/T cell lymphoma affects various organs, such as skin, gastrointestinal (GI) tract, liver, spleen, and bone marrow. Symptoms include enlarged lymph nodes of the neck. Most NK/T cell lymphoma subtypes are driven by Epstein bar viral infections.

Current treatments include chemotherapy (cyclophosphamide, doxorubicin, vincristine, prednisone), followed by stem cell transplant; but progression-free survival remains at 40-50%. Current treatments under investigation include Alemtuzumab, Carfilzomib (proteasome inhibitor), Romidepsin (HDAC inhibitor), Bevacizumab, Brentuximab vedotin (antibody-drug conjugate), Bortezomib (proteasome inhibitor), Belinostat (HDAC inhibitor), Pralatrexate, Vorinostat (HDAC inhibitor), and Avelumab. Despite the variety of drugs in development, many of them are often used off-label and have yielded mixed results.

There are currently no effective therapies for the treatment of NK/T cell lymphoma, and no therapy that selectively targets NK/T cell lymphoma has been developed. Current therapies for NK/T cell lymphoma may have off-target effects and are not entirely effective. The high disease mortality combined with the lack of effective treatments emphasize the need for therapeutic advancements in NK/T cell lymphoma.

Accordingly, there is a need in the art to develop safe and effective therapies for treating diseases mediated by NK cells and/or T cells that express CD94, such as NK/T cell lymphoma.

SUMMARY OF THE DISCLOSURE

To meet these and other needs, the present disclosure provides, inter alia, antibodies that bind specifically to CD94 (e.g., human CD94), methods of treating diseases or injuries associated with NK cells and/or T cells that express CD94, e.g., NK/T cell lymphomas and leukemias (e.g., LGL leukemia), and methods of depleting or reducing the numbers of NK cells and/or T cells that express CD94 in a subject upon administration of an antibody that specifically binds to CD94. These antibodies of the present disclosure may have one or more of the following characteristics: high affinity binding to human CD94 (e.g., cells expressing human CD94 on their surface), cross-reactivity to cynomolgus monkey CD94 (useful for preclinical studies), ability to bind human CD94 without blocking its interaction with HLA-E, minimal internalization following binding to CD94, and/or induction of ADCC against cells expressing CD94, such as leukemic cells. These characteristics are thought to be advantageous, e.g., for testing, development, and use in treating NK/T cell-based diseases, such as lymphomas and leukemias. For example, without wishing to be bound to theory, it is thought that targeting CD94 on NK cells for ADCC may induce cancer cells (e.g., LGL leukemic or lymphoma cells) to kill other cancer cells.

In some aspects, provided herein are human or humanized antibodies that bind to human CD94, wherein binding of the antibody to human CD94 does not block binding between human CD94 and human HLA-E. In some embodiments, the antibody binds human CD94 expressed on the surface of a cell (e.g., a human natural killer (NK) cell). In some embodiments, the antibody binds an extracellular domain of human CD94. In some embodiments, the antibody binds cynomolgus CD94 expressed on the surface of a cell. In some embodiments, binding of the antibody to cells expressing human CD94 blocks less than 20% of HLA-E binding to the human CD94. In other aspects, provided herein are human or humanized antibodies that bind to human CD94 and cynomolgus CD94 (e.g., that are capable of binding to human CD94 and cynomolgus CD94 separately). In some embodiments, the antibody binds human CD94 expressed on the surface of a cell (e.g., a human natural killer (NK) cell). In some embodiments, the antibody binds cynomolgus CD94 expressed on the surface of a cell (e.g., a cynomolgus NK cell, or a cell such as a human cell that overexpresses cynomolgus CD94). In some embodiments, binding of the antibody to human CD94 does not block binding between human CD94 and human HLA-E. In some embodiments, incubating the antibody with a cell expressing human CD94 on its surface for 24 hours at 37° C. results in a decrease in surface antibody staining of less than 50% due to internalization.

In some embodiments, the antibody comprises a heavy chain variable (VH) domain and a light chain variable (VL) domain, wherein the VH domain comprises a CDR-H1 comprising an amino acid sequence with at least 80% sequence identity to the amino acid sequence of SEQ ID NO:1, a CDR-H2 comprising an amino acid sequence with at least 80% sequence identity to the amino acid sequence of SEQ ID NO:2, and a CDR-H3 comprising an amino acid sequence with at least 80% sequence identity to the amino acid sequence of SEQ ID NO:3; and wherein the VL domain comprises a CDR-L1 comprising an amino acid sequence with at least 80% sequence identity to the amino acid sequence of SEQ ID NO:4, a CDR-L2 comprising an amino acid sequence with at least 80% sequence identity to the amino acid sequence of SEQ ID NO:5, and a CDR-L3 comprising an amino acid sequence with at least 80% sequence identity to the amino acid sequence of SEQ ID NO:6. In some embodiments, the antibody comprises a heavy chain variable (VH) domain and a light chain variable (VL) domain, wherein the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, the VH domain comprises an amino acid sequence with at least 80% sequence identity to the amino acid sequence of SEQ ID NO:19, and the VL domain comprises an amino acid sequence with at least 80% sequence identity to the amino acid sequence of SEQ ID NO:20. In some embodiments, the VH domain comprises an amino acid sequence with at least 90% sequence identity to the amino acid sequence of SEQ ID NO:19, and the VL domain comprises an amino acid sequence with at least 90% sequence identity to the amino acid sequence of SEQ ID NO:20. In some embodiments, the VH domain comprises an amino acid sequence with at least 95% sequence identity to the amino acid sequence of SEQ ID NO:19, and the VL domain comprises an amino acid sequence with at least 95% sequence identity to the amino acid sequence of SEQ ID NO:20. In some embodiments, the VH domain comprises an amino acid sequence with at least 99% sequence identity to the amino acid sequence of SEQ ID NO:19, and the VL domain comprises an amino acid sequence with at least 99% sequence identity to the amino acid sequence of SEQ ID NO:20. In some embodiments, the VH domain comprises the amino acid sequence of SEQ ID NO:19, and the VL domain comprises the amino acid sequence of SEQ ID NO:20. In some embodiments, the antibody comprises a heavy chain variable (VH) domain and a light chain variable (VL) domain, wherein the VH domain comprises a CDR-H1 comprising an amino acid sequence with at least 80% sequence identity to the amino acid sequence of SEQ ID NO:7, a CDR-H2 comprising an amino acid sequence with at least 80% sequence identity to the amino acid sequence of SEQ ID NO:8, and a CDR-H3 comprising an amino acid sequence with at least 80% sequence identity to the amino acid sequence of SEQ ID NO:9; and wherein the VL domain comprises a CDR-L1 comprising an amino acid sequence with at least 80% sequence identity to the amino acid sequence of SEQ ID NO:10, a CDR-L2 comprising an amino acid sequence with at least 80% sequence identity to the amino acid sequence of SEQ ID NO:11, and a CDR-L3 comprising an amino acid sequence with at least 80% sequence identity to the amino acid sequence of SEQ ID NO:12. In some embodiments, the antibody comprises a heavy chain variable (VH) domain and a light chain variable (VL) domain, wherein the VH domain comprises a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and wherein the VL domain comprises a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12. In some embodiments, the VH domain comprises an amino acid sequence with at least 80% sequence identity to the amino acid sequence of SEQ ID NO:21, and the VL domain comprises an amino acid sequence with at least 80% sequence identity to the amino acid sequence of SEQ ID NO:22. In some embodiments, the VH domain comprises an amino acid sequence with at least 90% sequence identity to the amino acid sequence of SEQ ID NO:21, and the VL domain comprises an amino acid sequence with at least 90% sequence identity to the amino acid sequence of SEQ ID NO:22. In some embodiments, the VH domain comprises an amino acid sequence with at least 95% sequence identity to the amino acid sequence of SEQ ID NO:21, and the VL domain comprises an amino acid sequence with at least 95% sequence identity to the amino acid sequence of SEQ ID NO:22. In some embodiments, the VH domain comprises an amino acid sequence with at least 99% sequence identity to the amino acid sequence of SEQ ID NO:21, and the VL domain comprises an amino acid sequence with at least 99% sequence identity to the amino acid sequence of SEQ ID NO:22. In some embodiments, the VH domain comprises the amino acid sequence of SEQ ID NO:21, and the VL domain comprises the amino acid sequence of SEQ ID NO:22. In some embodiments, the antibody comprises a heavy chain variable (VH) domain and a light chain variable (VL) domain, wherein the VH domain comprises a CDR-H1 comprising an amino acid sequence with at least 80% sequence identity to the amino acid sequence of SEQ ID NO:13, a CDR-H2 comprising an amino acid sequence with at least 80% sequence identity to the amino acid sequence of SEQ ID NO:14, and a CDR-H3 comprising an amino acid sequence with at least 80% sequence identity to the amino acid sequence of SEQ ID NO:15; and wherein the VL domain comprises a CDR-L1 comprising an amino acid sequence with at least 80% sequence identity to the amino acid sequence of SEQ ID NO:16, a CDR-L2 comprising an amino acid sequence with at least 80% sequence identity to the amino acid sequence of SEQ ID NO:17, and a CDR-L3 comprising an amino acid sequence with at least 80% sequence identity to the amino acid sequence of SEQ ID NO:18. In some embodiments, the antibody comprises a heavy chain variable (VH) domain and a light chain variable (VL) domain, wherein the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the VH domain comprises an amino acid sequence with at least 80% sequence identity to the amino acid sequence of SEQ ID NO:23, and the VL domain comprises an amino acid sequence with at least 80% sequence identity to the amino acid sequence of SEQ ID NO:24. In some embodiments, the VH domain comprises an amino acid sequence with at least 90% sequence identity to the amino acid sequence of SEQ ID NO:23, and the VL domain comprises an amino acid sequence with at least 90% sequence identity to the amino acid sequence of SEQ ID NO:24. In some embodiments, the VH domain comprises an amino acid sequence with at least 95% sequence identity to the amino acid sequence of SEQ ID NO:23, and the VL domain comprises an amino acid sequence with at least 95% sequence identity to the amino acid sequence of SEQ ID NO:24. In some embodiments, the VH domain comprises an amino acid sequence with at least 99% sequence identity to the amino acid sequence of SEQ ID NO:23, and the VL domain comprises an amino acid sequence with at least 99% sequence identity to the amino acid sequence of SEQ ID NO:24. In some embodiments, the VH domain comprises the amino acid sequence of SEQ ID NO:23, and the VL domain comprises the amino acid sequence of SEQ ID NO:24. In some embodiments, the antibody comprises a heavy chain variable (VH) domain and a light chain variable (VL) domain, wherein: (a) the VH domain comprises a CDR-H1 comprising an amino acid sequence with at least 80% sequence identity to the amino acid sequence of SEQ ID NO:30, a CDR-H2 comprising an amino acid sequence with at least 80% sequence identity to the amino acid sequence of SEQ ID NO:31, and a CDR-H3 comprising an amino acid sequence with at least 80% sequence identity to the amino acid sequence of SEQ ID NO:32; and wherein the VL domain comprises a CDR-L1 comprising an amino acid sequence with at least 80% sequence identity to the amino acid sequence of SEQ ID NO:33, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:35; (b) the VH domain comprises a CDR-H1 comprising an amino acid sequence with at least 80% sequence identity to the amino acid sequence of SEQ ID NO:36, a CDR-H2 comprising an amino acid sequence with at least 80% sequence identity to the amino acid sequence of SEQ ID NO:37, and a CDR-H3 comprising an amino acid sequence with at least 80% sequence identity to the amino acid sequence of SEQ ID NO:38; and wherein the VL domain comprises a CDR-L1 comprising an amino acid sequence with at least 80% sequence identity to the amino acid sequence of SEQ ID NO:33, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:35; (c) the VH domain comprises a CDR-H1 comprising an amino acid sequence with at least 80% sequence identity to the amino acid sequence of SEQ ID NO:36, a CDR-H2 comprising an amino acid sequence with at least 80% sequence identity to the amino acid sequence of SEQ ID NO:39, and a CDR-H3 comprising an amino acid sequence with at least 80% sequence identity to the amino acid sequence of SEQ ID NO:40; and wherein the VL domain comprises a CDR-L1 comprising an amino acid sequence with at least 80% sequence identity to the amino acid sequence of SEQ ID NO:33, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:35; (d) the VH domain comprises a CDR-H1 comprising an amino acid sequence with at least 80% sequence identity to the amino acid sequence of SEQ ID NO:41, a CDR-H2 comprising an amino acid sequence with at least 80% sequence identity to the amino acid sequence of SEQ ID NO:42, and a CDR-H3 comprising an amino acid sequence with at least 80% sequence identity to the amino acid sequence of SEQ ID NO:43; and wherein the VL domain comprises a CDR-L1 comprising an amino acid sequence with at least 80% sequence identity to the amino acid sequence of SEQ ID NO:44, a CDR-L2 comprising an amino acid sequence with at least 80% sequence identity to the amino acid sequence of SEQ ID NO:45, and a CDR-L3 comprising an amino acid sequence with at least 80% sequence identity to the amino acid sequence of SEQ ID NO:46; (e) the VH domain comprises a CDR-H1 comprising an amino acid sequence with at least 80% sequence identity to the amino acid sequence of SEQ ID NO:47, a CDR-H2 comprising an amino acid sequence with at least 80% sequence identity to the amino acid sequence of SEQ ID NO:48, and a CDR-H3 comprising an amino acid sequence with at least 80% sequence identity to the amino acid sequence of SEQ ID NO:49; and wherein the VL domain comprises a CDR-L1 comprising an amino acid sequence with at least 80% sequence identity to the amino acid sequence of SEQ ID NO:50, a CDR-L2 comprising an amino acid sequence with at least 80% sequence identity to the amino acid sequence of SEQ ID NO:51, and a CDR-L3 comprising an amino acid sequence with at least 80% sequence identity to the amino acid sequence of SEQ ID NO:52; (f) the VH domain comprises a CDR-H1 comprising an amino acid sequence with at least 80% sequence identity to the amino acid sequence of SEQ ID NO:53, a CDR-H2 comprising an amino acid sequence with at least 80% sequence identity to the amino acid sequence of SEQ ID NO:54, and a CDR-H3 comprising an amino acid sequence with at least 80% sequence identity to the amino acid sequence of SEQ ID NO:55; and wherein the VL domain comprises a CDR-L1 comprising an amino acid sequence with at least 80% sequence identity to the amino acid sequence of SEQ ID NO:50, a CDR-L2 comprising an amino acid sequence with at least 80% sequence identity to the amino acid sequence of SEQ ID NO:45, and a CDR-L3 comprising an amino acid sequence with at least 80% sequence identity to the amino acid sequence of SEQ ID NO:56; (g) the VH domain comprises a CDR-H1 comprising an amino acid sequence with at least 80% sequence identity to the amino acid sequence of SEQ ID NO:57, a CDR-H2 comprising an amino acid sequence with at least 80% sequence identity to the amino acid sequence of SEQ ID NO:58, and a CDR-H3 comprising an amino acid sequence with at least 80% sequence identity to the amino acid sequence of SEQ ID NO:59; and wherein the VL domain comprises a CDR-L1 comprising an amino acid sequence with at least 80% sequence identity to the amino acid sequence of SEQ ID NO:60, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:61; (h) the VH domain comprises a CDR-H1 comprising an amino acid sequence with at least 80% sequence identity to the amino acid sequence of SEQ ID NO:83, a CDR-H2 comprising an amino acid sequence with at least 80% sequence identity to the amino acid sequence of SEQ ID NO:84, and a CDR-H3 comprising an amino acid sequence with at least 80% sequence identity to the amino acid sequence of SEQ ID NO:85; and wherein the VL domain comprises a CDR-L1 comprising an amino acid sequence with at least 80% sequence identity to the amino acid sequence of SEQ ID NO:86, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:61; or (i) the VH domain comprises a CDR-H1 comprising an amino acid sequence with at least 80% sequence identity to the amino acid sequence of SEQ ID NO:47, a CDR-H2 comprising an amino acid sequence with at least 80% sequence identity to the amino acid sequence of SEQ ID NO:48, and a CDR-H3 comprising an amino acid sequence with at least 80% sequence identity to the amino acid sequence of SEQ ID NO:62; and wherein the VL domain comprises a CDR-L1 comprising an amino acid sequence with at least 80% sequence identity to the amino acid sequence of SEQ ID NO:63, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:64. In some embodiments, the antibody comprises a heavy chain variable (VH) domain and a light chain variable (VL) domain, wherein: (a) the VH domain comprises a CDR-H1 comprising an amino acid sequence with at least 80% sequence identity to the amino acid sequence of SEQ ID NO:87, a CDR-H2 comprising an amino acid sequence with at least 80% sequence identity to the amino acid sequence of SEQ ID NO:88, and a CDR-H3 comprising an amino acid sequence with at least 80% sequence identity to the amino acid sequence of SEQ ID NO:89; and wherein the VL domain comprises a CDR-L1 comprising an amino acid sequence with at least 80% sequence identity to the amino acid sequence of SEQ ID NO:90, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:35; (b) the VH domain comprises a CDR-H1 comprising an amino acid sequence with at least 80% sequence identity to the amino acid sequence of SEQ ID NO:87, a CDR-H2 comprising an amino acid sequence with at least 80% sequence identity to the amino acid sequence of SEQ ID NO:92, and a CDR-H3 comprising an amino acid sequence with at least 80% sequence identity to the amino acid sequence of SEQ ID NO:93; and wherein the VL domain comprises a CDR-L1 comprising an amino acid sequence with at least 80% sequence identity to the amino acid sequence of SEQ ID NO:90, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:35; (c) the VH domain comprises a CDR-H1 comprising an amino acid sequence with at least 80% sequence identity to the amino acid sequence of SEQ ID NO:87, a CDR-H2 comprising an amino acid sequence with at least 80% sequence identity to the amino acid sequence of SEQ ID NO:92, and a CDR-H3 comprising an amino acid sequence with at least 80% sequence identity to the amino acid sequence of SEQ ID NO:94; and wherein the VL domain comprises a CDR-L1 comprising an amino acid sequence with at least 80% sequence identity to the amino acid sequence of SEQ ID NO:90, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:35; (d) the VH domain comprises a CDR-H1 comprising an amino acid sequence with at least 80% sequence identity to the amino acid sequence of SEQ ID NO:95, a CDR-H2 comprising an amino acid sequence with at least 80% sequence identity to the amino acid sequence of SEQ ID NO:96, and a CDR-H3 comprising an amino acid sequence with at least 80% sequence identity to the amino acid sequence of SEQ ID NO:97; and wherein the VL domain comprises a CDR-L1 comprising an amino acid sequence with at least 80% sequence identity to the amino acid sequence of SEQ ID NO:98, a CDR-L2 comprising an amino acid sequence with at least 80% sequence identity to the amino acid sequence of SEQ ID NO:99, and a CDR-L3 comprising an amino acid sequence with at least 80% sequence identity to the amino acid sequence of SEQ ID NO:100; (e) the VH domain comprises a CDR-H1 comprising an amino acid sequence with at least 80% sequence identity to the amino acid sequence of SEQ ID NO:109, a CDR-H2 comprising an amino acid sequence with at least 80% sequence identity to the amino acid sequence of SEQ ID NO:110, and a CDR-H3 comprising an amino acid sequence with at least 80% sequence identity to the amino acid sequence of SEQ ID NO:114; and wherein the VL domain comprises a CDR-L1 comprising an amino acid sequence with at least 80% sequence identity to the amino acid sequence of SEQ ID NO:115, a CDR-L2 comprising an amino acid sequence with at least 80% sequence identity to the amino acid sequence of SEQ ID NO:99, and a CDR-L3 comprising an amino acid sequence with at least 80% sequence identity to the amino acid sequence of SEQ ID NO:52; (f) the VH domain comprises a CDR-H1 comprising an amino acid sequence with at least 80% sequence identity to the amino acid sequence of SEQ ID NO:116, a CDR-H2 comprising an amino acid sequence with at least 80% sequence identity to the amino acid sequence of SEQ ID NO:117, and a CDR-H3 comprising an amino acid sequence with at least 80% sequence identity to the amino acid sequence of SEQ ID NO:118; and wherein the VL domain comprises a CDR-L1 comprising an amino acid sequence with at least 80% sequence identity to the amino acid sequence of SEQ ID NO:115, a CDR-L2 comprising an amino acid sequence with at least 80% sequence identity to the amino acid sequence of SEQ ID NO:99, and a CDR-L3 comprising an amino acid sequence with at least 80% sequence identity to the amino acid sequence of SEQ ID NO:56; (g) the VH domain comprises a CDR-H1 comprising an amino acid sequence with at least 80% sequence identity to the amino acid sequence of SEQ ID NO:101, a CDR-H2 comprising an amino acid sequence with at least 80% sequence identity to the amino acid sequence of SEQ ID NO:102, and a CDR-H3 comprising an amino acid sequence with at least 80% sequence identity to the amino acid sequence of SEQ ID NO:103; and wherein the VL domain comprises a CDR-L1 comprising an amino acid sequence with at least 80% sequence identity to the amino acid sequence of SEQ ID NO:104, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:61; (h) the VH domain comprises a CDR-H1 comprising an amino acid sequence with at least 80% sequence identity to the amino acid sequence of SEQ ID NO:105, a CDR-H2 comprising an amino acid sequence with at least 80% sequence identity to the amino acid sequence of SEQ ID NO:106, and a CDR-H3 comprising an amino acid sequence with at least 80% sequence identity to the amino acid sequence of SEQ ID NO:107; and wherein the VL domain comprises a CDR-L1 comprising an amino acid sequence with at least 80% sequence identity to the amino acid sequence of SEQ ID NO:108, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:61; or (i) the VH domain comprises a CDR-H1 comprising an amino acid sequence with at least 80% sequence identity to the amino acid sequence of SEQ ID NO:109, a CDR-H2 comprising an amino acid sequence with at least 80% sequence identity to the amino acid sequence of SEQ ID NO:110, and a CDR-H3 comprising an amino acid sequence with at least 80% sequence identity to the amino acid sequence of SEQ ID NO:111; and wherein the VL domain comprises a CDR-L1 comprising an amino acid sequence with at least 80% sequence identity to the amino acid sequence of SEQ ID NO:112, a CDR-L2 comprising an amino acid sequence with at least 80% sequence identity to the amino acid sequence of SEQ ID NO:113, and a CDR-L3 comprising an amino acid sequence with at least 80% sequence identity to the amino acid sequence of SEQ ID NO:64. In some embodiments, the antibody comprises a heavy chain variable (VH) domain and a light chain variable (VL) domain, wherein: (a) the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (b) the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (c) the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (d) the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46; (e) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52; (f) the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56; (g) the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61; (h) the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61; or (i) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64. In some embodiments, the antibody comprises a heavy chain variable (VH) domain and a light chain variable (VL) domain, wherein: (a) the VH domain comprises a CDR-H1 comprising the amino acid sequence of SEQ ID NO:87, a CDR-H2 comprising the amino acid sequence of SEQ ID NO:88, and a CDR-H3 comprising the amino acid sequence of SEQ ID NO:89; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35; (b) the VH domain comprises a CDR-H1 comprising the amino acid sequence of SEQ ID NO:87, a CDR-H2 comprising the amino acid sequence of SEQ ID NO:92, and a CDR-H3 comprising the amino acid sequence of SEQ ID NO:93; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:350; (c) the VH domain comprises a CDR-H1 comprising the amino acid sequence of SEQ ID NO:87, a CDR-H2 comprising the amino acid sequence of SEQ ID NO:92, and a CDR-H3 comprising the amino acid sequence of SEQ ID NO:94; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35; (d) the VH domain comprises a CDR-H1 comprising the amino acid sequence of SEQ ID NO:95, a CDR-H2 comprising the amino acid sequence of SEQ ID NO:96, and a CDR-H3 comprising the amino acid sequence of SEQ ID NO:97; and wherein the VL domain comprises a CDR-L1 comprising the amino acid sequence of SEQ ID NO:98, a CDR-L2 comprising the amino acid sequence of SEQ ID NO:99, and a CDR-L3 comprising the amino acid sequence of SEQ ID NO:100; (e) the VH domain comprises a CDR-H1 comprising the amino acid sequence of SEQ ID NO:109, a CDR-H2 comprising the amino acid sequence of SEQ ID NO:110, and a CDR-H3 comprising the amino acid sequence of SEQ ID NO:114; and wherein the VL domain comprises a CDR-L1 comprising the amino acid sequence of SEQ ID NO:115, a CDR-L2 comprising the amino acid sequence of SEQ ID NO:99, and a CDR-L3 comprising the amino acid sequence of SEQ ID NO:52; (f) the VH domain comprises a CDR-H1 comprising the amino acid sequence of SEQ ID NO:116, a CDR-H2 comprising the amino acid sequence of SEQ ID NO:117, and a CDR-H3 comprising the amino acid sequence of SEQ ID NO:118; and wherein the VL domain comprises a CDR-L1 comprising the amino acid sequence of SEQ ID NO:115, a CDR-L2 comprising the amino acid sequence of SEQ ID NO:99, and a CDR-L3 comprising the amino acid sequence of SEQ ID NO:56; (g) the VH domain comprises a CDR-H1 comprising the amino acid sequence of SEQ ID NO:101, a CDR-H2 comprising the amino acid sequence of SEQ ID NO:102, and a CDR-H3 comprising the amino acid sequence of SEQ ID NO:103; and wherein the VL domain comprises a CDR-L1 comprising the amino acid sequence of SEQ ID NO:104, a CDR-L2 comprising the amino acid sequence of SEQ ID NO:91, and a CDR-L3 comprising the amino acid sequence of SEQ ID NO:61; (h) the VH domain comprises a CDR-H1 comprising the amino acid sequence of SEQ ID NO:105, a CDR-H2 comprising the amino acid sequence of SEQ ID NO:106, and a CDR-H3 comprising the amino acid sequence of SEQ ID NO:107; and wherein the VL domain comprises a CDR-L1 comprising the amino acid sequence of SEQ ID NO:108, a CDR-L2 comprising the amino acid sequence of SEQ ID NO:91, and a CDR-L3 comprising the amino acid sequence of SEQ ID NO:61; or (i) the VH domain comprises a CDR-H1 comprising the amino acid sequence of SEQ ID NO:109, a CDR-H2 comprising the amino acid sequence of SEQ ID NO:110, and a CDR-H3 comprising the amino acid sequence of SEQ ID NO:111; and wherein the VL domain comprises a CDR-L1 comprising the amino acid sequence of SEQ ID NO:112, a CDR-L2 comprising the amino acid sequence of SEQ ID NO:113, and a CDR-L3 comprising the amino acid sequence of SEQ ID NO:64. In some embodiments, the antibody comprises a heavy chain variable (VH) domain and a light chain variable (VL) domain, wherein: (a) the VH domain comprises an amino acid sequence with at least 80% sequence identity to the amino acid sequence of SEQ ID NO:65, and the VL domain comprises an amino acid sequence with at least 80% sequence identity to the amino acid sequence of SEQ ID NO:66; (b) the VH domain comprises an amino acid sequence with at least 80% sequence identity to the amino acid sequence of SEQ ID NO:67, and the VL domain comprises an amino acid sequence with at least 80% sequence identity to the amino acid sequence of SEQ ID NO:68; (c) the VH domain comprises an amino acid sequence with at least 80% sequence identity to the amino acid sequence of SEQ ID NO:69, and the VL domain comprises an amino acid sequence with at least 80% sequence identity to the amino acid sequence of SEQ ID NO:70; (d) the VH domain comprises an amino acid sequence with at least 80% sequence identity to the amino acid sequence of SEQ ID NO:71, and the VL domain comprises an amino acid sequence with at least 80% sequence identity to the amino acid sequence of SEQ ID NO:72; (e) the VH domain comprises an amino acid sequence with at least 80% sequence identity to the amino acid sequence of SEQ ID NO:73, and the VL domain comprises an amino acid sequence with at least 80% sequence identity to the amino acid sequence of SEQ ID NO:74; (f) the VH domain comprises an amino acid sequence with at least 80% sequence identity to the amino acid sequence of SEQ ID NO:75, and the VL domain comprises an amino acid sequence with at least 80% sequence identity to the amino acid sequence of SEQ ID NO:76; (g) the VH domain comprises an amino acid sequence with at least 80% sequence identity to the amino acid sequence of SEQ ID NO:77, and the VL domain comprises an amino acid sequence with at least 80% sequence identity to the amino acid sequence of SEQ ID NO:78; (h) the VH domain comprises an amino acid sequence with at least 80% sequence identity to the amino acid sequence of SEQ ID NO:79, and the VL domain comprises an amino acid sequence with at least 80% sequence identity to the amino acid sequence of SEQ ID NO:80; or (i) the VH domain comprises an amino acid sequence with at least 80% sequence identity to the amino acid sequence of SEQ ID NO:81, and the VL domain comprises an amino acid sequence with at least 80% sequence identity to the amino acid sequence of SEQ ID NO:82. In some embodiments, the antibody comprises a heavy chain variable (VH) domain and a light chain variable (VL) domain, wherein: (a) the VH domain comprises an amino acid sequence with at least 90% sequence identity to the amino acid sequence of SEQ ID NO:65, and the VL domain comprises an amino acid sequence with at least 90% sequence identity to the amino acid sequence of SEQ ID NO:66; (b) the VH domain comprises an amino acid sequence with at least 90% sequence identity to the amino acid sequence of SEQ ID NO:67, and the VL domain comprises an amino acid sequence with at least 90% sequence identity to the amino acid sequence of SEQ ID NO:68; (c) the VH domain comprises an amino acid sequence with at least 90% sequence identity to the amino acid sequence of SEQ ID NO:69, and the VL domain comprises an amino acid sequence with at least 90% sequence identity to the amino acid sequence of SEQ ID NO:70; (d) the VH domain comprises an amino acid sequence with at least 90% sequence identity to the amino acid sequence of SEQ ID NO:71, and the VL domain comprises an amino acid sequence with at least 90% sequence identity to the amino acid sequence of SEQ ID NO:72; (e) the VH domain comprises an amino acid sequence with at least 90% sequence identity to the amino acid sequence of SEQ ID NO:73, and the VL domain comprises an amino acid sequence with at least 90% sequence identity to the amino acid sequence of SEQ ID NO:74; (f) the VH domain comprises an amino acid sequence with at least 90% sequence identity to the amino acid sequence of SEQ ID NO:75, and the VL domain comprises an amino acid sequence with at least 90% sequence identity to the amino acid sequence of SEQ ID NO:76; (g) the VH domain comprises an amino acid sequence with at least 90% sequence identity to the amino acid sequence of SEQ ID NO:77, and the VL domain comprises an amino acid sequence with at least 90% sequence identity to the amino acid sequence of SEQ ID NO:78; (h) the VH domain comprises an amino acid sequence with at least 90% sequence identity to the amino acid sequence of SEQ ID NO:79, and the VL domain comprises an amino acid sequence with at least 90% sequence identity to the amino acid sequence of SEQ ID NO:80; or (i) the VH domain comprises an amino acid sequence with at least 90% sequence identity to the amino acid sequence of SEQ ID NO:81, and the VL domain comprises an amino acid sequence with at least 90% sequence identity to the amino acid sequence of SEQ ID NO:82. In some embodiments, the antibody comprises a heavy chain variable (VH) domain and a light chain variable (VL) domain, wherein: (a) the VH domain comprises an amino acid sequence with at least 95% sequence identity to the amino acid sequence of SEQ ID NO:65, and the VL domain comprises an amino acid sequence with at least 95% sequence identity to the amino acid sequence of SEQ ID NO:66; (b) the VH domain comprises an amino acid sequence with at least 95% sequence identity to the amino acid sequence of SEQ ID NO:67, and the VL domain comprises an amino acid sequence with at least 95% sequence identity to the amino acid sequence of SEQ ID NO:68; (c) the VH domain comprises an amino acid sequence with at least 95% sequence identity to the amino acid sequence of SEQ ID NO:69, and the VL domain comprises an amino acid sequence with at least 95% sequence identity to the amino acid sequence of SEQ ID NO:70; (d) the VH domain comprises an amino acid sequence with at least 95% sequence identity to the amino acid sequence of SEQ ID NO:71, and the VL domain comprises an amino acid sequence with at least 95% sequence identity to the amino acid sequence of SEQ ID NO:72; (e) the VH domain comprises an amino acid sequence with at least 95% sequence identity to the amino acid sequence of SEQ ID NO:73, and the VL domain comprises an amino acid sequence with at least 95% sequence identity to the amino acid sequence of SEQ ID NO:74; (f) the VH domain comprises an amino acid sequence with at least 95% sequence identity to the amino acid sequence of SEQ ID NO:75, and the VL domain comprises an amino acid sequence with at least 95% sequence identity to the amino acid sequence of SEQ ID NO:76; (g) the VH domain comprises an amino acid sequence with at least 95% sequence identity to the amino acid sequence of SEQ ID NO:77, and the VL domain comprises an amino acid sequence with at least 95% sequence identity to the amino acid sequence of SEQ ID NO:78; (h) the VH domain comprises an amino acid sequence with at least 95% sequence identity to the amino acid sequence of SEQ ID NO:79, and the VL domain comprises an amino acid sequence with at least 95% sequence identity to the amino acid sequence of SEQ ID NO:80; or (i) the VH domain comprises an amino acid sequence with at least 95% sequence identity to the amino acid sequence of SEQ ID NO:81, and the VL domain comprises an amino acid sequence with at least 95% sequence identity to the amino acid sequence of SEQ ID NO:82. In some embodiments, the antibody comprises a heavy chain variable (VH) domain and a light chain variable (VL) domain, wherein: (a) the VH domain comprises an amino acid sequence with at least 99% sequence identity to the amino acid sequence of SEQ ID NO:65, and the VL domain comprises an amino acid sequence with at least 99% sequence identity to the amino acid sequence of SEQ ID NO:66; (b) the VH domain comprises an amino acid sequence with at least 99% sequence identity to the amino acid sequence of SEQ ID NO:67, and the VL domain comprises an amino acid sequence with at least 99% sequence identity to the amino acid sequence of SEQ ID NO:68; (c) the VH domain comprises an amino acid sequence with at least 99% sequence identity to the amino acid sequence of SEQ ID NO:69, and the VL domain comprises an amino acid sequence with at least 99% sequence identity to the amino acid sequence of SEQ ID NO:70; (d) the VH domain comprises an amino acid sequence with at least 99% sequence identity to the amino acid sequence of SEQ ID NO:71, and the VL domain comprises an amino acid sequence with at least 99% sequence identity to the amino acid sequence of SEQ ID NO:72; (e) the VH domain comprises an amino acid sequence with at least 99% sequence identity to the amino acid sequence of SEQ ID NO:73, and the VL domain comprises an amino acid sequence with at least 99% sequence identity to the amino acid sequence of SEQ ID NO:74; (f) the VH domain comprises an amino acid sequence with at least 99% sequence identity to the amino acid sequence of SEQ ID NO:75, and the VL domain comprises an amino acid sequence with at least 99% sequence identity to the amino acid sequence of SEQ ID NO:76; (g) the VH domain comprises an amino acid sequence with at least 99% sequence identity to the amino acid sequence of SEQ ID NO:77, and the VL domain comprises an amino acid sequence with at least 99% sequence identity to the amino acid sequence of SEQ ID NO:78; (h) the VH domain comprises an amino acid sequence with at least 99% sequence identity to the amino acid sequence of SEQ ID NO:79, and the VL domain comprises an amino acid sequence with at least 99% sequence identity to the amino acid sequence of SEQ ID NO:80; or (i) the VH domain comprises an amino acid sequence with at least 99% sequence identity to the amino acid sequence of SEQ ID NO:81, and the VL domain comprises an amino acid sequence with at least 99% sequence identity to the amino acid sequence of SEQ ID NO:82. In some embodiments, the antibody comprises a heavy chain variable (VH) domain and a light chain variable (VL) domain, wherein: (a) the VH domain comprises the amino acid sequence of SEQ ID NO:65, and the VL domain comprises the amino acid sequence of SEQ ID NO:66; (b) the VH domain comprises the amino acid sequence of SEQ ID NO:67, and the VL domain comprises the amino acid sequence of SEQ ID NO:68; (c) the VH domain comprises the amino acid sequence of SEQ ID NO:69, and the VL domain comprises the amino acid sequence of SEQ ID NO:70; (d) the VH domain comprises the amino acid sequence of SEQ ID NO:71, and the VL domain comprises the amino acid sequence of SEQ ID NO:72; (e) the VH domain comprises the amino acid sequence of SEQ ID NO:73, and the VL domain comprises the amino acid sequence of SEQ ID NO:74; (f) the VH domain comprises the amino acid sequence of SEQ ID NO:75, and the VL domain comprises the amino acid sequence of SEQ ID NO:76; (g) the VH domain comprises the amino acid sequence of SEQ ID NO:77, and the VL domain comprises the amino acid sequence of SEQ ID NO:78; (h) the VH domain comprises the amino acid sequence of SEQ ID NO:79, and the VL domain comprises the amino acid sequence of SEQ ID NO:80; or (i) the VH domain comprises the amino acid sequence of SEQ ID NO:81, and the VL domain comprises the amino acid sequence of SEQ ID NO:82.

In some aspects, provided herein are antibodies that bind to human CD94. In some embodiments, the antibody comprises a heavy chain variable (VH) domain and a light chain variable (VL) domain, wherein the VH domain comprises a CDR-H1 comprising an amino acid sequence with at least 80% sequence identity to the amino acid sequence of SEQ ID NO:1, a CDR-H2 comprising an amino acid sequence with at least 80% sequence identity to the amino acid sequence of SEQ ID NO:2, and a CDR-H3 comprising an amino acid sequence with at least 80% sequence identity to the amino acid sequence of SEQ ID NO:3; and wherein the VL domain comprises a CDR-L1 comprising an amino acid sequence with at least 80% sequence identity to the amino acid sequence of SEQ ID NO:4, a CDR-L2 comprising an amino acid sequence with at least 80% sequence identity to the amino acid sequence of SEQ ID NO:5, and a CDR-L3 comprising an amino acid sequence with at least 80% sequence identity to the amino acid sequence of SEQ ID NO:6. In some embodiments, the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, the VH domain comprises an amino acid sequence with at least 80% sequence identity to the amino acid sequence of SEQ ID NO:19, and the VL domain comprises an amino acid sequence with at least 80% sequence identity to the amino acid sequence of SEQ ID NO:20. In some embodiments, the VH domain comprises the amino acid sequence of SEQ ID NO:19, and the VL domain comprises the amino acid sequence of SEQ ID NO:20. In some embodiments, the antibody comprises a heavy chain variable (VH) domain and a light chain variable (VL) domain, wherein the VH domain comprises a CDR-H1 comprising an amino acid sequence with at least 80% sequence identity to the amino acid sequence of SEQ ID NO:7, a CDR-H2 comprising an amino acid sequence with at least 80% sequence identity to the amino acid sequence of SEQ ID NO:8, and a CDR-H3 comprising an amino acid sequence with at least 80% sequence identity to the amino acid sequence of SEQ ID NO:9; and wherein the VL domain comprises a CDR-L1 comprising an amino acid sequence with at least 80% sequence identity to the amino acid sequence of SEQ ID NO:10, a CDR-L2 comprising an amino acid sequence with at least 80% sequence identity to the amino acid sequence of SEQ ID NO:11, and a CDR-L3 comprising an amino acid sequence with at least 80% sequence identity to the amino acid sequence of SEQ ID NO:12. In some embodiments, the VH domain comprises a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and wherein the VL domain comprises a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12. In some embodiments, the VH domain comprises an amino acid sequence with at least 80% sequence identity to the amino acid sequence of SEQ ID NO:21, and the VL domain comprises an amino acid sequence with at least 80% sequence identity to the amino acid sequence of SEQ ID NO:22. In some embodiments, the VH domain comprises the amino acid sequence of SEQ ID NO:21, and the VL domain comprises the amino acid sequence of SEQ ID NO:22. In some embodiments, the antibody comprises a heavy chain variable (VH) domain and a light chain variable (VL) domain, wherein the VH domain comprises a CDR-H1 comprising an amino acid sequence with at least 80% sequence identity to the amino acid sequence of SEQ ID NO:13, a CDR-H2 comprising an amino acid sequence with at least 80% sequence identity to the amino acid sequence of SEQ ID NO:14, and a CDR-H3 comprising an amino acid sequence with at least 80% sequence identity to the amino acid sequence of SEQ ID NO:15; and wherein the VL domain comprises a CDR-L1 comprising an amino acid sequence with at least 80% sequence identity to the amino acid sequence of SEQ ID NO:16, a CDR-L2 comprising an amino acid sequence with at least 80% sequence identity to the amino acid sequence of SEQ ID NO:17, and a CDR-L3 comprising an amino acid sequence with at least 80% sequence identity to the amino acid sequence of SEQ ID NO:18. In some embodiments, the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the VH domain comprises an amino acid sequence with at least 80% sequence identity to the amino acid sequence of SEQ ID NO:23, and the VL domain comprises an amino acid sequence with at least 80% sequence identity to the amino acid sequence of SEQ ID NO:24. In some embodiments, the VH domain comprises the amino acid sequence of SEQ ID NO:23, and the VL domain comprises the amino acid sequence of SEQ ID NO:24. In some embodiments, the antibody is a human antibody.

In some aspects, provided herein are antibodies that bind to human CD94. In some embodiments, the antibody comprises a heavy chain variable (VH) domain and a light chain variable (VL) domain, wherein: (a) the VH domain comprises a CDR-H1 comprising an amino acid sequence with at least 80% sequence identity to the amino acid sequence of SEQ ID NO:30, a CDR-H2 comprising an amino acid sequence with at least 80% sequence identity to the amino acid sequence of SEQ ID NO:31, and a CDR-H3 comprising an amino acid sequence with at least 80% sequence identity to the amino acid sequence of SEQ ID NO:32; and wherein the VL domain comprises a CDR-L1 comprising an amino acid sequence with at least 80% sequence identity to the amino acid sequence of SEQ ID NO:33, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:35; (b) the VH domain comprises a CDR-H1 comprising an amino acid sequence with at least 80% sequence identity to the amino acid sequence of SEQ ID NO:36, a CDR-H2 comprising an amino acid sequence with at least 80% sequence identity to the amino acid sequence of SEQ ID NO:37, and a CDR-H3 comprising an amino acid sequence with at least 80% sequence identity to the amino acid sequence of SEQ ID NO:38; and wherein the VL domain comprises a CDR-L1 comprising an amino acid sequence with at least 80% sequence identity to the amino acid sequence of SEQ ID NO:33, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:35; (c) the VH domain comprises a CDR-H1 comprising an amino acid sequence with at least 80% sequence identity to the amino acid sequence of SEQ ID NO:36, a CDR-H2 comprising an amino acid sequence with at least 80% sequence identity to the amino acid sequence of SEQ ID NO:39, and a CDR-H3 comprising an amino acid sequence with at least 80% sequence identity to the amino acid sequence of SEQ ID NO:40; and wherein the VL domain comprises a CDR-L1 comprising an amino acid sequence with at least 80% sequence identity to the amino acid sequence of SEQ ID NO:33, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:35; (d) the VH domain comprises a CDR-H1 comprising an amino acid sequence with at least 80% sequence identity to the amino acid sequence of SEQ ID NO:41, a CDR-H2 comprising an amino acid sequence with at least 80% sequence identity to the amino acid sequence of SEQ ID NO:42, and a CDR-H3 comprising an amino acid sequence with at least 80% sequence identity to the amino acid sequence of SEQ ID NO:43; and wherein the VL domain comprises a CDR-L1 comprising an amino acid sequence with at least 80% sequence identity to the amino acid sequence of SEQ ID NO:44, a CDR-L2 comprising an amino acid sequence with at least 80% sequence identity to the amino acid sequence of SEQ ID NO:45, and a CDR-L3 comprising an amino acid sequence with at least 80% sequence identity to the amino acid sequence of SEQ ID NO:46; (e) the VH domain comprises a CDR-H1 comprising an amino acid sequence with at least 80% sequence identity to the amino acid sequence of SEQ ID NO:47, a CDR-H2 comprising an amino acid sequence with at least 80% sequence identity to the amino acid sequence of SEQ ID NO:48, and a CDR-H3 comprising an amino acid sequence with at least 80% sequence identity to the amino acid sequence of SEQ ID NO:49; and wherein the VL domain comprises a CDR-L1 comprising an amino acid sequence with at least 80% sequence identity to the amino acid sequence of SEQ ID NO:50, a CDR-L2 comprising an amino acid sequence with at least 80% sequence identity to the amino acid sequence of SEQ ID NO:51, and a CDR-L3 comprising an amino acid sequence with at least 80% sequence identity to the amino acid sequence of SEQ ID NO:52; (f) the VH domain comprises a CDR-H1 comprising an amino acid sequence with at least 80% sequence identity to the amino acid sequence of SEQ ID NO:53, a CDR-H2 comprising an amino acid sequence with at least 80% sequence identity to the amino acid sequence of SEQ ID NO:54, and a CDR-H3 comprising an amino acid sequence with at least 80% sequence identity to the amino acid sequence of SEQ ID NO:55; and wherein the VL domain comprises a CDR-L1 comprising an amino acid sequence with at least 80% sequence identity to the amino acid sequence of SEQ ID NO:50, a CDR-L2 comprising an amino acid sequence with at least 80% sequence identity to the amino acid sequence of SEQ ID NO:45, and a CDR-L3 comprising an amino acid sequence with at least 80% sequence identity to the amino acid sequence of SEQ ID NO:56; (g) the VH domain comprises a CDR-H1 comprising an amino acid sequence with at least 80% sequence identity to the amino acid sequence of SEQ ID NO:57, a CDR-H2 comprising an amino acid sequence with at least 80% sequence identity to the amino acid sequence of SEQ ID NO:58, and a CDR-H3 comprising an amino acid sequence with at least 80% sequence identity to the amino acid sequence of SEQ ID NO:59; and wherein the VL domain comprises a CDR-L1 comprising an amino acid sequence with at least 80% sequence identity to the amino acid sequence of SEQ ID NO:60, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:61; (h) the VH domain comprises a CDR-H1 comprising an amino acid sequence with at least 80% sequence identity to the amino acid sequence of SEQ ID NO:83, a CDR-H2 comprising an amino acid sequence with at least 80% sequence identity to the amino acid sequence of SEQ ID NO:84, and a CDR-H3 comprising an amino acid sequence with at least 80% sequence identity to the amino acid sequence of SEQ ID NO:85; and wherein the VL domain comprises a CDR-L1 comprising an amino acid sequence with at least 80% sequence identity to the amino acid sequence of SEQ ID NO:86, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:61; or (i) the VH domain comprises a CDR-H1 comprising an amino acid sequence with at least 80% sequence identity to the amino acid sequence of SEQ ID NO:47, a CDR-H2 comprising an amino acid sequence with at least 80% sequence identity to the amino acid sequence of SEQ ID NO:48, and a CDR-H3 comprising an amino acid sequence with at least 80% sequence identity to the amino acid sequence of SEQ ID NO:62; and wherein the VL domain comprises a CDR-L1 comprising an amino acid sequence with at least 80% sequence identity to the amino acid sequence of SEQ ID NO:63, a CDR-L2 comprising an amino acid sequence with at least 80% sequence identity to the amino acid sequence of SEQ ID NO:34, and a CDR-L3 comprising an amino acid sequence with at least 80% sequence identity to the amino acid sequence of SEQ ID NO:64. In some embodiments, (a) the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (b) the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (c) the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (d) the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46; (e) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52; (f) the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56; (g) the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61; (h) the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61; or (i) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64. In some embodiments, the antibody comprises a heavy chain variable (VH) domain and a light chain variable (VL) domain, wherein: (a) the VH domain comprises a CDR-H1 comprising an amino acid sequence with at least 80% sequence identity to the amino acid sequence of SEQ ID NO:87, a CDR-H2 comprising an amino acid sequence with at least 80% sequence identity to the amino acid sequence of SEQ ID NO:88, and a CDR-H3 comprising an amino acid sequence with at least 80% sequence identity to the amino acid sequence of SEQ ID NO:89; and wherein the VL domain comprises a CDR-L1 comprising an amino acid sequence with at least 80% sequence identity to the amino acid sequence of SEQ ID NO:90, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:35; (b) the VH domain comprises a CDR-H1 comprising an amino acid sequence with at least 80% sequence identity to the amino acid sequence of SEQ ID NO:87, a CDR-H2 comprising an amino acid sequence with at least 80% sequence identity to the amino acid sequence of SEQ ID NO:92, and a CDR-H3 comprising an amino acid sequence with at least 80% sequence identity to the amino acid sequence of SEQ ID NO:93; and wherein the VL domain comprises a CDR-L1 comprising an amino acid sequence with at least 80% sequence identity to the amino acid sequence of SEQ ID NO:90, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:35; (c) the VH domain comprises a CDR-H1 comprising an amino acid sequence with at least 80% sequence identity to the amino acid sequence of SEQ ID NO:87, a CDR-H2 comprising an amino acid sequence with at least 80% sequence identity to the amino acid sequence of SEQ ID NO:92, and a CDR-H3 comprising an amino acid sequence with at least 80% sequence identity to the amino acid sequence of SEQ ID NO:94; and wherein the VL domain comprises a CDR-L1 comprising an amino acid sequence with at least 80% sequence identity to the amino acid sequence of SEQ ID NO:90, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:35; (d) the VH domain comprises a CDR-H1 comprising an amino acid sequence with at least 80% sequence identity to the amino acid sequence of SEQ ID NO:95, a CDR-H2 comprising an amino acid sequence with at least 80% sequence identity to the amino acid sequence of SEQ ID NO:96, and a CDR-H3 comprising an amino acid sequence with at least 80% sequence identity to the amino acid sequence of SEQ ID NO:97; and wherein the VL domain comprises a CDR-L1 comprising an amino acid sequence with at least 80% sequence identity to the amino acid sequence of SEQ ID NO:98, a CDR-L2 comprising an amino acid sequence with at least 80% sequence identity to the amino acid sequence of SEQ ID NO:99, and a CDR-L3 comprising an amino acid sequence with at least 80% sequence identity to the amino acid sequence of SEQ ID NO:100; (e) the VH domain comprises a CDR-H1 comprising an amino acid sequence with at least 80% sequence identity to the amino acid sequence of SEQ ID NO:109, a CDR-H2 comprising an amino acid sequence with at least 80% sequence identity to the amino acid sequence of SEQ ID NO:110, and a CDR-H3 comprising an amino acid sequence with at least 80% sequence identity to the amino acid sequence of SEQ ID NO:114; and wherein the VL domain comprises a CDR-L1 comprising an amino acid sequence with at least 80% sequence identity to the amino acid sequence of SEQ ID NO:115, a CDR-L2 comprising an amino acid sequence with at least 80% sequence identity to the amino acid sequence of SEQ ID NO:99, and a CDR-L3 comprising an amino acid sequence with at least 80% sequence identity to the amino acid sequence of SEQ ID NO:52; (f) the VH domain comprises a CDR-H1 comprising an amino acid sequence with at least 80% sequence identity to the amino acid sequence of SEQ ID NO:116, a CDR-H2 comprising an amino acid sequence with at least 80% sequence identity to the amino acid sequence of SEQ ID NO:117, and a CDR-H3 comprising an amino acid sequence with at least 80% sequence identity to the amino acid sequence of SEQ ID NO:118; and wherein the VL domain comprises a CDR-L1 comprising an amino acid sequence with at least 80% sequence identity to the amino acid sequence of SEQ ID NO:115, a CDR-L2 comprising an amino acid sequence with at least 80% sequence identity to the amino acid sequence of SEQ ID NO:99, and a CDR-L3 comprising an amino acid sequence with at least 80% sequence identity to the amino acid sequence of SEQ ID NO:56; (g) the VH domain comprises a CDR-H1 comprising an amino acid sequence with at least 80% sequence identity to the amino acid sequence of SEQ ID NO:101, a CDR-H2 comprising an amino acid sequence with at least 80% sequence identity to the amino acid sequence of SEQ ID NO:102, and a CDR-H3 comprising an amino acid sequence with at least 80% sequence identity to the amino acid sequence of SEQ ID NO:103; and wherein the VL domain comprises a CDR-L1 comprising an amino acid sequence with at least 80% sequence identity to the amino acid sequence of SEQ ID NO:104, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:61; (h) the VH domain comprises a CDR-H1 comprising an amino acid sequence with at least 80% sequence identity to the amino acid sequence of SEQ ID NO:105, a CDR-H2 comprising an amino acid sequence with at least 80% sequence identity to the amino acid sequence of SEQ ID NO:106, and a CDR-H3 comprising an amino acid sequence with at least 80% sequence identity to the amino acid sequence of SEQ ID NO:107; and wherein the VL domain comprises a CDR-L1 comprising an amino acid sequence with at least 80% sequence identity to the amino acid sequence of SEQ ID NO:108, a CDR-L2 comprising an amino acid sequence with at least 80% sequence identity to the amino acid sequence of SEQ ID NO:91, and a CDR-L3 comprising an amino acid sequence with at least 80% sequence identity to the amino acid sequence of SEQ ID NO:61; or (i) the VH domain comprises a CDR-H1 comprising an amino acid sequence with at least 80% sequence identity to the amino acid sequence of SEQ ID NO:109, a CDR-H2 comprising an amino acid sequence with at least 80% sequence identity to the amino acid sequence of SEQ ID NO:110, and a CDR-H3 comprising an amino acid sequence with at least 80% sequence identity to the amino acid sequence of SEQ ID NO:111; and wherein the VL domain comprises a CDR-L1 comprising an amino acid sequence with at least 80% sequence identity to the amino acid sequence of SEQ ID NO:112, a CDR-L2 comprising an amino acid sequence with at least 80% sequence identity to the amino acid sequence of SEQ ID NO:113, and a CDR-L3 comprising an amino acid sequence with at least 80% sequence identity to the amino acid sequence of SEQ ID NO:64. In some embodiments, (a) the VH domain comprises a CDR-H1 comprising the amino acid sequence of SEQ ID NO:87, a CDR-H2 comprising the amino acid sequence of SEQ ID NO:88, and a CDR-H3 comprising the amino acid sequence of SEQ ID NO:89; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35; (b) the VH domain comprises a CDR-H1 comprising the amino acid sequence of SEQ ID NO:87, a CDR-H2 comprising the amino acid sequence of SEQ ID NO:92, and a CDR-H3 comprising the amino acid sequence of SEQ ID NO:93; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:350; (c) the VH domain comprises a CDR-H1 comprising the amino acid sequence of SEQ ID NO:87, a CDR-H2 comprising the amino acid sequence of SEQ ID NO:92, and a CDR-H3 comprising the amino acid sequence of SEQ ID NO:94; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35; (d) the VH domain comprises a CDR-H1 comprising the amino acid sequence of SEQ ID NO:95, a CDR-H2 comprising the amino acid sequence of SEQ ID NO:96, and a CDR-H3 comprising the amino acid sequence of SEQ ID NO:97; and wherein the VL domain comprises a CDR-L1 comprising the amino acid sequence of SEQ ID NO:98, a CDR-L2 comprising the amino acid sequence of SEQ ID NO:99, and a CDR-L3 comprising the amino acid sequence of SEQ ID NO:100; (e) the VH domain comprises a CDR-H1 comprising the amino acid sequence of SEQ ID NO:109, a CDR-H2 comprising the amino acid sequence of SEQ ID NO:110, and a CDR-H3 comprising the amino acid sequence of SEQ ID NO:114; and wherein the VL domain comprises a CDR-L1 comprising the amino acid sequence of SEQ ID NO:115, a CDR-L2 comprising the amino acid sequence of SEQ ID NO:99, and a CDR-L3 comprising the amino acid sequence of SEQ ID NO:52; (f) the VH domain comprises a CDR-H1 comprising the amino acid sequence of SEQ ID NO:116, a CDR-H2 comprising the amino acid sequence of SEQ ID NO:117, and a CDR-H3 comprising the amino acid sequence of SEQ ID NO:118; and wherein the VL domain comprises a CDR-L1 comprising the amino acid sequence of SEQ ID NO:115, a CDR-L2 comprising the amino acid sequence of SEQ ID NO:99, and a CDR-L3 comprising the amino acid sequence of SEQ ID NO:56; (g) the VH domain comprises a CDR-H1 comprising the amino acid sequence of SEQ ID NO:101, a CDR-H2 comprising the amino acid sequence of SEQ ID NO:102, and a CDR-H3 comprising the amino acid sequence of SEQ ID NO:103; and wherein the VL domain comprises a CDR-L1 comprising the amino acid sequence of SEQ ID NO:104, a CDR-L2 comprising the amino acid sequence of SEQ ID NO:91, and a CDR-L3 comprising the amino acid sequence of SEQ ID NO:61; (h) the VH domain comprises a CDR-H1 comprising the amino acid sequence of SEQ ID NO:105, a CDR-H2 comprising the amino acid sequence of SEQ ID NO:106, and a CDR-H3 comprising the amino acid sequence of SEQ ID NO:107; and wherein the VL domain comprises a CDR-L1 comprising the amino acid sequence of SEQ ID NO:108, a CDR-L2 comprising the amino acid sequence of SEQ ID NO:91, and a CDR-L3 comprising the amino acid sequence of SEQ ID NO:61; or (i) the VH domain comprises a CDR-H1 comprising the amino acid sequence of SEQ ID NO:109, a CDR-H2 comprising the amino acid sequence of SEQ ID NO:110, and a CDR-H3 comprising the amino acid sequence of SEQ ID NO:111; and wherein the VL domain comprises a CDR-L1 comprising the amino acid sequence of SEQ ID NO:112, a CDR-L2 comprising the amino acid sequence of SEQ ID NO:113, and a CDR-L3 comprising the amino acid sequence of SEQ ID NO:64. In some embodiments, (a) the VH domain comprises an amino acid sequence with at least 80% sequence identity to the amino acid sequence of SEQ ID NO:65, and the VL domain comprises an amino acid sequence with at least 80% sequence identity to the amino acid sequence of SEQ ID NO:66; (b) the VH domain comprises an amino acid sequence with at least 80% sequence identity to the amino acid sequence of SEQ ID NO:67, and the VL domain comprises an amino acid sequence with at least 80% sequence identity to the amino acid sequence of SEQ ID NO:68; (c) the VH domain comprises an amino acid sequence with at least 80% sequence identity to the amino acid sequence of SEQ ID NO:69, and the VL domain comprises an amino acid sequence with at least 80% sequence identity to the amino acid sequence of SEQ ID NO:70; (d) the VH domain comprises an amino acid sequence with at least 80% sequence identity to the amino acid sequence of SEQ ID NO:71, and the VL domain comprises an amino acid sequence with at least 80% sequence identity to the amino acid sequence of SEQ ID NO:72; (e) the VH domain comprises an amino acid sequence with at least 80% sequence identity to the amino acid sequence of SEQ ID NO:73, and the VL domain comprises an amino acid sequence with at least 80% sequence identity to the amino acid sequence of SEQ ID NO:74; (f) the VH domain comprises an amino acid sequence with at least 80% sequence identity to the amino acid sequence of SEQ ID NO:75, and the VL domain comprises an amino acid sequence with at least 80% sequence identity to the amino acid sequence of SEQ ID NO:76; (g) the VH domain comprises an amino acid sequence with at least 80% sequence identity to the amino acid sequence of SEQ ID NO:77, and the VL domain comprises an amino acid sequence with at least 80% sequence identity to the amino acid sequence of SEQ ID NO:78; (h) the VH domain comprises an amino acid sequence with at least 80% sequence identity to the amino acid sequence of SEQ ID NO:79, and the VL domain comprises an amino acid sequence with at least 80% sequence identity to the amino acid sequence of SEQ ID NO:80; or (i) the VH domain comprises an amino acid sequence with at least 80% sequence identity to the amino acid sequence of SEQ ID NO:81, and the VL domain comprises an amino acid sequence with at least 80% sequence identity to the amino acid sequence of SEQ ID NO:82. In some embodiments, (a) the VH domain comprises an amino acid sequence with at least 90% sequence identity to the amino acid sequence of SEQ ID NO:65, and the VL domain comprises an amino acid sequence with at least 90% sequence identity to the amino acid sequence of SEQ ID NO:66; (b) the VH domain comprises an amino acid sequence with at least 90% sequence identity to the amino acid sequence of SEQ ID NO:67, and the VL domain comprises an amino acid sequence with at least 90% sequence identity to the amino acid sequence of SEQ ID NO:68; (c) the VH domain comprises an amino acid sequence with at least 90% sequence identity to the amino acid sequence of SEQ ID NO:69, and the VL domain comprises an amino acid sequence with at least 90% sequence identity to the amino acid sequence of SEQ ID NO:70; (d) the VH domain comprises an amino acid sequence with at least 90% sequence identity to the amino acid sequence of SEQ ID NO:71, and the VL domain comprises an amino acid sequence with at least 90% sequence identity to the amino acid sequence of SEQ ID NO:72; (e) the VH domain comprises an amino acid sequence with at least 90% sequence identity to the amino acid sequence of SEQ ID NO:73, and the VL domain comprises an amino acid sequence with at least 90% sequence identity to the amino acid sequence of SEQ ID NO:74; (f) the VH domain comprises an amino acid sequence with at least 90% sequence identity to the amino acid sequence of SEQ ID NO:75, and the VL domain comprises an amino acid sequence with at least 90% sequence identity to the amino acid sequence of SEQ ID NO:76; (g) the VH domain comprises an amino acid sequence with at least 90% sequence identity to the amino acid sequence of SEQ ID NO:77, and the VL domain comprises an amino acid sequence with at least 90% sequence identity to the amino acid sequence of SEQ ID NO:78; (h) the VH domain comprises an amino acid sequence with at least 90% sequence identity to the amino acid sequence of SEQ ID NO:79, and the VL domain comprises an amino acid sequence with at least 90% sequence identity to the amino acid sequence of SEQ ID NO:80; or (i) the VH domain comprises an amino acid sequence with at least 90% sequence identity to the amino acid sequence of SEQ ID NO:81, and the VL domain comprises an amino acid sequence with at least 90% sequence identity to the amino acid sequence of SEQ ID NO:82. In some embodiments, (a) the VH domain comprises an amino acid sequence with at least 95% sequence identity to the amino acid sequence of SEQ ID NO:65, and the VL domain comprises an amino acid sequence with at least 95% sequence identity to the amino acid sequence of SEQ ID NO:66; (b) the VH domain comprises an amino acid sequence with at least 95% sequence identity to the amino acid sequence of SEQ ID NO:67, and the VL domain comprises an amino acid sequence with at least 95% sequence identity to the amino acid sequence of SEQ ID NO:68; (c) the VH domain comprises an amino acid sequence with at least 95% sequence identity to the amino acid sequence of SEQ ID NO:69, and the VL domain comprises an amino acid sequence with at least 95% sequence identity to the amino acid sequence of SEQ ID NO:70; (d) the VH domain comprises an amino acid sequence with at least 95% sequence identity to the amino acid sequence of SEQ ID NO:71, and the VL domain comprises an amino acid sequence with at least 95% sequence identity to the amino acid sequence of SEQ ID NO:72; (e) the VH domain comprises an amino acid sequence with at least 95% sequence identity to the amino acid sequence of SEQ ID NO:73, and the VL domain comprises an amino acid sequence with at least 95% sequence identity to the amino acid sequence of SEQ ID NO:74; (f) the VH domain comprises an amino acid sequence with at least 95% sequence identity to the amino acid sequence of SEQ ID NO:75, and the VL domain comprises an amino acid sequence with at least 95% sequence identity to the amino acid sequence of SEQ ID NO:76; (g) the VH domain comprises an amino acid sequence with at least 95% sequence identity to the amino acid sequence of SEQ ID NO:77, and the VL domain comprises an amino acid sequence with at least 95% sequence identity to the amino acid sequence of SEQ ID NO:78; (h) the VH domain comprises an amino acid sequence with at least 95% sequence identity to the amino acid sequence of SEQ ID NO:79, and the VL domain comprises an amino acid sequence with at least 95% sequence identity to the amino acid sequence of SEQ ID NO:80; or (i) the VH domain comprises an amino acid sequence with at least 95% sequence identity to the amino acid sequence of SEQ ID NO:81, and the VL domain comprises an amino acid sequence with at least 95% sequence identity to the amino acid sequence of SEQ ID NO:82. In some embodiments, (a) the VH domain comprises an amino acid sequence with at least 99% sequence identity to the amino acid sequence of SEQ ID NO:65, and the VL domain comprises an amino acid sequence with at least 99% sequence identity to the amino acid sequence of SEQ ID NO:66; (b) the VH domain comprises an amino acid sequence with at least 99% sequence identity to the amino acid sequence of SEQ ID NO:67, and the VL domain comprises an amino acid sequence with at least 99% sequence identity to the amino acid sequence of SEQ ID NO:68; (c) the VH domain comprises an amino acid sequence with at least 99% sequence identity to the amino acid sequence of SEQ ID NO:69, and the VL domain comprises an amino acid sequence with at least 99% sequence identity to the amino acid sequence of SEQ ID NO:70; (d) the VH domain comprises an amino acid sequence with at least 99% sequence identity to the amino acid sequence of SEQ ID NO:71, and the VL domain comprises an amino acid sequence with at least 99% sequence identity to the amino acid sequence of SEQ ID NO:72; (e) the VH domain comprises an amino acid sequence with at least 99% sequence identity to the amino acid sequence of SEQ ID NO:73, and the VL domain comprises an amino acid sequence with at least 99% sequence identity to the amino acid sequence of SEQ ID NO:74; (f) the VH domain comprises an amino acid sequence with at least 99% sequence identity to the amino acid sequence of SEQ ID NO:75, and the VL domain comprises an amino acid sequence with at least 99% sequence identity to the amino acid sequence of SEQ ID NO:76; (g) the VH domain comprises an amino acid sequence with at least 99% sequence identity to the amino acid sequence of SEQ ID NO:77, and the VL domain comprises an amino acid sequence with at least 99% sequence identity to the amino acid sequence of SEQ ID NO:78; (h) the VH domain comprises an amino acid sequence with at least 99% sequence identity to the amino acid sequence of SEQ ID NO:79, and the VL domain comprises an amino acid sequence with at least 99% sequence identity to the amino acid sequence of SEQ ID NO:80; or (i) the VH domain comprises an amino acid sequence with at least 99% sequence identity to the amino acid sequence of SEQ ID NO:81, and the VL domain comprises an amino acid sequence with at least 99% sequence identity to the amino acid sequence of SEQ ID NO:82. In some embodiments, (a) the VH domain comprises the amino acid sequence of SEQ ID NO:65, and the VL domain comprises the amino acid sequence of SEQ ID NO:66; (b) the VH domain comprises the amino acid sequence of SEQ ID NO:67, and the VL domain comprises the amino acid sequence of SEQ ID NO:68; (c) the VH domain comprises the amino acid sequence of SEQ ID NO:69, and the VL domain comprises the amino acid sequence of SEQ ID NO:70; (d) the VH domain comprises the amino acid sequence of SEQ ID NO:71, and the VL domain comprises the amino acid sequence of SEQ ID NO:72; (e) the VH domain comprises the amino acid sequence of SEQ ID NO:73, and the VL domain comprises the amino acid sequence of SEQ ID NO:74; (f) the VH domain comprises the amino acid sequence of SEQ ID NO:75, and the VL domain comprises the amino acid sequence of SEQ ID NO:76; (g) the VH domain comprises the amino acid sequence of SEQ ID NO:77, and the VL domain comprises the amino acid sequence of SEQ ID NO:78; (h) the VH domain comprises the amino acid sequence of SEQ ID NO:79, and the VL domain comprises the amino acid sequence of SEQ ID NO:80; or (i) the VH domain comprises the amino acid sequence of SEQ ID NO:81, and the VL domain comprises the amino acid sequence of SEQ ID NO:82.

In further aspects, provided herein are antibodies that bind the same epitope as an antibody according to any one of the above embodiments. In some embodiments, the antibodies of the present disclosure bind the same epitope as a reference antibody. In some embodiments, the reference antibody comprises a VH domain comprising a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and a VL domain comprising a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, the reference antibody comprises a VH domain comprising a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and a VL domain comprising a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12. In some embodiments, the reference antibody comprises a VH domain comprising a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the reference antibody comprises a heavy chain variable (VH) domain and a light chain variable (VL) domain, wherein: (a) the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (b) the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (c) the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (d) the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46; (e) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52; (f) the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56; (g) the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61; (h) the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61; or (i) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64.

In further aspects, provided herein are antibodies that compete with an antibody according to any one of the above embodiments for binding to human CD94. In some embodiments, the antibodies of the present disclosure compete for binding to human CD94 with a reference antibody. In some embodiments, the reference antibody comprises a VH domain comprising a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and a VL domain comprising a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6. In some embodiments, the reference antibody comprises a VH domain comprising a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and a VL domain comprising a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12. In some embodiments, the reference antibody comprises a VH domain comprising a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and a VL domain comprising a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18. In some embodiments, the reference antibody comprises a heavy chain variable (VH) domain and a light chain variable (VL) domain, wherein: (a) the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (b) the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (c) the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35; (d) the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46; (e) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52; (f) the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56; (g) the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61; (h) the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61; or (i) the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64.

In some embodiments according to any of the embodiments described herein, the antibody is an antigen-binding antibody fragment or single chain antibody. In some embodiments, the antibody further comprises an Fc region, e.g., a human IgG1 Fc region. In some embodiments, the antibody comprises a human Fc region that is non-fucosylated. In some embodiments, the antibody is produced in a cell line (e.g., a CHO cell line) deficient in an alpha-1,6-fucosyltransferase gene, such as FUT8. In some embodiments, the antibody binds to a human cellular Fc gamma receptor IIIA to a greater extent than an antibody comprising a wild type human IgG1 Fc region. In some embodiments, the antibody is capable of inducing antibody-dependent cellular cytotoxicity (ADCC) against a cell expressing human CD94 on its surface.

In further aspects, provided herein are polynucleotide(s) encoding the antibody according to any one of the above embodiments. Further provided herein are vectors (e.g., expression vectors) comprising the polynucleotide(s) according to any one of the above embodiments. Further provided herein are host cells (e.g., isolated host cells or cell lines) comprising the polynucleotide(s) or vectors according to any one of the above embodiments. Further provided herein are methods for producing an antibody, comprising culturing the host cell according to any one of the above embodiments under conditions suitable for production of the antibody. In some embodiments, the methods further comprise recovering the antibody from the host cell.

Further provided herein are compositions (e.g., pharmaceutical compositions) comprising the antibody according to any one of the above embodiments and a pharmaceutically acceptable carrier.

In further aspects, provided herein are methods for treating a disease or disorder in a subject, comprising administering to the subject an effective amount of the antibody or composition according to any one of the above embodiments. In some embodiments, administration of the antibody results in a reduction in the number of peripheral blood LGL or NK cells in the subject. In some embodiments, the disease or disorder is Felty's syndrome, and wherein administration of the antibody to the subject results in a reduction of one or more Felty's syndrome symptoms in the subject. In some embodiments, the disease or disorder is inclusion body myositis, and wherein administration of the antibody to the subject results in a reduction of one or more inclusion body myositis symptoms in the subject. In some embodiments, the disease or disorder is aggressive NK leukemia, and wherein administration of the antibody to the subject results in a reduction of one or more aggressive NK leukemia symptoms in the subject. In some embodiments, the disease or disorder is rheumatoid arthritis, and wherein administration of the antibody to the subject results in a reduction of one or more rheumatoid arthritis symptoms in the subject. In some embodiments, the disease or disorder is LGL leukemia, and wherein administration of the antibody to the subject results in a reduction of one or more LGL leukemia symptoms in the subject. In some embodiments, the disease or disorder is CLPD-NK, and wherein administration of the antibody to the subject results in a reduction of one or more CLPD-NK symptoms in the subject. In some embodiments, the disease or disorder is natural killer (NK) cell or T-cell lymphoma, and wherein administration of the antibody to the subject results in a reduction of one or more lymphoma symptoms in the subject. In some embodiments, the NK cell or T-cell lymphoma is extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL, angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL. In some embodiments, the NK cell or T-cell lymphoma is extranodal NK/T cell lymphoma, hepatosplenic TCL, or enteropathy-associated TCL. In some embodiments, the disease or disorder is microscopic colitis, and wherein administration of the antibody to the subject results in a reduction of one or more microscopic colitis symptoms in the subject.

In further aspects, provided herein are methods for reducing the number of peripheral blood LGL and/or NK cells in a subject, comprising administering to the subject an effective amount of the antibody or composition according to any one of the above embodiments. In further aspects, provided herein are methods for inducing ADCC activity in a subject comprising administering to the subject an effective amount of the antibody or composition according to any one of the above embodiments. In further aspects, provided herein are methods for treating CLPD-NK in a human subject in need thereof comprising administering to the subject an effective amount of the antibody or composition according to any one of the above embodiments. In some embodiments, administration of the antibody results in an improvement of one or more CLPD-NK symptoms in the subject.

In further aspects, provided herein are methods of treating natural killer (NK) cell or T-cell lymphoma, comprising administering to a subject in need thereof an effective amount of the antibody or composition according to any one of the above embodiments. In some embodiments, the antibody does not bind to the same epitope on human CD94 as anti-CD94 antibody clones HP-3D9, HP-3B1, DX22, 131412, or 12K45. In some embodiments, the antibody binds to human CD94 with a greater affinity than anti-CD94 antibody clones HP-3D9, HP-3B1, DX22, 131412, and 12K45. In some embodiments, the NK cell or T-cell lymphoma is extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL, angioimmunoblastic TCL, or adult TCL. In some embodiments, the NK cell or T-cell lymphoma is extranodal NK/T cell lymphoma, hepatosplenic TCL, or enteropathy-associated TCL.

In further aspects, provided herein are methods of enhancing chimeric antigen receptor T cell (CAR-T) therapy in a human subject in need thereof, comprising administering to the subject an effective amount of the antibody or composition according to any one of the above embodiments prior to administration of a CAR-T treatment to the subject. In some embodiments, administration of the antibody or composition results in depletion of NK cells in the subject prior to administration of the CAR-T treatment.

In further aspects, provided herein are methods of depleting CD8+CD94+ T cells in a human subject in need thereof, comprising administering to the subject an effective amount of the antibody or composition according to any one of the above embodiments. In some embodiments, administration of the antibody or composition results in depletion of CD8+CD94+ T cells in the subject.

In some embodiments according to any of the embodiments described herein, the methods further comprise administering an IL-2 polypeptide to the subject.

In some embodiments according to any of the embodiments described herein, the subject is a human.

In further aspects, provided herein are the antibodies or compositions according to any one of the above embodiments for use in: treating a disease or disorder in a subject, reducing the number of peripheral blood LGL and/or NK cells in a subject, treating CLPD-NK in a human subject in need thereof, treating natural killer (NK) cell or T-cell lymphoma, treating microscopic colitis in a subject, or enhancing CAR-T therapy in a subject in need thereof. In some embodiments, the NK cell or T-cell lymphoma is extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL, angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL. In some embodiments, the NK cell or T-cell lymphoma is extranodal NK/T cell lymphoma, hepatosplenic TCL, or enteropathy-associated TCL.

In further aspects, provided herein is the use of the antibodies or compositions according to any one of the above embodiments for manufacture of a medicament, e.g., for use in: treating a disease or disorder in a subject, reducing the number of peripheral blood LGL and/or NK cells in a subject, treating CLPD-NK in a human subject in need thereof, treating natural killer (NK) cell or T-cell lymphoma, treating microscopic colitis in a subject, or enhancing CAR-T therapy in a subject in need thereof. In some embodiments, the NK cell or T-cell lymphoma is extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL, angioimmunoblastic TCL, or adult TCL. In some embodiments, the NK cell or T-cell lymphoma is extranodal NK/T cell lymphoma, hepatosplenic TCL, or enteropathy-associated TCL.

In further aspects, provided herein are kits or articles of manufacture comprising the antibodies or compositions according to any one of the above embodiments. In some embodiments, the kits further comprise instructions for using the kits, e.g., in treating a disease or disorder in a subject, reducing the number of peripheral blood LGL and/or NK cells in a subject, treating CLPD-NK in a human subject in need thereof, treating natural killer (NK) cell or T-cell lymphoma, treating microscopic colitis in a subject, or enhancing CAR-T therapy in a subject in need thereof. In some embodiments, the NK cell or T-cell lymphoma is extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL, angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL. In some embodiments, the NK cell or T-cell lymphoma is extranodal NK/T cell lymphoma, hepatosplenic TCL, or enteropathy-associated TCL.

In some embodiments, which may be combined with any of the preceding embodiments, an antibody of the disclosure comprises six CDRs from a single antibody listed in Table 1 (e.g., antibody 18H3, 1M4, 1E4, ATX-122, ATX-123, ATX-124, ATX-125, ATX-126, ATX-127, ATX-128, ATX-129, or ATX-130). In some embodiments, which may be combined with any of the preceding embodiments, an antibody of the disclosure comprises a VH and VL domain from a single antibody listed in Table 2 (e.g., antibody 18H3, 1M4, 1E4, ATX-122, ATX-123, ATX-124, ATX-125, ATX-126, ATX-127, ATX-128, ATX-129, or ATX-130).

All references cited herein, including patent applications and publications, are incorporated by reference in their entirety.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows the cross-reactivity of hybridoma antibodies to cynomolgus CD94. Anti-CD94 hybridoma supernatants were screened on cynomolgus CD94-expressing HEK293 cells by flow cytometry for cross-reactivity to cynomolgus CD94. HP-3D9 is a commercial anti-CD94 antibody that was used as a negative control. Mouse IgG1, IgG2a, IgG2b and IgG3 were used as negative controls. 18H3, 1M4 and 1E4 cross-reacted with cynomolgus CD94, while 20F2 is an example of another CD94 antibody clone that reacts with human CD94 but did not cross-react with cynomolgus CD94. FIG. 3B shows the cross-reactivity of commercial antibodies to cynomolgus CD94. Commercially available anti-CD94 antibodies were used to test cynomolgus cross-reactivity. 18H3 was used as a positive control. The MFI of each antibody was normalized to the MFI of its respective isotype. HP-3B1, 131412, 12K45, DX22 and HP-3D9 did not cross-react with cynomolgus CD94, unlike 18H3.

FIG. 5A shows competition assays between 18H3 and commercially available anti-CD94 antibodies. Commercially available anti-CD94 antibodies were titrated and incubated with PBMCs concurrently with 18H3. FIG. 5B shows competition assays with 18H3 and other hybridoma anti-CD94 antibodies disclosed herein (1M4 and 1E4). To test competition between 18H3 and 1M4/1E4, 1M4 and 1E4 were incubated with cells at concentrations of 8.5 µg/ml and 11 µg/ml, respectively. 18H3 was fluorescently tagged with AF647 and incubated with cells concurrently with 18H3-AF647. 18H3 only partially competed with HP-3D9, and did not compete with DX22, HP-3B1, 131412, 12K45, 1E4 and 1M4. These results suggest that 18H3 antibody binds to an epitope that is not shared with commercially available antibodies.

FIG. 6A shows competition assays between 1M4 and commercially available anti-CD94 antibodies. Commercially available anti-CD94 antibodies were titrated and incubated with PBMCs concurrently with 1M4. FIG. 6B shows competition assays with 1M4 and 1E4 antibody. To test competition between 1M4 and 1E4, 1E4 was incubated with cells at a concentration of 11 µg/ml. 1M4 with anti-mouse secondary antibody were incubated with cells concurrently with 1E4. 1M4 antibody did not compete with commercially available antibodies, but did compete with 1E4.

FIG. 8A shows the results for commercially available antibodies HP-3D9 and DX22. Commercially available anti-CD94 antibodies were internalized in a time-dependent manner. FIG. 8B shows the results for 18H3, 1M4 and 1E4 antibodies. 18H3, 1M4 and 1E4 antibodies were not significantly internalized upon binding to CD94.

FIG. 9A shows the results for the ADCC assay using human IgG1 18H3 antibody, while FIG. 9B shows the results for the ADCC assay using fucosylated 1E4 antibody. Both human IgG1 18H3 and fucosylated 1E4 depleted human primary NK cells in a concentration dependent manner.

FIG. 11 depicts a summary of anti-CD94 antibody characteristics and functional assessment relative to commercially available anti-CD94 antibodies.

DETAILED DESCRIPTION OF THE INVENTION

Figure 1:
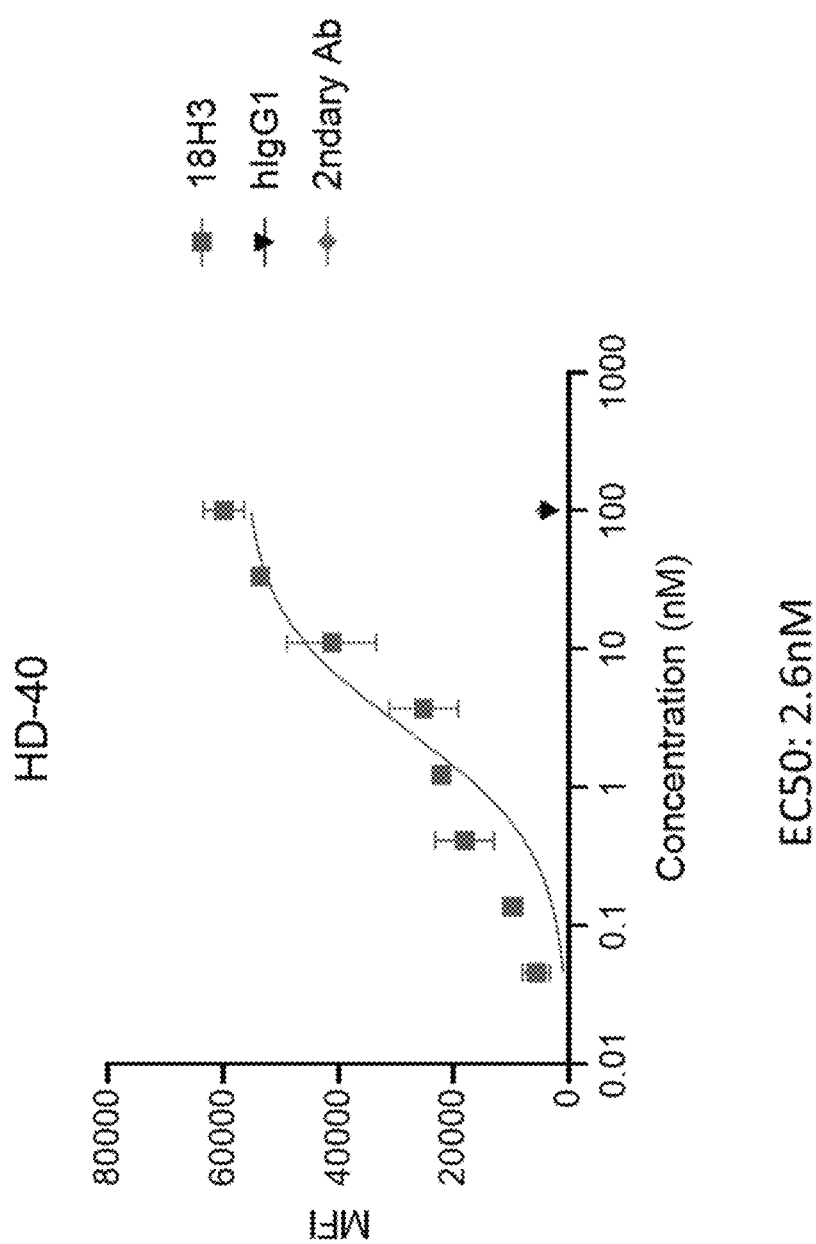
FIG. 1 shows the affinity of anti-CD94 antibody 18H3 for human primary natural killer (NK) cells as measured by flow cytometry. Peripheral blood mononuclear cells (PBMCs) of healthy donor HD-40 were used for antibody staining. 18H3 antibody was titrated from 100 nM to 0.046 nM in 1:3 dilutions and incubated with PBMCs. CD3 and CD56 antibodies were used to identify NK cells on the flow scatter. 18H3 antibody binding on CD3+ and CD56 bright NK cells was used to assess affinity of 18H3. Titration curves and EC50 were generated using Graphpad Prism. 18H3 bound to CD3+CD56 bright NK cells with an affinity of 2.6 nM. Human IgG1 isotype control with secondary antibody (hIgG1) and goat (Fab)2 fragment anti-human Fcγ-specific secondary antibody AF647 only (2ndary Ab) were used as controls.

Several aspects are described below with reference to example applications for illustration. It should be understood that numerous specific details, relationships, and methods are set forth to provide a full understanding of the features described herein. One having ordinary skill in the relevant art, however, will readily recognize that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

As used herein, the singular forms "a", "an", and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The term "comprising" as used herein is synonymous with "including" or "containing", and is inclusive or open-ended.

Any reference to "or" herein is intended to encompass "and/or" unless otherwise stated. As used herein, the term "about" with reference to a number refers to that number plus or minus 10% of that number. The term "about" with reference to a range refers to that range minus 10% of its lowest value and plus 10% of its greatest value.

I. Antibodies

In some embodiments, provided herein are antibodies that bind to CD94, e.g., human CD94 expressed on the surface of NK cells or T cells. Also provided herein are antibodies that bind to CD94 and that have immunoglobulin Fc part with modifications including reduced fucosylation, non-fucosylation, or mutations that enhance ADCC activities and/or improve affinity of the Fc region to Fc receptors such as CD16 (e.g., CD16a). Also provided herein are antibodies that bind to CD94 and that have one or more of the following characteristics: bind to human CD94 and cynomolgus monkey CD94, do not block binding of HLA-E to the CD94/NKG2A heterodimer, have a low degree of target (e.g., CD94) internalization, are non-fucosylated or have reduced fucosylation, and/or induce or promote ADCC activity.

A. Antibody Targets and Affinities

In some embodiments, the antibodies provided herein bind to CD94. In some embodiments, the antibodies provided herein bind to human CD94 (e.g., an extracellular domain of human CD94). In some embodiments, the antibodies provided herein bind to cynomolgus monkey CD94 (e.g., an extracellular domain of cynomolgus CD94). In some embodiments, the antibodies provided herein bind to human CD94 and to cynomolgus monkey CD94. In some embodiments, an antibody of the disclosure binds to CD94 on the surface of NK cells and/or T cells.

In some embodiments, an antibody of the disclosure binds to a human CD94 protein or a part thereof, or a protein having at least 80% (e.g., any of at least 80%, at least 85%, at least 90%, at least 95%, at least 96%, at least 97%, at least 98%, at least 99%, or 100%) homology to a human CD94 protein or a part thereof. Amino acid sequences of exemplary human CD94 proteins are provided in the sequences of SEQ ID NOs: 25-27:

(SEQ ID NO: 25)
MAVFKITLWRLISGTLGIICLSLMSTLGILLKNSFTKLSIEPAFTPGPNI

ELQKDSDCCSCQEKWVGYRCNCYFISSEQKTWNESRHLCASQKSSLLQLQ

NTDELDFMSSSQQFYWIGLSYSEEHTAWLWENGSALSQYLFPSFETFNTK

NCIAYNPNGNALDESCEDKNRYICKQQLI (SEQ ID NO: 26)
MAVFKTTLWRLISGTLGIICLSLMSTLGILLKNSFTKLSIEPAFTPGPNI

ELQKDSDCCSCQEKWVGYRCNCYFISSEQKTWNESRHLCASQKSSLLQLQ

NTDELQDFMSSSQQFYWIGLSYSEEHTAWLWENGSALSQYLFPSFETFNT

KNCIAYNPNGNALDESCEDKNRYICKQQLI (SEQ ID NO: 27)
MAAFTKLSIEPAFTPGPNIELQKDSDCCSCQEKWVGYRCNCYFISSEQKT

WNESRHLCASQKSSLLQLQNTDELDFMSSSQQFYWIGLSYSEEHTAWLWE

NGSALSQYLFPSFETFNTKKCIAYNPNGNALDESCEDKNRYICKQQLI

SYSEEHTAWLWENGSALSQYLFPSFETFNTKNCIAYNPNGNALDESCEDK

NRYICKQQLI

In some embodiments, the terms bind, specifically binds to, or is specific for refer to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant ($K_D$) of <1 µM, <100 nM, <10 nM, <1 nM, or <0.1 nM. In certain embodiments, an antibody specifically binds to an epitope on a protein that is conserved among the protein from different species. In another embodiment, specific binding can include, but does not require exclusive binding.

In some embodiments, the antibodies provided herein bind to human CD94 (Natural killer cells antigen CD94; CD94 Entrez Gene ID: 3824; KLRD1 (HGNC Symbol); UniProtKB identifier: Q13241; HGNC:6378; Ensembl: ENSG00000134539 OMIM: 602894; KP43).

In some embodiments, an antibody of the disclosure binds to a cynomolgus monkey CD94 protein or a part thereof, or a protein having at least 80% (e.g., any of at least 80%, at least 85%, at least 90%, at least 95%, at least 96%, at least 97%, at least 98%, at least 99%, or 100%) homology to a cynomolgus monkey CD94 protein or a part thereof. The amino acid sequences of cynomolgus monkey CD94 proteins are known in the art, for example, UniProtKB identifier: Q68VD4.

In certain embodiments, the affinity of an antibody for its target (e.g., CD94) may be represented by the dissociation constant ($K_D$). Affinity can be measured by common methods known in the art, such as flow cytometry or Western blotting, and using assays described herein (e.g., in the Examples). In some embodiments, the $K_D$ is measured using a radiolabeled antigen binding assay (RIA) performed with the Fab version of an antibody of the disclosure and its target (e.g., CD94). In some embodiments, the $K_D$ is measured using surface plasmon resonance assays. Exemplary assays are described, e.g., in Drake, A. W. and Klakamp, S. L. (2007) *J. Immunol. Methods* 318:147-152.

In some embodiments, the binding of an antibody of the disclosure to CD94, e.g., human CD94 and/or cynomolgus monkey CD94, may be assessed using any method known in the art. For example, binding of an antibody of the disclosure to human CD94 may be assessed in an ex vivo flow cytometry-based assay using peripheral blood mononuclear cells (PMBCs) and/or NK cells, e.g., as described in the Examples. Titration curves and EC50 may be generated and evaluated using methods known in the art, such as using Graphpad prism. In another example, binding of an antibody of the disclosure to cynomolgus monkey CD94 may be assessed in an ex vivo or in vitro flow cytometry-based assay using cynomolgus monkey CD94-expressing cells such as cynomolgus monkey CD94-expressing HEK293 cells, e.g., as described in the Examples.

In certain embodiments, an antibody of the disclosure has a $K_D$ of less than about 10 µM for binding to its target (e.g., human and/or cynomolgus CD94). In certain embodiments, an antibody of the disclosure has a $K_D$ of less than about 1 µM for binding to its target (e.g., human and/or cynomolgus CD94). In certain embodiments, an antibody of the disclosure has a $K_D$ of any of less than about 1000 nM, less than about 900 nM, less than about 800 nM, less than about 700 nM, less than about 600 nM, less than about 500 nM, less than about 400 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 0.5 nM, or less than about 0.1 nM for binding to its target (e.g., human and/or cynomolgus CD94). In some embodiments, an antibody of the disclosure has a $K_D$ of any of less than about 100 pM, less than about 75 pM, less than about 50 pM, less than about 25 pM, less than about 10 pM, less than about 5 pM, less than about 1 pM, less than about 0.5 pM, or less than about 0.1 pM for binding to its target (e.g., human and/or cynomolgus CD94).

In certain embodiments, an antibody of the disclosure has a $K_D$ of less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 0.5 nM, or less than about 0.1 nM for binding to human CD94 on human NK cells or T cells. In certain embodiments, an antibody of the disclosure has a $K_D$ of less than about 75 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 0.5 nM, or less than about 0.1 nM for binding to human CD94 on human NK cells or T cells. In certain embodiments, an antibody of the disclosure has a $K_D$ of between about 2 nM and about 80 nM for binding to human CD94 on human NK cells or T cells.

In certain embodiments, an antibody of the disclosure has a $K_D$ of less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 0.5 nM, or less than about 0.1 nM for binding to cynomolgus CD94 on cells expressing cynomolgus monkey CD94. In certain embodiments, an antibody of the disclosure has a $K_D$ of less than about 75 nM, less than about 80 nM, less than about 70 nM, less than about 60 nM, less than about 50 nM, less than about 40 nM, less than about 30 nM, less than about 20 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 0.5 nM, or less than about 0.1 nM for binding to cynomolgus CD94 on cells expressing cynomolgus monkey CD94. In certain embodiments, an antibody of the disclosure has a $K_D$ of between about 2 nM and about 80 nM for binding to cynomolgus CD94 on cells expressing cynomolgus monkey CD94.

In some embodiments, an antibody of the disclosure binds to its target (e.g., CD94) in the same or a different epitope as an antibody known in the art for that target. In some embodiments, an antibody of the disclosure binds to a different epitope as an antibody known in the art. In some embodiments, an antibody of the disclosure specifically binds to human CD94, wherein the antibody does not bind to the same epitope on human CD94 as anti-CD94 antibody clones HP-3D9, DX22, HP-3B1, 131412, or 12K45. In some embodiments, an antibody of the disclosure specifically binds to human CD94, wherein the antibody does not bind to the same epitope on human CD94 as anti-CD94 antibody clones DX22, HP-3B1, or 131412. In some embodiments, an antibody of the disclosure specifically binds to human CD94, wherein the antibody binds to the same epitope on human CD94 as anti-CD94 antibody clones HP-3D9, DX22, HP-3B1, 131412, or 12K45. In some embodiments, an antibody of the disclosure specifically binds to human CD94, wherein the antibody binds to the same epitope on human CD94 as anti-CD94 antibody clone HP-3D9. In some embodiments, an antibody of the disclosure specifically binds to human CD94, wherein the antibody binds to the same epitope on human CD94 as anti-CD94 antibody clone 12K45.

In some embodiments, if an antibody of the disclosure does not bind to its target (e.g., CD94) in the same epitope as another antibody for that target, e.g., a commercially available antibody or an antibody known in the art for that target, then the antibody of the disclosure does not block binding of the other antibody to the target in a competition assay (e.g., as described in the Examples), e.g., by 50% or more.

In some embodiments, an antibody of the disclosure binds to its target (e.g., CD94) with a higher affinity than an antibody known in the art for that target. In some embodiments, an antibody of the disclosure binds to its target (e.g., CD94) with a higher affinity than anti-CD94 antibody clones HP-3D9, DX22, HP-3B1, 131412, or 12K45. In some embodiments, an antibody of the disclosure binds to its target (e.g., CD94) with a higher affinity than anti-CD94 antibody clones HP-3B1, 131412, or 12K45.

In some embodiments, an antibody of the disclosure specifically binds to human CD94, wherein the antibody binds to human CD94 with a greater affinity than anti-CD94 antibody clones HP-3D9, DX22, HP-3B1, 131412, or 12K45. In some embodiments, an antibody of the disclosure specifically binds to human CD94, wherein the antibody binds to human CD94 with a greater affinity than anti-CD94 antibody clones HP-3B1, 131412, or 12K45.

In some embodiments, an antibody of the disclosure binds to its target (e.g., CD94) with any of at least 1.5-fold, at least 2-fold, at least 2.5-fold, at least 3-fold, at least 3.5-fold, at least 4-fold, at least 4.5-fold, at least 5-fold, at least 5.5-fold, at least 6-fold, at least 6.5-fold, at least 7-fold, at least 7.5-fold, at least 8-fold, at least 8.5-fold, at least 9-fold, at least 9.5-fold, at least 10-fold, or more, greater affinity than another antibody known in the art for that target.

B. Exemplary Anti-CD94 Antibodies

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:1, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:2, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:3; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:4, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:5, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:6.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:1, a CDR-H2 comprising an amino acid sequence comprising one, two, or three amino acid substitutions relative to the amino acid sequence of SEQ ID NO:2, and a CDR-H3 comprising an amino acid sequence comprising one, two, or three amino acid substitutions relative to the amino acid sequence of SEQ ID NO:3; and wherein the VL domain comprises a CDR-L1 comprising an amino acid sequence comprising one, two, or three amino acid substitutions relative to the amino acid sequence of SEQ ID NO:4, a CDR-L2 comprising an amino acid sequence comprising one, two, or three amino acid substitutions relative to the amino acid sequence of SEQ ID NO:5, and a CDR-L3 comprising an amino acid sequence comprising one, two, or three amino acid substitutions relative to the amino acid sequence of SEQ ID NO:6.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:19, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:20.

In some embodiments, an antibody of the disclosure comprises a heavy chain variable (VH) domain and a light chain variable (VL) domain, wherein the VH domain comprises the amino acid sequence of SEQ ID NO:19, and the VL domain comprises the amino acid sequence of SEQ ID NO:20.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:7, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO: 8, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:9; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:10, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:11, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:12.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:7, a CDR-H2 comprising an amino acid sequence comprising one, two, or three amino acid substitutions relative to the amino acid sequence of SEQ ID NO:8, and a CDR-H3 comprising an amino acid sequence comprising one, two, or three amino acid substitutions relative to the amino acid sequence of SEQ ID NO:9; and wherein the VL domain comprises a CDR-L1 comprising an amino acid sequence comprising one, two, or three amino acid substitutions relative to the amino acid sequence of SEQ ID NO:10, a CDR-L2 comprising an amino acid sequence comprising one, two, or three amino acid substitutions relative to the amino acid sequence of SEQ ID NO:11, and a CDR-L3 comprising an amino acid sequence comprising one, two, or three amino acid substitutions relative to the amino acid sequence of SEQ ID NO:12.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and wherein the VL domain comprises a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:21, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:22.

In some embodiments, an antibody of the disclosure comprises a heavy chain variable (VH) domain and a light chain variable (VL) domain, wherein the VH domain comprises the amino acid sequence of SEQ ID NO:21, and the VL domain comprises the amino acid sequence of SEQ ID NO:22.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:13, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:14, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:15; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:16, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:17, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:18.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:13, a CDR-H2 comprising an amino acid sequence comprising one, two, or three amino acid substitutions relative to the amino acid sequence of SEQ ID NO:14, and a CDR-H3 comprising an amino acid sequence comprising one, two, or three amino acid substitutions relative to the amino acid sequence of SEQ ID NO:15; and wherein the VL domain comprises a CDR-L1 comprising an amino acid sequence comprising one, two, or three amino acid substitutions relative to the amino acid sequence of SEQ ID NO:16, a CDR-L2 comprising an amino acid sequence comprising one, two, or three amino acid substitutions relative to the amino acid sequence of SEQ ID NO:17, and a CDR-L3 comprising an amino acid sequence comprising one, two, or three amino acid substitutions relative to the amino acid sequence of SEQ ID NO:18.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:23, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:24.

In some embodiments, an antibody of the disclosure comprises a heavy chain variable (VH) domain and a light chain variable (VL) domain, wherein the VH domain comprises the amino acid sequence of SEQ ID NO:23, and the VL domain comprises the amino acid sequence of SEQ ID NO:24.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:30, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:31, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:32; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:33, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:34, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:30, a CDR-H2 comprising an amino acid sequence comprising one, two, or three amino acid substitutions relative to the amino acid sequence of SEQ ID NO:31, and a CDR-H3 comprising an amino acid sequence comprising one, two, or three amino acid substitutions relative to the amino acid sequence of SEQ ID NO:32; and wherein the VL domain comprises a CDR-L1 comprising an amino acid sequence comprising one, two, or three amino acid substitutions relative to the amino acid sequence of SEQ ID NO:33, a CDR-L2 comprising an amino acid sequence comprising one, two, or three amino acid substitutions relative to the amino acid sequence of SEQ ID NO:34, and a CDR-L3 comprising an amino acid sequence comprising one, two, or three amino acid substitutions relative to the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:65, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:66.

In some embodiments, an antibody of the disclosure comprises a heavy chain variable (VH) domain and a light chain variable (VL) domain, wherein the VH domain comprises the amino acid sequence of SEQ ID NO:65, and the VL domain comprises the amino acid sequence of SEQ ID NO:66.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:36, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:37, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:38; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:33, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:34, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:36, a CDR-H2 comprising an amino acid sequence comprising one, two, or three amino acid substitutions relative to the amino acid sequence of SEQ ID NO:37, and a CDR-H3 comprising an amino acid sequence comprising one, two, or three amino acid substitutions relative to the amino acid sequence of SEQ ID NO:38; and wherein the VL domain comprises a CDR-L1 comprising an amino acid sequence comprising one, two, or three amino acid substitutions relative to the amino acid sequence of SEQ ID NO:33, a CDR-L2 comprising an amino acid sequence comprising one, two, or three amino acid substitutions relative to the amino acid sequence of SEQ ID NO:34, and a CDR-L3 comprising an amino acid sequence comprising one, two, or three amino acid substitutions relative to the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:67, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:68.

In some embodiments, an antibody of the disclosure comprises a heavy chain variable (VH) domain and a light chain variable (VL) domain, wherein the VH domain comprises the amino acid sequence of SEQ ID NO:67, and the VL domain comprises the amino acid sequence of SEQ ID NO:68.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:36, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:39, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:40; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:33, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:34, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:36, a CDR-H2 comprising an amino acid sequence comprising one, two, or three amino acid substitutions relative to the amino acid sequence of SEQ ID NO:39, and a CDR-H3 comprising an amino acid sequence comprising one, two, or three amino acid substitutions relative to the amino acid sequence of SEQ ID NO:40; and wherein the VL domain comprises a CDR-L1 comprising an amino acid sequence comprising one, two, or three amino acid substitutions relative to the amino acid sequence of SEQ ID NO:33, a CDR-L2 comprising an amino acid sequence comprising one, two, or three amino acid substitutions relative to the amino acid sequence of SEQ ID NO:34, and a CDR-L3 comprising an amino acid sequence comprising one, two, or three amino acid substitutions relative to the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:69, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:70.

In some embodiments, an antibody of the disclosure comprises a heavy chain variable (VH) domain and a light chain variable (VL) domain, wherein the VH domain comprises the amino acid sequence of SEQ ID NO:69, and the VL domain comprises the amino acid sequence of SEQ ID NO:70.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:41, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:42, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:43; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:44, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:45, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:46.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:41, a CDR-H2 comprising an amino acid sequence comprising one, two, or three amino acid substitutions relative to the amino acid sequence of SEQ ID NO:42, and a CDR-H3 comprising an amino acid sequence comprising one, two, or three amino acid substitutions relative to the amino acid sequence of SEQ ID NO:43; and wherein the VL domain comprises a CDR-L1 comprising an amino acid sequence comprising one, two, or three amino acid substitutions relative to the amino acid sequence of SEQ ID NO:44, a CDR-L2 comprising an amino acid sequence comprising one, two, or three amino acid substitutions relative to the amino acid sequence of SEQ ID NO:45, and a CDR-L3 comprising an amino acid sequence comprising one, two, or three amino acid substitutions relative to the amino acid sequence of SEQ ID NO:46.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:71, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:72.

In some embodiments, an antibody of the disclosure comprises a heavy chain variable (VH) domain and a light chain variable (VL) domain, wherein the VH domain comprises the amino acid sequence of SEQ ID NO:71, and the VL domain comprises the amino acid sequence of SEQ ID NO:72.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:47, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:48, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:49; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:50, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:51, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:52.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:47, a CDR-H2 comprising an amino acid sequence comprising one, two, or three amino acid substitutions relative to the amino acid sequence of SEQ ID NO:48, and a CDR-H3 comprising an amino acid sequence comprising one, two, or three amino acid substitutions relative to the amino acid sequence of SEQ ID NO:49; and wherein the VL domain comprises a CDR-L1 comprising an amino acid sequence comprising one, two, or three amino acid substitutions relative to the amino acid sequence of SEQ ID NO:50, a CDR-L2 comprising an amino acid sequence comprising one, two, or three amino acid substitutions relative to the amino acid sequence of SEQ ID NO:51, and a CDR-L3 comprising an amino acid sequence comprising one, two, or three amino acid substitutions relative to the amino acid sequence of SEQ ID NO:52.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:73, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:74.

In some embodiments, an antibody of the disclosure comprises a heavy chain variable (VH) domain and a light chain variable (VL) domain, wherein the VH domain comprises the amino acid sequence of SEQ ID NO:73, and the VL domain comprises the amino acid sequence of SEQ ID NO:74.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:53, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:54, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:55; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:50, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:45, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:56.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:53, a CDR-H2 comprising an amino acid sequence comprising one, two, or three amino acid substitutions relative to the amino acid sequence of SEQ ID NO:54, and a CDR-H3 comprising an amino acid sequence comprising one, two, or three amino acid substitutions relative to the amino acid sequence of SEQ ID NO:55; and wherein the VL domain comprises a CDR-L1 comprising an amino acid sequence comprising one, two, or three amino acid substitutions relative to the amino acid sequence of SEQ ID NO:50, a CDR-L2 comprising an amino acid sequence comprising one, two, or three amino acid substitutions relative to the amino acid sequence of SEQ ID NO:45, and a CDR-L3 comprising an amino acid sequence comprising one, two, or three amino acid substitutions relative to the amino acid sequence of SEQ ID NO:56.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:75, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:76.

In some embodiments, an antibody of the disclosure comprises a heavy chain variable (VH) domain and a light chain variable (VL) domain, wherein the VH domain comprises the amino acid sequence of SEQ ID NO:75, and the VL domain comprises the amino acid sequence of SEQ ID NO:76.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:57, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:58, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:59; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:60, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:34, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:61.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:57, a CDR-H2 comprising an amino acid sequence comprising one, two, or three amino acid substitutions relative to the amino acid sequence of SEQ ID NO:58, and a CDR-H3 comprising an amino acid sequence comprising one, two, or three amino acid substitutions relative to the amino acid sequence of SEQ ID NO:59; and wherein the VL domain comprises a CDR-L1 comprising an amino acid sequence comprising one, two, or three amino acid substitutions relative to the amino acid sequence of SEQ ID NO:60, a CDR-L2 comprising an amino acid sequence comprising one, two, or three amino acid substitutions relative to the amino acid sequence of SEQ ID NO:34, and a CDR-L3 comprising an amino acid sequence comprising one, two, or three amino acid substitutions relative to the amino acid sequence of SEQ ID NO:61.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:77, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:78.

In some embodiments, an antibody of the disclosure comprises a heavy chain variable (VH) domain and a light chain variable (VL) domain, wherein the VH domain comprises the amino acid sequence of SEQ ID NO:77, and the VL domain comprises the amino acid sequence of SEQ ID NO:78.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:83, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:84, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:85; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:86, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:34, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:61.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:83, a CDR-H2 comprising an amino acid sequence comprising one, two, or three amino acid substitutions relative to the amino acid sequence of SEQ ID NO:84, and a CDR-H3 comprising an amino acid sequence comprising one, two, or three amino acid substitutions relative to the amino acid sequence of SEQ ID NO:85; and wherein the VL domain comprises a CDR-L1 comprising an amino acid sequence comprising one, two, or three amino acid substitutions relative to the amino acid sequence of SEQ ID NO:86, a CDR-L2 comprising an amino acid sequence comprising one, two, or three amino acid substitutions relative to the amino acid sequence of SEQ ID NO:34, and a CDR-L3 comprising an amino acid sequence comprising one, two, or three amino acid substitutions relative to the amino acid sequence of SEQ ID NO:61.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:79, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:80.

In some embodiments, an antibody of the disclosure comprises a heavy chain variable (VH) domain and a light chain variable (VL) domain, wherein the VH domain comprises the amino acid sequence of SEQ ID NO:79, and the VL domain comprises the amino acid sequence of SEQ ID NO:80.

In some embodiments, an antibody of the disclosure comprises a heavy chain variable (VH) domain and a light chain variable (VL) domain, wherein the VH domain comprises a CDR-H1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:47, a CDR-H2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:48, and a CDR-H3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:62; and wherein the VL domain comprises a CDR-L1 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:63, a CDR-L2 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:34, and a CDR-L3 comprising an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:64.

In some embodiments, an antibody of the disclosure comprises a heavy chain variable (VH) domain and a light chain variable (VL) domain, wherein the VH domain comprises a CDR-H1 comprising an amino acid sequence comprising one, two, or three amino acid substitutions relative to the amino acid sequence of SEQ ID NO:47, a CDR-H2 comprising an amino acid sequence comprising one, two, or three amino acid substitutions relative to the amino acid sequence of SEQ ID NO:48, and a CDR-H3 comprising an amino acid sequence comprising one, two, or three amino acid substitutions relative to the amino acid sequence of SEQ ID NO:62; and wherein the VL domain comprises a CDR-L1 comprising an amino acid sequence comprising one, two, or three amino acid substitutions relative to the amino acid sequence of SEQ ID NO:63, a CDR-L2 comprising an amino acid sequence comprising one, two, or three amino acid substitutions relative to the amino acid sequence of SEQ ID NO:34, and a CDR-L3 comprising an amino acid sequence comprising one, two, or three amino acid substitutions relative to the amino acid sequence of SEQ ID NO:64.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64.

In some embodiments, an antibody of the disclosure comprises a heavy chain variable (VH) domain and a light chain variable (VL) domain, wherein the VH domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:81, and the VL domain comprises an amino acid sequence with at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the amino acid sequence of SEQ ID NO:82.

In some embodiments, an antibody of the disclosure comprises a heavy chain variable (VH) domain and a light chain variable (VL) domain, wherein the VH domain comprises the amino acid sequence of SEQ ID NO:81, and the VL domain comprises the amino acid sequence of SEQ ID NO:82.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:87, a CDR-H2 comprising the amino acid sequence of SEQ ID NO:88, and a CDR-H3 comprising the amino acid sequence of SEQ ID NO:89; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:87, a CDR-H2 comprising the amino acid sequence of SEQ ID NO:92, and a CDR-H3 comprising the amino acid sequence of SEQ ID NO:93; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:87, a CDR-H2 comprising the amino acid sequence of SEQ ID NO:92, and a CDR-H3 comprising the amino acid sequence of SEQ ID NO:94; and wherein the VL domain comprises a CDR-L1 comprising the amino acid sequence of SEQ ID NO:90, a CDR-L2 comprising the amino acid sequence of SEQ ID NO:91, and a CDR-L3 comprising the amino acid sequence of SEQ ID NO:35.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:95, a CDR-H2 comprising the amino acid sequence of SEQ ID NO:96, and a CDR-H3 comprising the amino acid sequence of SEQ ID NO:97; and wherein the VL domain comprises a CDR-L1 comprising the amino acid sequence of SEQ ID NO:98, a CDR-L2 comprising the amino acid sequence of SEQ ID NO:99, and a CDR-L3 comprising the amino acid sequence of SEQ ID NO:100.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:109, a CDR-H2 comprising the amino acid sequence of SEQ ID NO:110, and a CDR-H3 comprising the amino acid sequence of SEQ ID NO:114; and wherein the VL domain comprises a CDR-L1 comprising the amino acid sequence of SEQ ID NO:115, a CDR-L2 comprising the amino acid sequence of SEQ ID NO:99, and a CDR-L3 comprising the amino acid sequence of SEQ ID NO:52.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:116, a CDR-H2 comprising the amino acid sequence of SEQ ID NO:117, and a CDR-H3 comprising the amino acid sequence of SEQ ID NO:118; and wherein the VL domain comprises a CDR-L1 comprising the amino acid sequence of SEQ ID NO:115, a CDR-L2 comprising the amino acid sequence of SEQ ID NO:99, and a CDR-L3 comprising the amino acid sequence of SEQ ID NO:56.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:101, a CDR-H2 comprising the amino acid sequence of SEQ ID NO:102, and a CDR-H3 comprising the amino acid sequence of SEQ ID NO:103; and wherein the VL domain comprises a CDR-L1 comprising the amino acid sequence of SEQ ID NO:104, a CDR-L2 comprising the amino acid sequence of SEQ ID NO:91, and a CDR-L3 comprising the amino acid sequence of SEQ ID NO:61.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:105, a CDR-H2 comprising the amino acid sequence of SEQ ID NO:106, and a CDR-H3 comprising the amino acid sequence of SEQ ID NO:107; and wherein the VL domain comprises a CDR-L1 comprising the amino acid sequence of SEQ ID NO:108, a CDR-L2 comprising the amino acid sequence of SEQ ID NO:91, and a CDR-L3 comprising the amino acid sequence of SEQ ID NO:61.

In some embodiments, an antibody of the disclosure comprises a heavy chain variable (VH) domain and a light chain variable (VL) domain, wherein the VH domain comprises a CDR-H1 comprising the amino acid sequence of SEQ ID NO:109, a CDR-H2 comprising the amino acid sequence of SEQ ID NO:110, and a CDR-H3 comprising the amino acid sequence of SEQ ID NO:111; and wherein the VL domain comprises a CDR-L1 comprising the amino acid sequence of SEQ ID NO:112, a CDR-L2 comprising the amino acid sequence of SEQ ID NO:113, and a CDR-L3 comprising the amino acid sequence of SEQ ID NO:64.

In some embodiments, an antibody of the disclosure comprises a VH domain comprising 1, 2, or 3 CDRs from a single antibody listed in Table 1 and/or a VL domain comprising 1, 2, or 3 CDRs from a single antibody listed in Table 1. In some embodiments, an antibody of the disclosure comprises a VH and/or VL domain from a single antibody listed in Table 2.

TABLE 1

Anti-CD94 antibody CDR sequences

| Name | CDR-H1 | CDR-H2 | CDR-H3 | CDR-L1 | CDR-L2 | CDR-L3 |
|---|---|---|---|---|---|---|
| 18H3 | SYWIG (SEQ ID NO: 1) | IIYPGDSD TRYSPSF QG (SEQ ID NO: 2) | PFDYGGSP GYFDY (SEQ ID NO: 3) | RASQSIR SWLA (SEQ ID NO: 4) | KASSLES (SEQ ID NO: 5) | QQYNTFWT (SEQ ID NO: 6) |
| 1M4 | NYAMN (SEQ ID NO: 7) | VISGSGD TTYCADS VKG (SEQ ID NO: 8) | NCYGSGSY YNHFDY (SEQ ID NO: 9) | KSSQSVL YSSNRM NYLA (SEQ ID NO: 10) | WASTRES (SEQ ID NO: 11) | QQYYSIPLT (SEQ ID NO: 12) |
| 1E4 | TSDLCVS (SEQ ID NO: 13) | LIDWND DKYYSTS LQT (SEQ ID NO: 14) | TIAAAGPY DAFDI (SEQ ID NO: 15) | KSSQSVL YGSNNK NYLA (SEQ ID NO: 16) | WASTRKS (SEQ ID NO: 17) | QEYYSLRFT (SEQ ID NO: 18) |
| ATX-122 (Kabat) | SYGVS (SEQ ID NO: 30) | WISPYNG NTNYAH NLQG (SEQ ID NO: 31) | DRGRFGEL FFDY (SEQ ID NO: 32) | RASQGIS NYLA (SEQ ID NO: 33) | AASSLQS (SEQ ID NO: 34) | LQHNSYPFT (SEQ ID NO: 35) |
| ATX-122 (IMGT) | GYTFTSY G (SEQ ID NO: 87) | ISPYNGN T (SEQ ID NO: 88) | ARDRGRFG ELFFDY (SEQ ID NO: 89) | QGISNY (SEQ ID NO: 90) | AAS (SEQ ID NO: 91) | LQHNSYPFT (SEQ ID NO: 35) |
| ATX-123 (Kabat) | SYGIS (SEQ ID NO: 36) | WISAYNG NTNYAQ KFQG (SEQ ID NO: 37) | DRGRFGEL LSDY (SEQ ID NO: 38) | RASQGIS NYLA (SEQ ID NO: 33) | AASSLQS (SEQ ID NO: 34) | LQHNSYPFT (SEQ ID NO: 35) |
| ATX-123 (IMGT) | GYTFTSY G (SEQ ID NO: 87) | ISAYNGN T (SEQ ID NO: 92) | ARDRGRFG ELLSDY (SEQ ID NO: 93) | QGISNY (SEQ ID NO: 90) | AAS (SEQ ID NO: 91) | LQHNSYPFT (SEQ ID NO: 35) |
| ATX-124 (Kabat) | SYGIS (SEQ ID NO: 36) | WISAYNG NTNYAQ KLQG (SEQ ID NO: 39) | DRGRFGEL FFDH (SEQ ID NO: 40) | RASQGIS NYLA (SEQ ID NO: 33) | AASSLQS (SEQ ID NO: 34) | LQHNSYPFT (SEQ ID NO: 35) |

TABLE 1-continued

Anti-CD94 antibody CDR sequences

| Name | CDR-H1 | CDR-H2 | CDR-H3 | CDR-L1 | CDR-L2 | CDR-L3 |
|---|---|---|---|---|---|---|
| ATX-124 (IMGT) | GYTFTSYG (SEQ ID NO: 87) | ISAYNGNT (SEQ ID NO: 92) | ARDRGRFGELFFDH (SEQ ID NO: 94) | QGISNY (SEQ ID NO: 90) | AAS (SEQ ID NO: 91) | LQHNSYPFT (SEQ ID NO: 35) |
| ATX-125 (Kabat) | SIIYYWG (SEQ ID NO: 41) | SIYYSGSTYYNPSLKS (SEQ ID NO: 42) | LPLTGEFAFDI (SEQ ID NO: 43) | RASQSVSTYLA (SEQ ID NO: 44) | GASSRAT (SEQ ID NO: 45) | QQYGSSPIT (SEQ ID NO: 46) |
| ATX-125 (IMGT) | GGSISSIIYY (SEQ ID NO: 95) | IYYSGST (SEQ ID NO: 96) | ARLPLTGEFAFDI (SEQ ID NO: 97) | QSVSTY (SEQ ID NO: 98) | GAS (SEQ ID NO: 99) | QQYGSSPIT (SEQ ID NO: 100) |
| ATX-126 (Kabat) | SYSMN (SEQ ID NO: 47) | SISTSSNFIYYADSVKG (SEQ ID NO: 48) | DMGPFYSFYYMDV (SEQ ID NO: 49) | RASQSVSSYLA (SEQ ID NO: 50) | GASNRAT (SEQ ID NO: 51) | LQHNSYPPT (SEQ ID NO: 52) |
| ATX-126 (IMGT) | GFTFSSYS (SEQ ID NO: 109) | ISTSSNFI (SEQ ID NO: 110) | VRDMGPFYSFYYMDV (SEQ ID NO: 114) | QSVSSSY (SEQ ID NO: 115) | GAS (SEQ ID NO: 99) | LQHNSYPPT (SEQ ID NO: 52) |
| ATX-127 (Kabat) | SRYWWT (SEQ ID NO: 53) | EIYHSGTTNYNPSLES (SEQ ID NO: 54) | SPNWGYYYYYMDV (SEQ ID NO: 55) | RASQSVSSYLA (SEQ ID NO: 50) | GASSRAT (SEQ ID NO: 45) | QQYGRSLT (SEQ ID NO: 56) |
| ATX-127 (IMGT) | GGSISSRYW (SEQ ID NO: 116) | IYHSGTT (SEQ ID NO: 117) | ARSPNWGYYYYYMDV (SEQ ID NO: 118) | QSVSSSY (SEQ ID NO: 115) | GAS (SEQ ID NO: 99) | QQYGRSLT (SEQ ID NO: 56) |
| ATX-128 (Kabat) | GSTIQ (SEQ ID NO: 57) | RIRSKANSYATASAASVKG (SEQ ID NO: 58) | EGLGYYNVGYYYFYMDV (SEQ ID NO: 59) | RASQSISSYLN (SEQ ID NO: 60) | AASSLQS (SEQ ID NO: 34) | QQSYSTPIT (SEQ ID NO: 61) |
| ATX-128 (IMGT) | GFTFSGST (SEQ ID NO: 101) | IRSKANSYAT (SEQ ID NO: 102) | TREGLGYYNVGYYYFYMDV (SEQ ID NO: 103) | QSISSY (SEQ ID NO: 104) | AAS (SEQ ID NO: 91) | QQSYSTPIT (SEQ ID NO: 61) |
| ATX-129 (Kabat) | SYWMS (SEQ ID NO: 83) | NIKQDGSAKYYVDSVKG (SEQ ID NO: 84) | GYYFDY (SEQ ID NO: 85) | RVSQGISSYLN (SEQ ID NO: 86) | AASSLQS (SEQ ID NO: 34) | QQSYSTPIT (SEQ ID NO: 61) |
| ATX-129 (IMGT) | GFTFSSYW (SEQ ID NO: 105) | IKQDGSAK (SEQ ID NO: 106) | ARGYYFDY (SEQ ID NO: 107) | QGISSY (SEQ ID NO: 108) | AAS (SEQ ID NO: 91) | QQSYSTPIT (SEQ ID NO: 61) |
| ATX-130 (Kabat) | SYSMN (SEQ ID NO: 47) | SISTSSNFIYYADSVKG (SEQ ID NO: 48) | DLGRYYYYMDV (SEQ ID NO: 62) | RASQSISSWLA (SEQ ID NO: 63) | AASSLQS (SEQ ID NO: 34) | QKYNSAPFT (SEQ ID NO: 64) |
| ATX-130 (IMGT) | GFTFSSYS (SEQ ID NO: 109) | ISTSSNFI (SEQ ID NO: 110) | ARDLGRYYYYMDV (SEQ ID NO: 111) | QSISSW (SEQ ID NO: 112) | ASS (SEQ ID NO: 113) | QKYNSAPFT (SEQ ID NO: 64) |

TABLE 2

Anti-CD94 antibody variable domain sequences

| Name | VH | VL |
|------|----|----|
| 18H3 | EVQLVQSGAEVKKPGESLKISCKGS GYRFTSYWIGWVRQMPGKGLEWM GIIYPGDSDTRYSPSFQGQVIISADKS ITTAFLQWSSLKASDTAMYYCARPF DYGGSPGYFDYWGQGTLVTVSS (SEQ ID NO: 19) | DIQMTQSPSTLSASVGDRVTITCRASQSIRSW LAWYQQKPGKAPKLLIYKASSLESGVPSRFS GSGSGTEFTLTISSLQPDDFATYYCQQYNTF WTFGQGTKVEIK (SEQ ID NO: 20) |
| 1M4 | QLVESGGGLVQPGGSLRLACAASGF TFSNYAMNWVRQAPGKGLEWVSVI SGSGDTTYCADSVKGRFTISRDNSK NTLHLQLNSLRAEDTAVYYCAKNC YGSGSYYNHFDYWGQGTLVTVSS (SEQ ID NO: 21) | EIVMTQSPDSLAVSLGERATINCKSSQSVLYS SNRMNYLAWYQQKPGQPPNLLIYWASTRES GVPDRFSGSGSGTDFTLTISSLQAEDVAVYY CQQYYSIPLTFGGGTKVEIK (SEQ ID NO: 22) |
| 1E4 | QVTLRESGPALVKPTQTLTLTCTFSG FSLSTSDLCVSWIRQPPGKALEWLA LIDWNDDKYYSTSLQTRLTISKDTS KNQVVLTMTNMDPVDTATYYCAR TIAAAGPYDAFDIVVGQGTMVTVSS (SEQ ID NO: 23) | DIVMTQSPDSLSVSLGERATINCKSSQSVLY GSNNKNYLAWYQQKPGQPPKLLIYWASTR KSGVPDRFSGSGSGTDFTLTISSLQAEDVAV YYCQEYYSLRFTFGPGTKVDIK (SEQ ID NO: 24) |
| ATX-122 | QVQLVQSGAEVKKPGASLKVSCKA SGYTFTSYGVSWVRQAPGQGLEWV GWISPYNGNTNYAHNLQGRVAMTT DTSTSTAYMELRSLRSDDMAVYYC ARDRGRFGELFFDYWGQGTLVTVS S (SEQ ID NO: 65) | DIVMTQSPSSVSASVGDRVTITCRASQGISNY LAWYQQKPGKAPKLLIYAASSLQSGVPSRFS GSGSGTDFTLTISSLQPEDFATYYCLQHNSYP FTFGPGTKVDIK (SEQ ID NO: 66) |
| ATX-123 | QVQLVQSGAEVKKPGASVKVSCKA SGYTFTSYGISWVRQAPGQGLEWM GWISAYNGNTNYAQKFQGRVTMTT DTSTNTAYMELRSLRSDDTAVYYC ARDRGRFGELLSDYWGQGTLVTVS S (SEQ ID NO: 67) | DIVMTQSPSSVSASVGDRVTITCRASQGISNY LAWYQQKPGKAPKLLIYAASSLQSGVPSRFS GSGSGTDFTLTISSLQPEDFATYYCLQHNSYP FTFGPGTKVDIK (SEQ ID NO: 68) |
| ATX-124 | QVQLVQSGAEVKKPGASVKVSCKA SGYTFTSYGISWVRQAPGQGLEWM GWISAYNGNTNYAQKLQGRVTMTT DTSTSTAYMEVRSLRSDDTAVYYC ARDRGRFGELFFDHWGQGTLVTVS S (SEQ ID NO: 69) | DIVMTQSPSSVSASVGDRVTITCRASQGISNY LAWYQQKPGKAPKLLIYAASSLQSGVPSRFS GSGSGTDFTLTISSLQPEDFATYYCLQHNSYP FTFGPGTKVDIK (SEQ ID NO: 70) |
| ATX-125 | QVQLQQSGPGLVKPSETLSLTCTVS GGSISSIIYYWGWIRQPPGKGLEWIG SIYYSGSTYYNPSLKSRVTISVDTSK NQFSLNLSSVTAADTAVYYCARLPL TGEFAFDIWGQGTMVTVSS (SEQ ID NO: 71) | EIVLTQSPATLSLSPGERATLSCRASQSVSTY LAWFQQKPGQAPRLLIYGASSRATGIPDRFS GSGSGTDFTLTISRLEPEDFAVYYCQQYGSS PITFGQGTRLEIK (SEQ ID NO: 72) |
| ATX-126 | QVQLQESGGGLVQPGGSLKLSCAAS GFTFSSYSMNWVRQAPGKGLEWVS SISTSSNFIYYADSVKGRFTISRDNSK NTLYLQMNSLRAEDTAVYYCVRD MGPFYSFYYMDVWGNGTTVTVSS (SEQ ID NO: 73) | DIQVTQSPATLSLSPGERATLSCRASQSVSSS YLAWYQQKPGQAPRLLIYGASNRATGIPAR FSGSGSGTDFTLTISSLQPEDFATYYCLQHNS YPPTFGGGTKVDIK (SEQ ID NO: 74) |
| ATX-127 | QVQLQQSGPGLVKPSGTLSLTCAVS GGSISSRYWWTWVRQPPGKGLEWI GEIYHSGTTNYNPSLESRVTISVDKS KNQFSLKVSSVTAADTAVYYCARSP NWGYYYYYMDVWGKGTTVTVSS (SEQ ID NO: 75) | EIVMTQSPATLSVSPGERATLSCRASQSVSSS YLAWYQQKPGQAPRLLIYGASSRATGIPDRF SGSGSGTDFTLTISRLESEDFAVYYCQQYGR SLTFGGGTKVEIK (SEQ ID NO: 76) |
| ATX-128 | QVQLQESGGGLVQPGGSLKLSCAAS GFTFSGSTIQWVRQASGKGLEWVG RIRSKANSYATASAASVKGRFTISRD DSKNMAYLQMNSLKTEDTAVYYCT REGLGYYNVGYYYFYMDVWGKGT TVTVSS (SEQ ID NO: 77) | DIVMTQSPSSLSASVGDRVTITCRASQSISSY LNWYQQKPGKAPKLLIYAASSLQSGVPSKFS GSGSGTDFTLTISSLQPEDFATYYCQQSYSTP ITFGQGTRLEIK (SEQ ID NO: 78) |
| ATX-129 | EVQLVQSGGGLVQPGGSLRLSCAAS GFTFSSYWMSWVRQAPGKGLEWV ANIKQDGSAKYYVDSVKGRFTISRD NAKNSLYLQMNSLRAEDTAVYYCA RGYYFDYWGQGTLVTVSS (SEQ ID NO: 79) | EIVLTQSPSTLSASVGDRVTITCRVSQGISSYL NWYRQKPGKVPKLLIYAASSLQSGVPSRFSG SGSGTDFTLTISSLQPEDFATYYCQQSYSTPI TFGQGTRLEIK (SEQ ID NO: 80) |

TABLE 2-continued

Anti-CD94 antibody variable domain sequences

| Name | VH | VL |
|---|---|---|
| ATX-130 | EVQLLESGGGLVKPGGSLRLSCAAS GFTFSSYSMNWVRQAPGKGLEWVS SISTSSNFIYYADSVKGRFTISRDNA KNSLYLQMNSLRAEDTAVYYCARD LGRYYYYMDVWGKGTTVTVSS (SEQ ID NO: 81) | DIVMTQSPSSLSASVGDRVTITCRASQSISSW LAWYQQKPGKAPKSLIYAASSLQSGVPSKFS GSGSGTDFTLTISSLQPEDVATYYCQKYNSA PFTFGPGTKVDIK (SEQ ID NO: 82) |

Many definitions for CDR sequences of an antibody variable domain are known in the art and may be used to describe an antibody of the present disclosure, e.g., by CDR sequences. In some embodiments, antibody CDR sequences are defined as in Kabat (see, e.g., Kabat et al., Sequences of Proteins of Immunological Interest, 5th Ed. Public Health Service, National Institutes of Health, Bethesda, Md., 1991). In some embodiments, antibody CDR sequences are defined as in Chothia (see, e.g., Chothia and Lesk *J. Mol. Biol.* 196:901-917 (1987)). In some embodiments, antibody CDR sequences are defined as in IMGT (see, e.g., Lefranc, M. P. (1999) *The Immunologist* 7:132-136). In some embodiments, CDR sequences of a single antibody are defined as by mixing two or more definitions, e.g., Kabat, Chothia, and/or IMGT. In some embodiments, an antibody of the present disclosure comprises a VH domain comprising 1, 2, or all 3 CDR or HVR sequences present in the amino acid sequence of SEQ ID NO:65 and/or a VL domain comprising 1, 2, or all 3 CDR or HVR sequences present in the amino acid sequence of SEQ ID NO:66. In some embodiments, an antibody of the present disclosure comprises a VH domain comprising 1, 2, or all 3 CDR or HVR sequences present in the VH domain sequence of ATX-122 as described herein (see, e.g., Table 2) and/or a VL domain comprising 1, 2, or all 3 CDR or HVR sequences present in the VL domain sequence of ATX-122 as described herein (see, e.g., Table 2). In some embodiments, an antibody of the present disclosure comprises a VH domain comprising 1, 2, or all 3 CDR or HVR sequences present in the amino acid sequence of SEQ ID NO:67 and/or a VL domain comprising 1, 2, or all 3 CDR or HVR sequences present in the amino acid sequence of SEQ ID NO:68. In some embodiments, an antibody of the present disclosure comprises a VH domain comprising 1, 2, or all 3 CDR or HVR sequences present in the VH domain sequence of ATX-123 as described herein (see, e.g., Table 2) and/or a VL domain comprising 1, 2, or all 3 CDR or HVR sequences present in the VL domain sequence of ATX-123 as described herein (see, e.g., Table 2). In some embodiments, an antibody of the present disclosure comprises a VH domain comprising 1, 2, or all 3 CDR or HVR sequences present in the amino acid sequence of SEQ ID NO:69 and/or a VL domain comprising 1, 2, or all 3 CDR or HVR sequences present in the amino acid sequence of SEQ ID NO:70. In some embodiments, an antibody of the present disclosure comprises a VH domain comprising 1, 2, or all 3 CDR or HVR sequences present in the VH domain sequence of ATX-124 as described herein (see, e.g., Table 2) and/or a VL domain comprising 1, 2, or all 3 CDR or HVR sequences present in the VL domain sequence of ATX-124 as described herein (see, e.g., Table 2). In some embodiments, an antibody of the present disclosure comprises a VH domain comprising 1, 2, or all 3 CDR or HVR sequences present in the amino acid sequence of SEQ ID NO:71 and/or a VL domain comprising 1, 2, or all 3 CDR or HVR sequences present in the amino acid sequence of SEQ ID NO:72. In some embodiments, an antibody of the present disclosure comprises a VH domain comprising 1, 2, or all 3 CDR or HVR sequences present in the VH domain sequence of ATX-125 as described herein (see, e.g., Table 2) and/or a VL domain comprising 1, 2, or all 3 CDR or HVR sequences present in the VL domain sequence of ATX-125 as described herein (see, e.g., Table 2). In some embodiments, an antibody of the present disclosure comprises a VH domain comprising 1, 2, or all 3 CDR or HVR sequences present in the amino acid sequence of SEQ ID NO:73 and/or a VL domain comprising 1, 2, or all 3 CDR or HVR sequences present in the amino acid sequence of SEQ ID NO:74. In some embodiments, an antibody of the present disclosure comprises a VH domain comprising 1, 2, or all 3 CDR or HVR sequences present in the VH domain sequence of ATX-126 as described herein (see, e.g., Table 2) and/or a VL domain comprising 1, 2, or all 3 CDR or HVR sequences present in the VL domain sequence of ATX-126 as described herein (see, e.g., Table 2). In some embodiments, an antibody of the present disclosure comprises a VH domain comprising 1, 2, or all 3 CDR or HVR sequences present in the amino acid sequence of SEQ ID NO:75 and/or a VL domain comprising 1, 2, or all 3 CDR or HVR sequences present in the amino acid sequence of SEQ ID NO:76. In some embodiments, an antibody of the present disclosure comprises a VH domain comprising 1, 2, or all 3 CDR or HVR sequences present in the VH domain sequence of ATX-127 as described herein (see, e.g., Table 2) and/or a VL domain comprising 1, 2, or all 3 CDR or HVR sequences present in the VL domain sequence of ATX-127 as described herein (see, e.g., Table 2). In some embodiments, an antibody of the present disclosure comprises a VH domain comprising 1, 2, or all 3 CDR or HVR sequences present in the amino acid sequence of SEQ ID NO:77 and/or a VL domain comprising 1, 2, or all 3 CDR or HVR sequences present in the amino acid sequence of SEQ ID NO:78. In some embodiments, an antibody of the present disclosure comprises a VH domain comprising 1, 2, or all 3 CDR or HVR sequences present in the VH domain sequence of ATX-128 as described herein (see, e.g., Table 2) and/or a VL domain comprising 1, 2, or all 3 CDR or HVR sequences present in the VL domain sequence of ATX-128 as described herein (see, e.g., Table 2). In some embodiments, an antibody of the present disclosure comprises a VH domain comprising 1, 2, or all 3 CDR or HVR sequences present in the amino acid sequence of SEQ ID NO:79 and/or a VL domain comprising 1, 2, or all 3 CDR or HVR sequences present in the amino acid sequence of SEQ ID NO:80. In some embodiments, an antibody of the present disclosure comprises a VH domain comprising 1, 2, or all 3 CDR or HVR sequences present in the VH domain sequence of ATX-129 as described herein (see, e.g., Table 2) and/or a VL domain comprising 1, 2, or all 3 CDR or HVR sequences present in the VL domain sequence of ATX-129 as described herein (see, e.g., Table 2). In some embodiments, an antibody of the present disclosure comprises a VH domain comprising 1, 2, or all 3 CDR or HVR sequences present in the amino acid sequence of SEQ ID NO:81 and/or a VL domain comprising 1, 2, or all 3 CDR or HVR sequences present in the amino acid sequence of SEQ ID NO:82. In some embodiments, an antibody of the present disclosure comprises a VH domain comprising 1, 2, or all 3 CDR or HVR sequences present in the VH domain sequence of ATX-130 as described herein (see, e.g., Table 2) and/or a VL domain comprising 1, 2, or all 3 CDR or HVR sequences present in the VL domain sequence of ATX-130 as described herein (see, e.g., Table 2).

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:19, and the VL domain comprises the amino acid sequence of SEQ ID NO:20.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and wherein the VL domain comprises a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:21, and the VL domain comprises the amino acid sequence of SEQ ID NO:22.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:23, and the VL domain comprises the amino acid sequence of SEQ ID NO:24.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:65, and the VL domain comprises the amino acid sequence of SEQ ID NO:66.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:67, and the VL domain comprises the amino acid sequence of SEQ ID NO:68.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:69, and the VL domain comprises the amino acid sequence of SEQ ID NO:70.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:71, and the VL domain comprises the amino acid sequence of SEQ ID NO:72.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:73, and the VL domain comprises the amino acid sequence of SEQ ID NO:74.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:75, and the VL domain comprises the amino acid sequence of SEQ ID NO:76.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:77, and the VL domain comprises the amino acid sequence of SEQ ID NO:78.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:79, and the VL domain comprises the amino acid sequence of SEQ ID NO:80.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64.

In some embodiments, an antibody of the disclosure binds to an epitope on human or cynomolgus monkey CD94 that is the same as the CD94 epitope bound by an anti-CD94 antibody comprising a heavy chain variable (VH) domain and a light chain variable (VL) domain, wherein the VH domain comprises the amino acid sequence of SEQ ID NO:81, and the VL domain comprises the amino acid sequence of SEQ ID NO:82.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:1, a CDR-H2 comprising the amino acid sequence of SEQ ID NO:2, and a CDR-H3 comprising the amino acid sequence of SEQ ID NO:3; and wherein the VL domain comprises a CDR-L1 comprising the amino acid sequence of SEQ ID NO:4, a CDR-L2 comprising the amino acid sequence of SEQ ID NO:5, and a CDR-L3 comprising the amino acid sequence of SEQ ID NO:6.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:19, and the VL domain comprises the amino acid sequence of SEQ ID NO:20.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:7, a CDR-H2 comprising the amino acid sequence of SEQ ID NO:8, and a CDR-H3 comprising the amino acid sequence of SEQ ID NO:9; and wherein the VL domain comprises a CDR-L1 comprising the amino acid sequence of SEQ ID NO:10, a CDR-L2 comprising the amino acid sequence of SEQ ID NO:11, and a CDR-L3 comprising the amino acid sequence of SEQ ID NO:12.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:21, and the VL domain comprises the amino acid sequence of SEQ ID NO:22.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:13, a CDR-H2 comprising the amino acid sequence of SEQ ID NO:14, and a CDR-H3 comprising the amino acid sequence of SEQ ID NO:15; and wherein the VL domain comprises a CDR-L1 comprising the amino acid sequence of SEQ ID NO:16, a CDR-L2 comprising the amino acid sequence of SEQ ID NO:17, and a CDR-L3 comprising the amino acid sequence of SEQ ID NO:18.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:23, and the VL domain comprises the amino acid sequence of SEQ ID NO:24.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:30, a CDR-H2 comprising the amino acid sequence of SEQ ID NO:31, and a CDR-H3 comprising the amino acid sequence of SEQ ID NO:32; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:65, and the VL domain comprises the amino acid sequence of SEQ ID NO:66.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:67, and the VL domain comprises the amino acid sequence of SEQ ID NO:68.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:36, a CDR-H2 comprising the amino acid sequence of SEQ ID NO:39, and a CDR-H3 comprising the amino acid sequence of SEQ ID NO:40; and wherein the VL domain comprises a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:69, and the VL domain comprises the amino acid sequence of SEQ ID NO:70.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:41, a CDR-H2 comprising the amino acid sequence of SEQ ID NO:42, and a CDR-H3 comprising the amino acid sequence of SEQ ID NO:43; and wherein the VL domain comprises a CDR-L1 comprising the amino acid sequence of SEQ ID NO:44, a CDR-L2 comprising the amino acid sequence of SEQ ID NO:45, and a CDR-L3 comprising the amino acid sequence of SEQ ID NO:46.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:71, and the VL domain comprises the amino acid sequence of SEQ ID NO:72.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:49; and wherein the VL domain comprises a CDR-L1 comprising the amino acid sequence of SEQ ID NO:50, a CDR-L2 comprising the amino acid sequence of SEQ ID NO:51, and a CDR-L3 comprising the amino acid sequence of SEQ ID NO:52.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:73, and the VL domain comprises the amino acid sequence of SEQ ID NO:74.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:53, a CDR-H2 comprising the amino acid sequence of SEQ ID NO:54, and a CDR-H3 comprising the amino acid sequence of SEQ ID NO:55; and wherein the VL domain comprises a CDR-L1 comprising the amino acid sequence of SEQ ID NO:50, a CDR-L2 comprising the amino acid sequence of SEQ ID NO:45, and a CDR-L3 comprising the amino acid sequence of SEQ ID NO:56.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:75, and the VL domain comprises the amino acid sequence of SEQ ID NO:76.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:57, a CDR-H2 comprising the amino acid sequence of SEQ ID NO:58, and a CDR-H3 comprising the amino acid sequence of SEQ ID NO:59; and wherein the VL domain comprises a CDR-L1 comprising the amino acid sequence of SEQ ID NO:60, a CDR-L2 comprising the amino acid sequence of SEQ ID NO:34, and a CDR-L3 comprising the amino acid sequence of SEQ ID NO:61.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:77, and the VL domain comprises the amino acid sequence of SEQ ID NO:78.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:83, a CDR-H2 comprising the amino acid sequence of SEQ ID NO:84, and a CDR-H3 comprising the amino acid sequence of SEQ ID NO:85; and wherein the VL domain comprises a CDR-L1 comprising the amino acid sequence of SEQ ID NO:86, a CDR-L2 comprising the amino acid sequence of SEQ ID NO:34, and a CDR-L3 comprising the amino acid sequence of SEQ ID NO:61.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:79, and the VL domain comprises the amino acid sequence of SEQ ID NO:80.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64.

In some embodiments, an antibody of the disclosure competes for binding to human or cynomolgus monkey CD94 with an anti-CD94 antibody comprising a heavy chain variable (VH) domain and a light chain variable (VL) domain, wherein the VH domain comprises the amino acid sequence of SEQ ID NO:81, and the VL domain comprises the amino acid sequence of SEQ ID NO:82.

In some embodiments, an antibody of the disclosure comprises an Fc region. In some embodiments, the Fc region is a human IgG1 Fc region. In some embodiments, the antibody comprises a human Fc region that is non-fucosylated. In some embodiments, the antibody binds to a human cellular Fc gamma receptor MA to a greater extent than an antibody comprising a wild type human IgG1 Fc region. In some embodiments, the antibody is capable of inducing antibody-dependent cellular cytotoxicity (ADCC) against a cell expressing human CD94 on its surface.

In some embodiments, the term antibody is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. In some embodiments, an antibody of the disclosure is an isolated antibody. An "isolated" antibody is one which has been identified and separated and/or recovered from a component of its natural environment. Contaminant components of its natural environment are materials which would interfere with research, diagnostic, and/or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. An isolated antibody includes the antibody in situ within recombinant cells since at least one component of the antibody's natural environment will not be present. Ordinarily, however, an isolated antibody will be prepared by at least one purification step.

In some embodiments, a monoclonal antibody is an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, in some embodiments, a monoclonal antibody is obtained from a substantially homogeneous population of antibodies. Monoclonal antibodies may be produced using any method known in the art. For example, monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci.

C. Blocking of HLA-E Binding

Major histocompatibility complex class I, E (HLA-E) is the ligand of the CD94/NKG2A heterodimer and plays a crucial role in the inhibition of NK cell and CD8+ T cell activity when bound to the CD94/NKG2A heterodimer. Thus, without wishing to be bound to theory, blocking HLA-E and CD94/NKG2A interaction may result in activation and proliferation of target cells, e.g., cells expressing CD94. Thus, it may be beneficial that an anti-CD94 antibody does not block HLA-E interaction with the CD94/NKG2A heterodimer, e.g., in a subject with an NK/T cell lymphoma administered the anti-CD94 antibody. In some embodiments, HLA-E is human HLA-E, also known as QA1 and HLA-6.2. For an exemplary HLA-E gene, see, e.g., NCBI Gene ID No. 3133; for an exemplary HLA-E polypeptide, see, e.g., NP_005507.3.

In some embodiments, blocking of binding of HLA-E to the CD94/NKG2A heterodimer refers to blocking of binding of HLA-E to the CD94/NKG2A heterodimer, blocking of binding of HLA-E to CD94, and/or blocking of binding of HLA-E to NKG2A.

Blocking of binding of HLA-E to the CD94/NKG2A heterodimer by an antibody of the disclosure may be assessed using any method known in the art. For example, blocking of binding of HLA-E to the CD94/NKG2A heterodimer by an antibody of the disclosure may be assessed using an ex vivo assay using PBMCs and/or NK cells, e.g., as described in the Examples. In an exemplary assay, PBMCs, e.g., obtained from healthy donors, are incubated with human Fc block (Biolegend, San Diego, Calif.) and cell viability dye (Thermo Fisher, Carlsbad, Calif.) for 30 minutes on ice and protected from light. Cells are then washed once with FACS buffer (PBS with 2% IgG low FBS). Anti-CD94 antibodies or isotype control antibodies at saturating concentrations are incubated with the cells for 30 minutes on ice and protected from light. Cells are then washed and incubated with HLA-E tetramer PE (Creative Biolabs, Shirley, N.Y.), CD3 pacific blue, and CD56 FITC antibodies (Biolegend, San Diego, Calif.) for 30 minutes on ice and protected from light. Cells then receive a final wash in FACS buffer before quantification on a flow cytometer. Data acquisition and fluorescence compensation may be performed using methods known in the art, such as using a CytoFlex flow cytometer (Beckman Coulter, Chaska, Minn.). Data analysis may be performed using any method known in the art, such as using the FlowJo software. NK cells are identified through gating on lymphocytes on the forward and side scatter, followed by doublet and dead cell exclusion, and gated on the CD3–CD56+ population. HLA-E is then quantified on the CD3–CD56+NK cell population. Percent blocking of binding of HLA-E to the CD94/NKG2A heterodimer by an anti-CD94 antibody compared to a control antibody, e.g., an isotype control antibody, is calculated as: 100–((percent HLA-E positive for anti-CD94 antibody)/(percent HLA-E positive for isotype)*100).

In some embodiments, an antibody blocks binding of HLA-E to the CD94/NKG2A heterodimer if it blocks more than about 20% of HLA-E binding to the CD94/NKG2A heterodimer, e.g., compared to an isotype control antibody. In some embodiments, an antibody blocks binding of HLA-E to the CD94/NKG2A heterodimer if it blocks about 21%, about 25%, about 30%, about 35%, about 40%, about 45%, about 50%, about 55%, about 60%, about 65%, about 70%, about 75%, about 80%, about 85%, about 90%, about 95%, about 99%, or 100% of HLA-E binding to the CD94/NKG2A heterodimer, e.g., compared to an control antibody, e.g., an isotype control antibody In some embodiments, an antibody does not block binding of HLA-E to the CD94/NKG2A heterodimer if it blocks about 20% or less of HLA-E binding to the CD94/NKG2A heterodimer, e.g., compared to an isotype control antibody. In some embodiments, an antibody does not block binding of HLA-E to the CD94/NKG2A heterodimer if it blocks about 20%, about 18%, about 16%, about 14%, about 12%, about 10%, about 8%, about 6%, about 4%, about 2%, about 1%, about 0.5%, or 0% of HLA-E binding to the CD94/NKG2A heterodimer, e.g., compared to an control antibody, e.g., an isotype control antibody.

In some embodiments, an antibody provided herein does not block binding of HLA-E to the CD94/NKG2A heterodimer. In some embodiments, an antibody provided herein blocks about 20% or less, about 19% or less, about 18% or less, about 17% or less, about 16% or less, about 15% or less, about 14% or less, about 13% or less, about 12% or less, about 11% or less, about 10% or less, about 9% or less, about 8% or less, about 6% or less, about 5% or less, about 4% or less, about 3% or less, about 2% or less, about 1% or less, about 0.5% or less, or 0% of binding of HLA-E to the CD94/NKG2A heterodimer, compared to a control antibody, e.g., an isotype control antibody. In some embodiments, an antibody provided herein blocks 0% of binding of HLA-E to the CD94/NKG2A heterodimer, compared to a control antibody, e.g., an isotype control antibody.

D. Enhanced ADCC Activity

In some embodiments, antibody-dependent cell-mediated cytotoxicity, antibody-dependent cellular cytotoxicity, antibody directed cell cytotoxicity, or ADCC refer to a cell-mediated reaction in which non-specific cytotoxic cells producing Fc receptors, e.g. natural killer cells (NK cells), neutrophils, and macrophages, recognize an antibody bound to a target cell and then cause lysis of the target cell. The primary mediator cells are natural killer (NK) cells. NK cells express FcγRIII (Ravetch et al. (1991) Annu. Rev. Immunol., 9:457-92). In some embodiments, ADCC activity refers to the ability of an antibody or Fc fusion protein to elicit an ADCC reaction.

In some embodiments, the antibodies provided herein have enhanced antibody-dependent cellular cytotoxicity (ADCC) activity. In some embodiments, enhanced ADCC activity refers to an antibody or an Fc region of an antibody mediating or inducing ADCC more efficiently and/or more effectively than a native or wild type antibody and/or a native or wild type Fc region of an antibody in the presence of effector cells in vitro or in vivo, which may be determined using an ADCC assay, e.g., as described herein or as is commonly known in the art. In some embodiments, effector cells are leukocytes that produce one or more Fc receptors and perform effector functions. In some embodiments, such cells produce at least FcγRIII and perform the ADCC effector function. Examples of ADCC-mediated human leukocytes include peripheral blood mononuclear cells (PBMCs), natural killer cells (NK), monocytes, cytotoxic T cells, and neutrophils.

In some embodiments, ADCC activity can be assessed directly using an in vitro assay, using a $^{51}$Cr release assay using peripheral blood mononuclear cells (PBMC) and/or NK effector cells, see e.g., Shields et al. (2001) J. Biol. Chem., 276:6591-6604, or another suitable method. ADCC activity may be expressed as the number of remaining cells following an ADCC assay, or a concentration of antibody or Fc fusion protein at which the lysis of target cells is half-maximal (e.g., EC50 or IC50). In some embodiments, ADCC activity is determined using an ex vivo assay using PBMCs, LGL cells, and/or NK cells, e.g., as described in the Examples, and the ADCC activity of an antibody of the disclosure is described as the percent of target cells remaining after the ADCC assay and/or the IC50 or EC50 of the antibody (i.e., the concentration of an antibody of the disclosure at which half the maximum target cell depletion or cell lysis is achieved). The IC50 or EC50 of an antibody may be determined using any method known in the art, e.g., using a dosage response curve and GraphPad Prism.

In some embodiments, the antibodies provided herein induce ADCC activity with an IC50 or EC50 measured using an ex vivo assay of between about 1 ng/ml to about 100 ng/ml (e.g., any of about 1 ng/ml, about 2 ng/ml, about 3 ng/ml, about 4 ng/ml, about 5 ng/ml, about 10 ng/ml, about 15 ng/ml, about 20 ng/ml, about 25 ng/ml, about 30 ng/ml, about 35 ng/ml, about 40 ng/ml, about 45 ng/ml, about 50 ng/ml, about 55 ng/ml, about 60 ng/ml, about 65 ng/ml, about 70 ng/ml, about 75 ng/ml, about 80 ng/ml, about 85 ng/ml, about 90 ng/ml, about 95 ng/ml, or about 100 ng/ml). In some embodiments, the antibodies provided herein induce ADCC activity with an IC50 or EC50 measured using an ex vivo assay of about 20 ng/ml or less. In some embodiments, the antibodies provided herein induce ADCC activity with an IC50 or EC50 measured using an ex vivo assay of about 60 ng/ml or less. In some embodiments, an antibody of the disclosure exhibits an IC50 or EC50 that is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% lower than the IC50 or EC50 of a control antibody (e.g., a wild type control antibody, or an antibody known in the art or commercially available against the same target).

In some embodiments, IC50 or EC50 refers to the concentration of a compound (e.g., an antibody) which induces a response halfway between the baseline and maximum after a specified exposure time. For example, IC50 or EC50 may be used to measure the potency of an antibody for mediating and/or inducing an effector function, e.g., ADCC activity. In some embodiments, the IC50 or EC50 of a dose response curve represents the concentration of a compound (e.g., an antibody) where 50% of its maximal effect is observed.

In some embodiments, an antibody of the disclosure has a higher maximal target cell lysis compared to a control antibody (e.g., a wild type control antibody, or an antibody known in the art or commercially available against the same target). For example, antibodies of the disclosure may exhibit a maximal target cell lysis that is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than that of a control antibody (e.g., a wild type control antibody, or an antibody known in the art or commercially available against the same target).

(i) Enhanced Binding to Fc Receptors

In some embodiments, the antibodies provided herein include a human immunoglobulin Fc region that has enhanced ADCC activity compared to a wild type Fc region. In some embodiments, the antibodies provided herein bind to a human cellular Fc receptor to a greater extent than an antibody comprising a wild type Fc region. In some embodiments, an Fc receptor (FcR) is a receptor that is capable of binding to an Fc region of an antibody. Certain Fc receptors can bind to IgG (i.e., γ-receptor); such receptors include subclasses of FcγRI, FcγRII and FcγRIII, as well as their allelic variants and alternative splicing events. For an overview of the Fc receptors see Ravetch and China: Annu. Port. Immunol. 9, 457 (1991); Capel et al. Immunomethods, 4, 25 (1994); and de Haas et al., J. Leg. Clin. Med. 126, 330 (1995).

In some embodiments, the antibodies provided herein bind to a human cellular Fc gamma receptor IIIA to a greater extent than an antibody comprising a wild type Fc region. In some embodiments, the human cellular Fc gamma receptor MA comprises a valine residue or a phenylalanine residue at amino acid residue position 158. See, e.g., UniProt Accession P08637 or VAR_003960. In some embodiments, the human cellular Fc gamma receptor MA comprises the sequence of SEQ ID NO: 28 or 29.

Human cellular Fc gamma receptor IIIA 158F
(SEQ ID NO: 28)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

-continued

FHHNSDFYIPKATLKDSGSYFCRGLFGSKNVSSETVNITITQGLAVSTIS

SFFPPGYQVSFCLVMVLLFAVDTGLYFSVKTNIRSSTRDWKDHKFKWRKD

PQDK

Human cellular Fc gamma receptor IIIA 158V
(SEQ ID NO: 29)
MWQLLLPTALLLLVSAGMRTEDLPKAVVFLEPQWYRVLEKDSVTLKCQGA

YSPEDNSTQWFHNESLISSQASSYFIDAATVDDSGEYRCQTNLSTLSDPV

QLEVHIGWLLLQAPRWVFKEEDPIHLRCHSWKNTALHKVTYLQNGKGRKY

FHHNSDFYIPKATLKDSGSYFCRGLVGSKNVSSETVNITITQGLAVSTIS

SFFPPGYQVSFCLVMVLLFAVDTGLYFSVKTNIRSSTRDWKDHKFKWRKD

PQDK

In some embodiments, an antibody provided herein is of the IgG (e.g., IgG1, IgG2, IgG3, or IgG4), IgA (IgA1 or IgA2), IgD, IgM, or IgE isotype. In some embodiments, an antibody provided herein is of the IgG, isotype. In some embodiments, an antibody provided herein is of the IgG1, isotype. In some embodiments, antibodies provided herein bind to a human cellular Fc gamma receptor IIIA (FcγRIIIA) to a greater extent than an antibody comprising a wild type human IgG1 Fc region. In some embodiments, the human cellular Fc gamma receptor IIIA comprises a valine residue or a phenylalanine residue at amino acid residue position 158. Exemplary assays for determining binding to a human cellular Fc gamma receptor IIIA are known in the art; see, e.g., Lazar, G. A. et al. (2006) *Proc. Natl. Acad. Sci.* 103:4005-1010; and Ferrara, C. et al. (2011) *Proc. Natl. Acad. Sci.* 108:12669-12674.

In some embodiments, an Fc region is a C-terminal region of an immunoglobulin heavy chain that contains at least a portion of the constant region. In some embodiments, an Fc region includes a native Fc region or a variant Fc region. In one embodiment, a human IgG heavy chain Fc region extends from Cys226, or from Pro230, to the carboxyl-terminus of the heavy chain. However, the C-terminal lysine (Lys447) of the Fc region may or may not be present. In some embodiments, numbering of amino acid residues in an Fc region or constant region is according to the EU numbering system, also called the EU index, as described in Kabat et al., Sequences of Proteins of Immunological Interest, 5th Ed. Public Health Service, National Institutes of Health, Bethesda, Md., 1991. In some embodiments, a wild type Fc region or a native Fc region are an Fc region that comprises an amino acid sequence that is identical to the amino acid sequence of the Fc region found in nature. In some embodiments, a variant Fc region is an Fc region that comprises an amino acid sequence that differs from the native or wild type sequence of the Fc region in at least one amino acid. In some embodiments, a variant Fc region has at least one amino acid substitution, e.g., approximately 1-10 or 1-5 amino acid substitutions. In some embodiments, the Fc region variant is at least approximately 80% (e.g., at least about 90%, or at least about 95%) homologous to a native or wild type sequence Fc region and/or an Fc region of an original polypeptide. In some embodiments, the at least one amino acid substitution in the variant Fc region enhances the effector function of the variant Fc region compared to a native or wild type Fc region. In some embodiments, an effector function is a biological activity attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); antibody-dependent cell-mediated phagocytosis (ADCP); down regulation of cell surface receptors (e.g., B-cell receptor); and B-cell activation.

The binding affinity of an antibody for an Fc receptor may be assessed using any method known in the art, such as using surface plasmon resonance, and/or ELISA, e.g., as described in Shields et al. (2001) *J. Biol. Chem.*, 276:6591-6604. In some embodiments, the affinity of an antibody of the disclosure for FcγRIIIA may be above that of the wild-type control by any of at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 20 fold, at least about 30-fold, at least about 40-fold, at least about 50-fold, or higher.

In some embodiments, affinity refers to the strength of the sum total of noncovalent interactions between a single binding site of a molecule (e.g., an antibody) and its binding partner (e.g., an antigen or a target). For example, the affinity of a molecule X for its partner Y can generally be represented by the dissociation constant ($K_D$). Affinity can be measured by common methods known in the art, including those described herein.

In some embodiments, statements that a molecule (e.g., an antibody and/or an Fc region) binds to a greater extent than another molecule (e.g., an antibody and/or an Fc region), or that a molecule (e.g., an antibody and/or an Fc region) binds with a greater affinity than another molecule (e.g., an antibody and/or an Fc region), or other grammatical equivalents, refer to a molecule (e.g., an antibody and/or an Fc region) binding more tightly (e.g., having a lower dissociation constant) to a target (e.g., an Fc receptor, a cell surface protein) than another molecule (e.g., an antibody and/or an Fc region) in binding assays (e.g., as described herein and/or as commonly known in the art) under substantially the same conditions. For example, the statement that an antibody "X" binds to an Fc receptor to a greater extent than an antibody "Y" indicates that antibody "X" binds more tightly (e.g., has a lower dissociation constant) to an Fc receptor than antibody "Y" in binding assays (e.g., as described herein and/or as commonly known in the art) under substantially the same conditions. In another example, the statement that an antibody "X" binds to a target (e.g., a cell surface protein, such as CD94) with a greater affinity than an antibody "Y" indicates that antibody "X" binds more tightly (e.g., has a lower dissociation constant) to a target (e.g., a cell surface protein, such as CD94) than antibody "Y" in binding assays (e.g., as described herein and/or as commonly known in the art) under substantially the same conditions.

(ii) Reduced Fucosylation

In some embodiments, an antibody of the present disclosure is non-fucosylated or fucose-deficient, e.g., a glycosylation antibody variant comprising an Fc region wherein a carbohydrate structure attached to the Fc region has reduced fucose or lacks fucose. In some embodiments, an antibody with reduced fucose or lacking fucose has improved ADCC function. Non-fucosylated or fucose-deficient antibodies have reduced fucose relative to the amount of fucose on the same antibody produced in a cell line. In some embodiments, a non-fucosylated or fucose-deficient antibody composition of the present disclosure is a composition in which less than about 50% of the N-linked glycans attached to the Fc region of the antibodies in the composition comprise fucose.

In some embodiments, fucosylation or fucosylated refers to fucose residues within the oligosaccharides attached to the peptide backbone of an antibody of the present disclosure. Specifically, a fucosylated antibody comprises a (1,6)-linked fucose at the innermost N-acetylglucosamine (GlcNAc) residue in one or both of the N-linked oligosaccharides attached to the antibody Fc region, e.g., at position Asn 297 of the human IgG1 Fc domain (EU numbering of Fc region residues). Asn297 may also be located about +3 amino acids upstream or downstream of position 297, i.e., between positions 294 and 300, due to minor sequence variations in immunoglobulins.

In some embodiments, a degree of fucosylation is a percentage of fucosylated oligosaccharides relative to all oligosaccharides, e.g., as identified by methods known in the art, such as in an N-glycosidase F treated antibody composition assessed by matrix-assisted laser desorption-ionization time-of-flight mass spectrometry (MALDI-TOF MS). In a composition of a fully fucosylated antibody, at least 90% or essentially all oligosaccharides comprise fucose residues, i.e. are fucosylated. Accordingly, an individual antibody in such a composition typically comprises fucose residues in each of the two N-linked oligosaccharides in the Fc region. In some embodiments, in a composition of a fully non-fucosylated antibody, less than about 10% or essentially none of the oligosaccharides are fucosylated, and an individual antibody in such a composition does not contain fucose residues in either of the two N-linked oligosaccharides in the Fc region. In a composition of a partially fucosylated antibody, only part of the oligosaccharides comprise fucose. An individual antibody in such a composition can comprise fucose residues in none, one or both of the N-linked oligosaccharides in the Fc region, provided that the composition does not comprise essentially all individual antibodies that lack fucose residues in the N-linked oligosaccharides in the Fc region, nor essentially all individual antibodies that contain fucose residues in both of the N-linked oligosaccharides in the Fc region. In one embodiment, a composition of a partially fucosylated antibody has a degree of fucosylation of about 10% to about 80% (e.g., about 50% to about 80%, about 60% to about 80%, or about 70% to about 80%).

In some embodiments, a glycosylation antibody variant comprises an Fc region, wherein a carbohydrate structure attached to the Fc region lacks fucose. Such variants have improved ADCC function. Examples of defucosylated or fucose-deficient antibodies are described in: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004).

Antibodies with reduced fucosylation, or antibodies that are non-fucosylated may be produced using any method known in the art. In some embodiments of the antibodies of the disclosure, at least one or two of the heavy chains of the antibody can be non-fucosylated. For example, antibodies of the disclosure with reduced fucosylation, or antibodies of the disclosure that are non-fucosylated may be produced in a cell line having a alpha1,6-fucosyltransferase (Fut8) knockout, and/or overexpressing β1,4-N-acetylglycosminyltransferase III (GnT-III), and/or overexpressing Golgi μ-mannosidase II (ManII). Antibodies with reduced fucosylation, or antibodies that are non-fucosylated may also be generated using a cell line that is deficient for 'FUT8', alpha-1,6 fucosyltransferase, which catalyzes the transfer of fucose; using Chinese hamster ovary (CHO) cells, e.g., that are deficient in FUT8 (Yamane-Ohnuki et al., 2004); or using small interfering RNAs (siRNAs) to block the expression of the FUT8 gene (Mori et al., 2004). Other cell lines that may be used to produce non-fucosylated or defucosylated antibodies or antibodies with reduced fucosylation are known in the art, e.g., include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)), and cells overexpressing β1,4-N-acetylglycosminyltransferase III (GnT-III) and Golgi μ-mannosidase II (ManII).

In some embodiments, antibodies of the present disclosure have reduced fucose relative to the amount of fucose on the same antibody produced in a wild-type CHO cell. For example, an antibody can have a lower amount of fucose than it would otherwise have if produced by native CHO cells (e.g., a CHO cell that produce a native glycosylation pattern, such as, a CHO cell containing a native FUT8 gene). In some embodiments, an antibody provided herein is one wherein less than about 50%, 40%, 30%, 20%, 10%, 5% or 1% of the N-linked glycans thereon comprise fucose. In certain embodiments, an antibody provided herein is one wherein none of the N-linked glycans thereon comprise fucose, i.e., wherein the antibody is completely without fucose, or has no fucose, or is non-fucosylated, or is afucosylated. The amount of fucose can be determined by one of skill in the art, e.g., by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. In some embodiments, at least one or two of the heavy chains of the antibody is non-fucosylated.

Antibodies lacking 1,6-fucose on their heavy chain glycosylation may have enhanced binding affinity to the FcγRIII receptor and increased ADCC activity (see, e.g., Shields et al., 2002; Shinkawa et al, 2002; Okazaki, 2004; Dall'Ozzo, 2004). In some embodiments, the antibodies provided herein include an Fc region with modifications including reduced fucosylation, non-fucosylation, and/or mutations that enhance ADCC activities and/or improve affinity of the Fc region for Fc receptors such as FcγRIII and CD16 (e.g., CD16a). In some embodiments, the molecules (e.g., the antibodies provide herein) induce antibody directed cell cytotoxicity (ADCC) and deplete or reduce the number of NK cells and/or T cells that express CD94 to a higher extent over a fucosylated or wild type antibody.

In some embodiments, an antibody of the disclosure is engineered to improve ADCC activity by reducing fucosylation. In some embodiments, the molecules provided herein (e.g., the antibodies provided herein) can induce antibody directed cell cytotoxicity (ADCC) and deplete or reduce number of NK cells and/or T cells that express CD94 to a higher extent than a fucosylated or wild type antibody. In some embodiments, at least one or two of the heavy chains of an antibody of the disclosure are non-fucosylated. In some embodiments, an antibody of the disclosure is modified such that the carbohydrates of the antibody are non-fucosylated. In some embodiments, an antibody of the disclosure is modified such that less than about 90%, e.g., less than any of about 90%, about 80%, about 70%, about 60%, about 50%, about 40%, about 30%, about 20%, about 10%, about 5%, or about 1%, of the carbohydrates of the antibody contain fucose. In some embodiments, an antibody of the disclosure is modified such that less than about 40% of the carbohydrates of the antibody contain fucose. In some embodiments, the antibodies provided herein are non-fucosylated.

In some embodiments, the molecules (e.g., antibodies) provided herein induce antibody directed cell cytotoxicity (ADCC) and deplete or reduce the number of NK cells and/or T cells that express CD94 to a higher extent over a fucosylated or wild type antibody.

(iii) Mutations that Enhance ADCC Activity

An antibody of the disclosure may comprise a variant Fc region. In some embodiments, the variant Fc region includes at least one amino acid substitution in the Fc region that improves ADCC activity. For example, an antibody of the disclosure may have a variant IgG1 Fc region which comprises one or more of the Fc mutations selected from S239D, A330L, I332E, F243L and G236A. In another example, an antibody of the disclosure may have a human IgG1 Fc variant region which comprises one or more of the Fc mutations selected from S239D, A330L, I332E, F243L and G236A. Other amino acid substitutions that are known to enhance ADCC activity may be used, for example, as described in Lazar et al., PNAS 103, 4005-4010 (2006); Shields et al., J. Biol. Chem. 276, 6591-6604 (2001); Stewart et al., Protein Engineering, Design and Selection 24, 671-678 (2011), and Richards et al., Mol Cancer Ther 7, 2517-2527 (2008).

(iv) Reduced Internalization

In some embodiments, an antibody of the disclosure has a low degree of internalization, e.g., receptor-induced internalization or target internalization (i.e., internalization of surface expressed CD94), e.g., as compared to a wild type control antibody, or an antibody known in the art or commercially available for the same target. Antibodies with lower internalization have a higher receptor (e.g., CD94) occupancy on the cell surface and higher level of the receptor-antibody complexes on the cell surface, which may enhance ADCC activity. An antibody of the disclosure may be tested in vitro for its internalization capabilities. An antibody of the disclosure may be tested in an ex vivo assay, e.g., using PBMCs and/or NK cells, for its internalization capabilities, e.g., as described in the Examples. The internalization of the target (e.g., CD94) may be expressed as the percent decrease in mean fluorescence intensity (MFI) over a period of time using a flow cytometry-based assay, e.g., as described in the Examples. For example, the internalization of the target (i.e., the internalization capabilities of an antibody of the disclosure) may be expressed as the percent decrease in MFI, calculated by computing the difference in MFI over a 24 hour period (e.g., between 0.5 and 24 hours) in cells incubated with the antibody at 37 degrees Celsius, and multiplying by 100, e.g., as described in the Examples.

In some embodiments, an antibody has a high degree of internalization if it results in an MFI decrease of greater than 50%, calculated by computing the difference in MFI over a 24 hour period (e.g., between 0.5 and 24 hours) in cells incubated with antibody at 37° C., and multiplying by 100, as measured by an ex vivo assay, e.g., using PBMCs and/or NK cells, as described in the Examples. In some embodiments, an antibody has a high degree of internalization if incubating the antibody with a cell expressing human CD94 on its surface for 24 hours at 37° C. results in a decrease in surface antibody staining of greater than 50% due to internalization, assessed using methods known in the art and/or as described above.

In some embodiments, an antibody has a low degree of internalization if it results in an MFI decrease of less than 50% (e.g., any of about 50% or less, 45% or less, 40% or less, 35% or less, 30% or less, 25% or less, 20% or less, 15% or less, 10% or less, 5% or less, 1% or less, or 0%), calculated by computing the difference in MFI over a 24 hour period (e.g., between 0.5 and 24 hours) in cells incubated with antibody at 37° C., and multiplying by 100, as measured by an ex vivo assay, e.g., using PBMCs and/or NK cells, as described in the Examples. In some embodiments, an antibody of the disclosure has a low degree of internalization and results in an MFI decrease of about 50% or less, about 40% or less, about 35% or less, about 30% or less, about 25% or less, about 20% or less, about 15% or less, about 10% or less, about 5% or less, about 2.5% or less, about 1% or less, or about 0%, calculated as described above. In some embodiments, an antibody has a low degree of internalization if incubating the antibody with a cell expressing human CD94 on its surface for 24 hours at 37° C. results in a decrease in surface antibody staining of less than 50% due to internalization, assessed using methods known in the art and/or as described above.

In some embodiments, an antibody of the disclosure has or results in internalization activity that is at least about 5%, at least about 10%, at least about 20%, at least about 30%, at least about 40%, at least about 50%, at least about 60%, at least about 70%, at least about 80%, at least about 90%, at least about 99%, or about 100% lower the internalization of a control antibody, e.g., a commercial or wild type control antibody, or an isotype control antibody, wherein internalization is assessed as described above and/or using any suitable method known in the art.

Antibody candidates with no or low internalization activity may be further tested for binding to a target from cynomolgus monkeys and/or from humans (e.g., cynomolgus and/or human CD94). Antibodies that bind to a cynomolgus monkey and/or human target may be used for cell killing assays (e.g., ADCC assays) in vitro and in vivo. The cell killing activity (e.g., ADCC activity) of the selected antibodies may be compared to the commercially available antibodies or antibodies known in the art.

E. Generation of Antibodies

An antibody of the disclosure may be generated using any technologies and/or methods known in the art. Techniques for preparing antibodies, e.g., monoclonal antibodies (mAbs), against virtually any target antigen are well known in the art. See, for example, Köhler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen (e.g., CD94, or a part thereof), removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures. The person of ordinary skill will realize that where antibodies are to be administered to human subjects, the antibodies will bind to human antigens (e.g., human CD94, or a part thereof).

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

After the initial raising of antibodies to the immunogen (e.g., CD94, or a part thereof), the antibodies can be sequenced and subsequently prepared by recombinant techniques. Humanization and chimerization of murine antibodies and antibody fragments are well known to those skilled in the art, as discussed below.

In an exemplary method of generating an antibody of the disclosure, recombinant targets (e.g., CD94) may be utilized for immunization of mice. Antibodies generated following immunization of mice, e.g., as described above, may be analyzed for specific or selective binding to its target (e.g., CD94) by ELISA and flow cytometry. Antibodies may be selected based on their ability to bind to a target (e.g., CD94).

In some embodiments, non-human primate antibodies may be generated. General techniques for raising therapeutically useful antibodies in baboons may be found, for example, in Goldenberg et al., WO 91/11465 (1991), and in Losman et al., Int. J. Cancer 46: 310 (1990).

In some embodiments, an antibody may be a human antibody. In some embodiments, an antibody may be a monoclonal human antibody. In some embodiments, a human antibody possesses an amino acid sequence which corresponds to that of an antibody produced by a human or a human cell or derived from a non-human source that utilizes human antibody repertoires or other human antibody-encoding sequences. Such antibodies may be obtained from transgenic mice that have been engineered to produce specific human antibodies in response to antigenic challenge e.g., CD94, or a part thereof. Methods for producing fully human antibodies using either combinatorial approaches or transgenic animals transformed with human immunoglobulin loci are known in the art (e.g., Mancini et al., 2004, New Microbiol. 27:315-28; Conrad and Scheller, 2005, Comb. Chem. High Throughput Screen. 8:117-26; Brekke and Loset, 2003, Curr. Opin. Phamacol. 3:544-50). In certain embodiments, the claimed methods and procedures may utilize human antibodies produced by such techniques. Other methods of producing fully human antibodies include phage display, e.g., as described in Dantas-Barbosa et al., 2005, Genet. Mol. Res. 4:126-40, generation of antibodies in normal humans or from humans that exhibit a particular disease state, e.g., as described in Dantas-Barbosa et al., 2005, or using transgenic animals (e.g., mice) that have been genetically engineered to produce human antibodies using standard immunization protocols as discussed above, e.g., as described in Green et al., 1999, J. Immunol. Methods 231:11-23, Green et al., Nature Genet. 7:13 (1994), Lonberg et al., Nature 368:856 (1994), and Taylor et al., Int. Immun. 6: 579 (1994).

(i) In Vitro Cell Killing Assays

Generation of an antibody of the disclosure may involve testing the in vitro ADCC activity of the antibody. The improved cell killing or ADCC activity of an antibody of the disclosure may be tested as described above, as described in the Examples, and/or using methods known in the art. The improved cell killing or ADCC activity of an antibody of the disclosure may be tested for depletion of NK cells and/or T cells that express CD94. Depletion of NK cells and/or T cells that express CD94 may be tested using an exemplary in vitro model that recapitulates activity in humans (Tomasevic, et al, Growth Factors, 2014; 32(6): 223-235; Huang, et al, JCI insight, 2016; 1(7):e86689). Peripheral blood lymphocytes (PBL) isolated from the blood of normal (i.e., healthy) donors are incubated with antibodies that have a human Fc region with and without fucose and/or with and without Fc region mutations. The level of killing of NK cells and/or T cells that express CD94 in the PBLs (e.g., in a PBL sample) is measured using any method known in the art, such as flow cytometry (e.g., as described in the Examples). The cell killing activity (e.g., ADCC activity) of antibodies may be tested as described above, e.g., using the assay described above, using a variety of biospecimens such as blood, synovial fluid, bone marrow and spleen intact cell homogenates from patients with diseases such as NK/T cell lymphomas, e.g., extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, chronic lymphoproliferative disorder of NK cells (CLPD-NK), LGL leukemia, Felty's syndrome, CLPD-NK, IBM and RA with LGL and/or aggressive NK leukemia.

In addition to the cell killing assay described above, in vitro ADCC and antibody-dependent cellular phagocytosis (ADCP) assays using antibodies of the disclosure, purified target cells (e.g., NK cells and/or T cells that express CD94), and/or effector cells such as NK cells or monocytes/macrophages may be performed to assay the cell killing, ADCC and/or ADCP activity of antibodies of the disclosure. Cell killing, ADCC and/or ADCP assays, and other assay methods known in the art may be used, for example, as described in Kolbeck et al., J Allergy Clin Immunol. 2010; 125(6): 1344-1353.e2; Gomez-Roman et al., J. Immunol. Methods, 2006, 308, pp. 53-67; and Ackerman et al., J. Immunol. Methods, 2011, 366, pp. 8-19. The in vitro activity of an antibody of the disclosure may be compared to a commercially available antibody or an antibody known in the art against the same target.

(ii) In Vivo Cell Killing Assays

Generation of an antibody of the disclosure may involve testing the in vivo ADCC activity of the antibody, e.g., to show activity of the selected antibody candidates in vivo for depletion or reduction in the levels of NK cells and/or T cells that express CD94. The in vivo cell killing activity (e.g., ADCC and/or ADCP activity) of an antibody of the disclosure may be determined using any method known in the art. For example, the ability of an antibody of the disclosure to deplete or reduce NK cells and/or T cells that express CD94 in vivo may be tested in cynomolgus monkeys using methods known in the art. For example, in an exemplary method to test the in vivo cell killing activity (e.g., ADCC and/or ADCP activity) of an antibody of the disclosure, a cohort of cynomolgus monkeys are bled one day prior to administration of a single dose of an antibody of the disclosure, e.g., antibody treatment, to identify the pre-dose levels of NK cells and/or T cells that express CD94 by flow cytometry. After administration of an antibody of the disclosure, e.g., upon treatment with antibodies of the disclosure, the monkeys are bled at the following time points: 1 hour, 1 day, 7 days, 14 days and 30 days. The levels of NK cells and/or T cells that express CD94 in blood and other biospecimens such as synovial fluids, bone marrow and spleen are determined by flow cytometry at each of the time points. The in vivo activity of an antibody of the disclosure may be compared to a commercially available antibody or an antibody known in the art against the same target. An anti-CD94 antibody of the disclosure may be compared to anti-CD94 antibody clones DX22, HP-3D9, HP-3B1, 131412, or 12K45.

A skilled artisan will readily appreciate that other methods known in the art for testing ADCC activity in vivo may be used to assay the in vivo ADCC activity of antibodies of the disclosure (e.g., transgenic animals such as transgenic mice).

Other known antibodies against the target (e.g., CD94) may also be used in the methods provided herein. For example, an anti-CD94 antibody of the disclosure may be tested (e.g., for in vitro or in vivo ADCC activity, or for any other characteristic described herein) together with the following anti-CD94 antibodies: HP-3D9 (LSBio Catalog #LS-C134679-100; Abnova Catalog #: MAB6947); 212; 131412 (R&D Systems Catalog #: MAB1058); 13B146 (US Biological Catalog #: 030068); 13B147 (US Biological Catalog #: 030069); 1H1 (Abnova Catalog #: MAB10543); 3G2 (Biorbyt Catalog #: orb69389); DX22 (Biolegend Catalog #305502); REA113 (Miltenyi Biotec Catalog #: 130-098-967); KP43; EPR21003; AT13E3 (ATGen Catalog: ATGA0487); HP-3B1; 12K45; and B-D49.

(iii) Humanization

An antibody of the disclosure may be humanized according to any method known in the art. In some embodiments, a humanized antibody is a chimeric antibody comprising amino acid residues from non-human hypervariable regions (HVRs) and amino acid residues from human framework regions (FRs). In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. In some embodiments, a humanized form of an antibody, e.g., a non-human antibody, refers to an antibody that has undergone humanization.

For example, a monoclonal antibody may be humanized by transferring mouse CDRs from the heavy and light variable chains of a mouse immunoglobulin into the corresponding variable domains of a human antibody. The mouse framework regions (FR) in the chimeric monoclonal antibody may also be replaced with human FR sequences. To preserve the stability and antigen specificity of the humanized monoclonal antibody, one or more human FR residues may be replaced by the mouse counterpart residues. Humanized monoclonal antibodies may be used for therapeutic treatment of subjects. Techniques for the production of humanized monoclonal antibodies are well known in the art, e.g., as described in Jones et al., 1986, Nature, 321:522; Riechmann et al., Nature, 1988, 332:323; Verhoeyen et al., 1988, Science, 239:1534; Carter et al., 1992, Proc. Nat'l Acad. Sci. USA, 89:4285; Sandhu, Crit. Rev. Biotech., 1992, 12:437; Tempest et al., 1991, Biotechnology 9:266; Singer et al., J. Immun., 1993, 150:2844.

An antibody of the disclosure may have one or more of the characteristics described above, e.g., enhanced in vitro and/or in vivo cell killing activity (e.g., ADCC and/or ADCP activity), enhanced binding to one or more Fc receptors, reduced fucosylation or non-fucosylation, cross-reactivity (e.g., binding to human CD94 and to cynomolgus monkey CD94), lack of blocking of HLA-E binding to the CD94/NKG2A heterodimer, competition with commercially available antibodies (e.g., commercially available anti-CD94 antibodies), low internalization, and/or desirable affinity for its target protein (e.g., CD94, human CD94, and/or cynomolgus CD94).

In some embodiments, an antibody of the disclosure is soluble at concentrations higher than about 10 mg/mL. In some embodiments, an antibody of the disclosure forms a low level of soluble aggregates (e.g., less than 5%, less than 4%, less than 3%, less than 2%, or less than 1% soluble aggregates). In some embodiments, an antibody of the disclosure has an ability to maintain binding to its target (e.g., CD94) during storage, e.g., for at least 1 week, at least 2 weeks, at least 3 weeks, at least 1 month, at least 2 months, at least 3 months, at least 4 months, or more, at any of about 2° C., about 3° C., about 4° C., about 5° C., about 6° C., about 7° C., about 8° C. In some embodiments, an antibody of the disclosure has stability (e.g., lack of degradation products, e.g., as measured by SDS-PAGE) during storage, e.g., for at least 1 week, at least 2 weeks, at least 3 weeks, at least 1 month, at least 2 months, at least 3 months, at least 4 months, or more, at any of about 2° C., about 3° C., about 4° C., about 5° C., about 6° C., about 7° C., or about 8° C.

In some embodiments, an antibody of the disclosure is tested for toxicology. Toxicology analysis of an antibody of the disclosure may be carried out using any method known in the art. In an exemplary toxicology analysis, an antibody of the disclosure is tested for toxicity in cynomolgus monkeys at doses that are more than 5 times higher (e.g., any of about 5 times higher, about 10 times higher, about 15 times higher, about 20 times higher, about 25 times higher, about 30 times higher, about 35 times higher, about 40 times higher, about 45 times higher, about 50 times higher, about 55 times higher, about 60 times higher, about 65 times higher, about 70 times higher, about 75 times higher, about 80 times higher, about 85 times higher, about 90 times higher, about 95 times higher, about 100 times higher, or more) than the doses anticipated to be used in human subjects.

In some embodiments, an antibody of the disclosure is capable of depleting or reducing the level of NK cells and/or T cells that express CD94 in vitro and/or in vivo. Depletion or reduction in the level of NK cells and/or T cells that express CD94 may be measured using any method known in the art. For example, depletion of NK cells and/or T cells that express CD94 may be measured using a cell killing, ADCC, and/or ADCP assay, e.g., as described above and/or as described in the Examples.

In some embodiments, an antibody of the disclosure is soluble at concentrations higher than 10 mg/mL, has low level of soluble aggregates (<5%), maintains its binding to the target as measured by ELISA (>90% potency), with no degradation products as measured by SDS PAGE when incubated for 3 months at 2-8° C. In some embodiments, toxicology analysis of an antibody of the disclosure can be performed in cynomolgus monkeys at doses that are more than 5 times higher than the doses anticipated to be used in human subjects.

In some embodiments, the antibodies that bind to CD94 may deplete or reduce the level of NK cells and/or T cells that express CD94 and may have clear benefits for patients (e.g., human patients) with diseases or disorders such as LGL leukemia, Rheumatoid arthritis, Felty's syndrome, CLPD-NK, aggressive NK leukemia, IBM, IBD, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL. In addition, the antibody treatment may have better tolerability and fewer side-effects over the first and second line of therapies including chemotherapy, such as cyclophosphamide, doxorubicin, vincristine, prednisone; stem cell transplant; splenectomy; Alemtuzumab; Bevacizumab; Pralatrexate; Avelumab; proteasome inhibitors such as Carfilzomib and Bortezomib; HDAC inhibitors such as Romidepsin, Belinostat, and Vorinostat; and antibody-drug conjugates such as Brentuximab vedotin. The antibody treatment may demonstrate more selective depletion of the disease-inducing cells compared to the current therapies that are non-selective. Non-limiting examples of diseases and disorders in which NK cells and/or T cells that express CD94 may play a role are: LGL leukemia, Rheumatoid arthritis, Felty's syndrome, CLPD-NK, aggressive NK leukemia, IBM, IBD, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL. Accordingly, the invention provides a method of reducing the number of or depleting NK cells and/or T cells that express CD94 in a human subject upon administration of molecule that binds to CD94 and that comprises (a) a region that specifically binds to the target (e.g., CD94) and (b) an immunoglobulin Fc region.

II. Uses and Methods of Treatment

As discussed above, NK cells, CD4+ T cells, CD8+ T cells, and/or CD8+ and CD4+ T cells have been implicated in the pathogenesis of numerous diseases and disorders, such as NK/T cell lymphomas. Many of these disorders or diseases are characterized by a clonal expansion of NK cells and/or CD8+ and CD4+ T cells.

In some embodiments, provided herein are molecules (e.g., antibodies) that bind to CD94, e.g., expressed on the surface of NK cells and/or T cells. Also provided herein are molecules (e.g., antibodies) that bind to CD94 and that have reduced fucosylation, non-fucosylation (e.g., that have an immunoglobulin Fc part with modifications or mutations that reduce or eliminate fucosylation). Also provided herein are molecules (e.g., antibodies) that bind to CD94 and that have modifications or mutations that enhance ADCC activities and/or improve affinity of the Fc region to Fc receptors such as CD16 (e.g., CD16a). Also provided herein are molecules (e.g., antibodies) that bind to CD94 and that have one or more of the following characteristics: bind to human CD94 and cynomolgus CD94, do not block binding of HLA-E to the CD94/NKG2A heterodimer, have a low degree of internalization, are non-fucosylated or have reduced fucosylation, and/or induce, promote, or enhance ADCC activity.

In some embodiments, provided herein is a method for treating a disease or disorder in a subject, comprising administering to the subject an effective amount of an antibody described herein, that specifically binds to human CD94. In some embodiments, provided herein is a method for treating a disease or disorder in a subject, comprising administering to the subject an effective amount of an antibody that specifically binds to human CD94, wherein the antibody has one or more of the following characteristics: does not block binding of HLA-E to the CD94/NKG2A heterodimer, has a low degree of internalization, is non-fucosylated or has reduced fucosylation, and/or induces, promotes or enhances ADCC activity. In some embodiments, the disease or disorder is selected from chronic lymphoproliferative disorder of NK cells (CLPD-NK), LGL leukemia, Felty's syndrome, rheumatoid arthritis, aggressive NK leukemia, inclusion body myositis, inflammatory bowel disease, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, subcutaneous panniculitis TCL, or microscopic colitis. In some embodiments, administration of the antibody results in a reduction in the number of NK cells and/or T cells that express CD94. In some embodiments, administration of the antibody results in a reduction in the number of peripheral blood NK cells, CD8+, CD4+, or CD8+/CD4+ T cells, and/or LGL cells in the subject, e.g., that express CD94. In some embodiments, administration of the antibody results in a reduction in the number of peripheral blood LGL cells, e.g., that express CD94, in the subject. In some embodiments, administration of the antibody results in a reduction in the number of peripheral blood NK cells, e.g., that express CD94, in the subject. In some embodiments, administration of the antibody results in a reduction in the number of peripheral blood CD8+/CD4+ T cells, e.g., that express CD94, in the subject. In some embodiments, administration of the antibody results in a reduction in the number of peripheral blood CD8+ T cells, e.g., that express CD94, in the subject. In some embodiments, administration of the antibody results in a reduction in the number of peripheral blood CD4+ T cells, e.g., that express CD94, in the subject.

Also provided herein is a method for reducing the number of peripheral blood NK cells and/or T cells that express CD94, comprising administering to the subject an effective amount of an antibody of the disclosure that specifically binds to human CD94. In some embodiments, the antibody has one or more of the following characteristics: does not block binding of HLA-E to the CD94/NKG2A heterodimer, has a low degree of internalization, is non-fucosylated or has reduced fucosylation, and/or induces, promotes or enhances ADCC activity. In some embodiments, the subject has a disease or disorder selected from chronic lymphoproliferative disorder of NK cells (CLPD-NK), LGL leukemia, Felty's syndrome, rheumatoid arthritis, aggressive NK leukemia, inclusion body myositis, inflammatory bowel disease, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, subcutaneous panniculitis TCL, or microscopic colitis. In some embodiments, administration of the antibody to the subject results in a reduction in the number of peripheral blood NK cells and/or T cells that express CD94 compared to prior to administration of the antibody.

Also provided herein is a method for inducing ADCC activity in a subject, comprising administering to the subject an effective amount of an antibody of the disclosure that specifically binds to human CD94. In some embodiments, the antibody has one or more of the following characteristics: does not block binding of HLA-E to the CD94/NKG2A heterodimer, has a low degree of internalization, is non-fucosylated, has a reduced fucosylation, and/or induces, enhances or promotes ADCC activity. In some embodiments, the subject has a disease or disorder selected from chronic lymphoproliferative disorder of NK cells (CLPD-NK), LGL leukemia, Felty's syndrome, rheumatoid arthritis, aggressive NK leukemia, inclusion body myositis, inflammatory bowel disease, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, subcutaneous panniculitis TCL, or microscopic colitis. In some embodiments, administration of the antibody to the subject results in a reduction in the number of peripheral blood NK cells and/or T cells that express CD94 compared to prior to administration of the antibody.

In some embodiments, the disease or disorder is CLPD-NK. In some embodiments, the disease or disorder is LGL leukemia. In some embodiments, the disease or disorder is Felty's syndrome. In some embodiments, the disease or disorder is rheumatoid arthritis. In some embodiments, the disease or disorder is aggressive NK leukemia. In some embodiments, the disease or disorder is inclusion body myositis. In some embodiments, the disease or disorder is inflammatory bowel disease. In some embodiments, the disease or disorder is T-large granular lymphocyte leukemia (T-LGLL). In some embodiments, the disease or disorder is Natural Killer-large granular lymphocyte leukemia (NK-LGLL). In some embodiments, the disease or disorder is an NK/T cell lymphoma. In some embodiments, the disease or disorder is extranodal NK/T cell lymphoma. In some embodiments, the disease or disorder is hepatosplenic T cell lymphoma (TCL). In some embodiments, the disease or disorder is enteropathy-associated TCL. In some embodiments, the disease or disorder is cutaneous TCL. In some embodiments, the disease or disorder is anaplastic large cell lymphoma (ALK+). In some embodiments, the disease or disorder is anaplastic large cell lymphoma (ALK−). In some embodiments, the disease or disorder is peripheral TCL (not otherwise specified). In some embodiments, the disease or disorder is angioimmunoblastic TCL. In some embodiments, the disease or disorder is adult TCL. In some embodiments, the disease or disorder is monomorphic epitheliotropic intestinal TCL. In some embodiments, the disease or disorder is epidermotropic CD8+ cutaneous TCL. In some embodiments, the disease or disorder is primary cutaneous gamma/delta TCL. In some embodiments, the disease or disorder is subcutaneous panniculitis TCL. In some embodiments, the disease or disorder is microscopic colitis.

Also provided herein is a method for treating CLPD-NK in a human subject in need thereof, comprising administering to the human subject an effective amount of an antibody of the disclosure, wherein the antibody specifically binds to human CD94. In some embodiments, administration of the antibody to the human subject results in an improvement of CLPD-NK symptoms in the human.

Also provided herein is a method for treating NK/T cell lymphoma in a human subject in need thereof, comprising administering to the human subject an effective amount of an antibody of the disclosure, wherein the antibody specifically binds to human CD94. In some embodiments, administration of the antibody to the human subject results in an improvement of NK/T cell lymphoma symptoms in the human. In some embodiments, the NK/T cell lymphoma is selected from extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL.

Also provided herein is a method for treating CLPD-NK in a human subject in need thereof, comprising administering to the human subject an effective amount of an antibody of the disclosure, wherein the antibody specifically binds to human CD94, wherein the antibody has one or more of the following characteristics: does not block binding of HLA-E to the CD94/NKG2A heterodimer, has a low degree of internalization, is non-fucosylated or has reduced fucosylation, and/or induces, enhances or promotes ADCC activity. In some embodiments, administration of the antibody to the human subject results in an improvement of CLPD-NK symptoms in the human.

Also provided herein is a method for treating NK/T cell lymphoma in a human subject in need thereof, comprising administering to the human subject an effective amount of an antibody of the disclosure, wherein the antibody specifically binds to human CD94, wherein the antibody has one or more of the following characteristics: does not block binding of HLA-E to the CD94/NKG2A heterodimer, has a low degree of internalization, is non-fucosylated or has reduced fucosylation, and/or induces, enhances, or promotes ADCC activity. In some embodiments, administration of the antibody to the human subject results in an improvement of NK/T cell lymphoma symptoms in the human. In some embodiments, the NK/T cell lymphoma is selected from extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL. In some embodiments, the NK cell or T-cell lymphoma is extranodal NK/T cell lymphoma, hepatosplenic TCL, or enteropathy-associated TCL. In some embodiments, the NK cell or T-cell lymphoma is characterized by NK cells and/or T cells expressing CD94 (e.g., human CD94).

Also provided herein is a method for treating microscopic colitis in a human subject in need thereof, comprising administering to the human subject an effective amount of an antibody of the disclosure, wherein the antibody specifically binds to human CD94, wherein the antibody has one or more of the following characteristics: does not block binding of HLA-E to the CD94/NKG2A heterodimer, has a low degree of internalization, is non-fucosylated or has reduced fucosylation, and/or induces, enhances, or promotes ADCC activity. In some embodiments, administration of the antibody to the human subject results in an improvement of microscopic colitis symptoms in the human. Microscopic colitis is a gastrointestinal disease characterized by inflammation of the colon leading to persistent non-bloody, watery diarrhea. It is termed microscopic because tissue destruction can only be seen under a microscope, not through gross examination. The colon in these patients appear macroscopically normal or have near normal colonic mucosa. Two subtypes of microscopic colitis currently exists: Collagenous colitis, which is characterized by the buildup of a layer of collagen in the intestinal lining and Lymphocytic colitis, which is characterized by an increase in lymphocytes in colon tissue. It currently affects 100/100,000 individuals worldwide, of which 39.3% of the cases are of the lymphocytic subtype (Hisamatsu et al. (2016) *Inflamm. Intest. Dis.* 2:52-62). The current causes of microscopic colitis are unknown, but common factors include medication, bacterial and viral infections, autoimmune disease such as rheumatoid arthritis, celiac disease or psoriasis and buildup of bile acid. Current methods for diagnosis is histological examination of intestinal tissue, as the disease cannot be diagnosed without histopathological examination of biopsy material. Common symptoms of microscopic colitis include persistent, watery diarrhea, resulting in weight loss, bloating, anemia, malnourishment, etc. There is no cure or proper treatment for microscopic colitis except anti-diarrhetic medication, low-fat, low-fiber and low-dairy diet, steroids, bile acid blockers, anti-inflammatory meds, TNF inhibitors or in the rarest circumstances surgery to remove part or all of the colon. Although it is not clear what are the major disease-causing cells in microscopic colitis, studies have shown that there are elevations in the CD8+ intraepithelial lymphocytes (IELs) in the colon of microscopic colitis patients (Goranzon et al. (2013) *J. Crohns Colitis* 7:e434-442). There is evidence in the literature to suggest that CD94 is highly expressed on IELs in microscopic colitis (Barmeyer et al. (2016) *Inflamm. Bowel Dis.* 22:539-547). Without wishing to be bound to theory, it is thought that anti-CD94 (e.g., a non-fucosylated IgG1 antibody) could execute ADCC on the IEL cells via fratricide. The literature has also suggested that CD16 is highly elevated in microscopic colitis biopsies vs. normal controls, suggesting that IELs may engage anti-CD94 to induce ADCC on other IEL cells (Barmeyer et al. (2016) *Inflamm. Bowel Dis.* 22:539-547). Without wishing to be bound to theory, it is thought that the IEL cells are cytotoxic and could serve as an effector as well as target cells.

Also provided herein is a method for enhancing chimeric antigen receptor T cell (CAR-T) therapy in a human subject in need thereof, comprising administering to the human subject an effective amount of an antibody of the disclosure prior to administration of a CAR-T treatment to the subject, wherein the antibody specifically binds to human CD94, wherein the antibody has one or more of the following characteristics: does not block binding of HLA-E to the CD94/NKG2A heterodimer, has a low degree of internalization, is non-fucosylated or has reduced fucosylation, and/or induces, enhances, or promotes ADCC activity. In some embodiments, administration of the antibody to the human subject results in depletion of NK cells in the subject prior to administration of the CAR-T treatment. In some embodiments, the CAR-T therapy is for treatment of cancer, i.e., the subject has/is being treated for cancer. The short half-life of CAR-T cells for the treatment of various hematological and solid cancers significantly hampers the development of cell therapy. Lymphodepleting chemotherapy is commonly used prior to CAR-T treatments such as cyclophosphamide with or without fludarabine (Flu). However, these standard chemotherapies do not adequately deplete NK cells, resulting in elimination of off the shelf CAR-T cells shortly after infusion. Without wishing to be bound to theory, it is thought that anti-CD94 antibody treatment could potentially transiently deplete NK cells to enable engraftment of HLA class I-deficient cells ("universal CAR T cells") or organs to prevent NK cell-mediated rejection. Transient depletion of NK cells should provide a window for engraftment of HLA class I-negative cells and pose no safety risk. After CD94 depleting antibodies are gone, NK cell numbers could return to normal. Newly arising NK cells should become tolerant to the transferred HLA class I-negative cells (based on mixed bone marrow chimera experiments). Thus, anti-CD94 antibody treatment could provide an opportunity for enhancing CAR-T therapy, e.g., in cancer patients.

In some embodiments, the terms treat, treating, treatment, ameliorate, ameliorating, reducing one or more symptoms, reducing symptoms, reduce one or more symptoms, reduce symptoms, and other grammatical equivalents, refer to alleviating, abating or ameliorating one or more symptoms of a disease or disorder, preventing additional symptoms, ameliorating or preventing the underlying causes of symptoms, inhibiting the disease or disorder, e.g., arresting the development of the disease or disorder, relieving the disease or disorder, causing regression of the disease or disorder, relieving a condition caused by the disease or disorder, or stopping the symptoms of the disease or disorder, and are intended to include prophylaxis. In some embodiments, the terms further include achieving a therapeutic benefit and/or a prophylactic benefit. In some embodiments, a therapeutic benefit refers to eradication or amelioration of the underlying disease or disorder being treated. Also, a therapeutic benefit is achieved with the eradication or amelioration of one or more of the physiological symptoms associated with the underlying disease or disorder such that an improvement is observed in the patient, notwithstanding that, in some embodiments, the patient is still afflicted with the underlying disease or disorder. For prophylactic benefit, the pharmaceutical compositions are administered to a patient at risk of developing a particular disease or disorder, or to a patient reporting one or more of the physiological symptoms of a disease or disorder, even if a diagnosis of the disease or disorder has not been made.

In some embodiments, an effective amount, a therapeutically effective amount or pharmaceutically effective amount may be a sufficient amount of at least one pharmaceutical composition or compound (e.g., an antibody of the disclosure) being administered which will relieve to some extent one or more of the symptoms of the disease or condition being treated.

In some embodiments, the reduction in the number of peripheral blood NK cells and/or T cells that express CD94 in the subject occurs within the first 24 hours, e.g., any of within about 1 hour, within about 2 hours, within about 3 hours, within about 4 hours, within about 5 hours, within about 6 hours, within about 7 hours, within about 8 hours, within about 9 hours, within about 10 hours, within about 11 hours, within about 12 hours, within about 13 hours, within about 14 hours, within about 15 hours, within about 16 hours, within about 17 hours, within about 18 hours, within about 19 hours, within about 20 hours, within about 21 hours, within about 22 hours, within about 23 hours, or within about 24 hours after administration of the antibody to the subject.

In some embodiments, the number of peripheral blood NK cells and/or T cells that express CD94 in the subject (e.g., in a peripheral blood sample obtained from the subject) is reduced to below the limit for clinical diagnosis of the disease or disorder. In some embodiments, the number of peripheral blood NK cells and/or T cells that express CD94 in the subject is reduced to less than or equal to $2 \times 10^9$ cells/L (e.g., in a peripheral blood sample obtained from the subject). See, e.g., Lamy, T. et al. (2017) *Blood* 129:1082-1094. In some embodiments, the reduction in the number of peripheral blood NK cells and/or T cells that express CD94 in the subject to below the limit for clinical diagnosis of the disease or disorder is present in the subject for at least about 1 week, e.g., any of at least about 1 week, at least about 2 weeks, at least about 3 weeks, at least about 4 weeks, at least about 1 month, at least about 2 months, at least about 3 months, at least about 4 months, at least about 5 months, at least about 6 months, or more, after administration of the antibody to the subject. In some embodiments, the reduction in the number of peripheral blood NK cells and/or T cells that express CD94 in the subject to less than or equal to $2\times10^9$ cells/L in the subject (e.g., in a peripheral blood sample obtained from the subject) is present in the subject for at least about 1 week, e.g., any of at least about 1 week, at least about 2 weeks, at least about 3 weeks, at least about 4 weeks, at least about 1 month, at least about 2 months, at least about 3 months, at least about 4 months, at least about 5 months, at least about 6 months, or more, after administration of the antibody to the subject.

In some embodiments, the number of peripheral blood NK cells and/or T cells that express CD94 in the subject is reduced to below the limit of detection for the peripheral blood NK cells and/or T cells that express CD94 in the subject. In some embodiments, the reduction in the number of peripheral blood NK cells and/or T cells that express CD94 in the subject to below the limit of detection for the peripheral blood NK cells and/or T cells that express CD94 is present in the subject for at least about 1 week, e.g., any of at least about 1 week, at least about 2 weeks, at least about 3 weeks, at least about 4 weeks, at least about 1 month, at least about 2 months, at least about 3 months, at least about 4 months, at least about 5 months, at least about 6 months, or more, after administration of the antibody to the subject. In some embodiments, peripheral blood NK cells and/or T cells that express CD94 are detected by flow cytometry (e.g., as performed on a peripheral blood sample from the subject).

In some embodiments, the peripheral blood NK cells that express CD94 are CD3+CD56 bright. In some embodiments, the peripheral blood T cells that express CD94 are CD4+, CD8+, or CD8+ and CD4+.

In some embodiments, the reduction in the number of peripheral blood NK cells and/or T cells that express CD94 in the subject is reversible. In some embodiments, the reduction in the number of peripheral blood NK cells and/or T cells that express CD94 in the subject is reversible within any of about 1 week, about 2 weeks, about 3 weeks, about 4 weeks, about 1 month, about 2 months, about 3 months, about 4 months, about 5 months, about 6 months, or more, after administration of the antibody to the subject.

In some embodiments, a statement that a cell or a population of cells is positive (+) for, or expresses a particular marker (e.g., CD3, CD4, CD8, CD16, CD94, NKG2A, etc.), refers to the detectable presence on or in the cell of the particular marker. In some embodiments, a statement that a cell or a population of cells is positive for, +, or expresses a surface marker (e.g., a cell surface protein) refers to the presence of cell surface expression of the particular marker, for example, as detected by flow cytometry, for example, by staining with an antibody that specifically binds to the marker and detecting said antibody, wherein the staining is detectable by flow cytometry at a level substantially above the staining detected carrying out the same procedure with an isotype-matched control and/or fluorescence minus one (FMO) gating control under otherwise identical conditions, and/or at a level substantially similar to that for cell known to be positive for the marker, and/or at a level substantially higher than that for a cell known to be negative for the marker.

In some embodiments, a statement that a cell or a population of cells is negative (−) for, or does not express a particular marker (e.g., CD3, CD4, CD8, CD16, CD94, NKG2A, etc.) refers to the absence of a detectable presence on or in the cell of the particular marker. In some embodiments, a statement that a cell or a population of cells is negative for, −, or does not express a surface marker (e.g., a cell surface protein) refers to the absence of cell surface expression of the particular marker, for example, as detected by flow cytometry, for example, by staining with an antibody that specifically binds to the marker and detecting said antibody, wherein the staining is detectable by flow cytometry at a level substantially similar or below the staining detected carrying out the same procedure with an isotype-matched control and/or fluorescence minus one (FMO) gating control under otherwise identical conditions, and/or at a level below that for cell known to be positive for the marker, and/or at a level substantially similar or below that for a cell known to be negative for the marker.

In some embodiments, the antibody has an EC50 or IC50 for reducing peripheral blood NK cells and/or T cells that express CD94 in the subject of between about 1 ng/ml and about 100 ng/ml, e.g., any of about 1 ng/ml, about 5 ng/ml, about 10 ng/ml, about 15 ng/ml, about 20 ng/ml, about 25 ng/ml, about 30 ng/ml, about 35 ng/ml, about 40 ng/ml, about 45 ng/ml, about 50 ng/ml, about 55 ng/ml, about 60 ng/ml, about 65 ng/ml, about 70 ng/ml, about 75 ng/ml, about 80 ng/ml, about 85 ng/ml, about 90 ng/ml, about 95 ng/ml, or about 100 ng/ml. In some embodiments, the antibody has an IC50 or EC50 for reducing peripheral blood NK cells and/or T cells that express CD94 in the subject of between about 10 ng/ml and about 80 ng/ml. In some embodiments, the antibody has an IC50 or EC50 for reducing peripheral blood NK cells and/or T cells that express CD94 in the subject of about 20 ng/ml. In some embodiments, the antibody has an IC50 or EC50 for reducing peripheral blood NK cells and/or T cells that express CD94 in the subject of about 60 ng/ml. EC50 or IC50 may be measured using any method known in the art, e.g., as described in the Examples.

In some embodiments, the subject is a human, a primate, a non-human primate (e.g., African green monkeys, cynomolgus monkey, rhesus monkeys, etc.), a farm mammal, a game mammal, or a domestic mammal. In some embodiments, the subject is a human. In some embodiments, the human subject is an infant, a toddler, a child, a young adult, an adult or a geriatric. In some embodiments, the subject has a disease involving T cells and/or NK cells that express CD94, e.g., CLPD-NK, LGL leukemia, Felty's syndrome, rheumatoid arthritis, aggressive NK leukemia, inclusion body myositis, inflammatory bowel disease, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL.

In some embodiments, administration of the antibody to the subject does not result in tumor lysis syndrome in the subject. Tumor lysis syndrome may be measured or diagnosed according to any method known in the art, such as the Cairo-Bishop classification system for tumor lysis syndrome (see, e.g., Cairo and Bishop (2004) Br J Haematol, 127(1):3-11.)

In some embodiments, an antibody of the disclosure binds to CD94. In some embodiments, an antibody of the disclosure depletes and/or reduces the level of NK cells and/or T cells that express CD94. In some embodiments, an antibody of the disclosure has clear benefits for a patient (e.g., a human patient) having a disease or disorder, such as CLPD-NK, LGL leukemia, rheumatoid arthritis, Felty's syndrome, aggressive NK leukemia, IBM, IBD, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, subcutaneous panniculitis TCL or other diseases associated with LGL, T cells, and/or NK cells. In some embodiments, an antibody of the disclosure has better tolerability and fewer side effects over the first and second line of therapies for the disease or disorder (e.g., CLPD-NK, LGL leukemia, Felty's syndrome, rheumatoid arthritis, aggressive NK leukemia, inclusion body myositis, inflammatory bowel disease, or an NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, or adult TCL), such as chemotherapy, e.g., cyclophosphamide, doxorubicin, vincristine, prednisone; stem cell transplant; splenectomy; Alemtuzumab; Bevacizumab; Pralatrexate; Avelumab; proteasome inhibitors such as Carfilzomib and Bortezomib; HDAC inhibitors such as Romidepsin, Belinostat, and Vorinostat; and antibody-drug conjugates such as Brentuximab vedotin. In some embodiments, an antibody of the disclosure demonstrates more selective depletion of the disease-inducing cells, e.g., NK cells and/or T cells that express CD94, compared to current therapies that are non-selective, such as chemotherapy, e.g., cyclophosphamide, doxorubicin, vincristine, prednisone; stem cell transplant; splenectomy; Alemtuzumab; Bevacizumab; Pralatrexate; Avelumab; proteasome inhibitors such as Carfilzomib and Bortezomib; HDAC inhibitors such as Romidepsin, Belinostat, and Vorinostat; and antibody-drug conjugates such as Brentuximab vedotin. Accordingly, in some embodiments, the disclosure provides a method of reducing the number or depleting NK cells and/or T cells that express CD94 in a human subject upon administration of molecule (e.g., an antibody of the disclosure) that binds to a cell surface protein on NK cells and/or T cells, such as CD94, and that comprises (a) a region that specifically binds to the target and (b) an immunoglobulin Fc region.

In some embodiments, the methods provided herein further comprise administering to the subject an IL-2 polypeptide, e.g., a therapeutic IL-2 polypeptide. IL-2 polypeptides, e.g., therapeutic IL-2 polypeptides, suitable for administration to a subject (e.g., a subject having a disease or disorder described herein) according to the methods provided herein are known in the art. Exemplary IL-2 polypeptides include, without limitation, Aldesleukin, Interking, and Neoleukin 2/15.

A. Administration and Dosing Regimens (i) Routes of Administration

In some embodiments, administer, administering, administration, and the like, refer to methods that are used to enable delivery of therapeutic or pharmaceutical compositions to the desired site of biological action. In some embodiments, an antibody of the disclosure (and any additional therapeutic agent) for use in any of the methods provided herein may be administered to the subject (e.g., a human) by any suitable means, including parenteral, intrapulmonary, intranasal, and intralesional administration. Parenteral infusions include intramuscular, intravenous, intraarterial, intraperitoneal, or subcutaneous administration. In some embodiments, an antibody of the disclosure is administered by intravenous infusion. Dosing of an antibody of the disclosure can be by any suitable route, e.g., by injections, such as intravenous or subcutaneous injections, depending in part on whether the administration is brief or chronic.

(ii) Dosing Regimens

An antibody of the disclosure for use in any of the methods provided herein may be administered to the subject using various dosing schedules or regimens, including but not limited to single or multiple administrations over various time-points, bolus administration, and pulse infusion. The specific dosage of the antibodies of the disclosure to be administered will vary according to the particular target specificity, the type of disease or disorder, the subject, and the nature and severity of the disease, the physical condition of the subject, the therapeutic regimen (e.g., whether a combination therapeutic agent is used), and the selected route of administration. In some embodiments, a dose of an antibody of the disclosure may range from about 0.0001 mg/kg to 100 mg/kg of the subject's body weight. An exemplary dosage regimen of an antibody of the disclosure entails administration of the antibody in multiple dosages over a prolonged period, for example, of at least six months.

Other known antibodies against CD94 may also be used in the methods provided herein. For example, the following anti-CD94 antibodies may be used: HP-3D9 (LSBio Catalog #LS-C134679-100; Abnova Catalog #: MAB6947); 212; 131412 (R&D Systems Catalog #: MAB1058); 13B146 (US Biological Catalog #: 030068); 13B147 (US Biological Catalog #: 030069); 1H1 (Abnova Catalog #: MAB10543); 3G2 (Biorbyt Catalog #: orb69389); DX22 (Biolegend Catalog #305502); REA113 (Miltenyi Biotec Catalog #: 130-098-967); KP43; EPR21003; AT13E3 (ATGen Catalog: ATGA0487); HP-3B1; 12K45; and B-D49.

B. Diseases

There are 9 distinct diseases involving NK/T cell lymphoma: extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL and adult TCL. See, e.g., Bajaj, 2019. NK/T cell lymphoma affects various organs such as skin, GI, liver, spleen, bone marrow. Symptoms of NK/T cell lymphoma include enlarged lymph nodes of the neck. Advantageously, the methods described herein may be used, e.g., to reduce the number of abnormal or pathologic NK cells and/or T cells (e.g., CD4+ T cells, CD8+ T cells, CD4+ and CD8+ T cells) that express CD94 via mechanisms such as ADCC that employ NK cells, essentially using the pathologic cells to eliminate each other.

The methods described herein may also be used, e.g., to reduce the number of abnormal or pathologic NK and/or T cells that express CD94 and are associated with a NK/T cell lymphoma, such as extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL (not otherwise specified), angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL, via mechanisms such as ADCC that employ NK cells, essentially using the pathologic cells to eliminate each other.

There are 3 distinct diseases involving LGLs: T-cell LGL (T-LGL) leukemia; chronic lymphoproliferative disorders of NK cells (CLPD-NK, formerly NK-LGL); and aggressive NK-cell leukemias, such as aggressive natural killer leukemia (ANKL) and extranodal NKL nasal type (ENKL).

In addition to the NK or T LGL leukemias, NK or LGL cells play key roles in rheumatoid arthritis (RA), Felty's syndrome, aggressive NK leukemia, Inclusion body myositis (IBM), inflammatory bowel disease (IBD), and other diseases. Non-limiting examples of diseases and disorders in which LGL and NK cells play a role include LGL leukemia, Rheumatoid arthritis, Felty's syndrome, aggressive NK leukemia, IBM, and IBD. Advantageously, the methods described herein may be used, e.g., to reduce the number of abnormal or pathologic NK cells (e.g., CLPD-NK, ANKL, or ENKL cells) via mechanisms such as ADCC that employ NK cells, essentially using the pathologic cells to eliminate each other. For exemplary descriptions of symptoms of these diseases, see, e.g., Lamy, et al, Blood, 2017 x Vol. 129, No. 9; Loughran Blood, VOl 82, NO 1 (July I), 1993: pp 1-14; Semenzato G, et al, Blood. 1997; 89(1):256-260; and Bourgault-Rouxel, et al, Leuk Res. 2008; 32(1):45-48.

(i) CLPD-NK

Chronic lymphoproliferative disorders of NK cells (CLPD-NK), also referred to as NK-LGL leukemia, chronic NK cell lymphocytosis, chronic NK-LGL lymphoproliferative disorder (LPD), NK cell lineage granular lymphocyte proliferative disorder, NK cell LGL lymphocytosis, or indolent granular NK cell LPD is generally characterized by a persistent (e.g., 6 months or greater) increase in peripheral blood NK cells (e.g., $\geq 2 \times 10^9$/L).

Symptoms of CLPD-NK include variable cytopenias such as neutropenia and anemia, fatigue, fever, night sweats, recurrent infections, rheumatoid arthritis, lymphadenopathy, hepatosplenomegaly, skin lesions, hematologic neoplasms, vasculitis, neuropathy, and autoimmune disorders.

In some embodiments of the methods provided herein, the disease or disorder is CLPD-NK, and administration of the antibody results in a reduction in one or more CLPD-NK symptoms in the subject. In some embodiments, the reduction in the number of peripheral blood LGL and/or NK cells in the subject after administration of the antibody results in a reduction in one or more CLPD-NK symptoms in the subject.

Symptoms of CLPD-NK may be measured by any method known in the art, such as using laboratory tests to measure anemia, neutropenia, complete blood counts, and/or magnetic resonance imaging (MRI), CT scan, palpation, or ultrasound (e.g., to determine hepatosplenomegaly), bone marrow exams, and flow cytometry. Methods for measuring symptoms of CLPD-NK are described, e.g., in Swerdlow, S. H. et al. (2016) Blood 127:2375-2390.

(ii) LGL Leukemia

Large granular lymphocytic (LGL) leukemia is a chronic lymphoproliferative disorder that exhibits a chronic elevation in large granular lymphocytes (LGLs) in the peripheral blood and is called T-cell LGL leukemia.

Symptoms of LGL leukemia include splenomegaly, B symptoms (e.g., systemic symptoms such as fever, night sweats, and weight loss), anemia, neutropenia, and recurrent infections. Rheumatoid arthritis is often also found in people with T-cell LGL leukemia.

In some embodiments of the methods provided herein, the disease or disorder is LGL leukemia, and administration of the antibody results in a reduction in one or more LGL leukemia symptoms in the subject. In some embodiments, the reduction in the number of peripheral blood LGL and/or NK cells in the subject after administration of the antibody results in a reduction in one or more LGL leukemia symptoms in the subject.

Symptoms of LGL leukemia may be measured by any method known in the art, such as using laboratory tests to measure anemia, neutropenia, and other cytopenias, complete blood counts, magnetic resonance imaging (MRI), CT scan, palpation, or ultrasound (e.g., to determine splenomegaly), bone marrow exams, and flow cytometry. Methods for measuring symptoms of LGL leukemia are described, e.g., in Swerdlow, S. H. et al. (2016) *Blood* 127:2375-2390.

(iii) Felty's Syndrome

Felty's syndrome is an autoimmune disease characterized by rheumatoid arthritis, splenomegaly (e.g., inflammatory splenomegaly), and a reduced number of neutrophils in the blood. Symptoms of Felty's syndrome include painful, stiff, and/or swollen joints, physical findings associated with rheumatoid arthritis, splenomegaly, neutropenia, infections, keratoconjunctivitis sicca, fever, weight loss, fatigue, discoloration of the skin, sores (e.g., ulcers), hepatomegaly, anemia, thrombocytopenia, abnormal liver function, enlarged lymph nodes, and vasculitis.

In some embodiments of the methods provided herein, the disease or disorder is Felty's syndrome, and administration of the antibody results in a reduction in one or more Felty's syndrome symptoms in the subject. In some embodiments, the reduction in the number of peripheral blood LGL and/or NK cells in the subject after administration of the antibody results in a reduction in one or more Felty's syndrome symptoms in the subject. Symptoms of Felty's syndrome include, without limitation, joint inflammation, joint pain, and splenomegaly.

Symptoms of Felty's syndrome may be measured by any method known in the art, such as using laboratory tests to measure anemia, neutropenia, thrombocytopenia, and other cytopenias, complete blood counts, magnetic resonance imaging (MRI), CT scan, or ultrasound (e.g., to determine splenomegaly and/or hepatomegaly), laboratory tests for abnormal liver function, palpation to determine splenomegaly and/or hepatomegaly, flow cytometry, disease activity score-28 (DAS-28, e.g., as used for monitoring rheumatoid arthritis symptoms), and DAS-28 with erythrocyte sedimentation rate (ESR).

(iv) Rheumatoid Arthritis

Rheumatoid arthritis is an autoimmune disorder that primarily affects the joints, but can also affect other organs and can be associated with cardiovascular disease, osteoporosis, interstitial lung disease, infection, cancer, fatigue, and depression. Symptoms of rheumatoid arthritis include swollen, tender, and warm joints, joint inflammation, joint pain, joint stiffness, splenomegaly, rheumatoid nodules (e.g., in the skin), necrotizing granuloma, vasculitis, pyoderma gangrenosum, Sweet's syndrome, drug reactions, erythema nodsum, lobe pannicultis, atrophy of finger skin, palmar erythema, skin fragility, diffuse alopecia areata, lung fibrosis, Caplan's syndrome, exudative pleural effusions, atherosclerosis, myocardial infarction, stroke, pericarditis, endocarditis, left ventricular failure, valvulitis, fibrosis of the heart and/or blood vessels, anemia, increased platelet count, low white blood cell count, renal amyloidosis, episcleritis, scleritis, keratoconjuctivitis sicca, keratitis, loss of vision, liver problems, peripheral neuropathy, mononeuritis multiplex, carpal tunnel syndrome, myelopathy, atlanto-axial subluxation, vertebrae slipping, fatigue, low grade fever, malaise, morning stiffness, loss of appetite, loss of weight, osteoporosis, cancer (e.g., lymphoma, skin cancer), and periodontitis.

In some embodiments of the methods provided herein, the disease or disorder is rheumatoid arthritis, and administration of the antibody results in a reduction in one or more rheumatoid arthritis symptoms in the subject. In some embodiments, the reduction in the number of peripheral blood LGL and/or NK cells in the subject after administration of the antibody results in a reduction in one or more rheumatoid arthritis symptoms in the subject.

In some embodiments, symptoms and disease status/progression of rheumatoid arthritis are measured according to the 2010 ACR/EULAR Rheumatoid Arthritis Classification Criteria (see, e.g., Aletaha et al., (2010) Annals of Rheumatic Diseases, 69(9):1580-8). Symptoms of rheumatoid arthritis may also be measured by any method known in the art, such as using laboratory tests to measure erythrocyte sedimentation rates, C-reactive protein, rheumatoid factor, anti-citrullinated protein antibodies, anemia and other cytopenias, increased platelet count, low white blood cell count, complete blood counts, renal amyloidosis, medical imaging such as X-rays, MRI, CT-scans, ultrasound (e.g., ultrasonography using a high-frequency transducer; Doppler ultrasound), flow cytometry, disease activity score-28 (DAS-28), and DAS-28 with erythrocyte sedimentation rate (ESR).

(v) Aggressive NK Leukemia

Aggressive NK-cell leukemia is an aggressive disease with systemic proliferation of NK cells and a rapidly declining clinical course. Aggressive NK leukemia may also be referred to as aggressive NK-cell lymphoma. Symptoms of aggressive NK-cell leukemia include constitutional symptoms (e.g., malaise, weight loss, fatigue), hepatosplenomegaly, lymphadenopathy, coagulopathies, hemophagocytic syndrome, multi-organ failure, infections such as Epstein-Barr virus, allergic reactions (e.g., allergic reactions to insect bites, such as mosquito bites) that may result in necrosis and systemic symptoms such as fever, swollen lymph nodes, abdominal pain, diarrhea, and anaphylaxis.

In some embodiments of the methods provided herein, the disease or disorder is aggressive NK-cell leukemia, and administration of the antibody results in a reduction in one or more aggressive NK-cell leukemia symptoms in the subject. In some embodiments, the reduction in the number of peripheral blood LGL and/or NK cells in the subject after administration of the antibody results in a reduction in one or more aggressive NK-cell leukemia symptoms in the subject.

Symptoms of aggressive NK leukemia may be measured by any method known in the art, such as using laboratory tests, e.g., to measure anemia, neutropenia, and other cytopenias, complete blood counts, and/or magnetic resonance imaging (MRI), CT scan, palpation, or ultrasound (e.g., to determine splenomegaly), bone marrow exams, and flow cytometry. Methods for measuring symptoms of aggressive NK leukemia are described, e.g., in Swerdlow, S. H. et al. (2016) *Blood* 127:2375-2390.

(vi) Inclusion Body Myositis

Inclusion Body Myositis (IBM), also referred to as sporadic inclusion body myositis, is an inflammatory muscle disease characterized by autoimmune and degenerative processes that result in progressive weakness and wasting of distal and/or proximal muscles. Generally, IBM is characterized by invasion of immune cells into muscle tissues. In some cases, patients with IBM have elevated creatine kinase levels in the blood. Symptoms of IBM include progressive muscle weakness, muscle wasting/atrophy, frequent tripping and falling, difficulty manipulating fingers, foot drop, restricted mobility, impaired balance, muscle pain, dysphagia, and fatigue.

In some embodiments of the methods provided herein, the disease or disorder is IBM, and administration of the antibody results in a reduction in one or more IBM symptoms in the subject. In some embodiments, the reduction in the number of peripheral blood LGL and/or NK cells in the subject after administration of the antibody results in a reduction in one or more IBM symptoms in the subject.

Symptoms of IBM may be measured by any method known in the art, such as muscle biopsies, blood tests (e.g., to measure creatine kinase), electromyography (EMG) studies, blood tests to measure antibodies to NT5C1A, flow cytometry, and myositis disease activity assessment tools including without limitation Myositis Intention to Treat Activity Index (MITAX) and Myositis Disease Activity Assessment Visual Analogue Scales (MYOACT).

(vii) Inflammatory Bowel Disease

Inflammatory bowel disease (IBD) refers to a class of inflammatory conditions of the colon and small intestine. Types of IBD include ulcerative colitis and Crohn's disease. Symptoms of IBD include diarrhea, fever, fatigue, abdominal pain, abdominal cramping, blood in the stool, reduced appetite, and weight loss.

In some embodiments of the methods provided herein, the disease or disorder is IBD, and administration of the antibody results in a reduction in one or more IBD symptoms in the subject. In some embodiments, the reduction in the number of peripheral blood LGL and/or NK cells in the subject after administration of the antibody results in a reduction in one or more IBD symptoms in the subject.

Symptoms of IBD may be measured by any method known in the art, such as laboratory blood tests for anemia, other cytopenias, or infections, fecal occult blood tests, colonoscopies, flexible sigmoidoscopy, upper endoscopy, capsule endoscopy, balloon-assisted enteroscopy, X-rays, CT-scans, MRI scans, ultrasound, and flow cytometry.

III. Pharmaceutical Formulations

In some embodiments, a pharmaceutical composition, a composition, or a pharmaceutical formulation refer to a biologically active compound (e.g., an antibody of the disclosure), optionally mixed with at least one pharmaceutically acceptable chemical component, such as, though not limited to carriers, stabilizers, diluents, dispersing agents, suspending agents, thickening agents, excipients and the like.

Pharmaceutical compositions, pharmaceutical formulations, and/or compositions of any of the antibodies of the disclosure for use in any of the methods as described herein may be prepared by mixing such antibody having the desired degree of purity with one or more optional pharmaceutically acceptable carriers (Remington's Pharmaceutical Sciences 16th edition, Osol, A. Ed. (1980)), in the form of lyophilized formulations or aqueous solutions.

Pharmaceutically acceptable carriers are generally non-toxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The formulation herein may also contain more than one active ingredient as necessary for the particular indication (e.g., a disease or disorder) being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g., films, or microcapsules.

The formulations to be used for in vivo administration are generally sterile. Sterility may be readily accomplished, e.g., by filtration through sterile filtration membranes.

IV. Kits and Articles of Manufacture

In another aspect of the disclosure, a kit or an article of manufacture containing materials useful for the methods provided herein, e.g., treatment of the diseases or disorders described above, reducing the number of peripheral blood NK cells and/or T cells that express CD94 in a subject, or inducing ADCC activity in a subject, are provided. The kit or article of manufacture may comprise a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for the methods provided herein, e.g., treatment of the diseases or disorders described above, reducing the number of peripheral blood NK cells and/or T cells that express CD94 in a subject, or inducing ADCC activity in a subject, and may have a sterile access port (for example the container may be an intravenous solution bag or a vial having a stopper pierceable by a hypodermic injection needle). At least one active agent in the composition is an antibody of the disclosure. The label or package insert indicates that the composition is used for the methods provided herein, e.g., treatment of the diseases or disorders described above, reducing the number of peripheral blood NK cells and/or T cells that express CD94 in a subject, or inducing ADCC activity in a subject. Moreover, the kit or article of manufacture may comprise (a) a first container with a composition contained therein, wherein the composition comprises an antibody of the disclosure; and (b) a second container with a composition contained therein, wherein the composition comprises a further therapeutic agent. The kit or article of manufacture in this embodiment of the invention may further comprise a package insert indicating that the compositions can be used to treat a particular disease or disorder, e.g., as described herein, to reduce the number of peripheral blood NK cells and/or T cells that express CD94 in a subject, or to induce ADCC activity in a subject. Alternatively, or additionally, the kit or article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Anti-CD94 Antibody Production and Evaluation

This example describes the production and characterization of antibodies specific to human CD94.
Materials and Methods
Anti-CD94 Antibody Production and Screening Four-week old, ATX-Gx Alloy transgenic mice (mice that produce human antibodies) were immunized subcutaneously with C-terminal His-tagged CD94 for five weeks, with one boost of antigen per week. Antibody titers in mouse serum were assessed during pre- and post-boosts via ELISA and flow cytometry. The mice with the highest serum antibody titer were selected to supply B cells for the generation of hybridomas.

Prior to cell fusion, mice were administered with one additional boost of CD94-His antigen. The mice were then sacrificed and their spleens harvested. Spleen cells and SP2/0-Ag14 myeloma cells were mixed, and fusion was then induced by incubation at 37° C. in the presence of polyethylene glycol (PEG) or electroporation. The cells were then harvested and plated into 96-well plates with limited dilution to achieve one cell per well. The cells were subsequently treated with hypoxanthine, aminopterin and thymidine (HAT) medium and selected for over 2 weeks in culture.

Hybridoma supernatant were screened using ELISA and flow cytometry to identify candidates specific towards CD94. For ELISA, CD94-His antigen was immobilized on plates and 100 μl of each supernatant was incubated with antigen. A fluorescently labeled secondary antibody was used to detect antibodies captured on the ELISA plate, and positive hits were validated by analysis of antibody binding on human primary NK cells using flow cytometry. Cynomolgus CD94 cross-reactivity was assessed by antibody binding to cyno-CD94-expressing BaF3 cells using flow cytometry.

Verification of VH and VL sequences were performed using standard RNA extraction of hybridomas, followed by reverse transcription of RNA to cDNA and PCR using Alloy ATC-Gx specific primers.

Healthy Donor and Patient Samples

Fresh healthy donor buffy coats were obtained from Stanford Blood Center. Peripheral blood mononuclear cells (PBMCs) were isolated via ficoll-paque (GE Healthcare, Chicago, Ill.) separation and cryopreserved in Bambanker cell freezing media (Bulldog-Bio, Portsmouth, N.H.). Briefly, buffy coats were diluted in phosphate buffered saline (PBS) in a 1:1 ratio, followed by layering of the diluted buffy coat and centrifugation at 760 g in ficoll. The PBMC layer was isolated and washed in PBS prior to downstream analysis. Peripheral blood leukocytes (PBLs) were isolated through red blood cell lysis.

Antibody Affinity Assays

Healthy donor PBMCs were seeded in 96 well plates at a density of 100,000 cells per well, incubated with human Fc block (Biolegend) and cell viability dye (Thermo Fisher) for 30 minutes on ice and protected from light. The cells were washed once with FACS buffer (PBS with 2% IgG low FBS). anti-CD94 antibodies at concentrations of 100 nM to 0.046 nM, 1:3-fold dilutions, were incubated with cells for 30 minutes on ice and protected from light. The cells were then washed and incubated with goat IgG anti-mouse Fcγ specific AF647 secondary antibody or goat (Fab)2 fragment anti-human Fcγ specific AF647 secondary antibody (Jackson immuno research), anti-CD3 pacific blue-labelled and anti-CD56 FITC-labelled antibodies (Biolegend) for 30 minutes on ice and protected from light. After incubation, the cells received a final wash in FACS buffer before quantification on the Cytoflex (Beckman Coulter). All data acquisition and fluorescence compensation were performed using CytoFlex (Beckman Coulter, Atlanta, Ga.). Data analysis was performed using FlowJo software. NK cells were identified through gating on lymphocytes on the forward and side scatter, followed by doublet and dead cell exclusion, and gated on the CD3−CD56+ population. CD94 expression was then quantified on the CD3−CD56+NK cell population. Antibody titration curves and EC50s were generated using Graphpad Prism.

Antibody Cynomolgus CD94 Cross-Reactivity Assay

Cynomolgus CD94-expressing HEK293 cells were seeded in 96-well plates at a density of 100,000 cells per well, incubated with cell viability dye (Thermo Fisher) for 30 minutes on ice and protected from light. The cells were washed once with FACS buffer (PBS with 2% IgG low FBS). Hybridoma supernatants, anti-CD94 antibodies and isotype controls were incubated with cells for 30 minutes on ice and protected from light. The cells were then washed and incubated with goat IgG anti-mouse Fcγ specific AF647 secondary antibody or goat (Fab)2 fragment anti-human Fcγ specific AF647 secondary antibody (Jackson ImmunoResearch) for 30 minutes on ice and protected from light. After incubation, the cells received a final wash in FACS buffer before quantification on the Cytoflex (Beckman Coulter). All data acquisition and fluorescence compensation were performed using CytoFlex (Beckman Coulter, Atlanta, Ga.). Data analysis was performed using FlowJo software. HEK293 cells were identified through gating on the major cell population using forward and side scatter, followed by doublet and dead cell exclusion. CD94 expression was then quantified on this population. MFI bar graphs were generated using Graphpad Prism.

HLA-E Blocking Assay

Healthy donor PBMCs were seeded in 96-well plates at a density of 100,000 cells per well, incubated with human Fc block (Biolegend) and cell viability dye (Thermo Fisher) for 30 minutes on ice and protected from light. The cells were washed once with FACS buffer (PBS with 2% IgG low FBS). anti-CD94 antibodies at EC80 concentrations were incubated with cells for 30 minutes on ice and protected from light. After incubation with the anti-CD94 antibodies, the cells were washed and incubated with HLA-E tetramer PE (Creative Biolabs), anti-CD3 pacific blue-labelled, and anti-CD56 FITC-labelled antibodies (Biolegend) for 30 minutes on ice and protected from light. The cells then received a final wash in FACS buffer before quantification on the Cytoflex (Beckman Coulter). All data acquisition and fluorescence compensation were performed using CytoFlex (Beckman Coulter, Atlanta, Ga.). Data analysis was performed using FlowJo software. NK cells were identified through gating on lymphocytes on the forward and side scatter, followed by doublet and dead cell exclusion, and gated on the CD3−CD56+ population. HLA-E expression was then quantified on the CD3−CD56+NK cell population. Percent blocking was calculated as 100−((percent HLA-E positive for anti-CD94 antibody)/(percent HLA-E positive for isotype)*100).

Antibody Competition Assay

Healthy donor PBMCs were seeded in 96-well plates at a density of 100,000 cells per well, incubated with human Fc block (Biolegend) and cell viability dye (Thermo Fisher) for 30 minutes on ice and protected from light. The cells were washed once with FACS buffer (PBS with 2% IgG low FBS). Unconjugated anti-CD94 antibodies at EC80 concentrations, CD3 FITC and CD56 PE antibodies, and APC-labeled anti-CD94 antibodies were incubated with cells for 30 minutes on ice and protected from light. The cells then received a final wash in FACS buffer before quantification on the Cytoflex (Beckman Coulter). All data acquisition and fluorescence compensation were performed using CytoFlex (Beckman Coulter, Atlanta, Ga.). Data analysis was performed using FlowJo software. NK cells were identified through gating on lymphocytes on the forward and side scatter, followed by doublet and dead cell exclusion, and gated on the CD3−CD56+ population. Anti-CD94 APC was then quantified on the CD3−CD56+NK cell population. All titration curves and EC50s were generated using Graphpad Prism.

Antibody Internalization Assay

Healthy donor PBMCs were seeded in 96-well plates at a density of 100,000 cells per well in RPMI with 10% IgG low FBS, incubated with human Fc block (Biolegend) for 10 minutes at room temperature. Unconjugated anti-CD94 antibodies were incubated with the cells at EC80 concentrations at 4° C. and 37° C. for 30 minutes to 24 hours. The cells were washed once with FACS buffer (PBS with 2% IgG low FBS) and kept on ice for the remaining procedure. Goat anti-mouse Fcγ specific antibodies were incubated with cells for 30 minutes on ice and protected from light. The cells were then washed once and CD94 expression was quantified on the Cytoflex. All data acquisition and fluorescence compensation were performed using CytoFlex (Beckman Coulter, Atlanta, Ga.). Data analysis was performed using FlowJo software. NK cells were identified through gating on lymphocytes on the forward and side scatter, followed by doublet and dead cell exclusion, and gated on the CD3−CD56+ population. Anti-CD94 APC was then quantified on the CD3−CD56+NK cell population. Percent decrease in MFI was calculated by computing the difference in MFI between 0.5 and 24 hours at 37° C. and multiplying by 100.

Antibody-Dependent Cellular Cytotoxicity Assay

Approximately $1 \times 10^5$-$2 \times 10^5$ fresh or frozen PBMCs were plated in tissue culture-treated 96-well U bottom plates in RPMI with 10% low IgG FBS. The cells were incubated overnight in $10^1$-$10^{-6}$ ug/ml in 10-fold dilutions of the human IgG1 isotype control antibody or the 1E4 fucosylated and 18H3-KIF antibody. The cells were then stained with fluorescently labelled antibodies against CD3, CD56 and CD16 to identify the remaining NK cells (see flow cytometry analysis). A minimum of 10,000 events were collected on the flow cytometer in the lymphocyte population. Percent NK/leukemic cell remaining was calculated by normalizing the absolute count by the cell numbers in the isotype treated conditions. The IC50 was determined using GraphPad Prism.

Results

Anti-CD94 antibodies were generated using a standard hybridoma technique, as described supra. Briefly, ATX-Gx Alloy transgenic mice were immunized with C-terminal His-tagged CD94 for five weeks. B cells from mice with the highest serum antibody titer after five weeks were used to generate hybridomas. The hybridomas were the screened through ELISA to identify candidates specific towards CD94.

Positive hits were validated by assessing binding to human NK cells by flow cytometry analysis. Binding of the anti-CD94 antibody clones to primary human NK cells was assessed by flow cytometry analysis. Supernatants from the anti-CD94 hybridomas were used to test binding of the anti-CD94 antibody clones. A commercially available anti-CD94 antibody, HP-3D9, and several IgG isotype controls were also tested for binding on NK cells.

Figure 2:
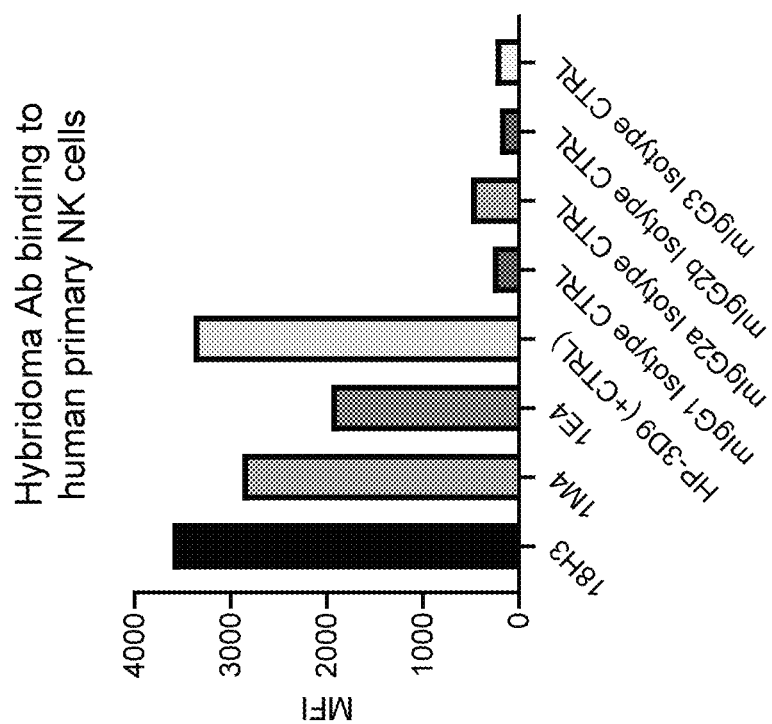
FIG. 2 shows the binding of anti-CD94 antibodies to human primary NK cells as measured by flow cytometry. Anti-CD94 hybridoma supernatants were screened on human primary NK cells by flow cytometry. HP-3D9 is a commercial anti-CD94 antibody that was used as a positive control. Mouse IgG1, IgG2a, IgG2b and IgG3 were used as negative controls. Anti-CD94 antibodies 18H3, 1M4 and 1E4 bound to CD94 expressed on human primary NK cells.

The affinity of the antibody clones was also assessed by flow cytometry analysis. FIG. 1 shows the titration curve generated for anti-CD94 antibody clone 18H3. Anti-CD94 antibody 18H3 showed an affinity of 2.6 nM on human primary NK cells. The affinities determined for the other anti-CD94 antibodies are listed in FIG. 11. As shown in FIG. 2, hybridoma supernatant screening revealed that 18H3, 1M4 and 1E4 bind to human primary NK cells, as measured by flow cytometry.

Figures 3A, 3B:
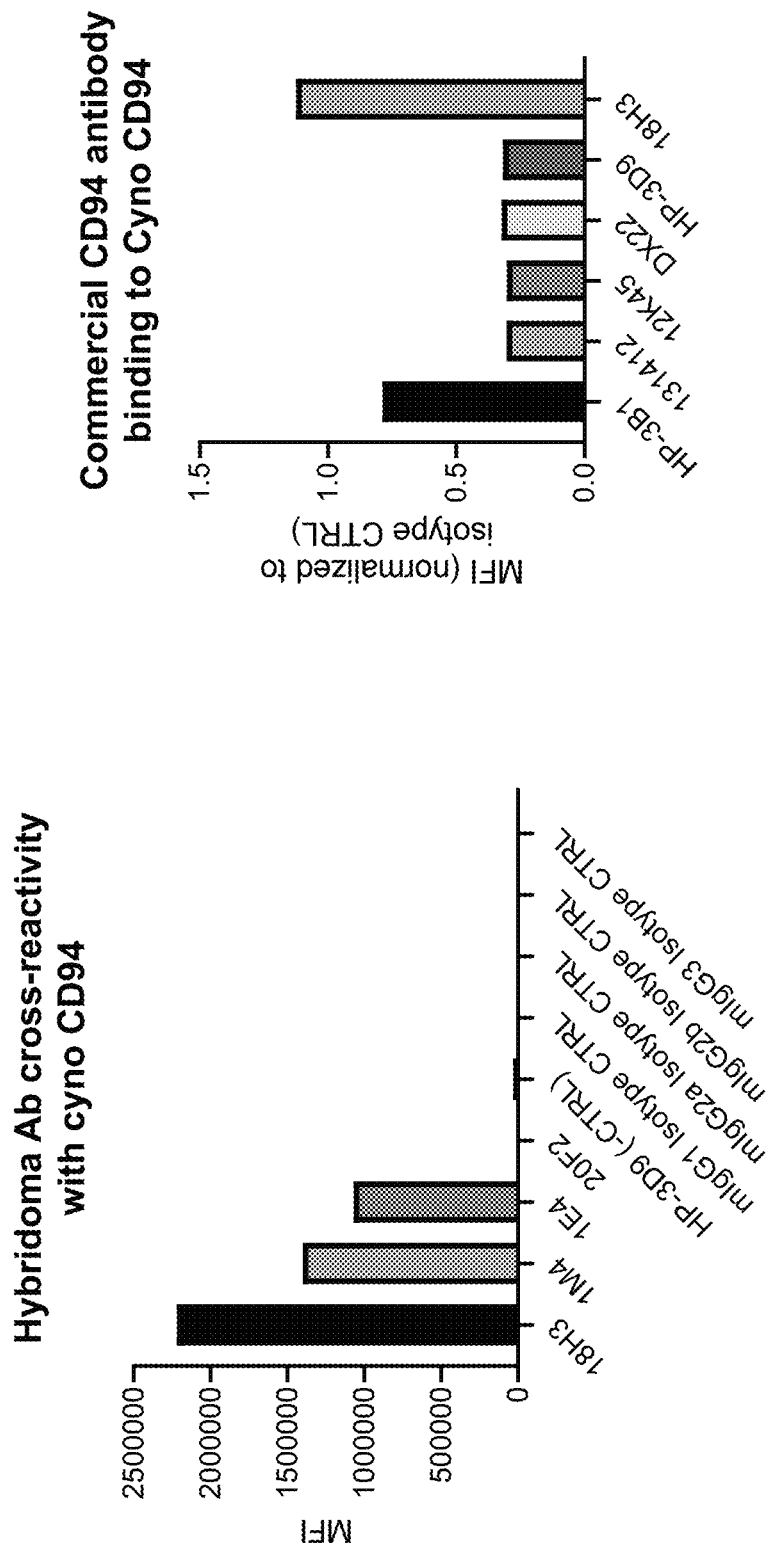
FIGS. 3A-3B show the cross-reactivity of anti-CD94 antibodies to cynomolgus CD94.
Figure 4A:
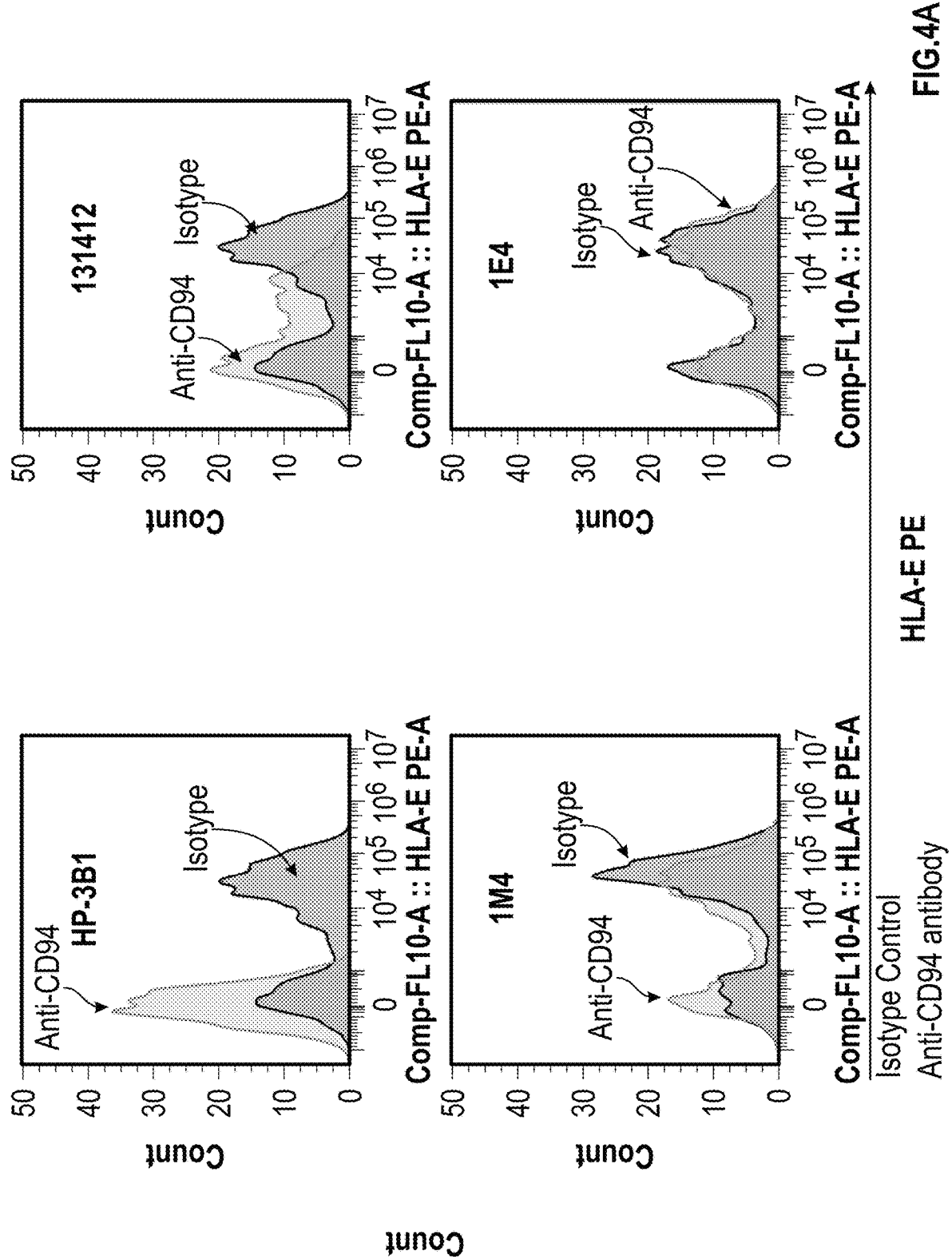
FIGS. 4A & 4B show the results of HLA-E tetramer blocking assays performed with anti-CD94 and commercially available anti-CD94 antibodies using flow cytometry. Healthy donor PBMCs were incubated with anti-CD94 antibodies. PE labeled HLA-E tetramer was then incubated with the cell and antibody mixture, and detected using flow cytometry. For HP-3B1, 131412, 12K45, DX22, 1M4 and 1E4, 2.5 µl of HLA-E tetramer reagent was used, while 5 µl was used for 18H3 and HP-3D9. Saturating concentrations of each antibody was used in this assay. The percent blocking was calculated as 100−((percent HLA-E positive for anti-CD94 antibody)/(percent HLA-E positive for isotype)*100). The 18H3 and 1E4 antibodies did not block HLA-E binding to CD94.
Figure 4B:
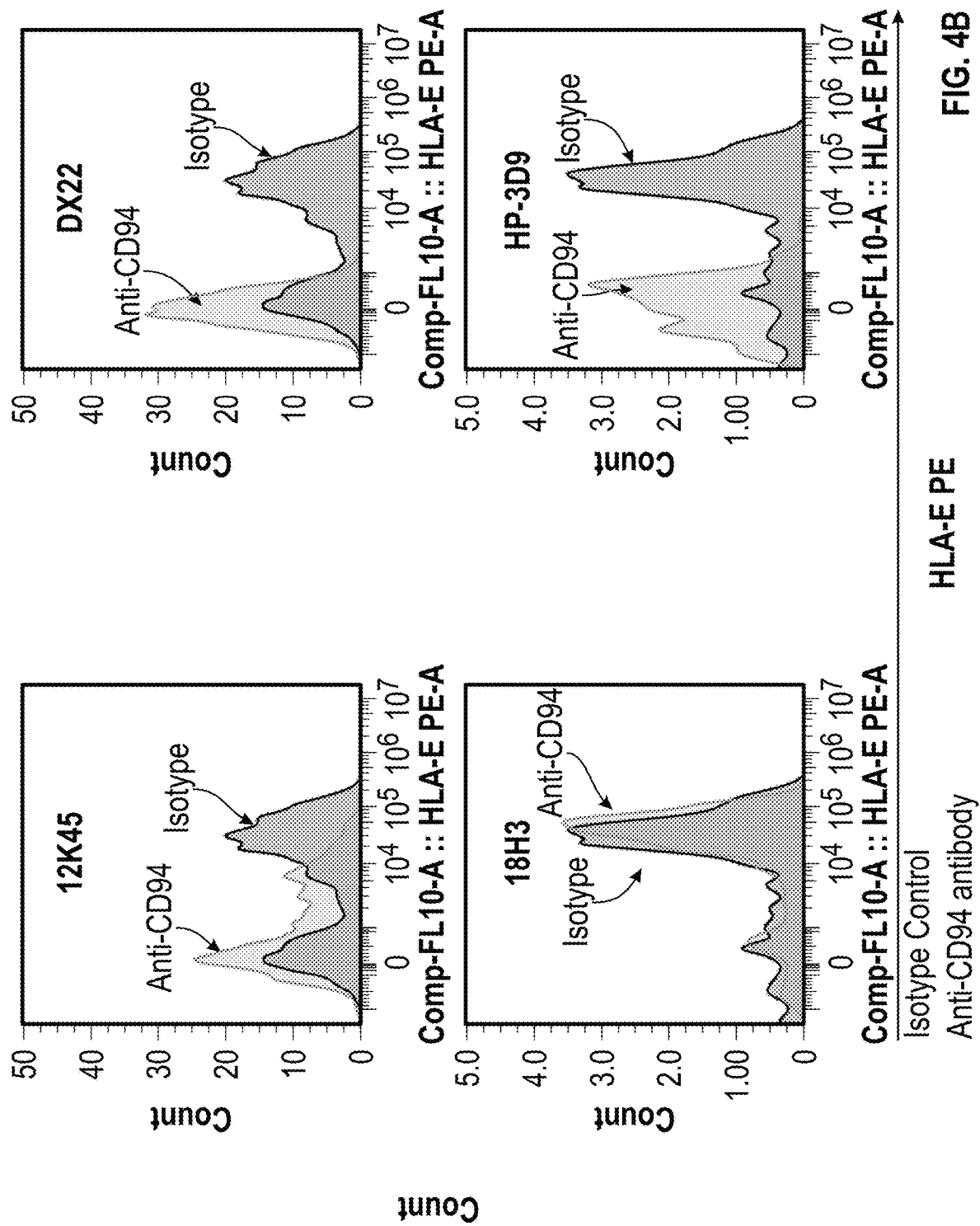
Figure 5A:
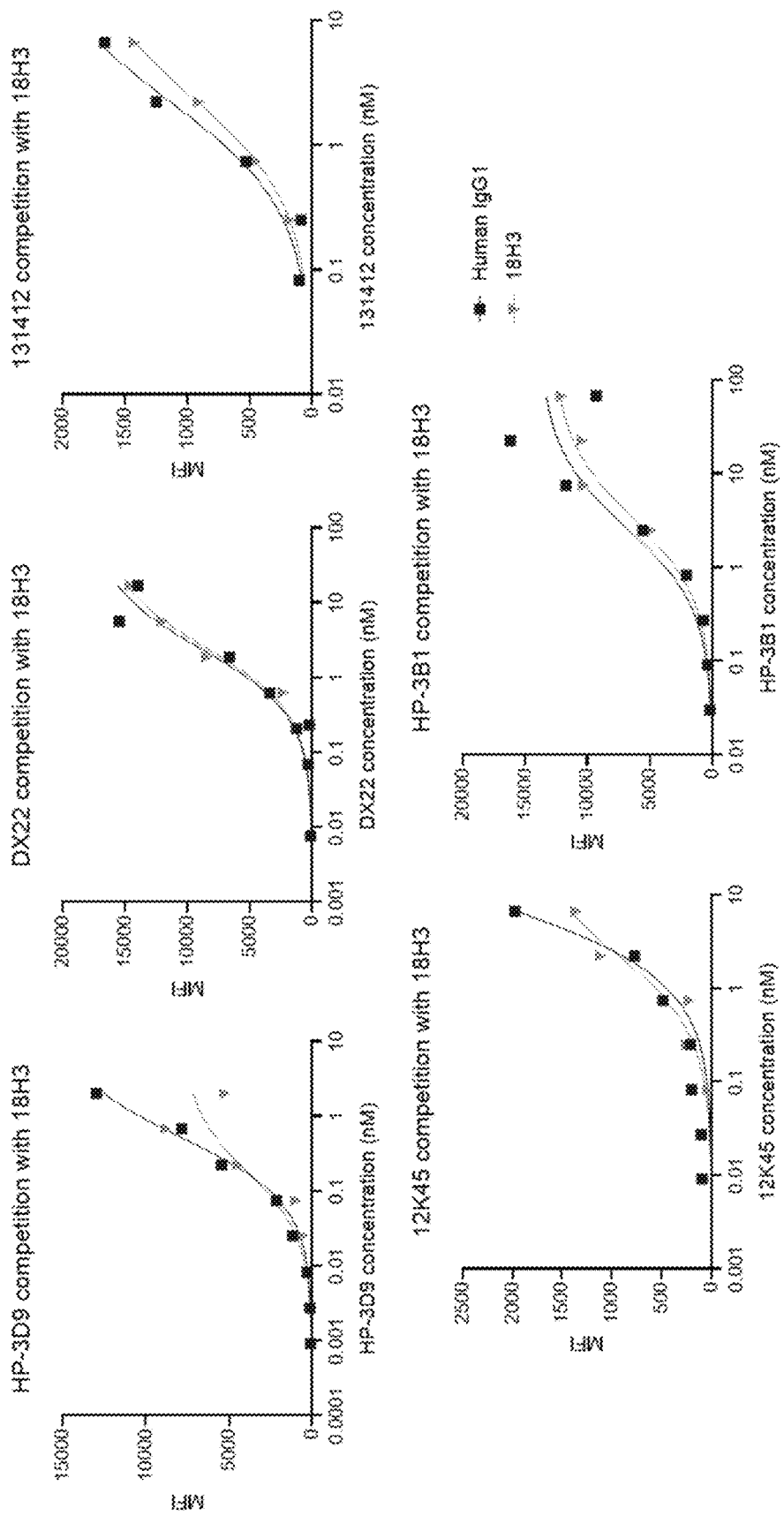
FIGS. 5A-5B show the results of competition assays performed for 18H3 anti-CD94 antibody evaluation. For all competition assays, 18H3 was incubated with PBMCs at a concentration of 1.3 µg/ml.
Figure 5B:
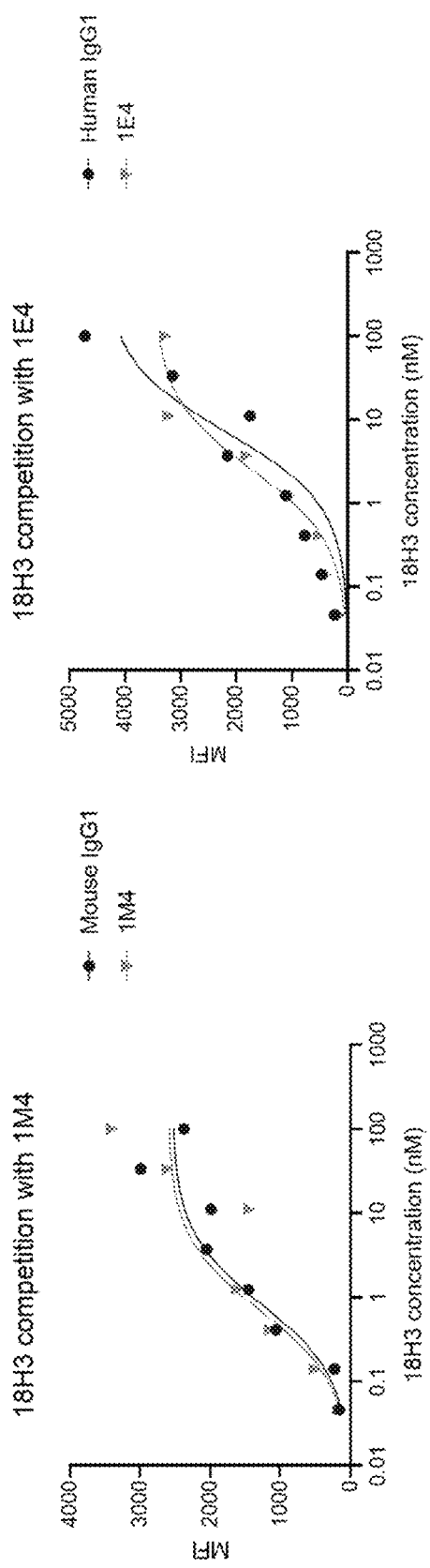
Figure 6A:
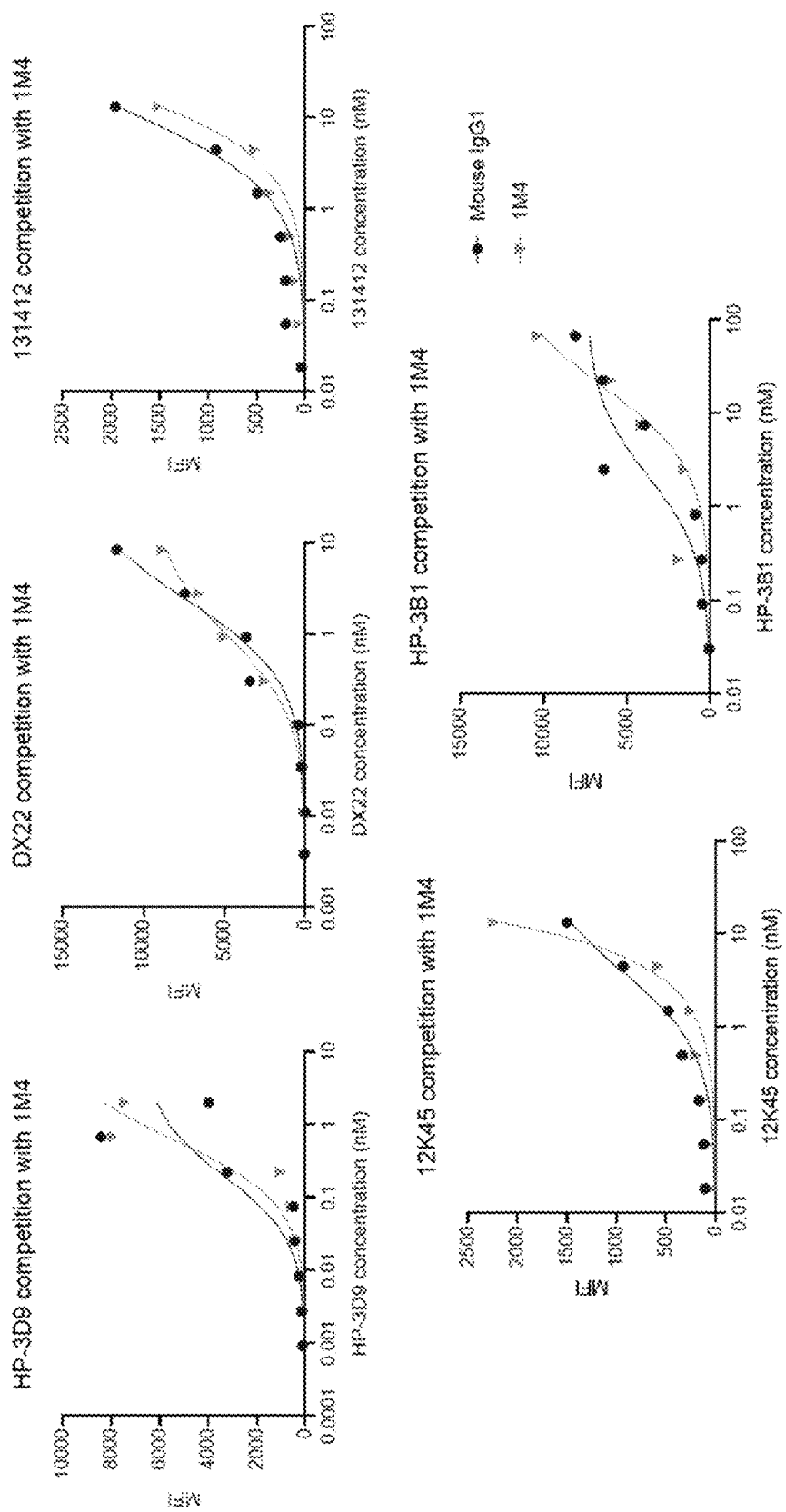
FIGS. 6A-6B show the results of competition assays performed for 1M4 anti-CD94 antibody evaluation. For all competition assays, 1M4 was incubated with PBMCs at a concentration of 8.5 µg/ml.
Figure 6B:
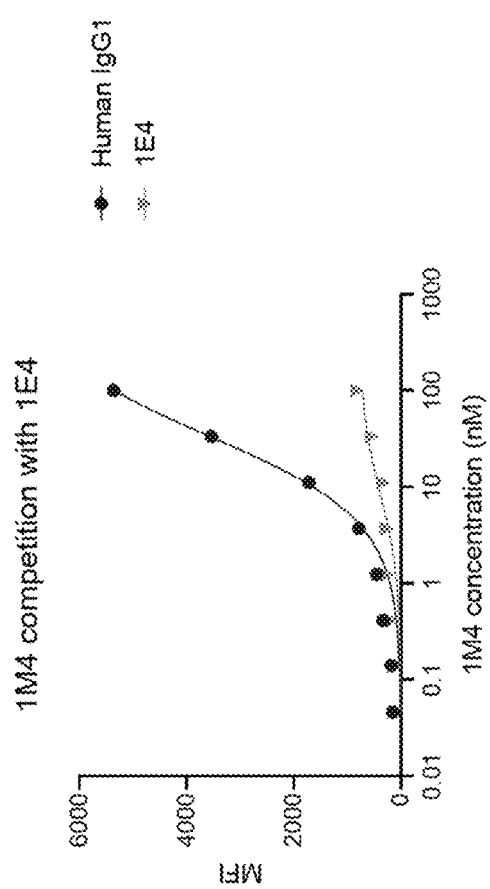

The anti-CD94 hybridoma supernatants were also tested for cross-reactivity to cynomolgus CD94. Hybridomas were screened for cross-reactivity to cynomolgus CD94 using cynomolgus CD94-expressing HEK293 cells by flow cytometry. As shown in FIG. 3A, this analysis revealed that clones 18H3, 1M4 and 1E4 cross-react with cynomolgus CD94. Supernatant from clone 20F2 did not cross-react with cynomolgus CD94, albeit being reactive to human CD94. The cross-reactivity of commercially available anti-CD94 antibodies was also evaluated. As shown in FIG. 3B, none of the commercially available anti-CD94 antibodies tested (HP-3D9, HP-3B1, 131412, 12K45, DX22) exhibited cross-reactivity to cynomolgus CD94.

These results indicate that anti-CD94 antibodies 18H3, 1M4 and 1E4 bind to an epitope that is not shared with HP-3D9, HP-3B1, 131412, 12K45, DX22, and 20F2 (not commercial) antibodies. The cross-reactivity of the 18H3, 1M4 and 1E4 antibodies suggests that they could be useful for cynomolgus monkey toxicity studies prior to phase I trials in human subjects.

Following validation, the VH and VL sequences were determined for the validated antibody clones. Table A summarizes the VH and VL sequences for three validated anti-CD94 clones, 18H3, 1M4 and 1E4. The framework and CDR sequences (bolded in Table A) were determined using the Kabat numbering scheme.

TABLE A

Sequences of anti-CD94 antibody clones

| Antibody clone | Heavy chain | Light chain |
|---|---|---|
| 18H3 | EVQLVQSGAEVKKPGESLKISCKGSGYRF TSYWIGWVRQMPGKGLEWMGIIYPGDS DTRYSPSFQGQVIISADKSITTAFLQWSSL KASDTAMYYCARPFDYGGSPGYFDYWG QGTLVTVSS (SEQ ID NO: 19) | DIQMTQSPSTLSASVGDRVTITCRAS QSIRSWLAWYQQKPGKAPKLLIYKA SSLESGVPSRFSGSGSGTEFTLTISSLQ PDDFATYYCQQYNTFWTFGQGTKV EIK (SEQ ID NO: 20) |
| 1M4 | QLVESGGGLVQPGGSLRLACAASGFTFSN YAMNWVRQAPGKGLEWVSVISGSGDTT YCADSVKGRFTISRDNSKNTLHLQLNSLR AEDTAVYYCAKNCYGSGSYYNHFDYWG QGTLVTVSS (SEQ ID NO: 21) | EIVMTQSPDSLAVSLGERATINCKSS QSVLYSSNRMNYLAWYQQKPGQPP NLLIYWASTRESGVPDRFSGSGSGTD FTLTISSLQAEDVAVYYCQQYYSIPL TFGGGTKVEIK (SEQ ID NO: 22) |
| 1E4 | QVTLRESGPALVKPTQTLTLTCTFSGFSLS TSDLCVSWIRQPPGKALEWLALIDWNDD KYYSTSLQTRLTISKDTSKNQVVLTMTN MDPVDTATYYCARTIAAAGPYDAFDIW GQGTMVTVSS (SEQ ID NO: 23) | DIVMTQSPDSLSVSLGERATINCKSS QSVLYGSNNKNYLAWYQQKPGQPP KLLIYWASTRKSGVPDRFSGSGSGT DFTLTISSLQAEDVAVYYCQEYYSL RFTEGPGTKVDIK (SEQ ID NO: 24) |

The validated anti-CD94 antibodies were further evaluated for their ability (or lack thereof) to block binding by HLA-E. HLA-E is the ligand of CD94/NKG2A heterodimers, and plays a crucial role in the inhibition of NK and CD8+ T cell activity when bound to CD94/NKG2A. Without wishing to be bound to theory, it is thought that the interaction between HLA-E and CD94/NKG2A may result in activation and proliferation of target cells. Thus, it is beneficial that the anti-CD94 antibody candidate does not block the CD94:HLA-E interaction in a diseased setting.

HLA-E blocking by anti-CD94 antibody clones and commercially available anti-CD94 antibodies was evaluated by flow cytometry. As shown in FIGS. 4A & 4B, 18H3 and 1E4 antibodies did not block HLA-E binding. Over 40% HLA-E blocking was observed for commercially available anti-CD94 antibodies, while 0% blocking was observed for the anti-CD94 antibodies. Because expression levels of CD94 varies from dim (~10,000 receptors) to bright (>100,000 receptors), we propose that if an antibody blocks more than 20% of HLA-E binding it can be considered as a ligand blocking antibody. Overall, this HLA-E blocking assay demonstrates that 18H3 and 1E4 antibodies do not block the interaction of CD94 with HLA-E, while commercially available CD94 antibodies block this interaction.

Competition assays were performed to determine if the newly identified antibodies bound to shared epitopes with themselves and existing antibodies. Anti-CD94 antibodies 18H3, 1M4, and 1E4 were assayed for competition with each other as well as with commercially available antibodies. As shown in FIGS. 5A-5B, 18H3 antibody binds to a unique epitope. 18H3 only partially competed with HP-3D9, and did not compete with the DX22, HP-3B1, 131412, 12K45, 1E4 and 1M4 antibodies. Thus, the 18H3 antibody binds to an epitope that is not shared with commercially available antibodies.

Similarly, 1M4 antibody did not compete with commercially available antibodies. As shown in FIGS. 6A-6B, 1M4 competed with 1E4 antibody, but did not compete with DX22, 131412, HP-3D9, 12K45 and HP-3B1.

Figure 7:
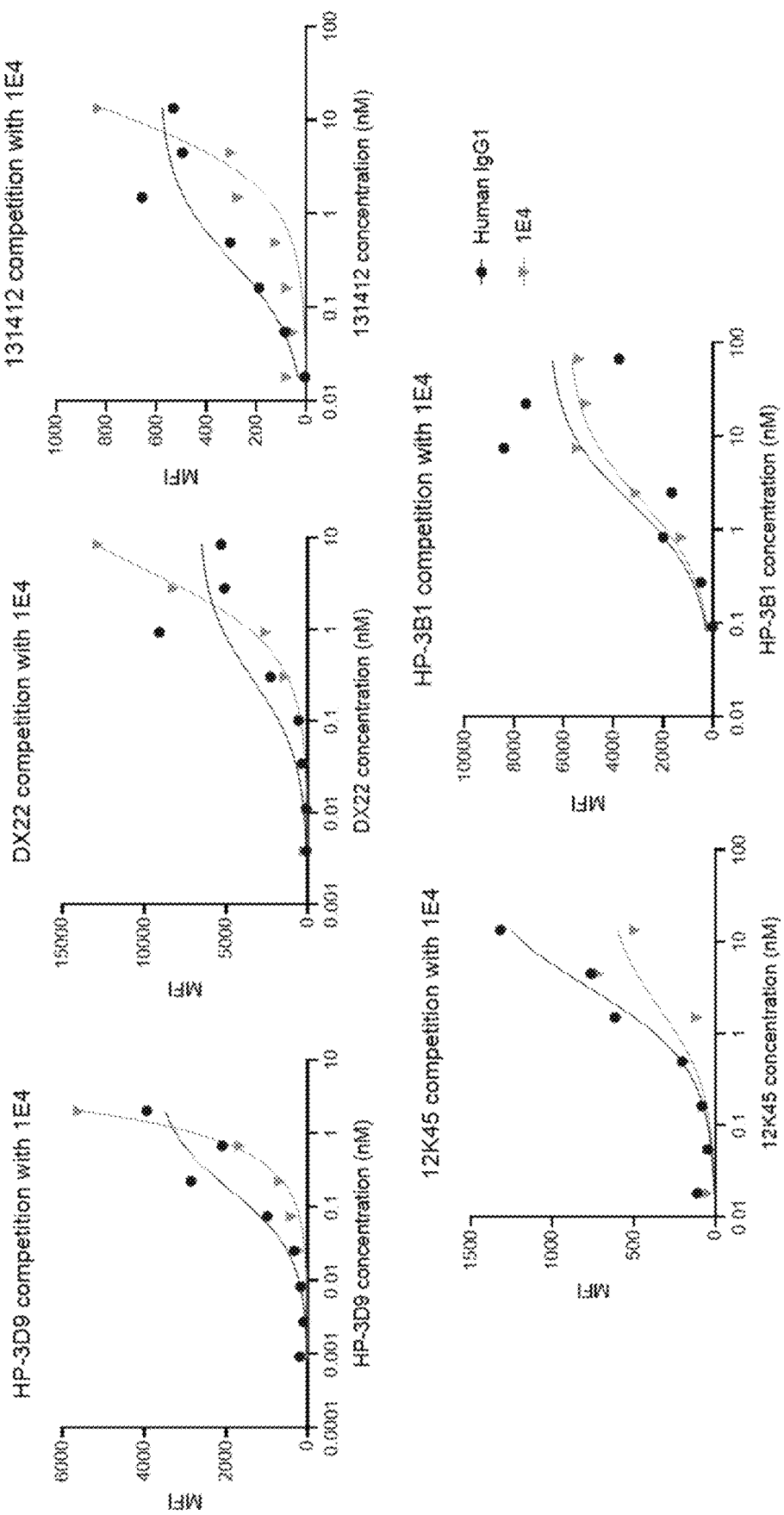
FIG. 7 shows the results of competition assays performed for 1E4 anti-CD94 antibody evaluation. For all competition assays, 1E4 was incubated with PBMCs at a concentration of 11 µg/ml. Commercially available anti-CD94 antibodies were titrated and incubated with PBMCs concurrently with 1E4. 1E4 antibody did not compete with four out of the five commercially available anti-CD94 antibodies tested, but partially competed with 12K45.

The 1E4 antibody did not compete with four out of the five commercially available anti-CD94 antibodies tested. As shown in FIG. 7, 1E4 partially competed with 12K45, but did not compete with HP-3D9, DX22, 131412 and HP-3B1.

Figure 8A:
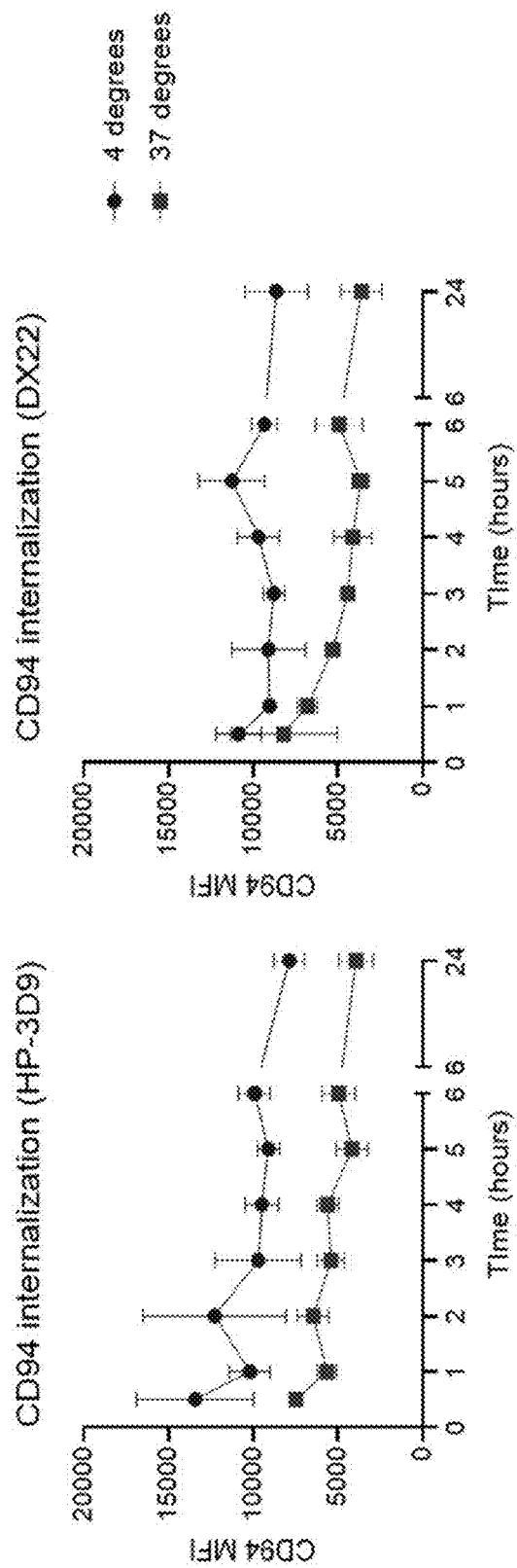
FIGS. 8A-8B show the results of an anti-CD94 antibody internalization assay. Healthy donor peripheral blood mononuclear cells (PBMCs) were incubated with unconjugated anti-CD94 antibodies at multiple time points ranging from 30 minutes to 24 hours. The cells were either kept at 4° C. to prevent internalization or 37° C. to induce internalization.
Figure 8B:
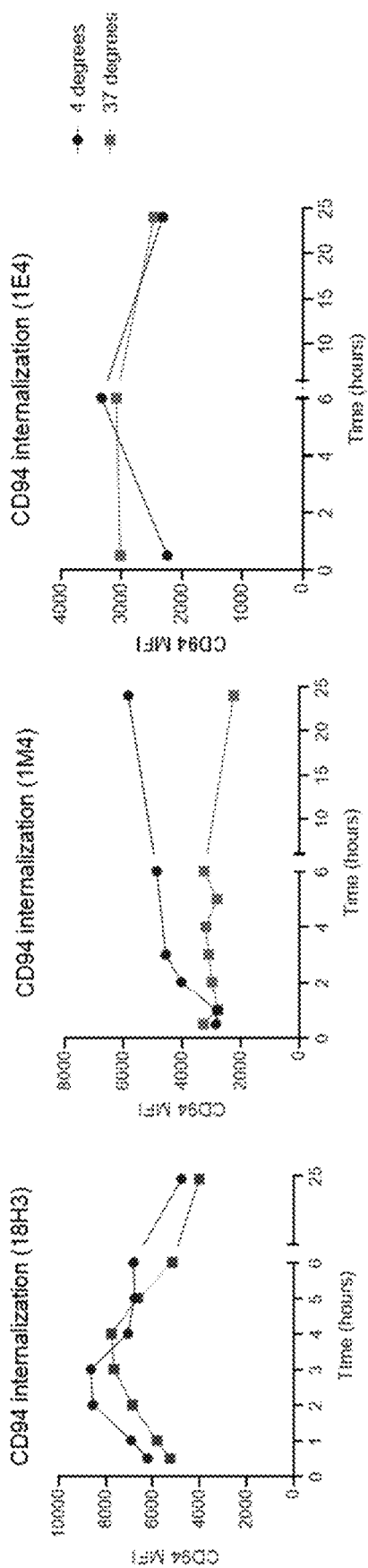

An antibody internalization assay was performed to evaluate internalization of CD94 receptors when bound by anti-CD94 antibody. In this assay, a cutoff of above 50% would be considered high degree of internalization. Without wishing to be bound to theory, it is thought that a low level of internalization would be beneficial for antibody-dependent cellular cytotoxicity (ADCC), as CD94 receptor would be retained on the cell surface and maintain a high receptor density for effector cells to execute ADCC. The results depicted in FIGS. 8A-8B show that CD94 receptor became internalized when bound to commercial anti-CD94 antibodies, but not when bound to 18H3, 1M4 and 1E4 antibodies. 18H3, 1M4, and 1E4 antibodies did not become internalized above 50% upon binding to CD94. In contrast, a 54%, 56%, 24%, 32%, 18% percent decrease in MFI was observed for HP-3D9, DX22, 18H3, 1M4 and 1E4, respectively, comparing 0.5 hours to 24 hours at 37° C.

Figure 9A:
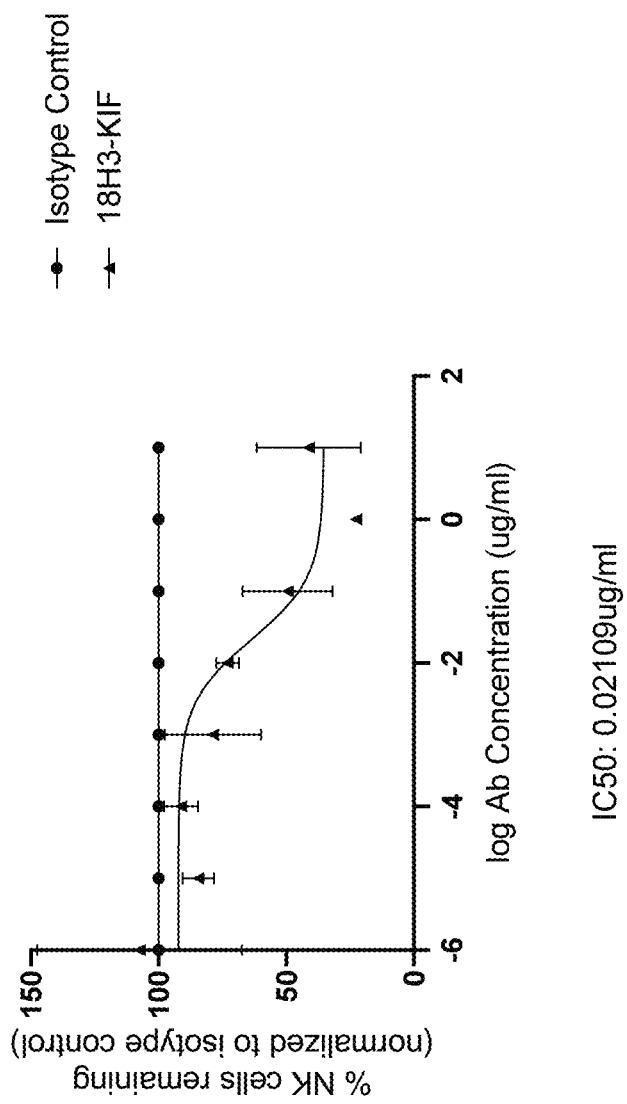
FIGS. 9A-9B show the results of an antibody-dependent cellular cytotoxicity (ADCC) assay for anti-CD94 antibody using healthy donor PBMCs. The 18H3 antibody was produced in Expi-CHO cells cultured in the presence of kifunensine, a potent inhibitor of the mannosidase I enzyme, which is used to produce 18H3-KIF mimicking non-fucosylated antibody. Fucosylated 1E4 antibody was used for the ADCC assay. PBMCs were plated in 96-well plates and incubated in the presence of anti-CD94 antibody ranging from $1 \times 10^{-6}$ to 10 µg/ml in 10-fold dilutions overnight. The number of NK cells was quantified by flow cytometry. The number of NK cells in the human IgG1 and anti-CD94 antibody treated conditions were normalized to NK cell number from human IgG1 treated wells.
Figure 9B:
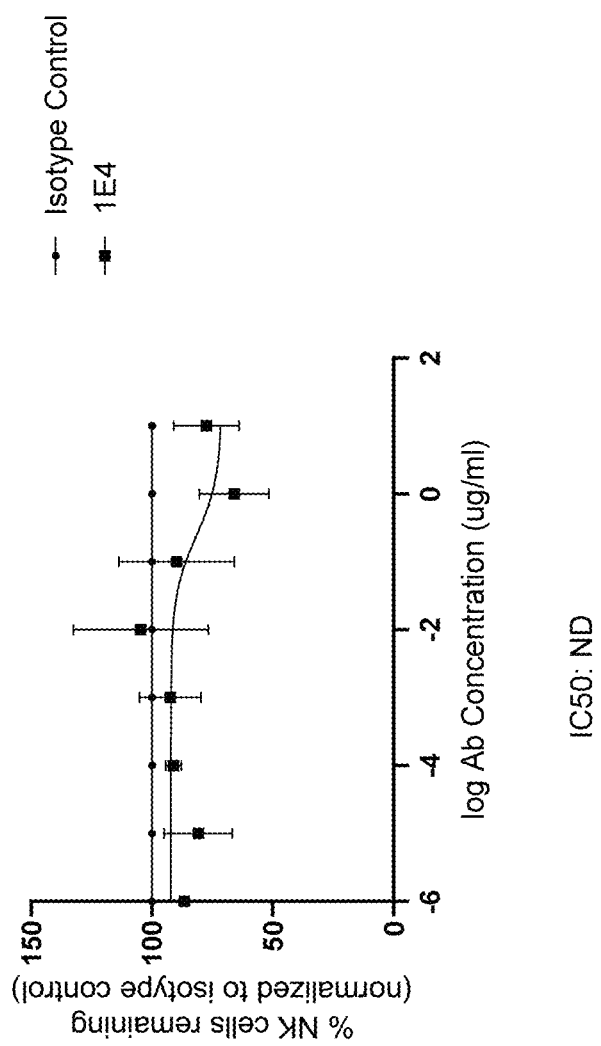

To test the ability of the anti-CD94 antibodies to induce ADCC of NK cells, an ADDC assay was performed using healthy donor PBMCs. For this assay, 18H3 antibody was produced in Expi-CHO cells cultured in the presence of kifunensine, a potent inhibitor of the mannosidase I enzyme, to produce 18H3-KIF mimicking non-fucosylated antibody. Fucosylated 1E4 antibody was also tested for ADCC. As shown in FIGS. 9A-9B, partially non-fucosylated, human IgG1 18H3 and fucosylated 1E4 depleted human NK cells in the PBMC pool of healthy donors in ex vivo culture after 24 hours of incubation. The depletion of NK cells by human IgG1 18H3 and 1E4 was concentration-dependent. The IC50 of 18H3-KIF was determined as 0.02 µg/ml, while the IC50 was undetermined for 1E4 antibody.

Figure 10:
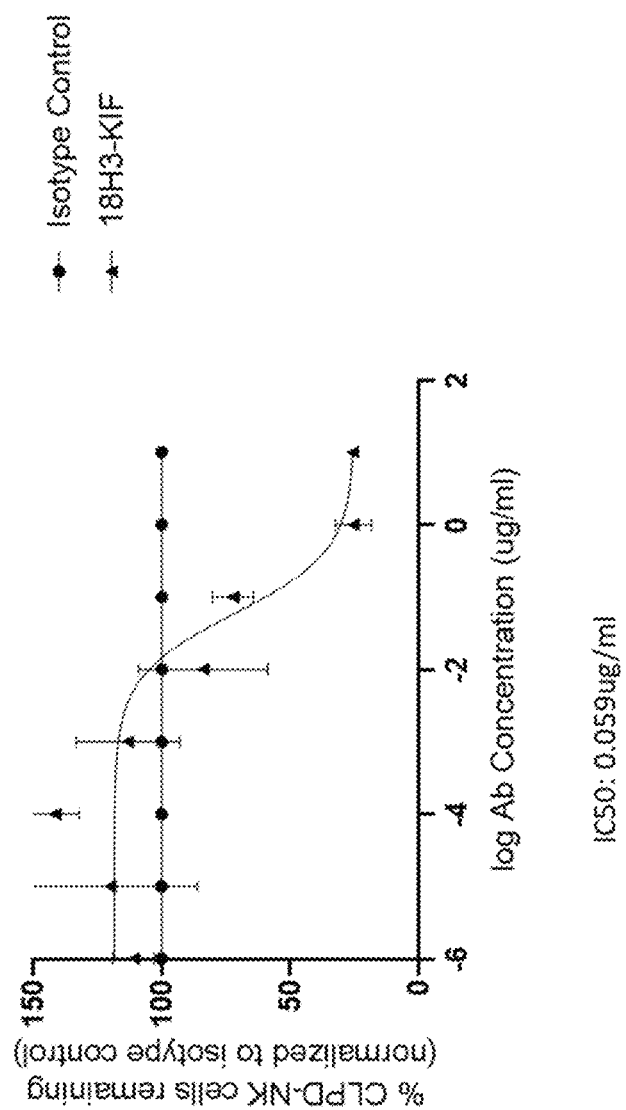
FIG. 10 shows the results of an anti-CD94 antibody ADCC assay using CLPD-NK patient PBMCs. 18H3 was produced in Expi-CHO cells cultured in the presence of kifunensine, a potent inhibitor of the mannosidase I enzyme, to produce 18H3-KIF mimicking non-fucosylated antibody. PBMCs were plated in 96-well plates and incubated in the presence of anti-CD94 antibody ranging from 1×10-6 to 10 ug/ml in 10-fold dilutions overnight. The number of CD3−CD16+ leukemic cells was quantified by flow cytometry. The number of leukemic cells in the human IgG1 and anti-CD94 antibody treated conditions were normalized to leukemic cell number from human IgG1 treated wells. Partially non-fucosylated, human IgG1 18H3 depleted human CLPD-NK leukemic cells in a concentration dependent manner.

Finally, the ability of the 18H3 antibody to induce ADCC of human leukemic cells was evaluated through an ADCC assay using cells from chronic lymphoproliferative disorder of NK cells (CLPD-NK) patients. For this assay, 18H3 antibody was produced in Expi-CHO cells cultured in the presence of kifunensine to produce 18H3-KIF mimicking non-fucosylated antibody. As shown in FIG. 10, partially non-fucosylated, human IgG1 18H3 depleted human CLPD-NK leukemic cells in a PBMC pool of a CLPD-NK patient in ex vivo culture after 24 hours of incubation. The 18H3 antibody depleted human CLPD-NK leukemic cells in a concentration dependent manner, with an IC50 of 0.059 µg/ml. This depletion was selective, as no other cell types were affected.

FIG. 11 summarizes the characteristics and functional assessment of the anti-CD94 antibodies relative to the commercially available antibodies as described above.

Example 2: Anti-CD94 Antibody ATX-130 Characterization

This example describes the characterization of an antibody specific to human CD94.

Materials and Methods

Materials and methods used in this experiment are detailed below. Unless otherwise noted, donor samples and primary cells were prepared as described in Example 1. Unless otherwise noted, antibody affinity assays, HLA-E blocking assay, antibody competition assay, antibody internalization assay, and antibody-dependent cellular cytotoxicity assay were performed as described in Example 1.

Interferon Gamma ELISA

Approximately $1 \times 10^5$-$2 \times 10^5$ fresh or frozen PBMCs were plated in tissue culture-treated 96-well U bottom plates in RPMI with 10% low IgG FBS. The cells were incubated overnight in hATX-130, mATX-130, human IgG1 isotype control and media alone (1, 5, and 10 ug/ml). Cell culture supernatants were collected 24 hours post-incubation and assessed for IFNgamma secretion using Human IFN-gamma Quantikine ELISA Kit (R&D systems, Minneapolis, Minn.).

Results

Four-week old, ATX-Gx Alloy transgenic mice (mice that produce human antibodies) were immunized subcutaneously with C-terminal His-tagged CD94 for five weeks, with one boost of antigen per week. Antibody titers in mouse serum were assessed during pre- and post-boosts via ELISA and flow cytometry. The mice with the highest serum antibody titer were selected for spleen harvest. The B-cells were isolated from the spleen and then the repertoires of manipulated V-genes are cloned into phage library vectors. The phage library was then screened for high affinity binders against immobilized CD94 antigen through 2-3 cycles, followed by elution of phage candidates. The eluted phage was used to infect bacteria and the DNA was sequenced to identify VL and VH sequences. The VL and VH sequences were reformatted on human IgG1 to generate human anti-CD94 antibodies.

Figure 12:
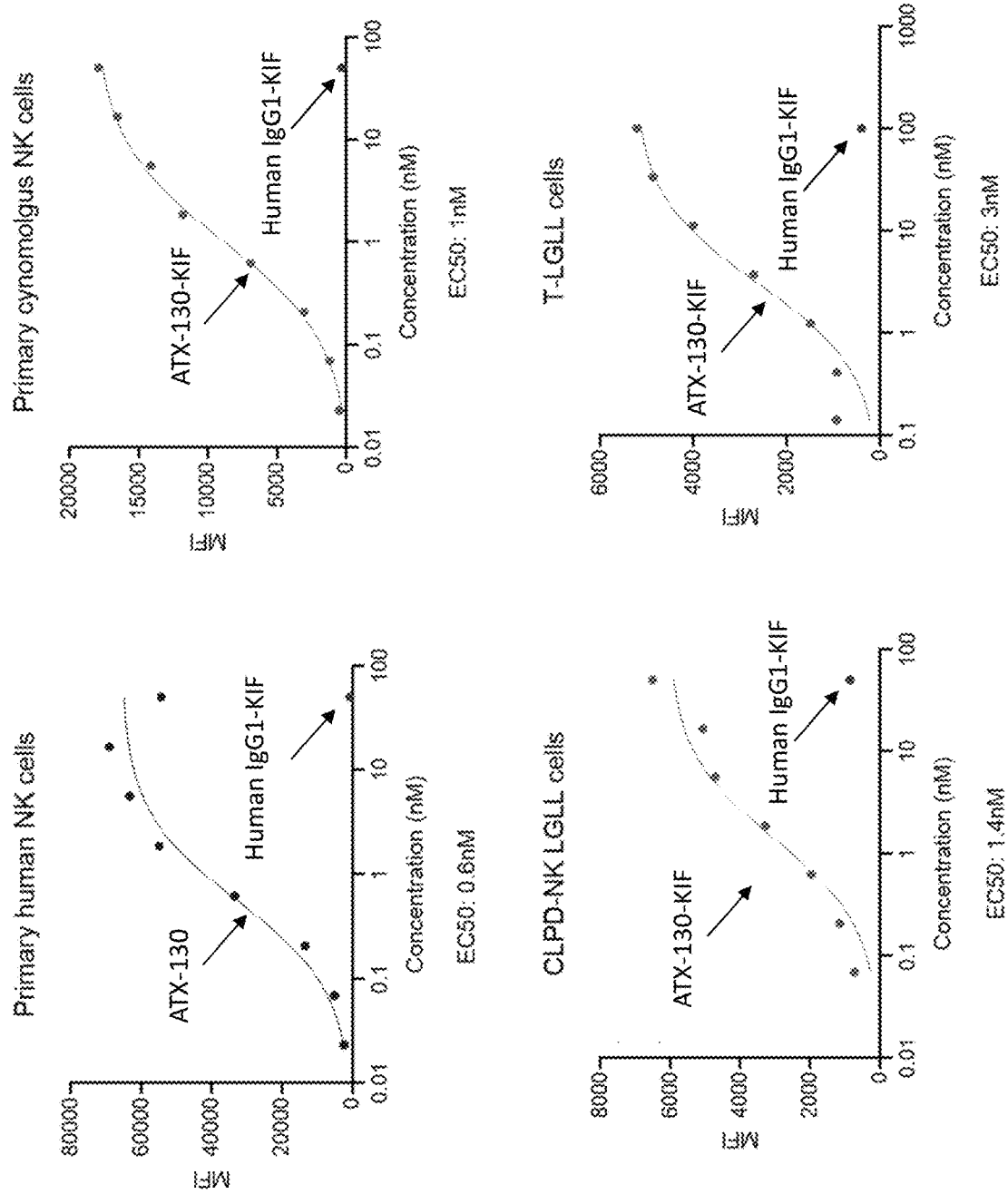
FIG. 12 shows the affinity of anti-CD94 antibody ATX-130 for human primary natural killer (NK) cells and anti-CD94 antibody ATX-130-KIF for cynomolgus primary natural killer (NK) cells, chronic lymphoproliferative disorder of NK cells (CLPD-NK), and T-large granular lymphocyte leukemia cells (T-LGLL) as measured by flow cytometry. The ATX-130 antibody was produced in Expi-CHO cells cultured in the presence of kifunensine, a potent inhibitor of the mannosidase I enzyme, which is used to produce ATX-130-KIF mimicking non-fucosylated antibody. PBMCs of healthy donors were used for antibody staining ATX-130 antibody was titrated from 50 nM to 0.02 nM. Secondary anti-human antibody labeled with Alexa Fluor 647 was used to detect binding on CD3−CD56 bright NK cells. ATX-130-KIF antibody conjugated with Alexa Fluor 647 was titrated from 50 nM to 0.02 nM. T-LGLL cells were identified using CD3+CD16+ gating, while CLPD-NK cells were identified using CD3−CD16+ gating strategy. Titration curves and EC50 were generated using Graphpad Prism. ATX-130 bound to CD3−CD56 bright NK cells with an affinity of 0.6 nM. ATX-130-KIF showed an affinity of 1 nM on primary cynomolgus NK cells, 1.4 nM on CLPD-NK cells, and 3 nM on T-LGLL cells. Fluorescently labeled human IgG1-KIF isotype-KIF antibody was used as control. Arrows indicate ATX-130 and Human IgG1-KIF data points.

The affinity of the antibody clones was assessed by flow cytometry analysis. ATX-130-KIF mimicking non-fucosylated antibody was produced by culturing Expi-CHO cells cultured in the presence of kifunensine, a potent inhibitor of the mannosidase I enzyme. FIG. 12 shows titration curves generated for anti-CD94 antibody clones ATX-130 and ATX-130-KIF. anti-CD94 antibody ATX-130 showed an affinity of 0.6 nM on human primary NK cells. ATX-130-KIF showed an affinity of 1 nM on primary cynomolgus NK cells, 1.4 nM on chronic lymphoproliferative disorder of NK cells (CLPD-NK), and 3 nM on T-large granular lymphocyte leukemia cells (T-LGLL). Thus, ATX-130 and ATX-130-

KIF have similar binding affinity on primary human NK cells, cynomolgus NK cells, CLPD-NK cells, and T-LGLL cells.

Figure 13:
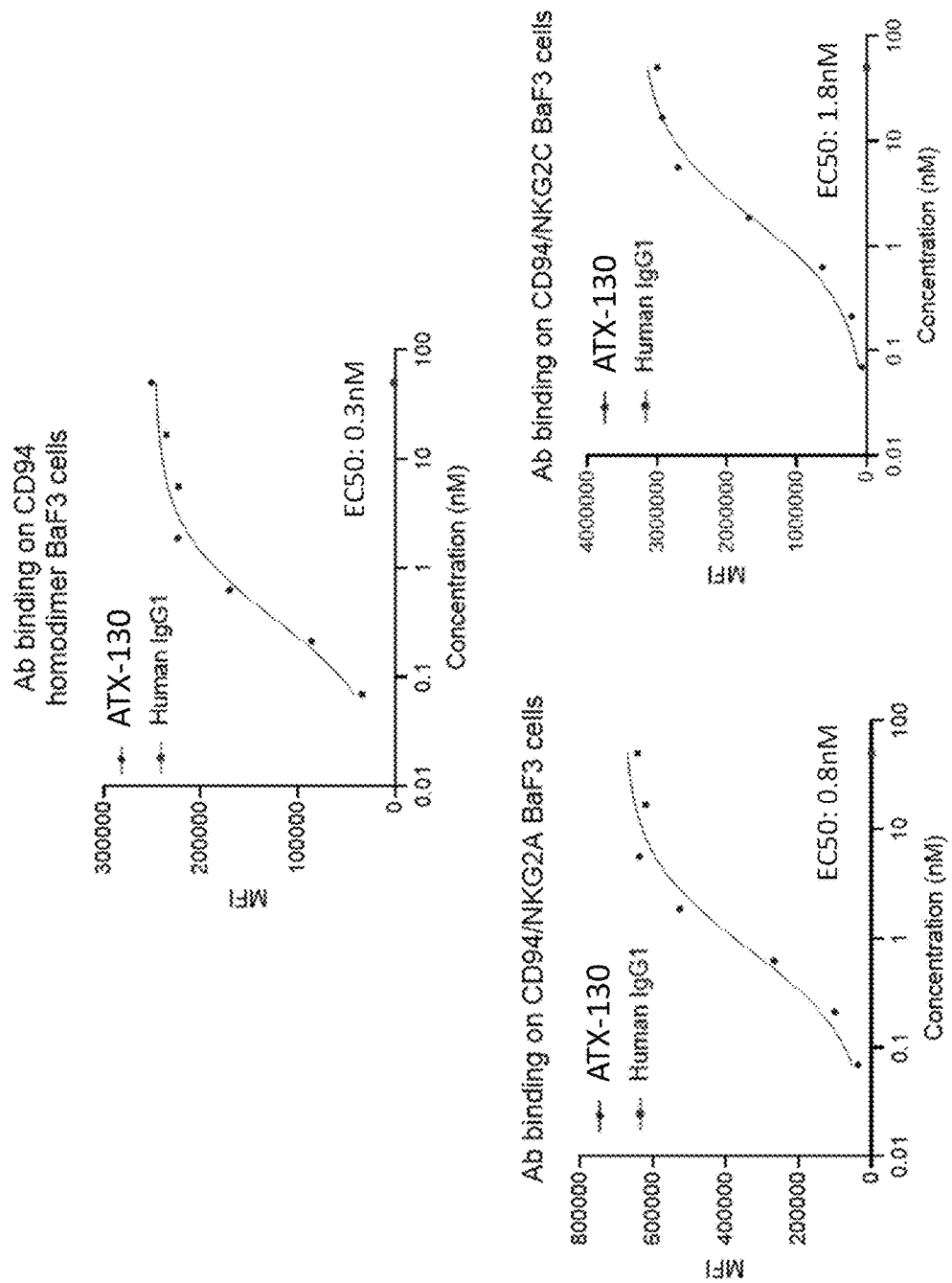
FIG. 13 shows affinity of anti-CD94 antibody ATX-130 on CD94 homodimer or heterodimer. BaF3 cells overexpressing CD94 homodimer (top panel), CD94/NKG2A heterodimer (lower left panel), and CD94/NKG2C heterodimer (lower right panel) were incubated with unconjugated ATX-130 antibody in a dilution series from 50 nM to 0.02 nM. Secondary anti-human antibody labeled with Alexa Fluor 647 was used to detect ATX-130 binding on cells. ATX-130 binds to CD94 homodimer, CD94/NKG2A, and CD94/NKG2C heterodimer BaF3 cells with affinity of 0.3, 0.8, and 1.8 nM, respectively.

The affinity of the antibody clone ATX-130 on CD94 homodimer and heterodimer was also assessed by flow cytometry analysis. FIG. 13 shows titration curves generated for anti-CD94 antibody clone ATX-130. anti-CD94 antibody clone ATX-130 showed an affinity of 0.3 nM on BaF3 cells overexpressing CD94 homodimer (top panel). anti-CD94 antibody clone ATX-130 showed an affinity of 0.8 nM and 1.8 nM on BaF3 cells overexpressing either CD94/NKG2A heterodimer or CD94/NKG2C, respectively (lower panels). These results show that ATX-130 binds to CD94 homodimer, CD94/NKG2A, and CD94/NKG2C heterodimer BaF3 cells with similar affinity.

Figure 14:
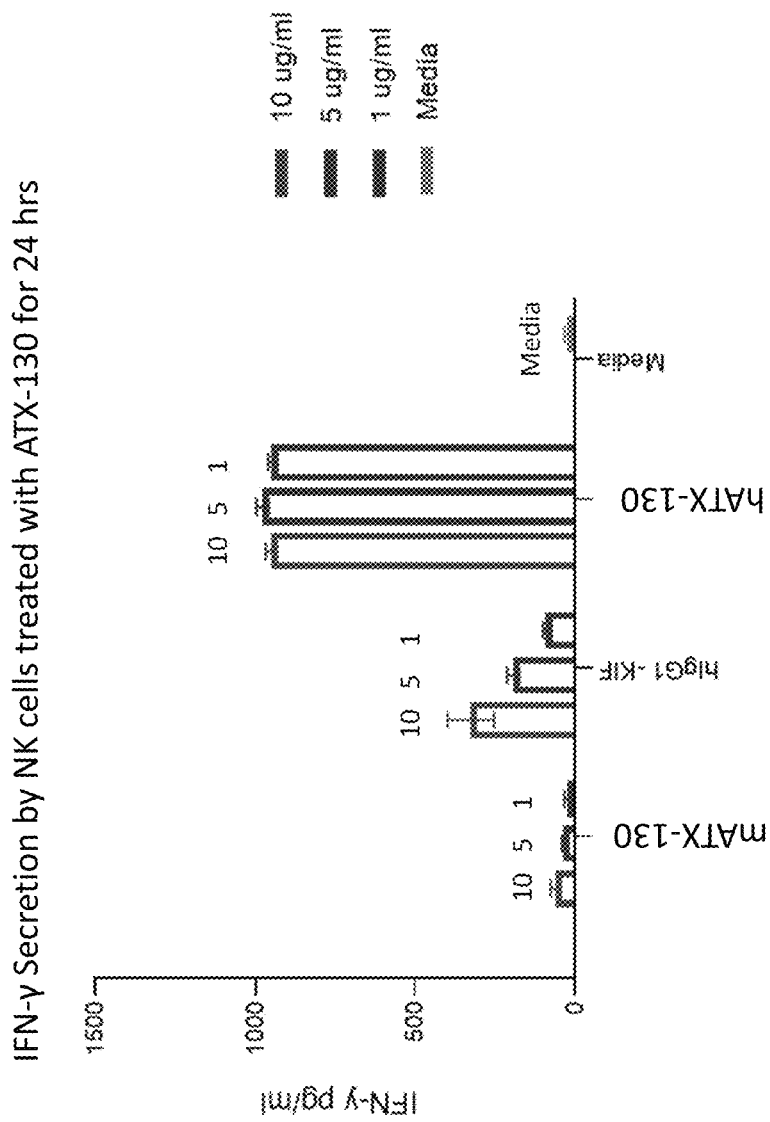
FIG. 14 shows IFN-gamma secretion on human NK cells in the presence of ATX-130 antibodies as assessed by ELISA. NK cells were isolated from healthy donor PBMCs and cultured in the presence of ATX-130 with mouse IgG1 inactive Fc (mATX-130), human IgG1-KIF isotype control, ATX-130 (hATX-130), and media alone. After 24 hours of incubation, cell culture supernatants were collected and ELISA was performed to detect secreted IFN-gamma. Concentration of ATX-130 (10 µg/mL, 5 µg/mL, 1 µg/mL, or media) is depicted at the top of each bar and corresponds to concentrations depicted in figure legend.

An Interferon gamma ELISA was performed to evaluate ATX-130 agonistic or antagonistic effect on CD94/NKG2A and NKG2C heterodimers. As shown in FIG. 14, NK cells did not secrete IFN-gamma in the presence of ATX-130 with mouse inactive Fc (mATX-130), suggesting that binding to CD94 alone in the absence of active human Fc does not activate downstream signaling of NKG2A and NKG2C. Thus, the ATX-130 antibody is not agonist or antagonistic on CD94/NKG2A and NKG2C on NK cells.

Figure 15:
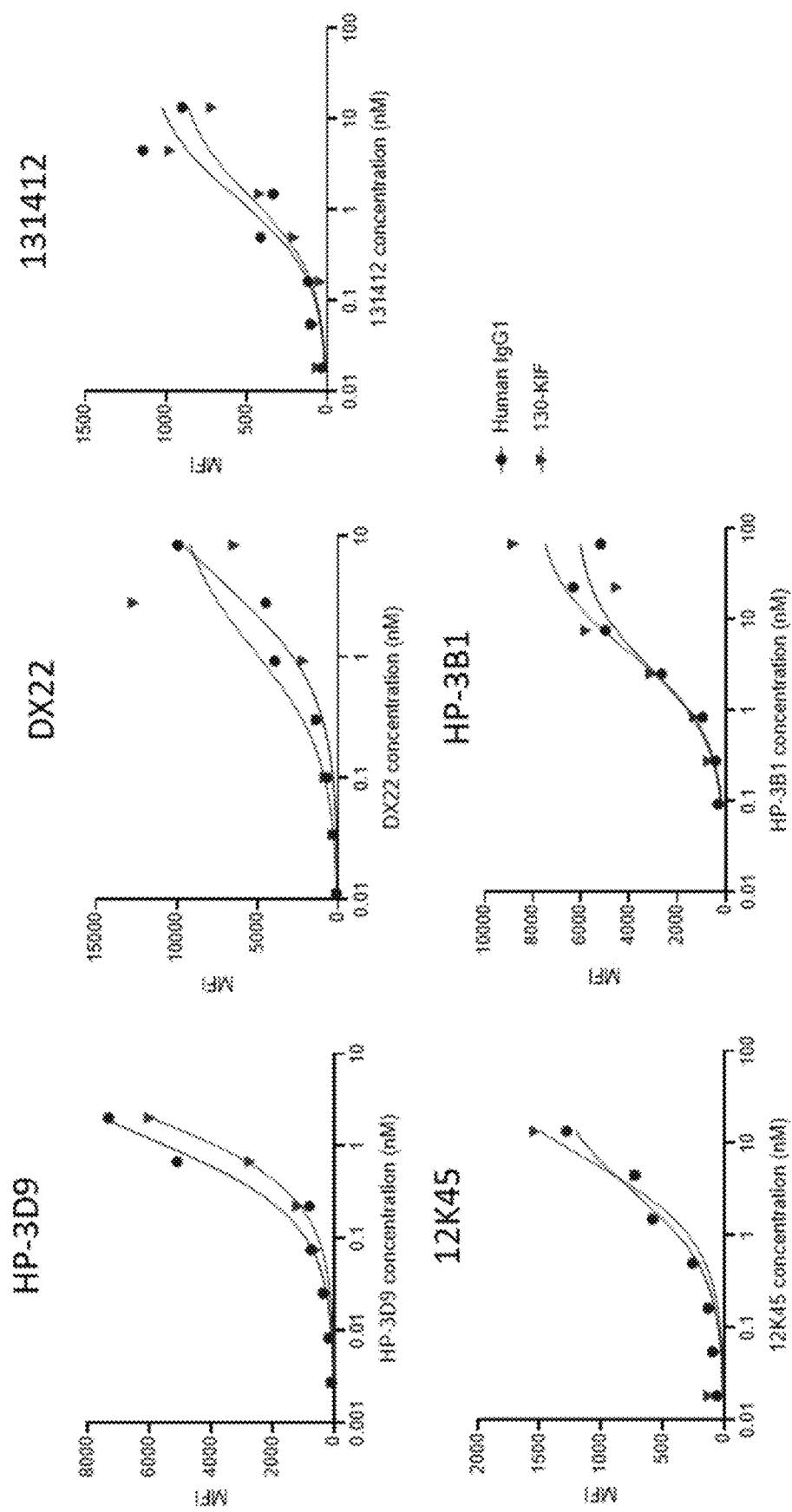
FIG. 15 shows the results of competition assays performed for ATX-130 anti-CD94 antibody evaluation. For all competition assays, ATX-130 was incubated with PBMCs at a concentration of 7.5 µg/ml. Commercially available anti-CD94 antibodies (clones HP-3D9, DX22, 131412, 12K45, and HP-3B1) were titrated and incubated with PBMCs concurrently with ATX-130. Competition was assessed by plotting the MFI of the titrated commercially available anti-CD94 antibodies. ATX-130 does not compete with HP-3D9, DX22, 131412, 12K45, or HP-3B1.

Competition assays were performed to determine if the newly identified antibodies bound to shared epitopes with existing antibodies. Anti-CD94 antibody ATX-130 was assayed for competition with commercially available anti-CD94 antibodies. As shown in FIG. 15, ATX-130 binds to a unique epitope. ATX-130 did not compete with HP-3D9, DX22, 131412, 12K45, or HP-3B1. Thus, the ATX-130 antibody binds to an epitope that is not shared with commercially available antibodies.

Following validation, the VH and VL sequences were determined for the validated antibody clones. Table 2 summarizes the VH and VL sequences for the validated anti-CD94 clone, ATX-130. The framework and CDR sequences (see Table 1) were determined using the Kabat numbering scheme.

Figure 16:
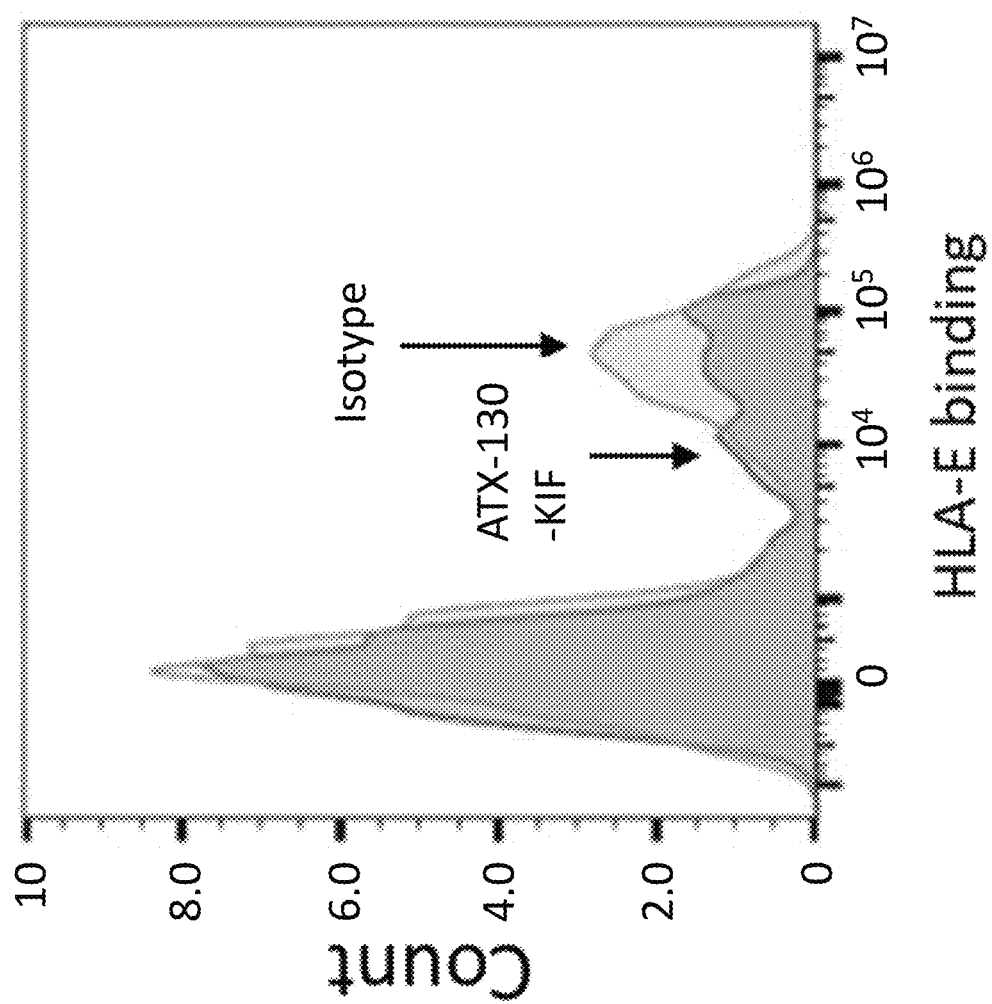
FIG. 16 shows the results of HLA-E tetramer blocking assays performed with ATX-130-KIF and isotype control antibody using flow cytometry. Healthy donor PBMCs were incubated with ATX-130-KIF. PE labeled HLA-E tetramer was then incubated with cells and antibody mixture and detected by flow cytometry. Saturating concentrations of ATX-130-KIF were used in this assay. The percent blocking was calculated as 100−((percent HLA-E positive for anti-CD94 antibody)/(percent HLA-E positive for isotype)*100). Arrows indicate ATX-130-KIF and isotype histograms. ATX-130-KIF did not block HLA-E binding to CD94.

The validated anti-CD94 antibody was further evaluated for its ability (or lack thereof) to block binding by HLA-E, as described in Example 1. HLA-E blocking by anti-CD94 antibody ATX-130-KIF and an isotype control were evaluated by flow cytometry. As shown in FIG. 16, saturating concentrations of ATX-130-KIF did not block HLA-E binding.

Figure 17:
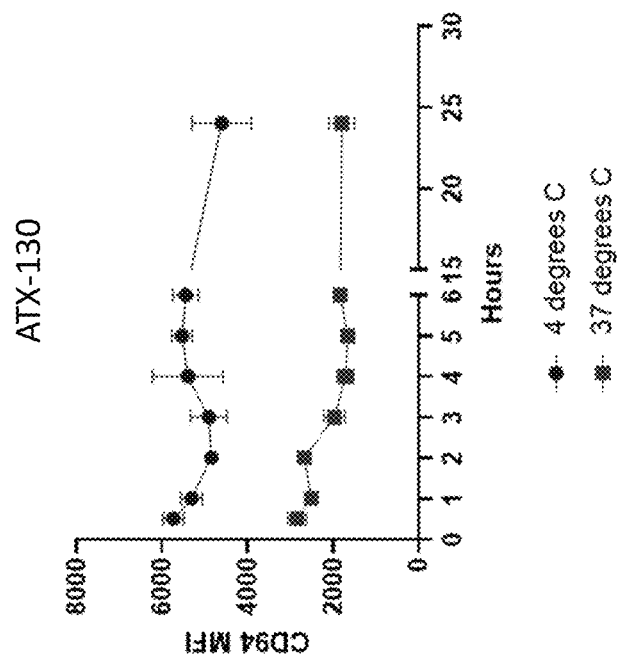
FIG. 17 shows the results of an anti-CD94 antibody internalization assay. Healthy donor PBMCs were incubated with unconjugated ATX-130 at multiple time points ranging from 30 minutes to 24 hours. Cells were either kept at 4° C. to prevent internalization or at 37° C. to induce internalization. ATX-130 does not become significantly internalized within 24 hours.

An antibody internalization assay was performed to evaluate internalization of CD94 receptors when bound by anti-CD94 antibody, as described in Example 1. As shown in FIG. 17, CD94 receptor did not become internalized for up to 24 hours at 37° C. when bound to unconjugated ATX-130.

Figure 18:
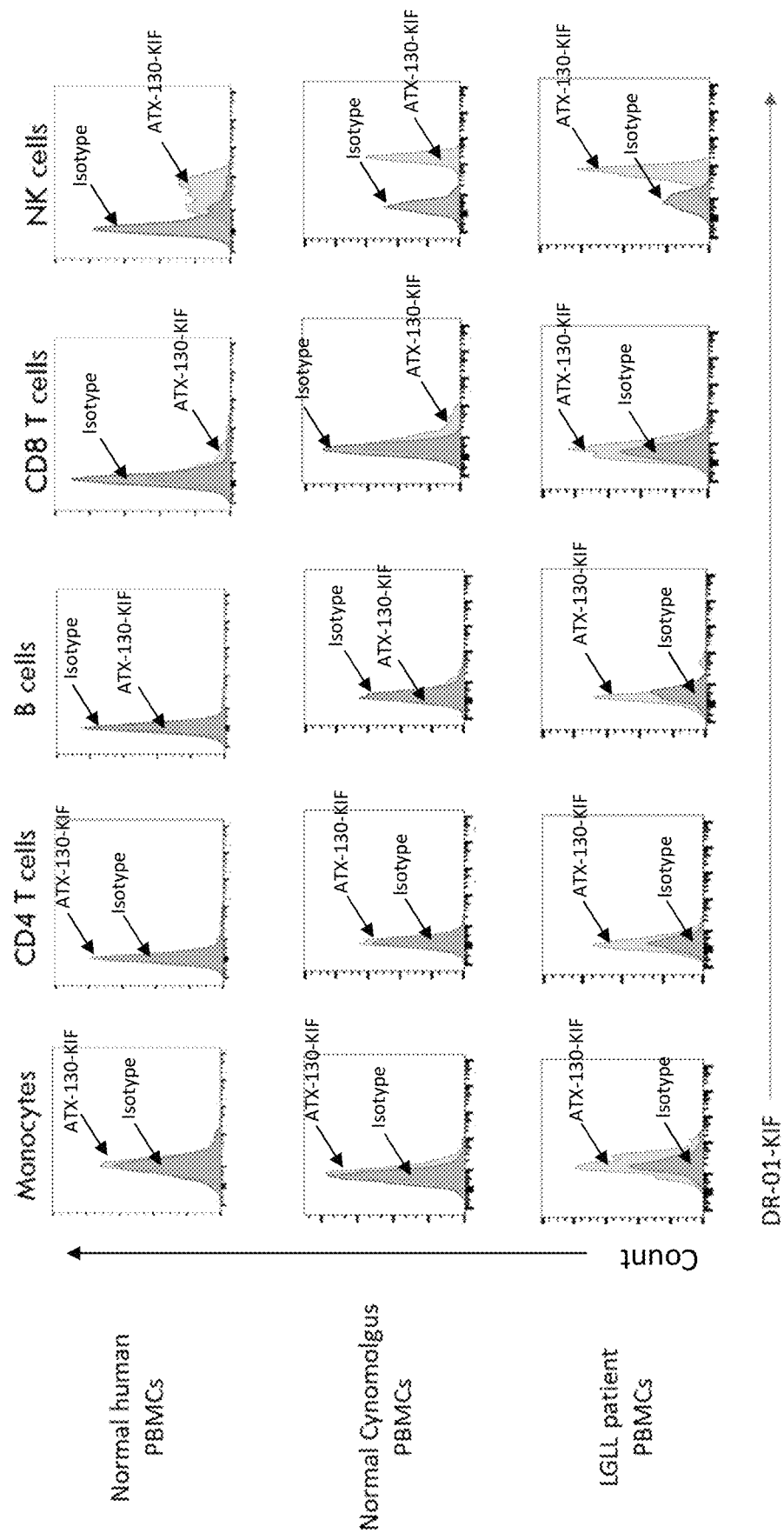
FIG. 18 shows the binding of ATX-130-KIF to immune cell types as measured by flow cytometry. Immune cell types (monocytes, CD4 T cells, B cells, CD8 T cells, and NK cells) of PBMCs from normal human, cynomolgus, and LGL leukemia patient samples were stained with ATX-130-KIF Alexa Fluor 647 (50 nM) and assessed for binding. ATX-130-KIF selectively binds to NK cells (CD3−CD56+/CD16+), subset of normal CD8 T cells (CD3+CD8+), and all LGLL cells (CD3−CD16+). Arrows indicate ATX-130-KIF and isotype histograms.

KIF-treated (ATX-130-KIF) non-fucosylated antibody binding selectivity was assessed by flow cytometry analysis on healthy human, cynomolgus, and LGLL patient immune cells. As shown in FIG. 18, ATX-130-KIF did not bind on monocytes, CD4+ T cells, or B cells in normal human and cynomolgus PBMCs, and LGL leukemia patient PBMCs. Small subsets of CD8+ T cells were recognized by ATX-130-KIF in all three sample types. Thus, ATX-130-KIF selectively binds to normal and LGLL NK cells from all three sample types.

Figure 19:
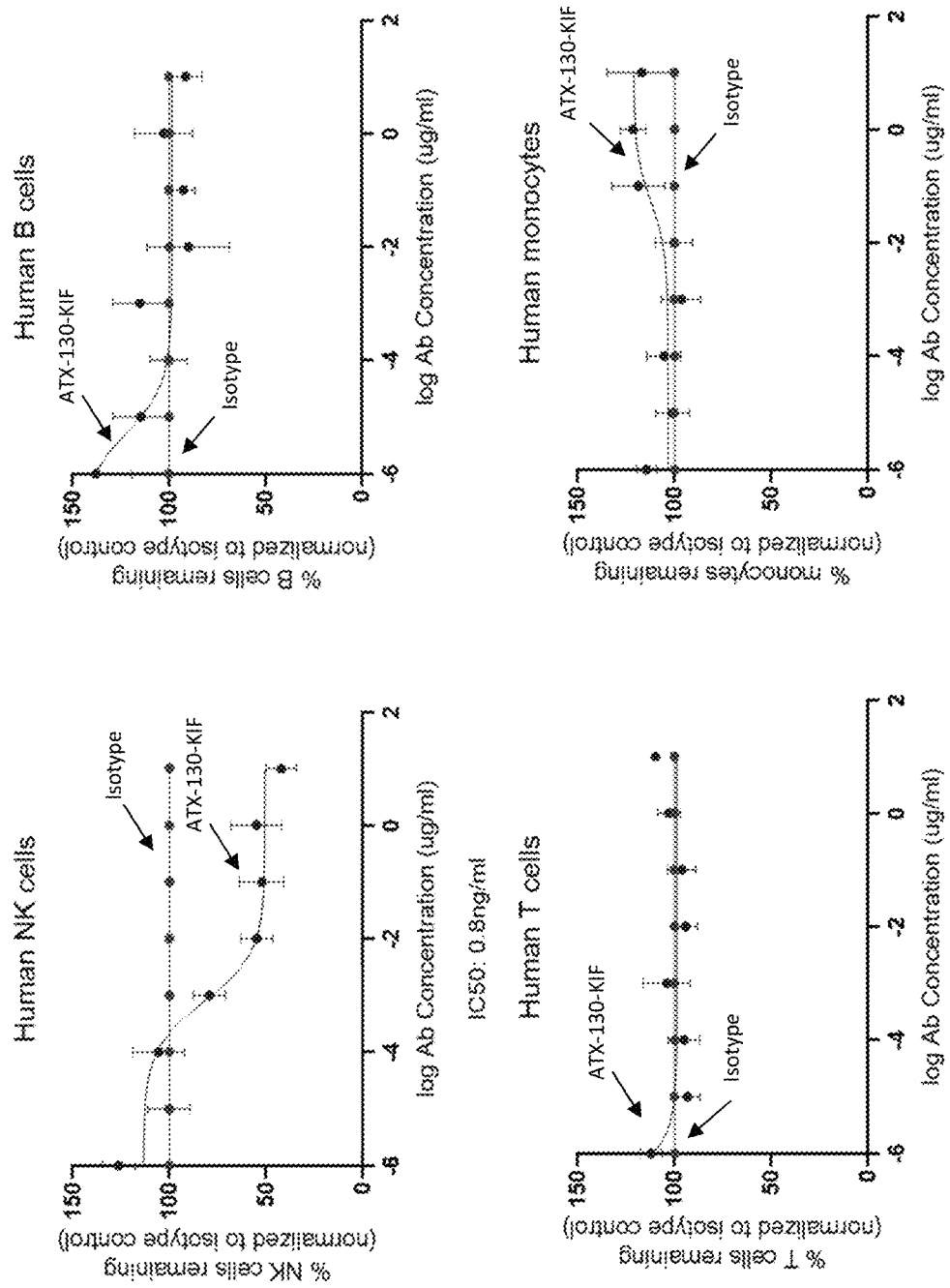
FIG. 19 shows the results of an ADCC assay for ATX-130-KIF using healthy donor PBMCs. Healthy donor PBMCs were plated in 96-well plates and incubated with ATX-130 (titrated in 10-fold dilutions) for 24 hours. Depletion of different immune cell types was assessed by quantifying the remaining number of cells by flow cytometry. Arrows indicate ATX-130-KIF and isotype curves. ATX-130 depletes human NK cells with a potency of 0.8 ng/ml while sparing other immune cell types.

To test the ability of the anti-CD94 antibodies to induce ADDC of NK cells, an ADDC assay was performed using human healthy donor PBMCs. For this assay, anti-CD94 non-fucosylated antibody (ATX-130-KIF) was tested for ADCC in human NK cells, B cells, T cells, and monocytes. As shown in FIG. 19, ATX-130-KIF depleted human NK cells in the PBMC pool of healthy donors in ex vivo culture after 24 hours of incubation, whereas human B cells, T cells, and monocytes were unaffected. The depletion of NK cells by ATX-130-KIF was concentration-dependent. The IC50 of ATX-130-KIF was determined as 0.8 ng/ml. Depletion of over 50% of NK cells was observed at the highest concentration ex vivo. ATX-130 potency on NK cells and preservation of other immune cells suggests that this molecule can exhibit high efficacy and favorable toxicity profile in vivo.

Figure 20:
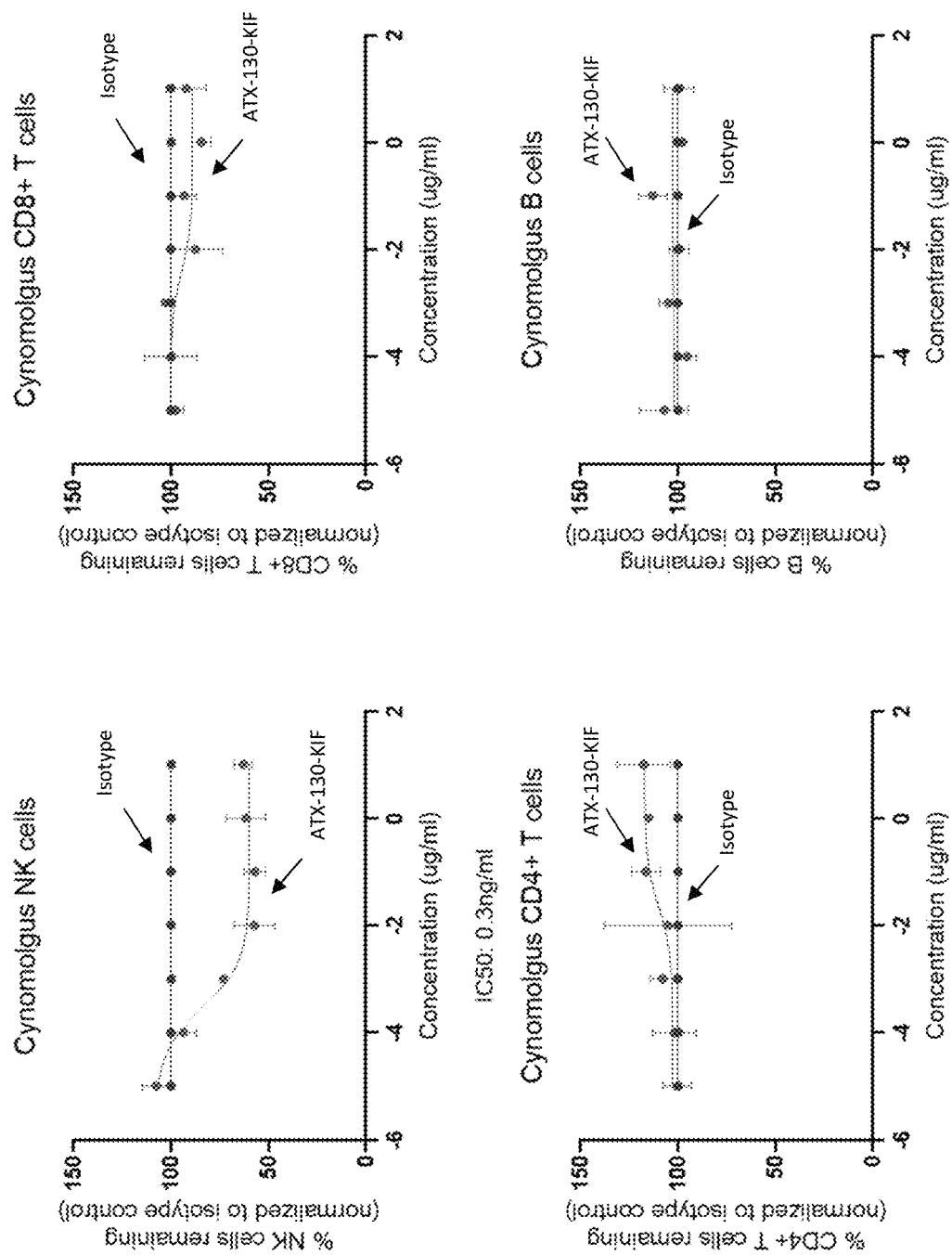
FIG. 20 shows the results of an anti-CD94 antibody ADCC assay using cynomolgus PBMCs. Cynomolgus PBMCs were plated in 96-well plates and incubated with ATX-130-KIF (titrated in 10-fold dilutions) for 24 hours. Depletion of different immune cell types (NK cells, CD8 T cells, CD4 T cells, and B cells) was assessed by quantifying the remaining number of cells by flow cytometry. Arrows indicate ATX-130-KIF and isotype curves. ATX-130-KIF depletes cynomolgus NK cells with a potency of 0.3 ng/ml while sparing other immune cell types.

Next, to test the ability of the anti-CD94 antibodies to induce ADCC of NK cells, an ADDC assay was performed using cynomolgus PBMCs. For this assay, anti-CD94 non-fucosylated antibody (ATX-130-KIF) was tested for ADCC in cynomolgus NK cells, B cells, T cells, and monocytes. As shown in FIG. 20, ATX-130-KIF depleted cynomolgus NK cells in the cynomolgus PBMC pool in ex vivo culture after 24 hours of incubation, whereas cynomolgus B cells, T cells, and monocytes were unaffected. The depletion of NK cells by ATX-130-KIF was concentration-dependent. The IC50 of ATX-130-KIF was determined as 0.3 ng/ml. Depletion of over 50% of NK cells was observed at the highest concentration ex vivo. ATX-130 potency on NK cells and preservation of other immune cells suggested that this molecule can exhibit high efficacy and favorable toxicity profile in vivo.

Figure 21:
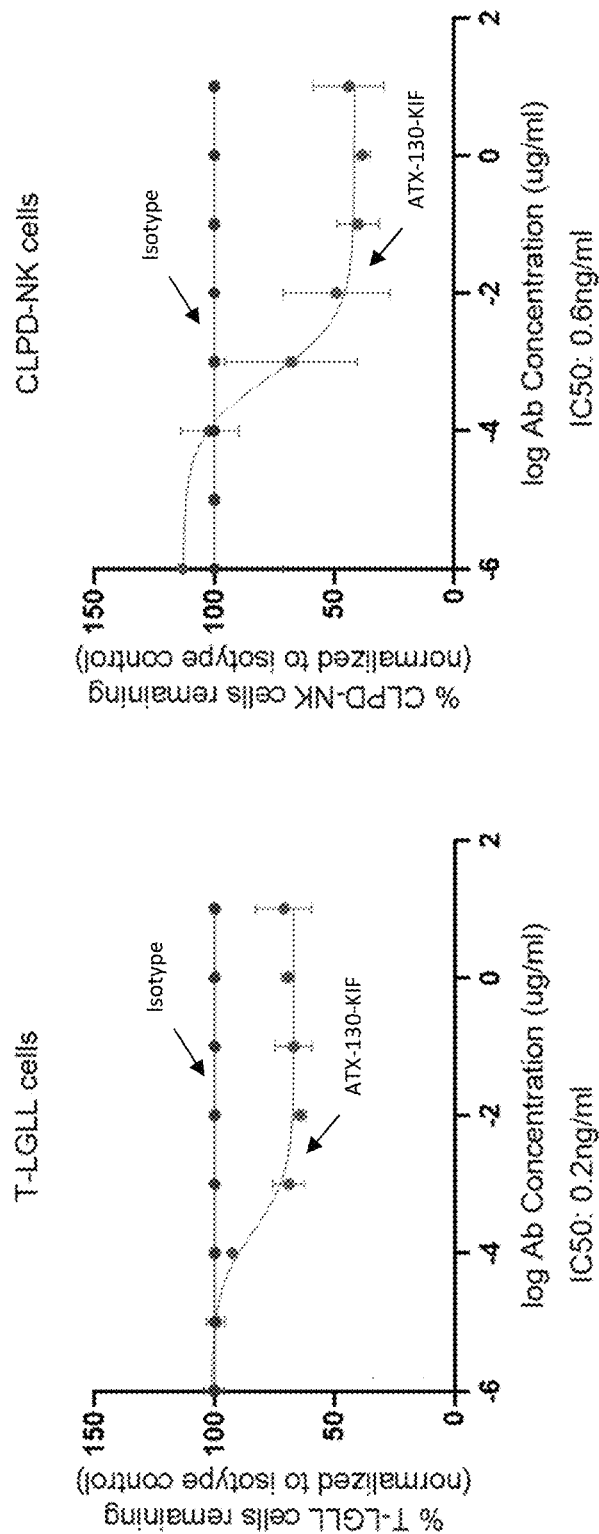
FIG. 21 shows the results of an anti-CD94 antibody ADCC assay using T-LGLL and CLPD-NK PBMCs. T-LGLL and CLPD-NK PBMCs were plated in 96-well plates and incubated with ATX-130-KIF (titrated in 10-fold dilutions) for 24 hours. Depletion of different immune cell types was assessed by quantifying the remaining number of cells by flow cytometry. Arrows indicate ATX-130-KIF and isotype curves. ATX-130-KIF depletes T-LGLL and CLPD-NK cells with a potency of 0.2 and 0.6 ng/ml, respectively while sparing other immune cell types.

Finally, the ability of the ATX-130-KIF antibody to induce ADCC of human leukemic cells was evaluated through an ADCC assay using cells from chronic lymphoproliferative disorder of NK cells (CLPD-NK) and T-large granular lymphocyte leukemia (T-LGLL) patients. As shown in FIG. 21, the ATX-130-KIF antibody depleted human T-LGLL and CLPD-NK leukemic cells in a concentration dependent manner, with an IC50 of 0.2 ng/ml and 0.6 ng/ml, respectively. Depletion of over 30% and 50% of T-LGLL and CLPD-NK leukemic cells, was observed at the highest concentration ex vivo, respectively. This depletion was selective, as no other cell types were affected.

Example 4: Anti-CD94 Antibody ATX-130-KIF Study in Non-Human Primates

This example describes an exploratory pharmacodynamic (PD) in cynomolgus macaques to evaluate the efficacy of ATX-130-KIF in vivo.

Materials and Methods

In Vivo Non-Human Primate Exploratory Study

Figure 24A:
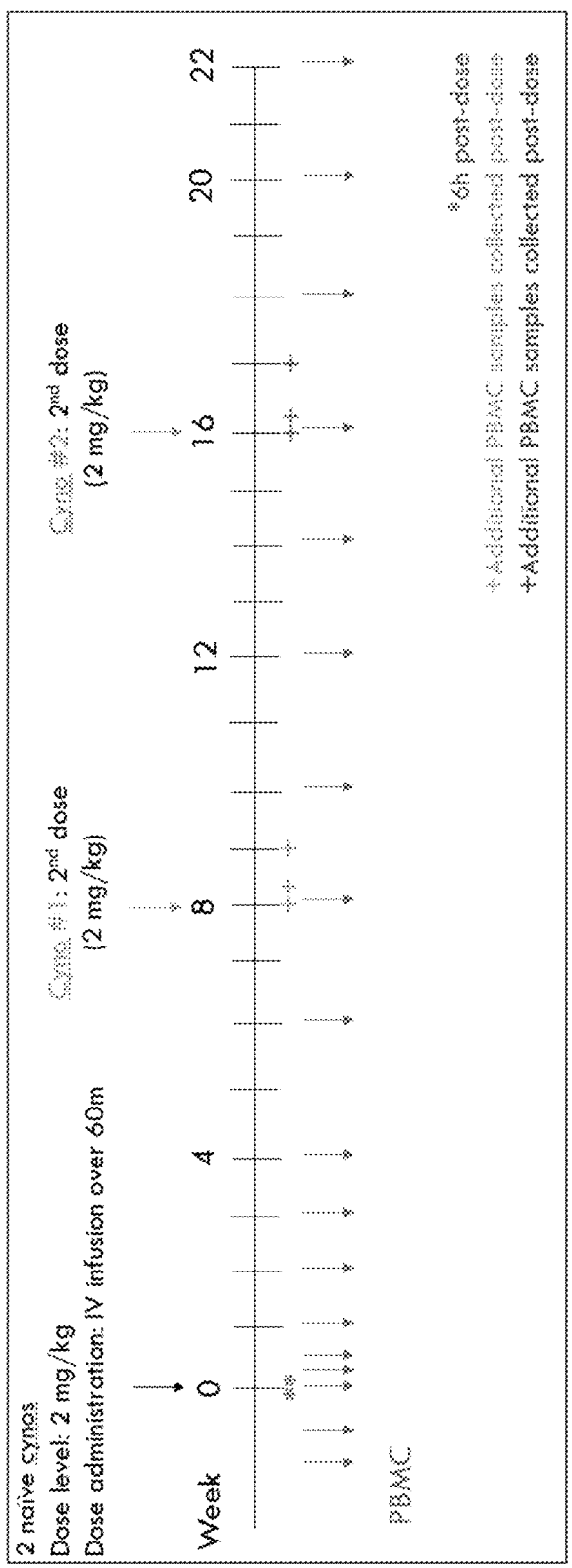
FIG. 24A shows the design of an exploratory pharmacodynamic (PD) study in non-human primates to evaluate efficacy of ATK-130 in vivo.

Two healthy male cynomolgus monkeys, ages 6.5 and 9.2 years and weighing 6.54 and 7.18 kg, respectively, naïve to all compounds prior to study commencement and with no prior history of illness were selected for the study. As shown in FIG. 24A, two doses of ATX-130-KIF (2 mg/kg) were administered to Cyno #1 through intravenous (IV) infusion at a rate of approximately 0.25 mL/min over 60 minutes on Week 0 and 8. Two doses of ATX-130-KIF (2 mg/kg) were administered to Cyno #2 through IV infusion at a rate of approximately 0.25 mL/min over 60 minutes on Week 0 and 16. Blood, serum and PBMCs were collected at various time intervals at pre- and post-dose as shown in FIG. 24A. PD was determined via target cell depletion by flow cytometry analysis. The study endpoint was projected at 22 weeks.

Results

To evaluate the efficacy of ATX-130-KIF in vivo, a PD study was completed in non-human primates (NHP). Two healthy male cynomolgus monkeys, ages 6.5 and 9.2 years and weighing 6.54 and 7.18 kg (Cyno #1 and Cyno #2), respectively, naïve to all compounds prior to study commencement and with no prior history of illness were selected for the study. Pharmacodynamic (PD) activity was determined via target cell depletion by flow cytometry analysis. All bioanalytical data were presented up to 18 weeks, with the study endpoint projected at 22 weeks.

Figure 24B:
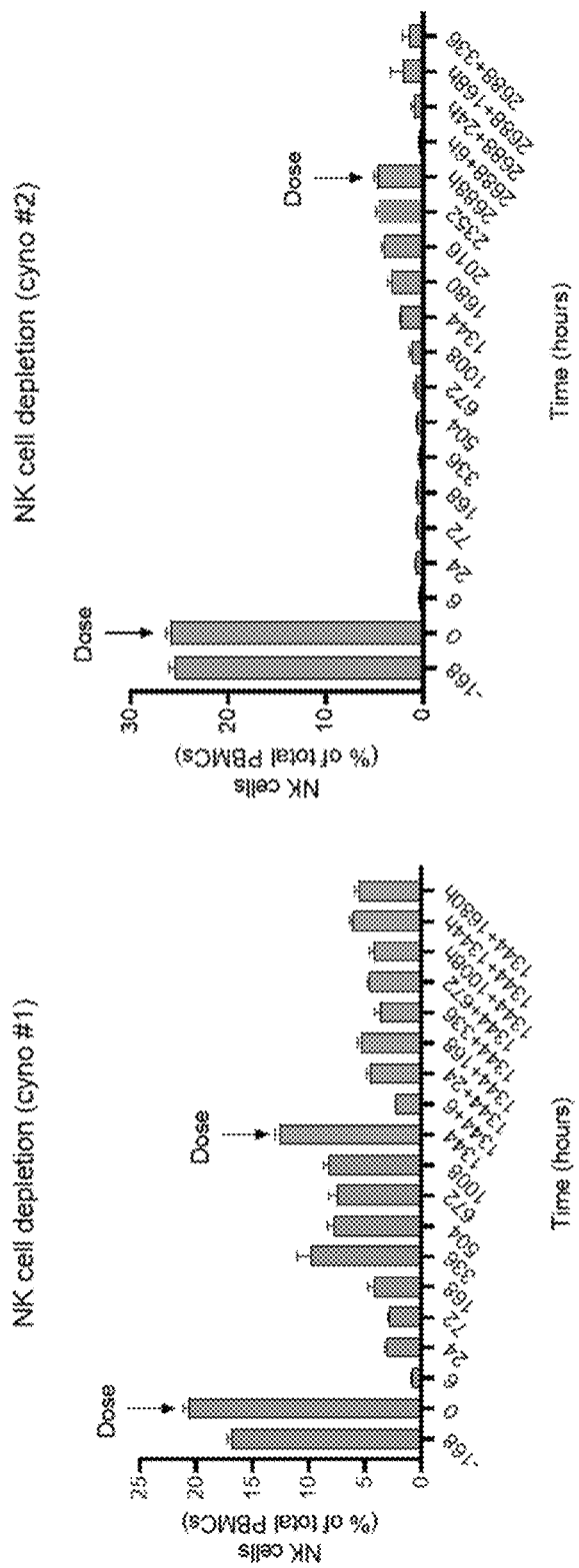
FIG. 24B shows depletion of cynomolgus NK cells in vivo with ATX-130-KIF dosing at 2 mg/kg as assessed by flow cytometry. Two naïve cynomolgus macaques (Cyno #1 and Cyno #2) were administered ATX-130-KIF (2 mg/kg) via intravenous (IV) infusion for 60 minutes. An additional 2 mg/kg of ATX-130-KIF was administered to Cyno #1 at 8 weeks and Cyno #2 at 16 weeks. Body weight and clinical observations were recorded periodically. PBMCs were isolated from 5 mL blood draws per time point per animal. $0.3 \times 10^6$ cells were plated per well in technical triplicates and stained with antibody panel. CD3−CD8+ gating strategy was used to identify cynomolgus NK cells. NK cells were quantified by calculating the percentage of the cell population out of total PBMCs. Arrows indicate time points at which doses were administered.

The ability (or lack thereof) of ATX-130-KIF to deplete cynomolgus NK cells in blood was assessed by flow cytometry analysis. As shown in FIG. 24B, the composition of NK cells in total PBMCs in Cyno #1 (left panel) and Cyno #2 (right panel) were 20% and 25% at baseline, respectively. For each dose, depletion of targets cells (NK cells) to <5% of PBMCs was detected in both animals 6 hours post-administration of ATX-130-KIF. In Cyno #1, a steady increase in percent NK cells was observed from 6 hours to 336 hours, which then stabilized at 50% of baseline up to administration of the second dose at 1008 hours. Stabilization of NK cell count at 50% of baseline was observed after 168 hours following the 2nd dose. In Cyno #2, NK cell recovery was slower than in Cyno #1. NK cell count remained at low levels 6 weeks following dose 1, with an increase over Weeks 8 to 14. Administration of ATX-130-KIF at Week 16 reduced NK cell levels 6 hours post-dose and remained low up to the latest sample collection. Overall, the current results show that ATX-130-KIF can demonstrate efficacy in vivo in cynomolgus macaques.

Figure 25A:
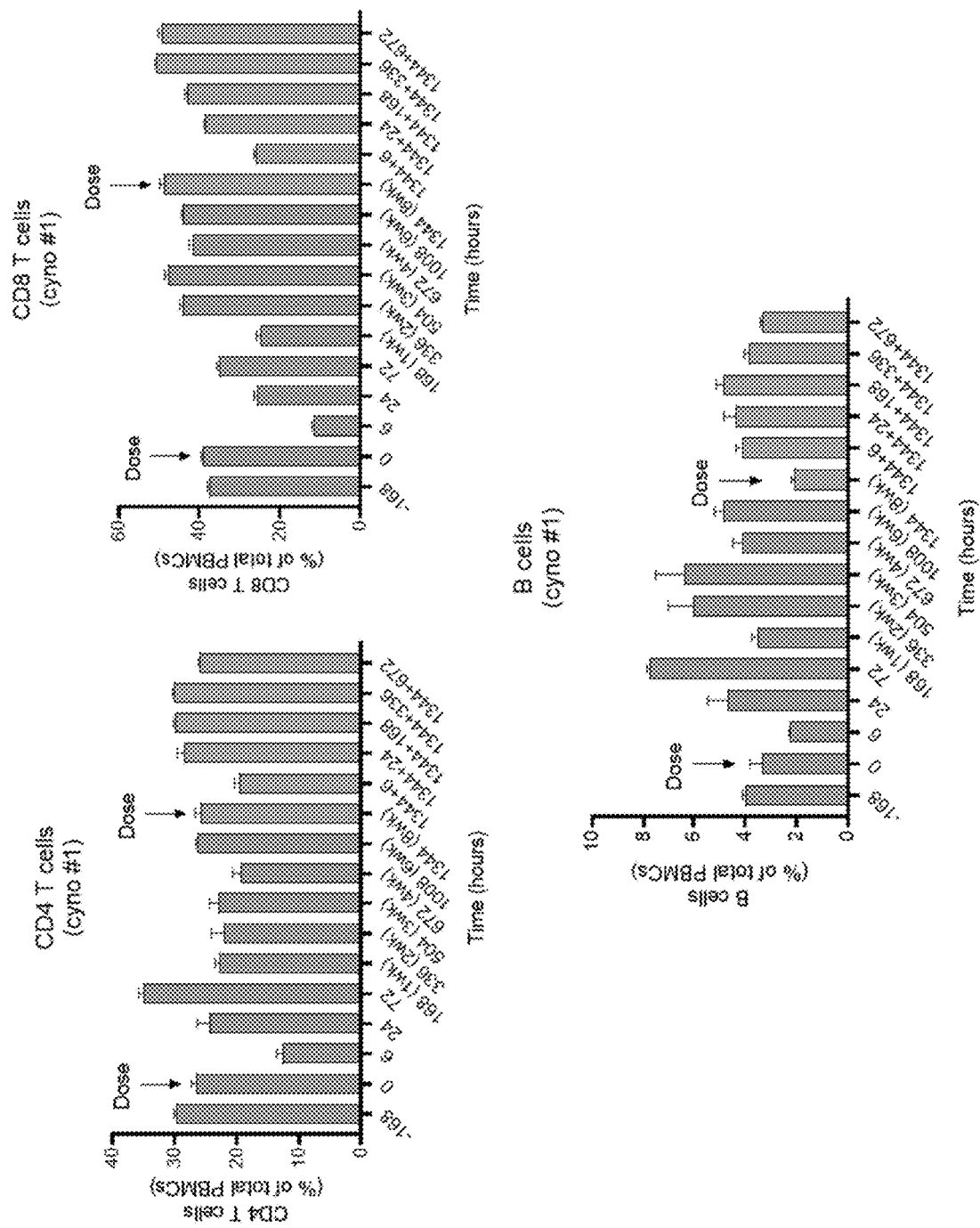
FIGS. 25A-25B show the assessment of depletion of cynomolgus CD4 T, CD8 T, and B cells. PBMCs were isolated from 5 mL blood draws per time point for Cyno #1 and Cyno #2. $0.3 \times 10^6$ cells were plated per well in technical triplicates and stained with antibody panel. CD3+CD4+, CD3+CD8+, and CD3−CD20+ gating strategy were used to identify Cyno #1 (FIG. 25A) and Cyno #2 (FIG. 25B) CD4+ T cells, CD8+ T cells, and B cells, respectively. Cells were quantified by calculating the percentage of the cell population out of total PBMCs.
Figure 25B:
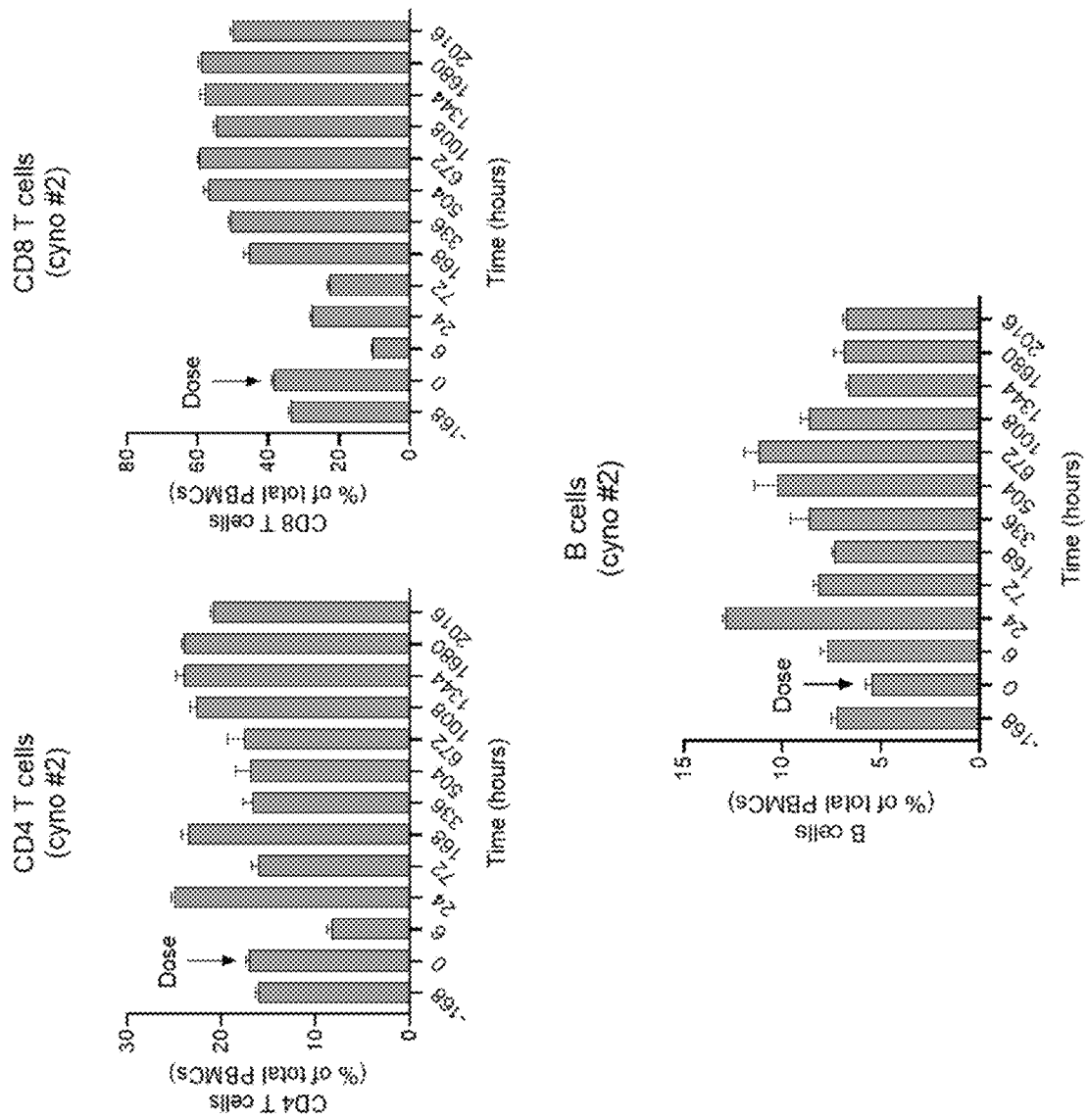

The ability (or lack thereof) of ATX-130-KIF to deplete cynomolgus CD4 T, CD8 T, and B cells in blood was assessed by flow cytometry analysis. As shown in FIG. 25A, the composition of CD4+ T cells, CD8+ T cells, and B cells of total PBMCs in Cyno #1 was 27%, 40%, and 4% at baseline, respectively. As shown in FIG. 25B, the composition of CD4+ T cells, CD8+ T cells, and B cells of total PBMCs in Cyno #2 was 26%, 40%, and 5% at baseline, respectively. Depletion of T and B cells was detected in both animals 6 hours post-administration of ATX-130-KIF. However, these immune cell populations returned to baseline levels 24 hours post-dose. The results from this study show that ATX-130-KIF only transiently depletes other immune cells, without depletion of non-CD94 expressing cells.

Figure 26:
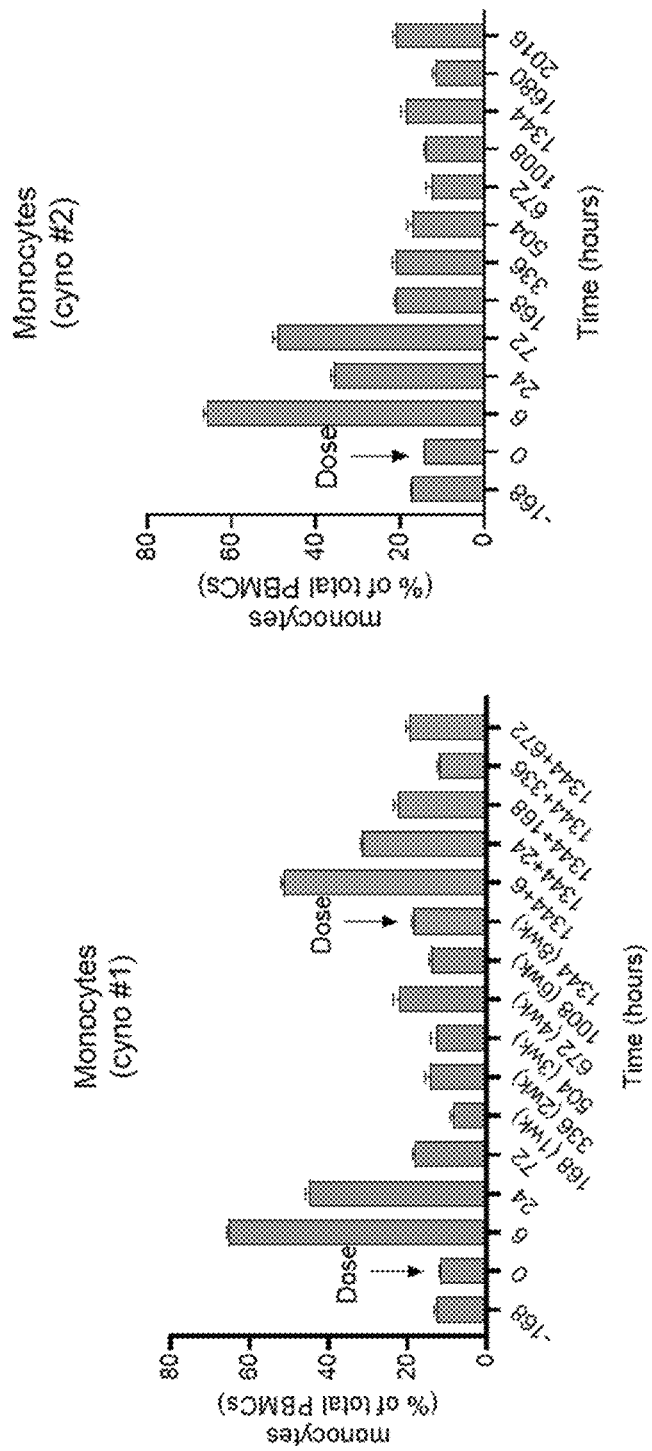
FIG. 26 shows the results of assessment of monocyte depletion by flow cytometry. PBMCs were isolated from 5 mL blood draws per time point for Cyno #1 (left panel) and Cyno #2 (right panel). 0.3×10$^6$ cells were plated per well in technical triplicates and stained with antibody panel. CD3−CD14+ gating strategy was used to identify monocytes. Cells were quantified by calculating the percentage of the cell population out of total PBMCs.

Cynomolgus monocyte depletion was assessed by flow cytometry. As shown in FIG. 26, elevation of monocytes was observed 6 hours post-dose, but returned to baseline levels after 7 days. The results from the study show that ATX-130-KIF transiently elevates monocytes, suggesting that ATX-130-KIF can engage monocytes to perform ADCC and contribute to targeted depletion of NK cells.

Figure 27:
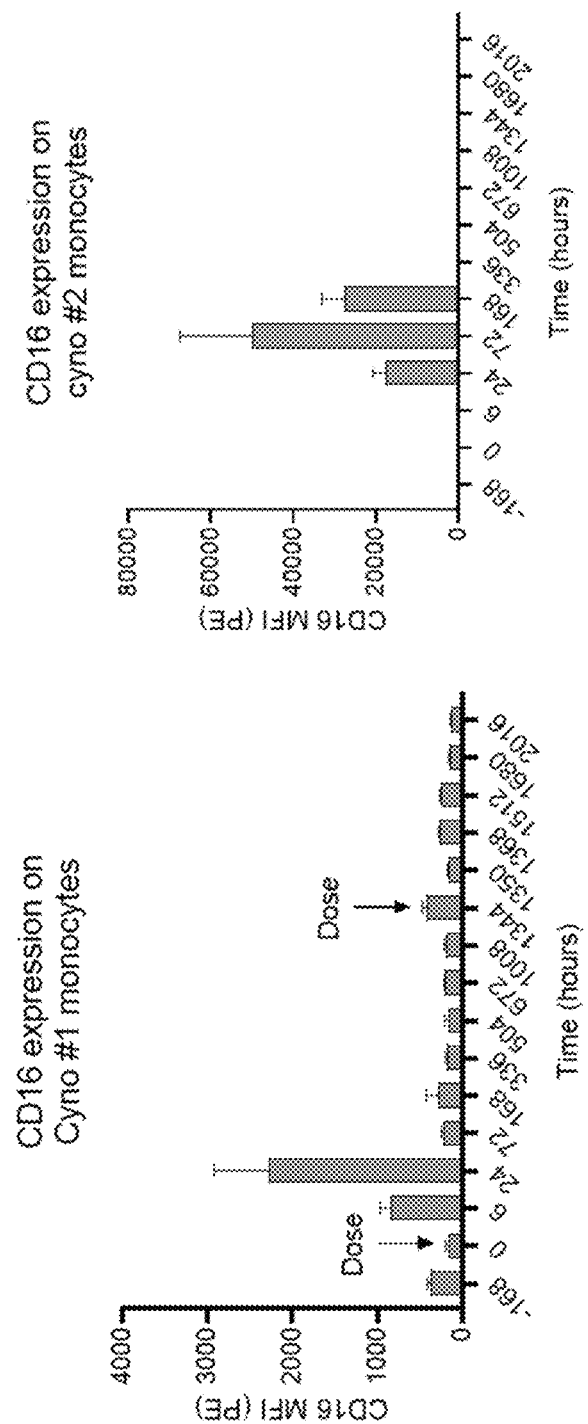
FIG. 27 shows the results of assessment of CD16 expression on monocytes by flow cytometry. PBMCs were isolated from 5 mL blood draws per time point for Cyno #1 (left panel) and Cyno #2 (right panel). 0.3×10$^6$ cells were plated per well in technical triplicates and stained with antibody panel. CD3−CD14+ gating strategy was used to identify monocytes. CD16 MFI was assessed on monocytes.

Cynomolgus CD16 expression on monocytes was assessed by flow cytometry. As shown in FIG. 27, elevation of CD16 on monocytes was observed 24 hours post-dose, but returned to baseline levels after 7 days. The results from the study show that ATX-130-KIF transiently elevates CD16 on monocytes, suggesting that ATX-130-KIF engages monocytes to perform ADCC and contribute to targeted depletion of NK cells.

Example 3: Anti-CD94 Antibody ATX-130 In Vivo Mouse Study

Figure 22A:
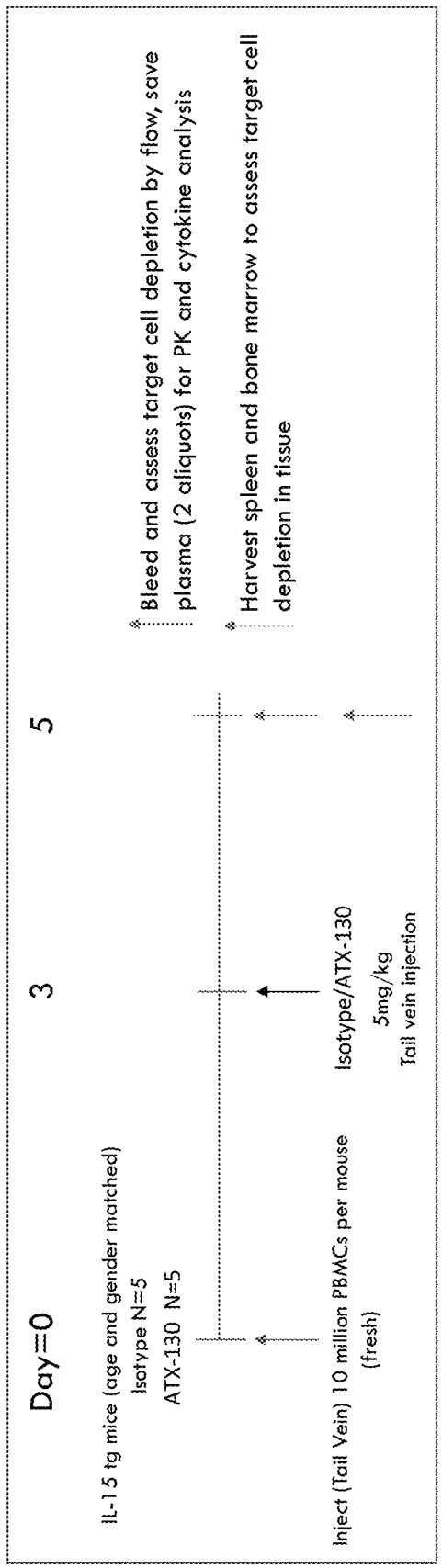
FIG. 22A shows study design examining effects of ATK-130 or isotype control on humanized IL-15 transgenic mice engrafted with healthy human donor PBMCs.
Figure 22B:
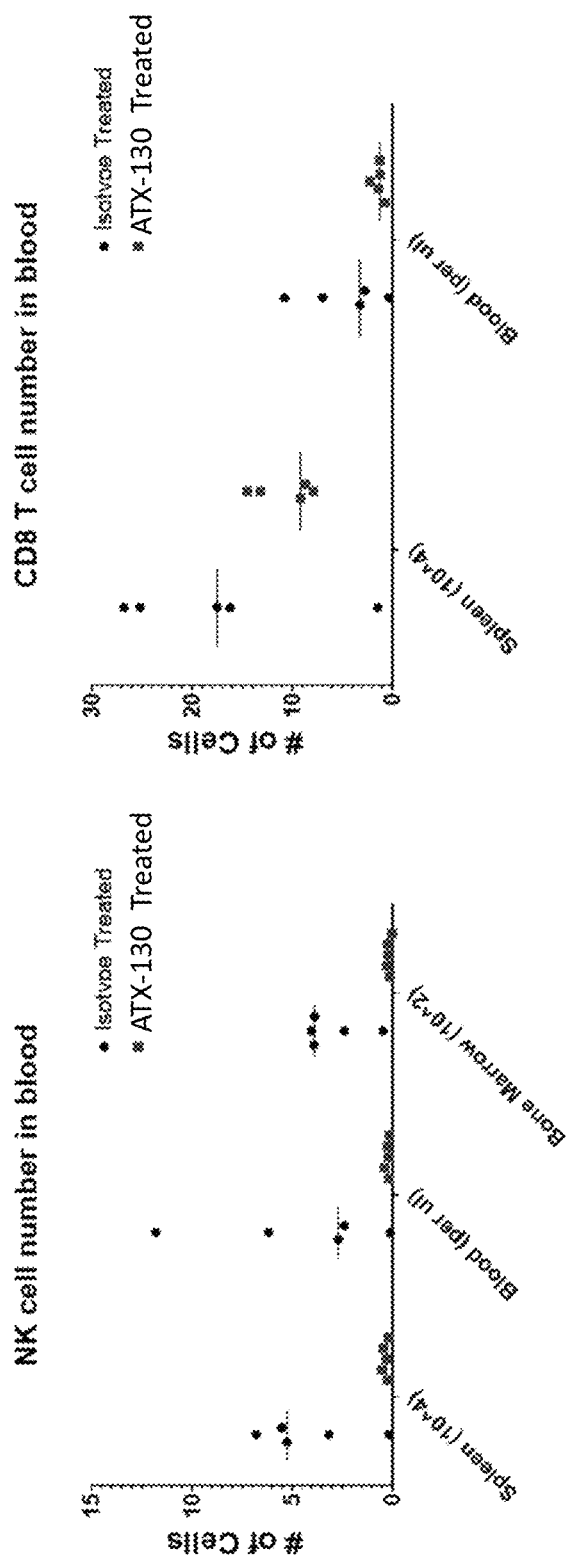
FIG. 22B shows depletion of normal human NK and CD8 T cells in IL-15 transgenic mice. Mice were engrafted with healthy donor PBMCs for three days. One dose of human IgG1 isotype control or ATX-130 (5 mg/kg) were injected into mice (5 mice per arm), and depletion of NK cells (top panel) and CD8 T cells (lower panel) in the blood, spleen, and bone marrow were assessed by flow cytometry 48 hours post-dose. Depletion was quantified by the number of NK and CD8 T cells remaining in respective samples.

This example describes the characterization of antibodies specific to human CD94 using in vivo mouse studies.
Materials and Methods
In Vivo Humanized IL-15 Transgenic Mouse Studies The humanized NSG™-IL-15 transgenic mouse was obtained from the Jackson Lab. Mice are engrafted with healthy donor and LGLL donor PBMCs for 3 and 28 days, respectively. One dose of human IgG1 isotype control or ATX-130 (5 mg/kg) was injected into mice, and depletion of normal NK cells, normal CD8 T cells and CD8 T leukemic cells in the blood, spleen, bone marrow and liver were assessed by flow cytometry 48 hours post-dose (FIG. 22A).
Results The ability (or lack thereof) of ATX-130 to deplete human NK and CD8 T cells was assessed in IL-15 transgenic mice (NSG™-IL-15). The humanized NSG™-IL-15 transgenic mouse is a mouse strain with a complete absence of the mouse IL-2R gamma gene, resulting in defective adaptive and innate immune systems. Expression of human IL-15 enables efficient engraftment of human immune cells, particularly cytotoxic immune cells, from healthy donors and leukemic patients. As shown in FIG. 22B, complete NK cell depletion was observed with ATX-130 treatment (5 mg/kg) relative to isotype control. Partial depletion (~50%) of CD8 T cells was observed. The remaining CD8 T cells were CD94-negative, and thus were not depleted. Overall, ATX-130 depletes CD94+ cells, which includes all human NK cells, and 50% of CD8 T cells.

Figure 23:
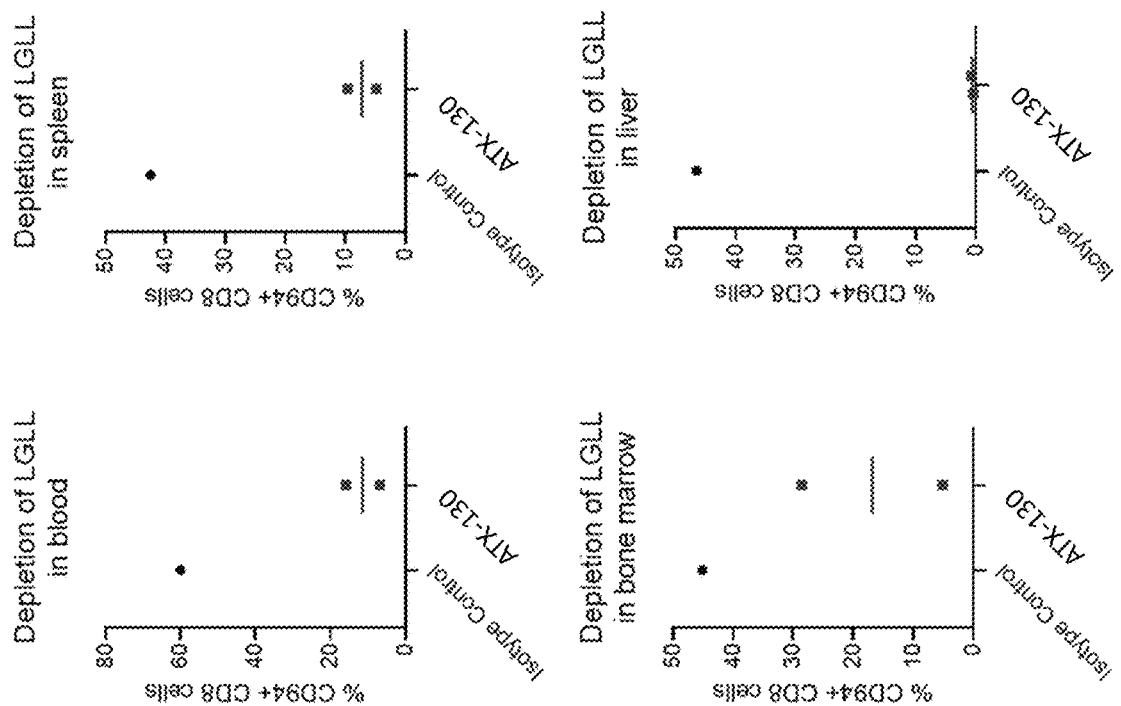
FIG. 23 shows depletion of LGLL cells in blood, spleen, bone marrow, and liver in IL-15 transgenic mice. Mice are engrafted with LGLL PBMCs for 28 days. One dose of human IgG1 isotype control or ATX-130 (5 mg/kg) were injected into mice (5 mice per arm), and depletion of LGLL cells in the blood, spleen, bone marrow, and liver were assessed by flow cytometry 48 hours post-dose. Depletion was quantified by the number of CD94+ LGLL cells remaining in respective samples.

The ability (or lack thereof) of ATX-130-KIF to deplete LGLL in blood, spleen, bone marrow, and liver was assessed in IL-15 transgenic mice (NSG™-IL-15). As shown in FIG. 23, more than 50% LGLL cell depletion was observed with ATX-130 treatment (5 mg/kg) relative to isotype control. The remaining LGLL cells were CD94-negative, and thus were not depleted. Overall, ATX-130 efficiently depletes CD94+ LGLL cells in mice in vivo.

Example 5: Anti-CD94 Antibody ATX-130 Non-GLP Study in Non-Human Primates

Figure 28A:
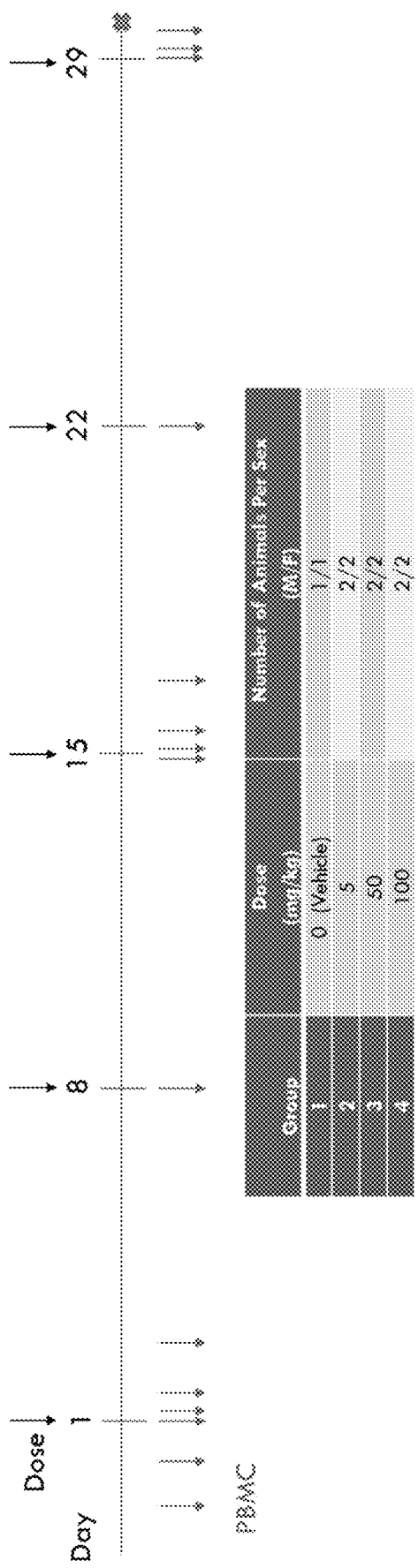
FIG. 28A shows design of a non-GLP PD study in non-human primates to evaluate efficacy of ATK-130 in vivo.

This example describes a second pharmacodynamic (PD) in cynomolgus macaques to evaluate the efficacy of ATX-130 in vivo.
Materials and Methods
In Vivo Non-Human Primate Non-GLP Study A second non-GLP pharmacodynamic (PD) study of 14 healthy cynomolgus monkeys naïve to all compounds prior to study commencement and with no prior history of illness were selected for the study. Five doses of ATX-130 (0-100 mg/kg) were administered through intravenous (IV) infusion at a rate of approximately 0.25 mL/min over 60 minutes weekly. PBMCs were collected at various time intervals at pre- and post-dose. PD was determined via NK cell depletion (CD3−CD16+) and CD8 T cell depletion (CD3+CD8+ NKG2A+) in blood by flow cytometry analysis. Depletion of the same target cells was determined in tissues that were harvested at the time of necropsy.
Results To evaluate the efficacy of ATX-130 in vivo, a second pharmacodynamic (PD) study was completed in NHP (cynomolgus macaques; FIG. 28A). To demonstrate in vivo activity of ATX-130 in NHP, ATX-130 was used as the test article. Fourteen healthy cynomolgus macaques naïve to all compounds prior to study commencement and with no prior history of illness were selected for the study.

Figure 28B:
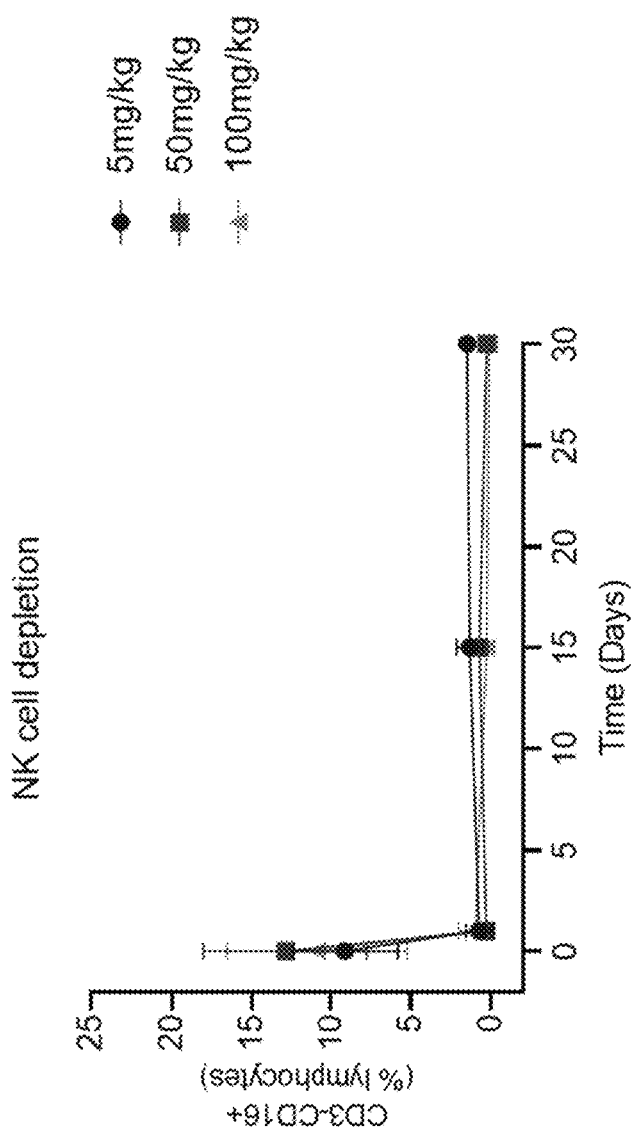
FIG. 28B shows depletion of cynomolgus NK cells in vivo with ATX-130 dosing at 5, 50, and 100 mg/kg. PBMCs were isolated from 0.5 mL blood draws per time point per animal. 0.3×10$^6$ cells were plated per well in technical triplicates and stained with antibody panel. CD3−CD16+ gating strategy was used to identify cynomolgus NK cells. NK cells were quantified by calculating the percentage of the cell population out of total PBMCs.

The ability (or lack thereof) of ATX-130 to deplete cynomolgus NK cells in blood was assessed by flow cytometry analysis. As shown in FIG. 28B, depletion of targets cells (NK cells) to <5% of PBMCs was detected in all animals 6 hours post-administration of ATX-130 at each dose. Overall, the current results show that ATX-130 can demonstrate efficacy in vivo in cynomolgus macaques at 5, 50, and 100 mg/kg.

Figure 29:
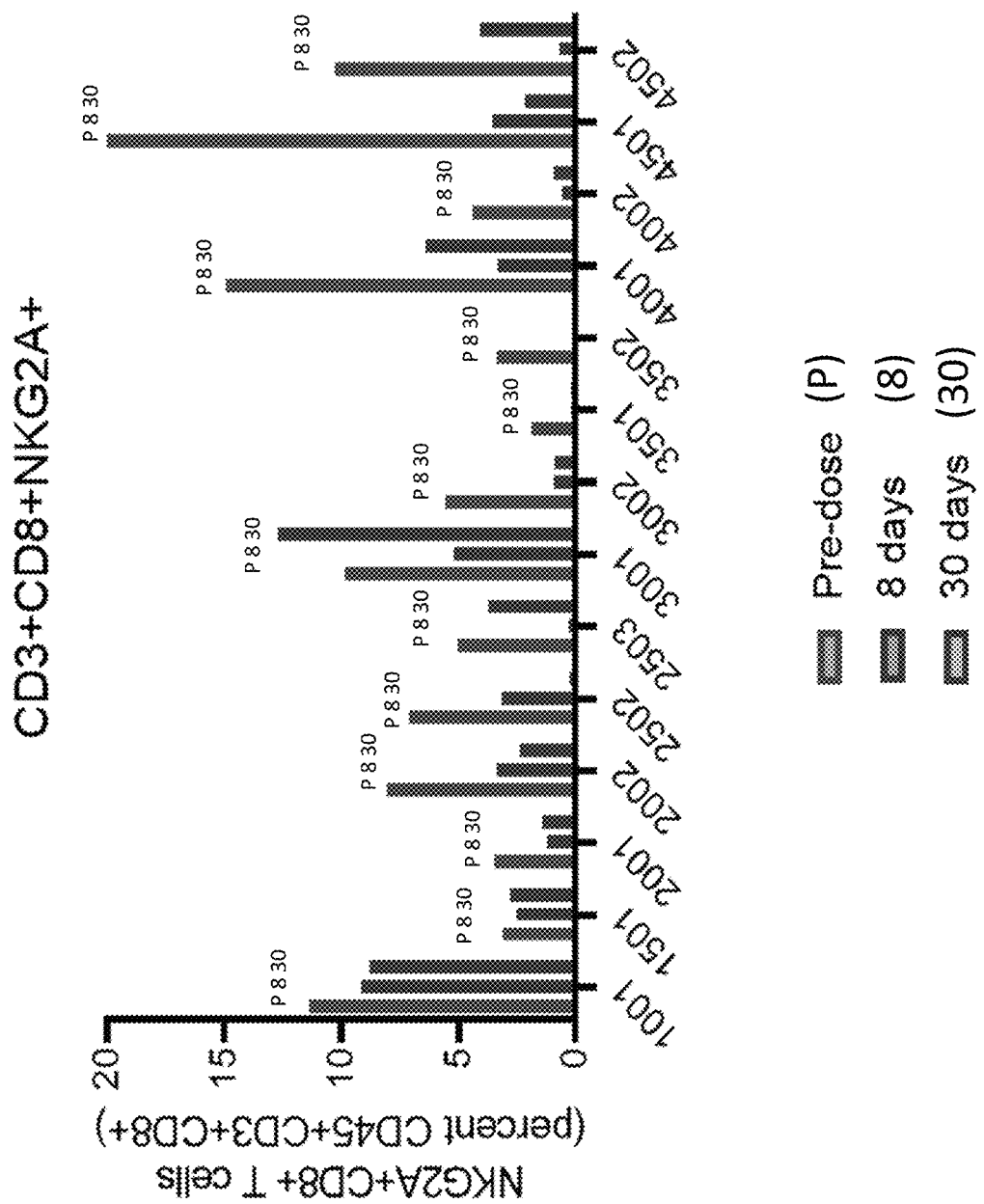
FIG. 29 shows depletion of cynomolgus CD94+CD8+NKG2A+ cells in vivo with ATX-130 dosing at 5, 50, and 100 mg/kg. PBMCs were isolated from 0.5 mL blood draws per time point per animal. 0.3×10$^6$ cells were plated per well in technical triplicates and stained with antibody panel. CD3+CD8+NKG2A+ gating strategy was used to identify cynomolgus CD8+ T cells. CD8 T cells were quantified by calculating the percentage of the cell population out of total PBMCs. Identifiers at the top of each bar indicate time point at which PMBCs were isolated and correspond to time points depicted in figure legend.

The ability (or lack thereof) of ATX-130 to deplete cynomolgus CD94+CD8+NKG2A+ cells in blood at 5, 50, and 100 mg/kg was assessed by flow cytometry. As shown in FIG. 29, depletion of targets cells (CD8 T cells) to <50% of PBMCs was detected in all animals 8 days post-administration of ATX-130 at each dose. Overall, the current results showed that ATX-130 can demonstrate efficacy in vivo on CD94+CD8 T cells in cynomolgus macaques at 5, 50, and 100 mg/kg.

Figure 30:
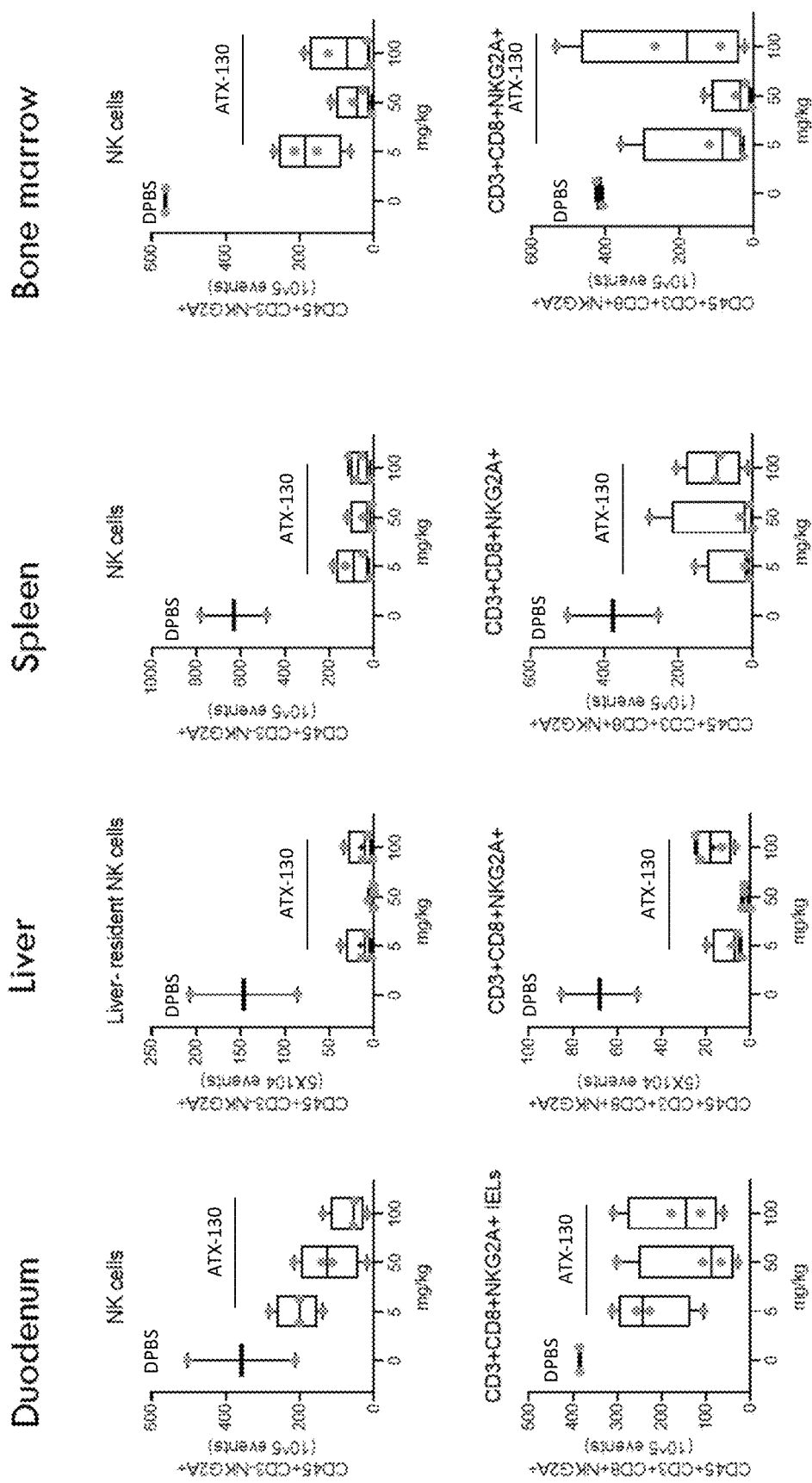
FIG. 30 shows depletion of cynomolgus NK and CD94+CD8+NKG2A+ T cells in vivo with ATX-130 dosing at 5, 50, and 100 mg/kg or vehicle control at 0 mg/kg (using Dulbecco's Phosphate Buffered Saline, PBS). Duodenum, liver, spleen, and bone marrow were harvested at study endpoint. Tissues were dissociated into single cell suspensions and 0.3×10$^6$ cells were plated per well in technical triplicates and stained with antibody panel. CD3+CD8+NKG2A+ gating strategy was used to identify cynomolgus CD8+ T cells. CD45+CD3−NKG2A+ markers were used to identify cynomolgus NK cells. Identifiers at the top of each boxplot indicate antibody used in the experiment.

The ability (or lack thereof) of ATX-130 to deplete cynomolgus NK and CD8+NKG2A+ T cells in tissue was assessed by flow. As shown in FIG. 30, depletion of targets cells (NK and CD8 T cells) to <50% of total cells in animals treated with 5, 50, and 100 mg/kg of ATX-130 relative to 0 mg/kg was detected at the end of study. Overall, the current results showed that ATX-130 can demonstrate efficacy in vivo on NK and CD94+CD8 T cells in cynomolgus macaque tissue.

Example 6: Characterization of Additional Anti-CD94 Antibodies

This example describes characterization of additional ATX anti-CD94 antibodies with respect to binding cells expressing CD94 and CD94 ligand blocking.

First, cell binding affinity of anti-CD94 antibodies ATX-122, -123, -124, -125, -126, -127, -128, -129, and -130 was examined. For human NK cell binding, PBMCs were freshly isolated from healthy donors and incubated with unconjugated antibodies in a dilution series from 100 nM to 0.046 nM. Secondary anti-human antibody labeled with Alexa Fluor 647 was used to detect binding on CD3−CD56bright NK cells. For cynomolgus CD94 binding, HEK293 cells overexpressing cynomolgus CD94 were incubated with unconjugated antibodies in a dilution series from 100 nM to 0.046 nM. Secondary anti-human antibody labeled with Alexa Fluor 647 was used to detect binding on the cells.

Figure 31A:
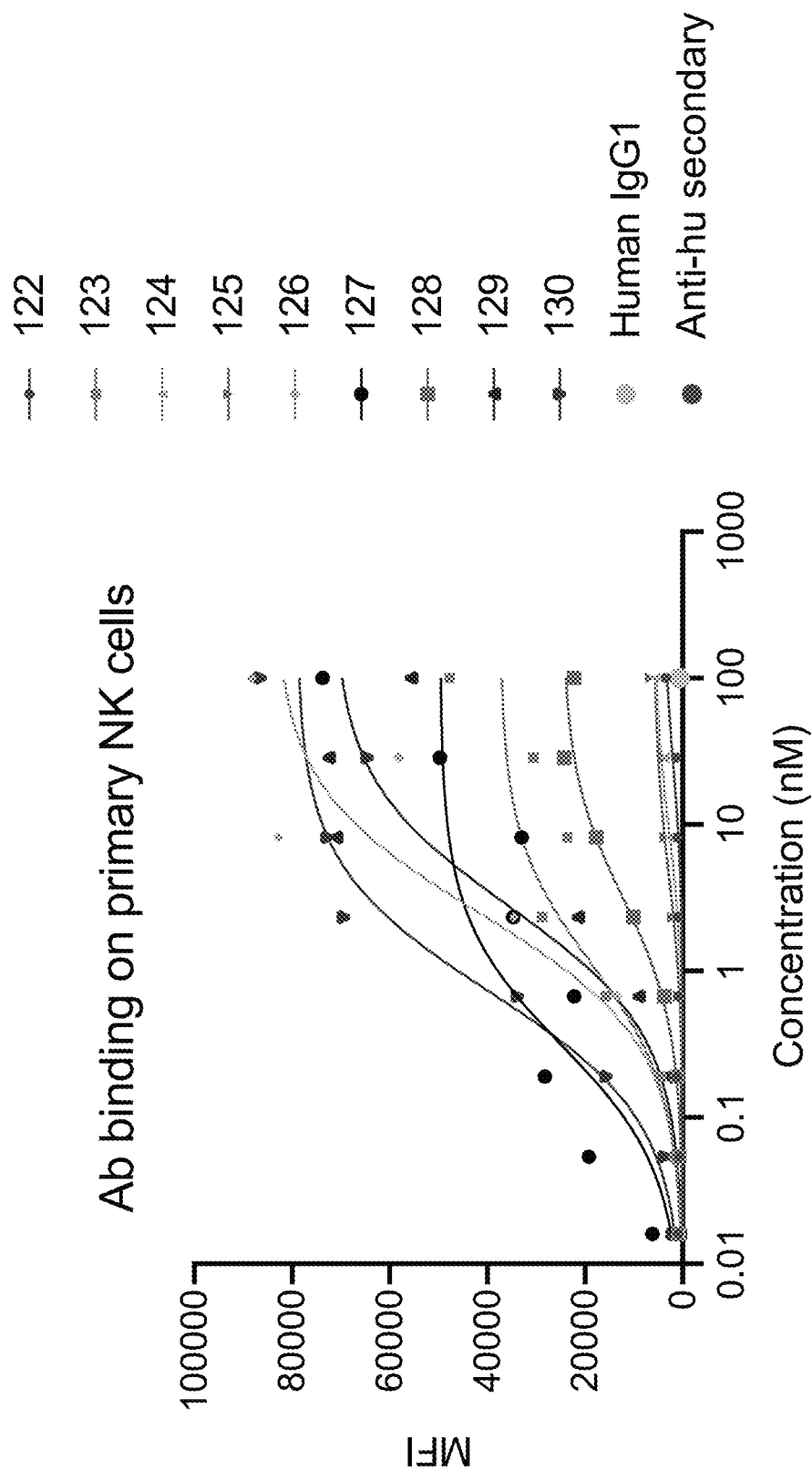
FIGS. 31A & 31B show binding of depicted anti-CD94 antibodies to normal human NK cells (FIG. 31A) or HEK293 cells expressing cynomolgus CD94 (FIG. 31B). Antibodies are shown by ATX numbers. The results showed that ATX-#anti-CD94 antibodies bound to human NK cells or cells expressing cynomolgus CD94.
Figure 31B:
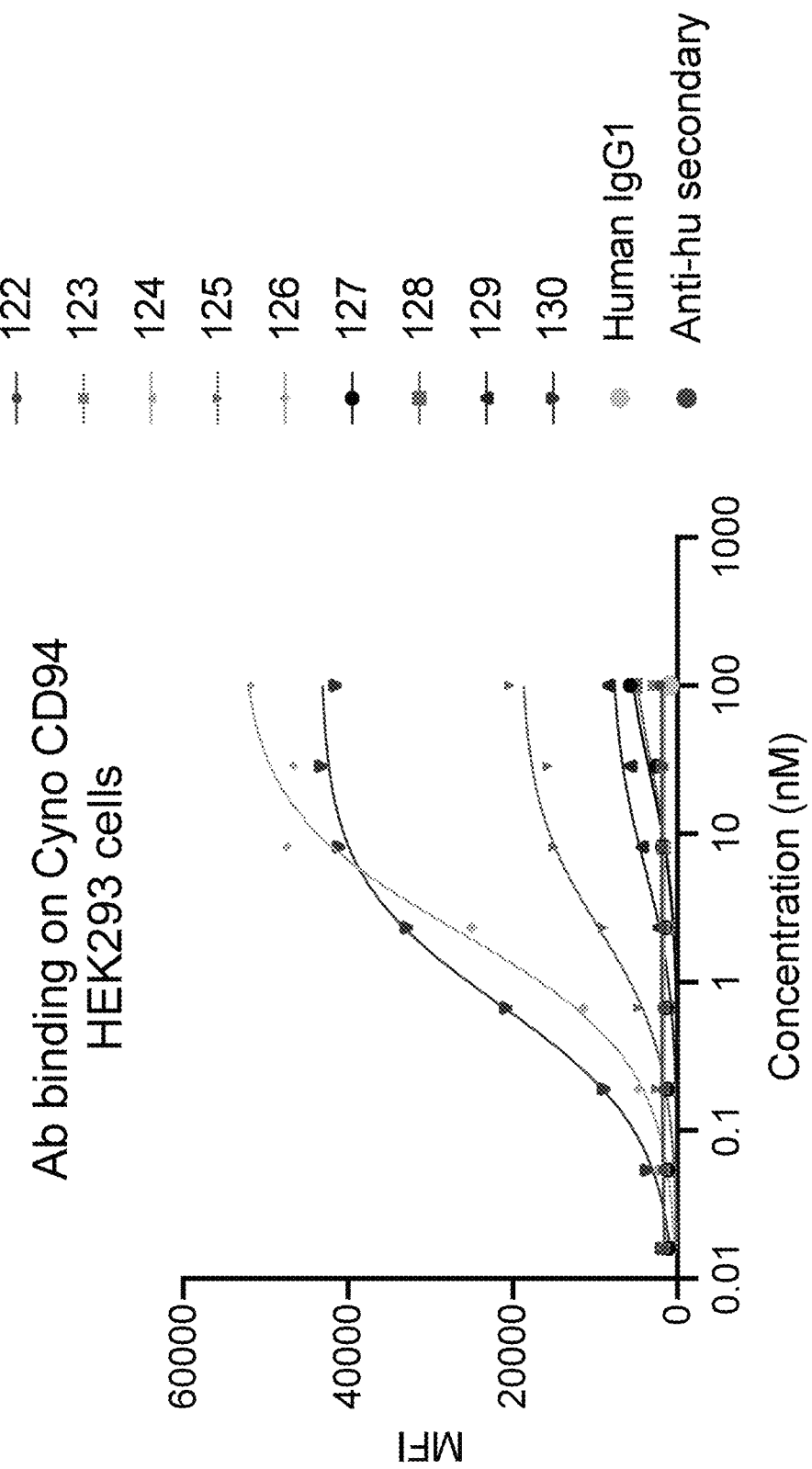
Figure 32A:
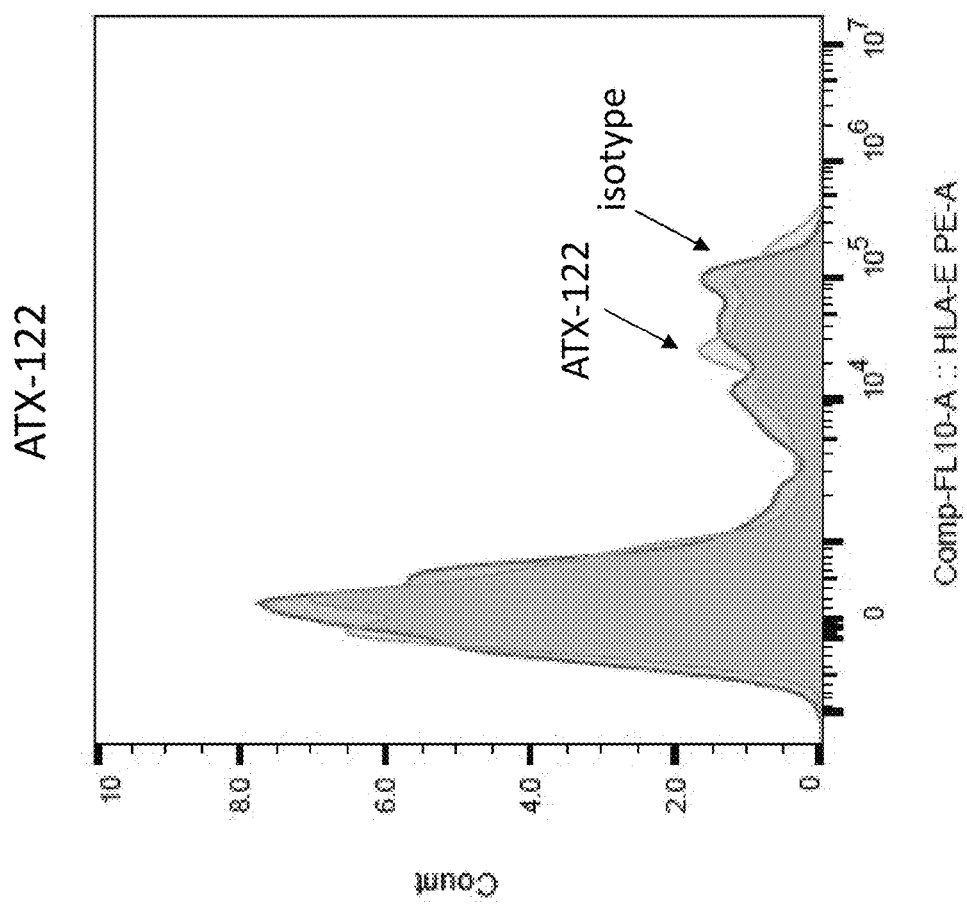
FIGS. 32A-32I show results of HLA-E tetramer blocking assays to determine whether the indicated anti-CD94 antibodies block HLA-E binding. Healthy donor PBMCs were incubated with anti-CD94 antibodies. PE labeled HLA-E tetramer was then incubated with cells and antibody mixture and detected by flow cytometry.
Figure 32B:
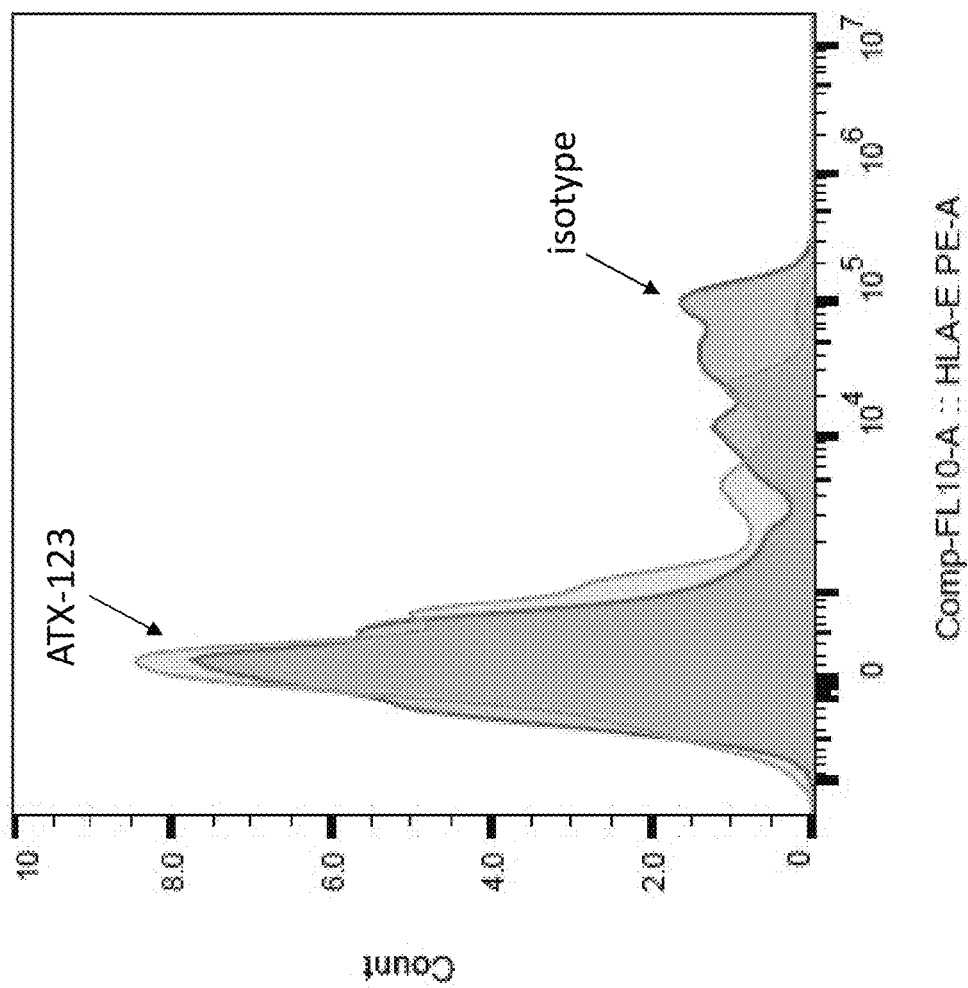
Figure 32C:
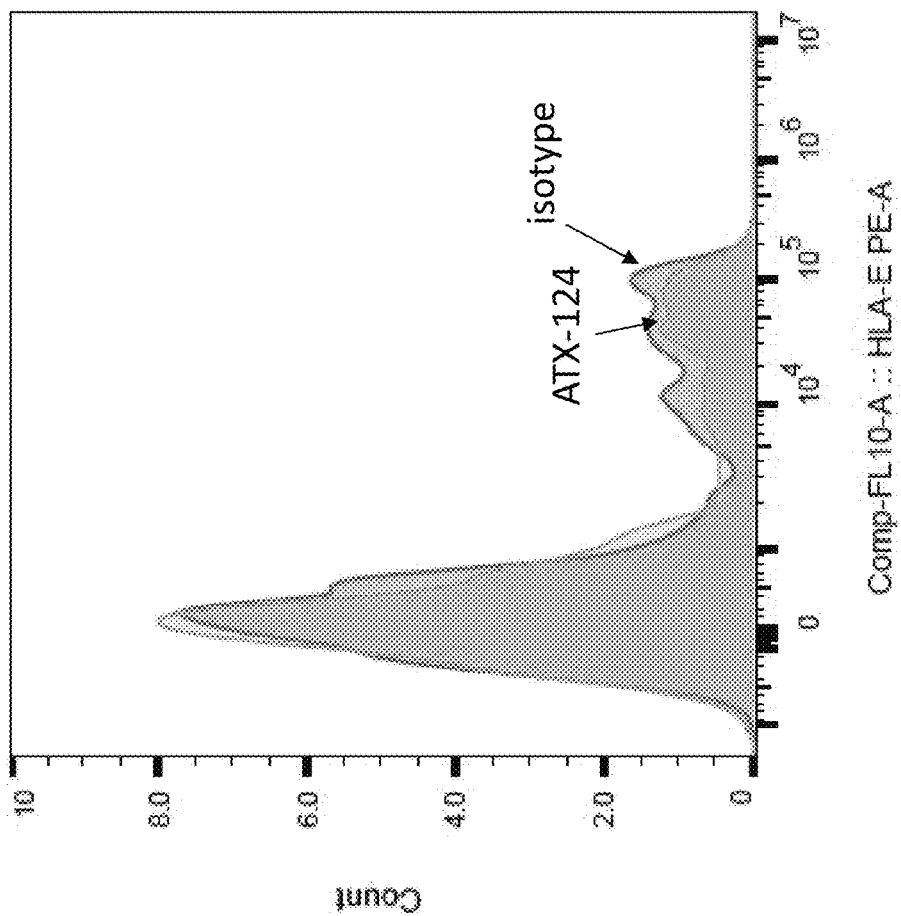
Figure 32D:
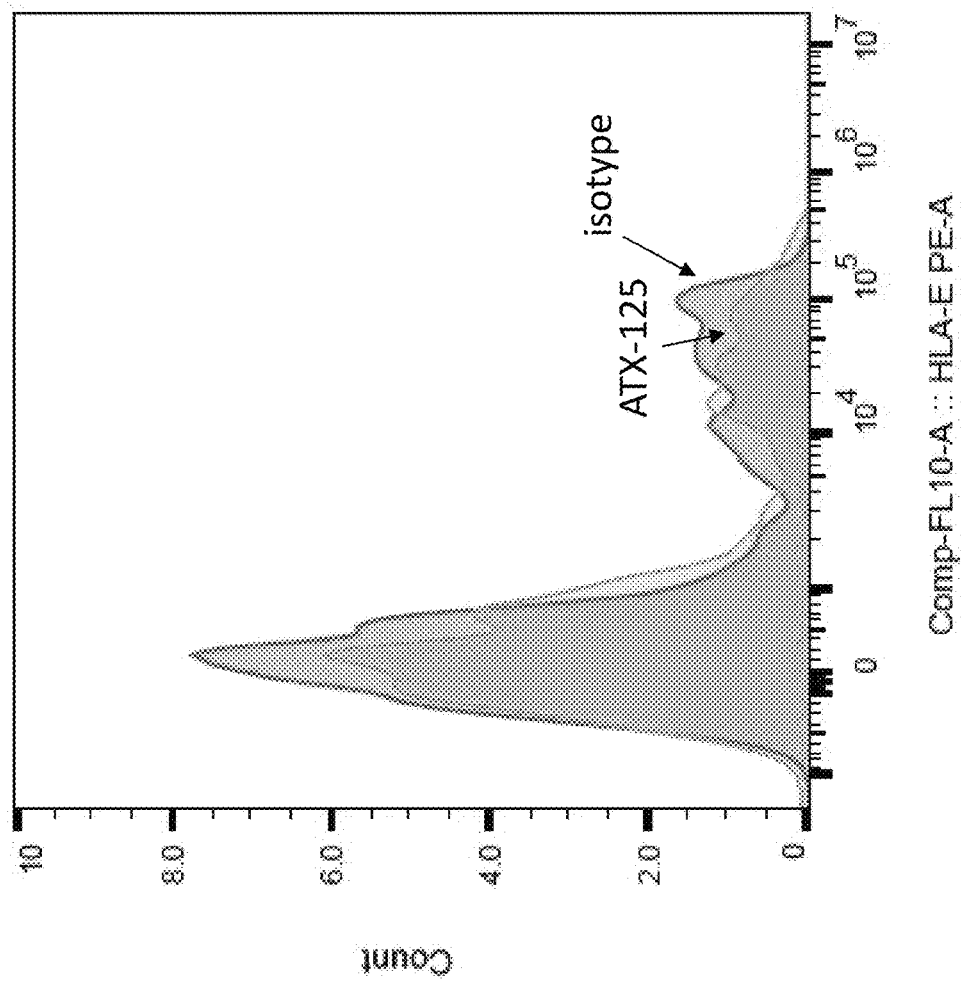
Figure 32E:
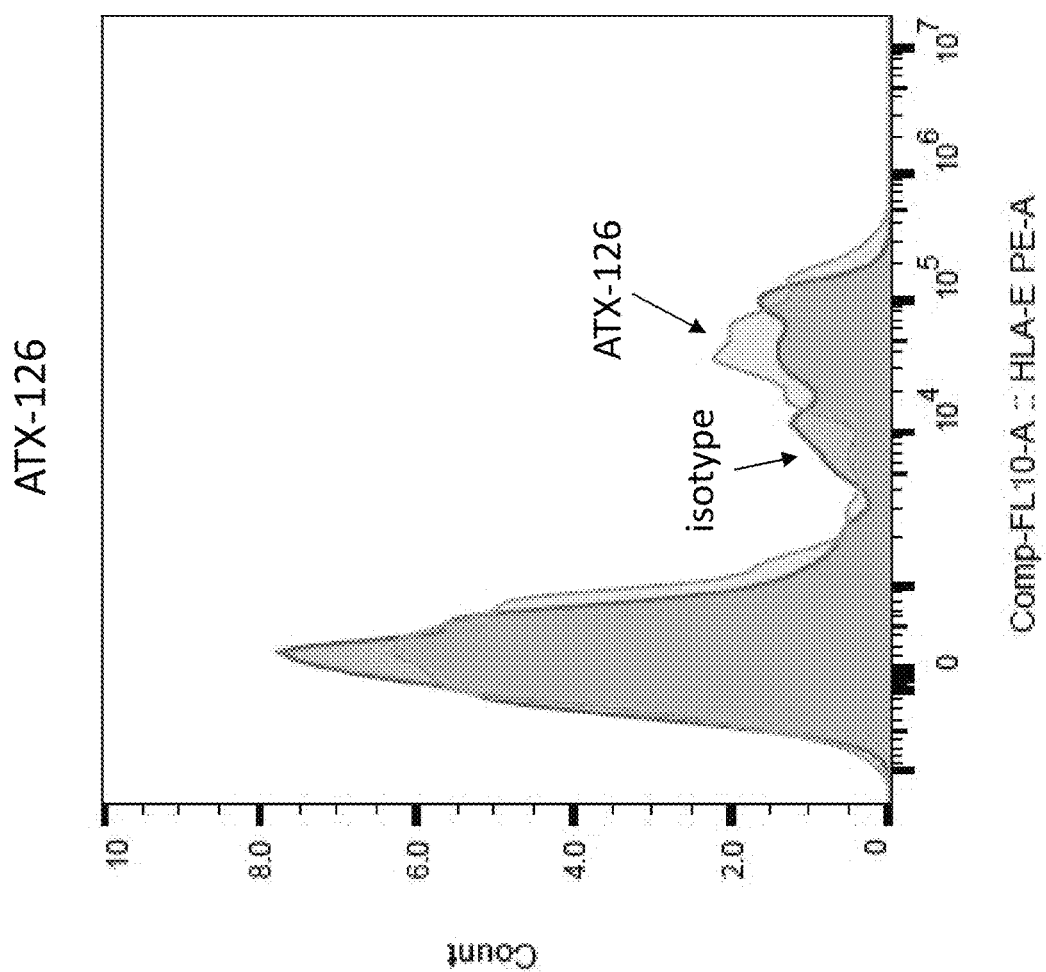
Figure 32F:
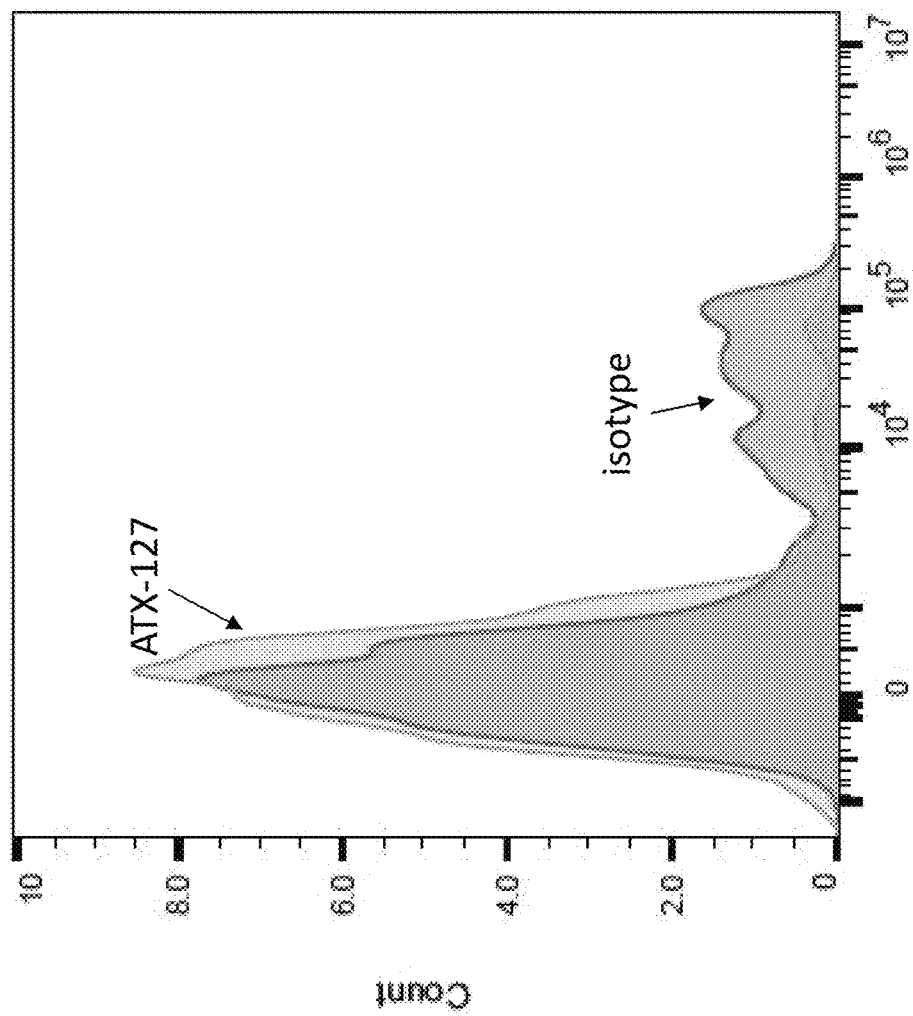
Figure 32G:
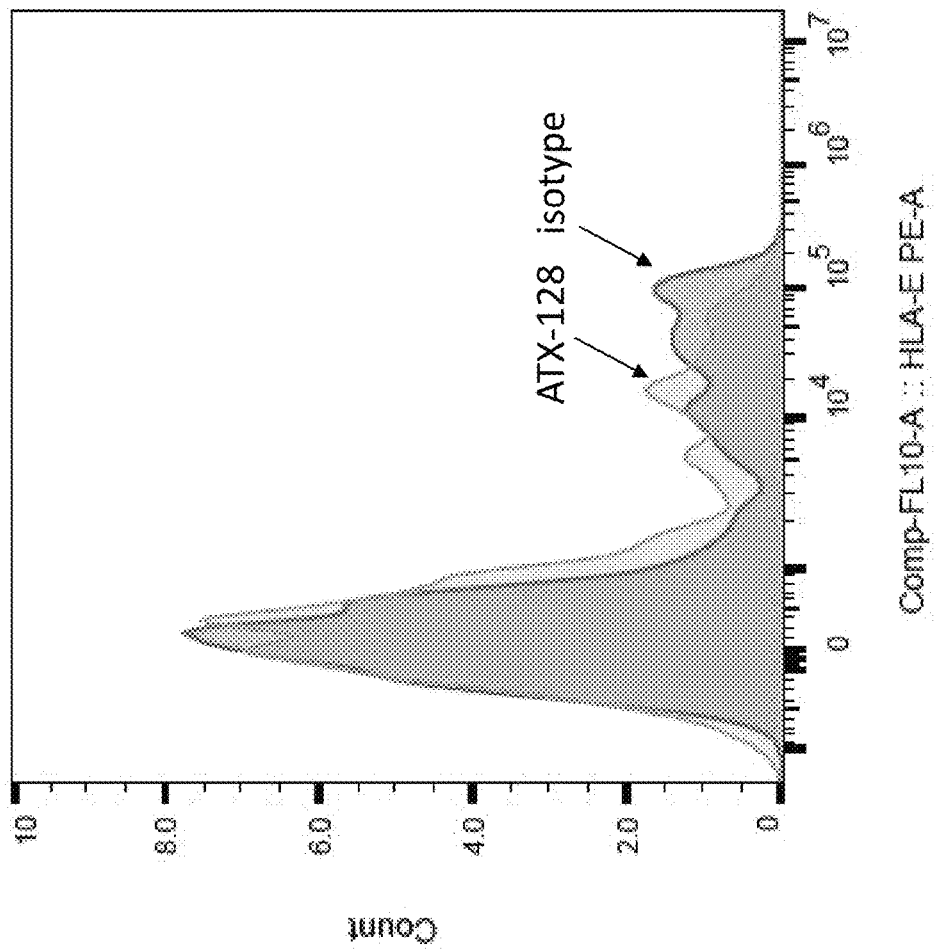
Figure 32H:
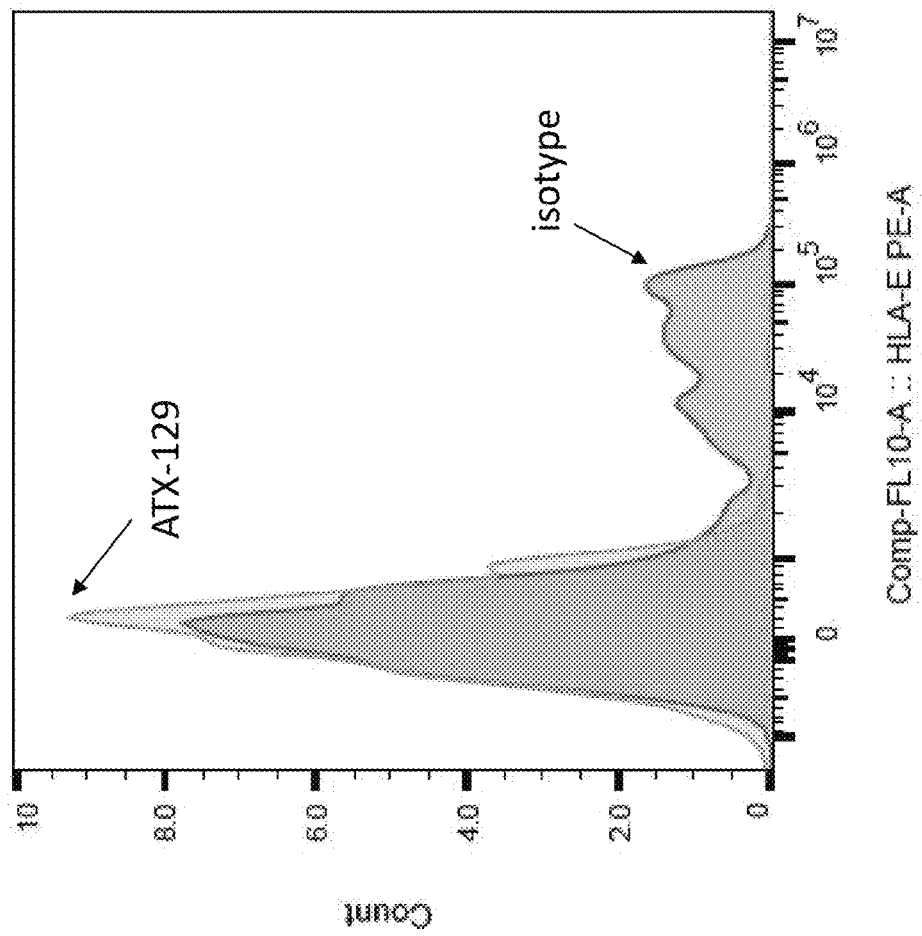
Figure 32I:
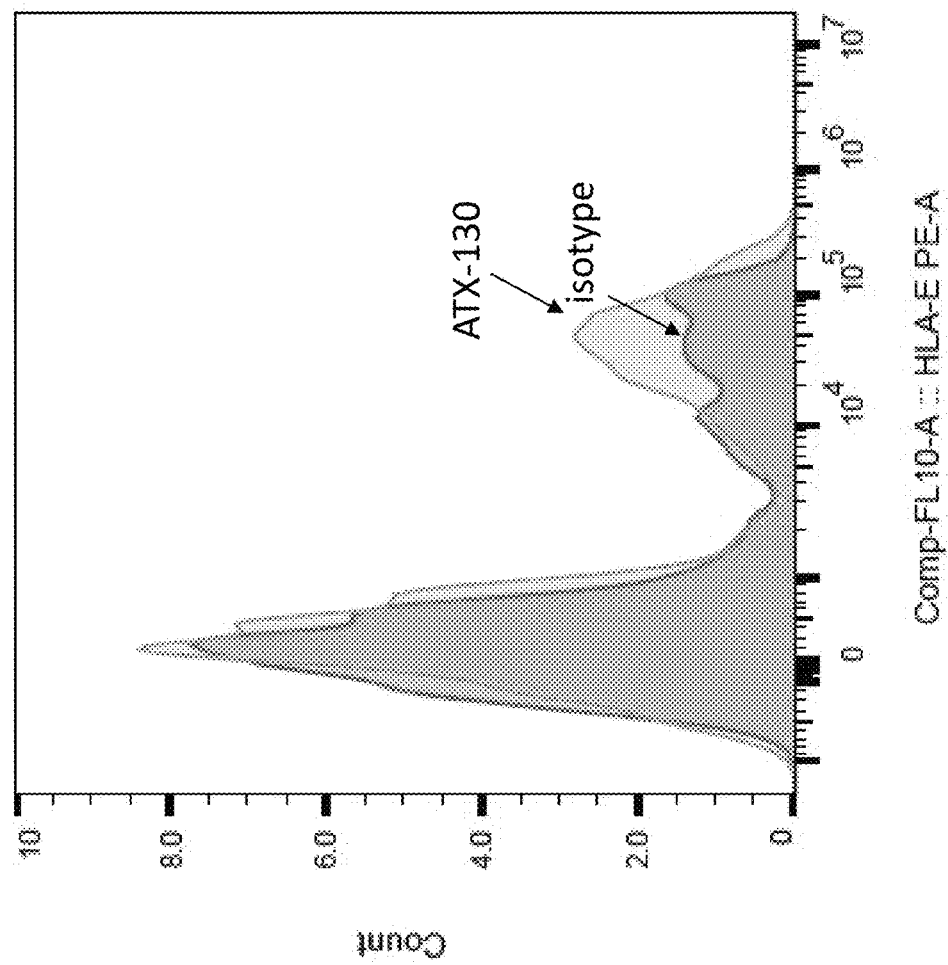

The results demonstrated that the ATX series anti-CD94 antibodies bound human NK cells (FIG. 31A) and cells overexpressing cynomolgus CD94 (mimicking cynomolgus NK cells; FIG. 31B). In freshly isolated PBMCs from healthy donors and HEK293 cells expressing cynomolgus CD94, ATX anti-CD94 antibodies bound with affinities (EC50) ranging from 0.3 to 27 nM.

Second, anti-CD94 antibodies ATX-122, -123, -124, -125, -126, -127, -128, -129, and -130 were characterized in HLA-E tetramer blocking assays to determine whether they block HLA-E binding. Healthy donor PBMCs were incubated with anti-CD94 antibodies. PE labeled HLA-E tetramer was then incubated with cells and antibody mixture and detected by flow cytometry.

The results demonstrated that most anti-CD94 antibodies did not block HLA-E binding (FIGS. 32A-32I). Percent blocking was calculated as 100−((percent HLA-E positive for anti-CD94 antibody)/(percent HLA-E positive for isotype)*100). If an antibody blocked more than 20% of HLA-E binding, it was considered a ligand-blocking antibody. Overall, 6 out of 9 ATX series anti-CD94 antibodies did not block HLA-E binding, whereas commercially available anti-CD94 antibodies block this interaction (see Example 1). A summary of ATX series anti-CD94 antibody characteristics is provided in Table 3.

TABLE 3

Summary of ATX series anti-CD94 antibody characteristics.

| Antibody | Affinity on human NK cells (nM) | Cyno CD94 cross-reactivity | HLA-E blocking |
|---|---|---|---|
| ATX-122 | 27.04 | No | 0% |
| ATX-123 | 1.12 | Yes | 39% |
| ATX-124 | 10.03 | No | 18% |
| ATX-125 | 4.63 | Yes | 11% |
| ATX-126 | 2.52 | Yes | 0% |
| ATX-127 | 0.31 | Yes | 77% |
| ATX-128 | 0.32 | No | 10% |
| ATX-129 | 2.8 | Yes | 96% |
| ATX-130 | 0.6 | Yes | 0% |

Although the present disclosure has been described in some detail by way of illustration and example for purposes of clarity of understanding, the descriptions and examples should not be construed as limiting the scope of the present disclosure. The disclosures of all patent and scientific literature cited herein are expressly incorporated in the entirety by reference.

What is claimed is:

1. An antibody that binds to human CD94, wherein the antibody comprises a heavy chain variable (VH) domain and a light chain variable (VL) domain, wherein:
the VH domain comprises a CDR-H1 comprising the amino acid sequence of SEQ ID NO:47, a CDR-H2 comprising the amino acid sequence of SEQ ID NO:48, and a CDR-H3 comprising the amino acid sequence of SEQ ID NO:62; and wherein the VL domain comprises a CDR-L1 comprising the amino acid sequence of SEQ ID NO:63, a CDR-L2 comprising the amino acid sequence of SEQ ID NO:34, and a CDR-L3 comprising the amino acid sequence of SEQ ID NO:64.

2. An antibody that binds to human CD94, wherein the antibody comprises a heavy chain variable (VH) domain and a light chain variable (VL) domain, wherein:
the VH domain comprises a CDR-H1 comprising the amino acid sequence of SEQ ID NO: 109, a CDR-H2 comprising the amino acid sequence of SEQ ID NO:110, and a CDR-H3 comprising the amino acid sequence of SEQ ID NO: 111; and wherein the VL domain comprises a CDR-L1 comprising the amino acid sequence of SEQ ID NO: 112, a CDR-L2 comprising the amino acid sequence of SEQ ID NO:113, and a CDR-L3 comprising the amino acid sequence of SEQ ID NO:64.

3. The antibody of claim 1, wherein:
the VH domain comprises an amino acid sequence with at least 80% sequence identity to the amino acid sequence of SEQ ID NO:81, and the VL domain comprises an amino acid sequence with at least 80% sequence identity to the amino acid sequence of SEQ ID NO:82.

4. The antibody of claim 3, wherein:
the VH domain comprises the amino acid sequence of SEQ ID NO:81, and the VL domain comprises the amino acid sequence of SEQ ID NO:82.

5. The antibody of claim 1, wherein the antibody is a human antibody.

6. The antibody of claim 1, wherein the antibody is an antigen-binding antibody fragment or single chain antibody.

7. The antibody of claim 1, wherein the antibody further comprises an Fc region.

8. The antibody of claim 7, wherein the Fc region is a human IgG1 Fc region.

9. The antibody of claim 7, wherein the antibody comprises a human Fc region that is non-fucosylated.

10. The antibody of claim 7, wherein the antibody binds to a human cellular Fc gamma receptor IIIA to a greater extent than an antibody comprising a wild type human IgG1 Fc region.

11. The antibody of claim 7, wherein the antibody is capable of inducing antibody-dependent cellular cytotoxicity (ADCC) against a cell expressing human CD94 on its surface.

12. A polynucleotide encoding the antibody of claim 1.

13. A vector comprising the polynucleotide of claim 12.

14. The vector of claim 13, wherein the vector is an expression vector.

15. An isolated host cell comprising the polynucleotide of claim 12.

16. A method of producing an antibody, comprising culturing the host cell of claim 15 under conditions suitable for production of the antibody.

17. The method of claim 16, further comprising recovering the antibody from the host cell.

18. A pharmaceutical composition comprising the antibody of claim 1 and a pharmaceutically acceptable carrier.

19. A method for treating a disease or disorder in a subject, comprising administering to the subject an effective amount of the composition of claim 18; wherein the disease or disorder is Felty's syndrome, inclusion body myositis, aggressive NK leukemia, rheumatoid arthritis, LGL leukemia, or chronic lymphoproliferative disorder of NK cells (CLPD-NK).

20. A method for reducing the number of peripheral blood LGL and/or NK cells in a subject, comprising administering to the subject an effective amount of the composition of claim 18.

21. A method for inducing ADCC activity in a subject, comprising administering to the subject an effective amount of the composition of claim 18.

22. A method for treating CLPD-NK in a human subject in need thereof, comprising administering to the subject an effective amount of the composition of claim 18.

23. A method of treating natural killer (NK) cell or T-cell lymphoma, comprising administering to a subject in need thereof an effective amount of the composition of claim 18.

24. The method of claim 23, wherein the NK cell or T-cell lymphoma is extranodal NK/T cell lymphoma, hepatosplenic T cell lymphoma (TCL), enteropathy-associated TCL, cutaneous TCL, anaplastic large cell lymphoma (ALK+), anaplastic large cell lymphoma (ALK−), peripheral TCL, angioimmunoblastic TCL, adult TCL, monomorphic epitheliotropic intestinal TCL, epidermotropic CD8+ cutaneous TCL, primary cutaneous gamma/delta TCL, or subcutaneous panniculitis TCL.

25. The method of claim 24, wherein the NK cell or T-cell lymphoma is extranodal NK/T cell lymphoma, hepatosplenic TCL, or enteropathy-associated TCL.

26. A method for enhancing chimeric antigen receptor T cell (CAR-T) therapy in a human subject in need thereof, comprising administering to the subject an effective amount of the composition of claim 18 prior to administration of a CAR-T treatment to the subject.

27. A method for depleting CD8+CD94+ T cells in a human subject in need thereof, comprising administering to the subject an effective amount of the composition of claim 18.

28. The method of claim 19, further comprising administering an IL-2 polypeptide to the subject.

29. The method of claim 19, wherein the subject is a human.

30. The antibody of claim 1, wherein the antibody comprises a heavy chain comprising a VH domain that comprises the amino acid sequence of SEQ ID NO:81 and a human IgG1 Fc region, and a light chain comprising a VL domain that comprises the amino acid sequence of SEQ ID NO:82.

31. The antibody of claim 30, wherein the human IgG1 Fc region is non-fucosylated.

32. A method for depleting NK cells in a human subject in need thereof, comprising administering to the subject an effective amount of the composition of claim 18.

33. The method of claim 32, wherein the antibody that binds to human CD94 further comprises an Fc region.

34. The antibody of claim 8, wherein the human IgG1 Fc region is non-fucosylated.

35. The antibody of claim 4, wherein the antibody further comprises a human IgG1 Fc region.

36. The antibody of claim 35, wherein the human IgG1 Fc region is non-fucosylated.

37. A polynucleotide encoding the antibody of claim 4.

38. A vector comprising the polynucleotide of claim 37.

39. An isolated host cell comprising the polynucleotide of claim 37.

40. A method of producing an antibody, comprising culturing the host cell of claim 39 under conditions suitable for production of the antibody.

41. A pharmaceutical composition comprising the antibody of claim 4 and a pharmaceutically acceptable carrier.

42. A method for treating a disease or disorder in a subject, comprising administering to the subject an effective amount of the composition of claim 41; wherein the disease or disorder is Felty's syndrome, inclusion body myositis, aggressive NK leukemia, rheumatoid arthritis, LGL leukemia, or chronic lymphoproliferative disorder of NK cells (CLPD-NK).

43. A method for reducing the number of peripheral blood LGL and/or NK cells in a subject, comprising administering to the subject an effective amount of the composition of claim 41.

44. A method for inducing ADCC activity in a subject, comprising administering to the subject an effective amount of the composition of claim 41.

45. A method for treating CLPD-NK in a human subject in need thereof, comprising administering to the subject an effective amount of the composition of claim 41.

46. A method of treating natural killer (NK) cell or T-cell lymphoma, comprising administering to a subject in need thereof an effective amount of the composition of claim 41.

47. A method for enhancing chimeric antigen receptor T cell (CAR-T) therapy in a human subject in need thereof, comprising administering to the subject an effective amount of the composition of claim 41 prior to administration of a CAR-T treatment to the subject.

48. A method for depleting CD8+CD94+ T cells in a human subject in need thereof, comprising administering to the subject an effective amount of the composition of claim 41.

49. A method for depleting NK cells in a human subject in need thereof, comprising administering to the subject an effective amount of the composition of claim 41.

50. A polynucleotide encoding the antibody of claim 35.

51. A vector comprising the polynucleotide of claim 50.

52. An isolated host cell comprising the polynucleotide of claim 50.

53. A method of producing an antibody, comprising culturing the host cell of claim 52 under conditions suitable for production of the antibody.

54. A pharmaceutical composition comprising the antibody of claim 35 and a pharmaceutically acceptable carrier.

55. A method for treating a disease or disorder in a subject, comprising administering to the subject an effective amount of the composition of claim 54; wherein the disease or disorder is Felty's syndrome, inclusion body myositis, aggressive NK leukemia, rheumatoid arthritis, LGL leukemia, or chronic lymphoproliferative disorder of NK cells (CLPD-NK).

56. A method for reducing the number of peripheral blood LGL and/or NK cells in a subject, comprising administering to the subject an effective amount of the composition of claim 54.

57. A method for inducing ADCC activity in a subject, comprising administering to the subject an effective amount of the composition of claim 54.

58. A method for treating CLPD-NK in a human subject in need thereof, comprising administering to the subject an effective amount of the composition of claim 54.

59. A method of treating natural killer (NK) cell or T-cell lymphoma, comprising administering to a subject in need thereof an effective amount of the composition of claim 54.

60. A method for enhancing chimeric antigen receptor T cell (CAR-T) therapy in a human subject in need thereof, comprising administering to the subject an effective amount of the composition of claim 54 prior to administration of a CAR-T treatment to the subject.

61. A method for depleting CD8+CD94+ T cells in a human subject in need thereof, comprising administering to the subject an effective amount of the composition of claim 54.

62. A method for depleting NK cells in a human subject in need thereof, comprising administering to the subject an effective amount of the composition of claim 54.

63. A polynucleotide encoding the antibody of claim 36.

64. A vector comprising the polynucleotide of claim 63.

65. An isolated host cell comprising the polynucleotide of claim 63.

66. A method of producing an antibody, comprising culturing the host cell of claim 65 under conditions suitable for production of the antibody.

67. A pharmaceutical composition comprising the antibody of claim 36 and a pharmaceutically acceptable carrier.

68. A method for treating a disease or disorder in a subject, comprising administering to the subject an effective amount of the composition of claim 67; wherein the disease or disorder is Felty's syndrome, inclusion body myositis, aggressive NK leukemia, rheumatoid arthritis, LGL leukemia, or chronic lymphoproliferative disorder of NK cells (CLPD-NK).

69. A method for reducing the number of peripheral blood LGL and/or NK cells in a subject, comprising administering to the subject an effective amount of the composition of claim 67.

70. A method for inducing ADCC activity in a subject, comprising administering to the subject an effective amount of the composition of claim 67.

71. A method for treating CLPD-NK in a human subject in need thereof, comprising administering to the subject an effective amount of the composition of claim 67.

72. A method of treating natural killer (NK) cell or T-cell lymphoma, comprising administering to a subject in need thereof an effective amount of the composition of claim 67.

73. A method for enhancing chimeric antigen receptor T cell (CAR-T) therapy in a human subject in need thereof, comprising administering to the subject an effective amount of the composition of claim 67 prior to administration of a CAR-T treatment to the subject.

74. A method for depleting CD8+CD94+ T cells in a human subject in need thereof, comprising administering to the subject an effective amount of the composition of claim 67.

75. A method for depleting NK cells in a human subject in need thereof, comprising administering to the subject an effective amount of the composition of claim 67.

* * * * *

UNITED STATES PATENT AND TRADEMARK OFFICE
CERTIFICATE OF CORRECTION

PATENT NO. : 11,795,228 B2  
APPLICATION NO. : 17/489385  
DATED : October 24, 2023  
INVENTOR(S) : Nenad Tomasevic et al.

Page 1 of 1

It is certified that error appears in the above-identified patent and that said Letters Patent is hereby corrected as shown below:

On the Title Page

Item (71), delete "Redwood City, CA (US)" and insert --Foster City, CA (US)--

Signed and Sealed this  
Thirteenth Day of May, 2025

Coke Morgan Stewart  
*Acting Director of the United States Patent and Trademark Office*